US007160542B2

(12) United States Patent
Le et al.

(10) Patent No.: US 7,160,542 B2
(45) Date of Patent: *Jan. 9, 2007

(54) METHOD OF TREATING PSORIASIS USING HUMAN ANTI-TNF ANTIBODIES AND FRAGMENTS

(75) Inventors: Junming Le, Jackson Heights, NY (US); Jan Vilcek, New York, NY (US); Peter Daddona, Menlo Park, CA (US); John Ghrayeb, Thorndale, PA (US); David Knight, Berwyn, PA (US); Scott Siegel, Westborough, MA (US)

(73) Assignees: New York University, New York, NY (US); Centocor, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/170,753

(22) Filed: Jun. 29, 2005

(65) Prior Publication Data
US 2006/0013816 A1    Jan. 19, 2006

Related U.S. Application Data

(60) Division of application No. 09/927,703, filed on Aug. 10, 2001, which is a continuation of application No. 09/756,398, filed on Jan. 8, 2001, now Pat. No. 6,835,823, which is a division of application No. 09/133,119, filed on Aug. 12, 1998, now Pat. No. 6,277,969, which is a division of application No. 08/570,674, filed on Dec. 11, 1995, now abandoned, which is a continuation-in-part of application No. 08/324,799, filed on Oct. 18, 1994, now Pat. No. 5,698,195, which is a continuation-in-part of application No. 08/192,102, filed on Feb. 4, 1994, now Pat. No. 5,656,272, and a continuation-in-part of application No. 08/192,861, filed on Feb. 4, 1994, now Pat. No. 5,919,452, and a continuation-in-part of application No. 08/192,093, filed on Feb. 4, 1994, now Pat. No. 6,284,471, which is a continuation-in-part of application No. 08/010,406, filed on Jan. 29, 1993, now abandoned, and a continuation-in-part of application No. 08/013,413, filed on Feb. 2, 1993, now abandoned, which is a continuation-in-part of application No. 07/943,852, filed on Sep. 11, 1992, now abandoned, which is a continuation-in-part of application No. 07/853,606, filed on Mar. 18, 1992, now abandoned, which is a continuation-in-part of application No. 07/670,827, filed on Mar. 18, 1991, now abandoned.

(51) Int. Cl.
*A61K 39/395* (2006.01)
*C07K 16/28* (2006.01)

(52) U.S. Cl. .............. 424/145.1; 424/130.1; 424/133.1; 424/141.1; 424/158.1; 530/387.1; 530/387.3; 530/388.1; 530/388.2; 530/388.23

(58) Field of Classification Search .............. None
See application file for complete search history.

(56) References Cited

U.S. PATENT DOCUMENTS

| | | |
|---|---|---|
| 4,603,106 A | 7/1986 | Cerami et al. |
| 4,816,567 A | 3/1989 | Cabilly et al. |
| 4,822,776 A | 4/1989 | Cerami et al. |
| 5,075,236 A | 12/1991 | Yone et al. |
| 5,223,395 A | 6/1993 | Gero |
| 5,231,024 A | 7/1993 | Moeller et al. |
| 5,342,613 A | 8/1994 | Creaven et al. |
| 5,360,716 A | 11/1994 | Ohmoto et al. |
| 5,436,154 A | 7/1995 | Barbanti et al. |
| 5,654,407 A | 8/1997 | Boyle et al. |
| 5,656,272 A | 8/1997 | Le et al. |
| 5,658,570 A | 8/1997 | Newman et al. |
| 5,698,195 A | 12/1997 | Le et al. |
| 5,700,788 A | 12/1997 | Mongelli et al. |
| 5,730,975 A | 3/1998 | Hotamisligil et al. |
| 5,741,488 A | 4/1998 | Feldman et al. |
| 5,750,105 A | 5/1998 | Newman et al. |
| 5,776,947 A | 7/1998 | Kroemer et al. |
| 5,874,441 A * | 2/1999 | Magolda et al. ............ 514/285 |
| 5,888,511 A | 3/1999 | Skurkovich et al. |
| 5,919,452 A * | 7/1999 | Le et al. ............... 424/133.1 |
| 5,958,413 A | 9/1999 | Anagnostopulos et al. |
| 5,959,087 A | 9/1999 | Rathjen et al. |
| 5,993,833 A | 11/1999 | DeLacharriere et al. |
| 5,994,510 A * | 11/1999 | Adair et al. ............. 530/387.3 |
| 6,015,558 A | 1/2000 | Hotamisligil et al. |

(Continued)

FOREIGN PATENT DOCUMENTS

EP    0212489 A2    3/1987

(Continued)

OTHER PUBLICATIONS

The Merck Manual of Diagnosis and Therapy, Sixteenth Edition, edited by Berkow et al., Merck Research Laboratories, Rahway, NJ, 1992; see pp. 2435-2437.*

(Continued)

*Primary Examiner*—Phillip Gambel
(74) *Attorney, Agent, or Firm*—Hamilton, Brook, Smith & Reynolds, P.C.

(57) ABSTRACT

Anti-TNF antibodies, fragments and regions thereof which are specific for human tumor necrosis factor-α (TNFα) and are useful in vivo diagnosis and therapy of a number of TNFα-mediated pathologies and conditions, as well as polynucleotides coding for murine and chimeric antibodies, methods of producing the antibody, methods of use of the anti-TNF antibody, or fragment, region or derivative thereof, in immunoassays and immunotherapeutic approaches are provided.

18 Claims, 37 Drawing Sheets

U.S. PATENT DOCUMENTS

| | | |
|---|---|---|
| 6,172,202 B1 | 1/2001 | Marcucci et al. |
| 6,190,691 B1 | 2/2001 | Mak |
| 6,194,451 B1 | 2/2001 | Alpegiani et al. |
| 6,277,969 B1 | 8/2001 | Le et al. |
| 6,284,471 B1 | 9/2001 | Le et al. |
| 6,309,640 B1 | 10/2001 | Cerami et al. |
| 6,419,927 B1 | 7/2002 | Cerami et al. |
| 6,790,444 B1 | 9/2004 | Le et al. |
| 6,835,823 B1 | 12/2004 | Le et al. |
| 6,991,791 B1 | 1/2006 | Le et al. |
| 7,070,775 B1 | 7/2006 | Le et al. |

FOREIGN PATENT DOCUMENTS

| | | |
|---|---|---|
| EP | 0218868 A2 | 4/1987 |
| EP | 0260610 B1 | 3/1988 |
| EP | 0350690 A2 | 1/1990 |
| EP | 0351789 A2 | 1/1990 |
| EP | 0351789 B1 | 1/1990 |
| EP | 0380068 A1 | 8/1990 |
| EP | 0393438 A2 | 10/1990 |
| EP | 0453898 A2 | 10/1991 |
| EP | 0486526 B2 | 5/1992 |
| EP | 0512528 B1 | 11/1992 |
| EP | 0526905 A2 | 2/1993 |
| EP | 0288 088 B1 | 3/1994 |
| EP | 0585705 A1 | 3/1994 |
| EP | 0614984 A2 | 9/1994 |
| EP | 0308378 B1 | 11/1994 |
| EP | 0412486 B1 | 11/1994 |
| EP | 0101681 B1 | 12/1994 |
| EP | 0398327 B1 | 3/1995 |
| EP | 0433900 B1 | 9/1995 |
| EP | 0663836 B1 | 7/1997 |
| JP | 61-047500 | 3/1986 |
| JP | 02-227095 | 9/1990 |
| WO | WO 89/08460 | 9/1989 |
| WO | WO 90/00902 | 2/1990 |
| WO | WO 90/01950 | 3/1990 |
| WO | WO 91/02078 | 2/1991 |
| WO | WO 91/04054 | 4/1991 |
| WO | WO 91/09967 | 7/1991 |
| WO | WO 92/01059 | 1/1992 |
| WO | WO 92/01472 | 2/1992 |
| WO | WO 92/07076 | 4/1992 |
| WO | WO 92/11383 | 7/1992 |
| WO | WO 92/13095 | 8/1992 |
| WO | WO 92/16553 | 10/1992 |
| WO | WO 93/02108 | 2/1993 |
| WO | WO 93/11236 | 6/1993 |
| WO | WO 94/08609 | 4/1994 |
| WO | WO 94/08619 | 4/1994 |

OTHER PUBLICATIONS

Beutler, B. et al., "Identity of tumour necrosis factor and the macrophage-secreted factor cachectin," *Nature*, 316:552-554 (1985).

Beutler, B. et al., "Passive Immunization Against Cachectin/Tumor Necrosis Factor Protects Mice from Lethal Effect of Endotoxin," *Science*, 229:869-871 (1985).

Morrison, Sherie L., "Transfectomas Provide Novel Chimeric Antibodies," *Science*, 229:1202-1207 (1985).

Liang, Chi-Ming et al., "Production and Characterization of Monoclonal Antibodies Against Recombinant Human Tumor Necrosis Factor/Cachectin," *Biochem. & Biophy. Res. Comm.*, 137(2):847-854 (1986).

Hirai, Makoto et al., "Production and characterization of monoclonal antibodies to human tumor necrosis factor," *J. of Immun. Methods*, 96:57-62 (1987).

Piguet, Pierre-Francois et al., "Tumor Necrosis Factor/Cachectin is an Effector of Skin and Gut Lesions of the Acute Phase of Graft-vs.-Host Disease," *J. Exp. Med.*, 166:1280-1289 (1987).

Meager, Anthony et al., "Preparation and Characterization of Monoclonal Antibodies Directed Against Antigenic Determinants of Recombinant Human Tumour Necrosis Factor (rTNF)," *Hybridoma*, 6(3):305-311 (1987).

Fendly, Brian M. et al., "Murine Monoclonal Antibodies Defining Neutralizing Epitopes on Tumor Necrosis Factor," *Hybridoma* , (4):359-370 (1987).

Bringman, Timothy S. and Aggarwal, Bharat B., "Monoclonal Antibodies to Human Tumor Necrosis Factors Alpha and Beta: Applications for Affinity Purification, Immunoassays, and as Structural Probes," *Hybridoma*, 6(5):489-507 (1987).

Tracey, Kevin J. et al., "Anti-cachectin/TNF monoclonal antibodies prevent septic shock during lethal bacteraemia," *Nature*, 330:662-664 (1987).

Nagai, M. et al., "Antibody to tumor necrosis factor (TNF) reduces endotoxin fever," *Experientia*, 44:606-607 (1988).

Shimamoto, Yoshinori et al., "Monoclonal antibodies against human recombinant tumor necrosis factor: prevention of endotoxic shock,"*Immunology Letters*, 17:311-318 (1988).

Di Giovine, Francesco, S. et al., "Tumour necrosis factor in synovial exudates," *Annals of the Rheumatic Diseases*, 47:768-772 (1988).

Collins, M.S. et al., "Immunoprophylaxis of Polymicrobic Cellulitis with a Human Monoclonal Antibody Against Lipopolysaccharide Antigen of *Pseudomonas aeruginosa*, " Abstract E-63, *Abstracts of Annual Meeting 1989*.

Exley, A.R. et al., "Monoclonal Antibody (Mab) to Recombinant Human Tumour Necrosis Factor (rhTNF) in the Prophylaxis and Treatment of Endotoxic Shock in Cynomolgus Monkeys," *Medical Research Society*, Abstract 184, p. 50 (1989).

Cross, A.S. et al., "Pretreatment with Recombinant Murine Tumor Necrosis Factor α/Cachectin and Murine Interleukin 1 α Protects Mice from Lethal Bacterial Infection," *J. of Exp. Med.*, 169:2021-2027 (1989).

Engelmann, Hartmut et al., "A Tumor Necrosis Factor-binding Protein Purified to Homogeneity from Human Urine Protects Cells from Tumor Necrosis Factor Toxicity," *J. of Bio. Chem.*, 264(20):11974-11980 (1989).

Silva, Ayona T. et al., "Prophylactic and Therapeutic Effects of a Monoclonal Antibody to Tumor Necrosis Factor-αin Experimental Gram-Negative Shock," *J. of Infectious Diseases*, 162:421-427 (1990).

Opal, Steven M. et al., "Efficacy of a Monoclonal Antibody Directed Against Tumor Necrosis Factor in Protecting Neutropenic Rats from Lethal Infection with *Pseudomonas aeruginosa*," *J. of Infectious Diseases*, 161:1148-1152 (1990).

Tavernier, Jan et al., "Analysis of the Structure-Function Relationship of Tumour Necrosis Factor. Human/Mouse Chimeric TNF Proteins: General Properties and Epitope Analysis," *J. Mol. Biol.*, 211:493-501 (1990).

Lucas, R. et al., "Generation and characterization of a neutralizing rat anti-rm TNF-α monoclonal antibody," *Immunology*, 71:218-223 (1990).

Hinshaw, L.B. et al., "Survival of Primates in $LD_{100}$ Septic Shock Following Therapy with Antibody to Tumor Necrosis Factor (TNFα)," *Circulatory Shock*, 30:279-292 (1990).

Nophar, Yaron et al., "Soluble forms of tumor necrosis factor receptors (TNF-Rs). The cDNA for the type 1 TNF-R, cloned using amino acid sequence data of its soluble form, encodes both the cell surface and a soluble form of the receptor," *The EMBO Journal*, 9(*10*):3269-3278 (1990).

Engelmann, Hartmut et al., "Two Tumor Necrosis Factor-binding Proteins Purified from Human Urine," *J. of Bio. Chem.*, 265(3):1531-1536 (1990).

Verhoef, J. and Torensma, R., "Prospects for Monoclonal Antibodies in the Diagnosis and Treatment of Bacterial Infections," *Eur. J. Clin. Microbiol. Dis.*, 9(4):247-250 (1990).

Loetscher, Hansruedi et al., "Molecular Cloning and Expression of the Human 55 kd Tumor Necrosis Factor Receptor," *Cell*, 61:351-359 (1990).

Schall, Thomas J. et al., "Molecular Cloning and Expression of a Receptor for Human Tumor Necrosis Factor," *Cell*, 61:361-370 (1990).

Akama, Hideto et al., "Mononuclear Cells Enhance Prostaglandin E$_2$ Production of Polymorphonuclear Leukocytes via Tumor Necrosis Factor α," *Biochemical and Biophysical Research Comm.*, 168(2):857-862 (1990).

Exley, A.R. et al., "Monoclonal antibody to TNF in severe septic shock," *The Lancet*, 335:1275-1277 (1990).

Möller, Achim et al., "Monoclonal Antibodies to Human Tumor Necrosis Factor α: *In Vitro* and *In Vivo* Application," *Cytokine*, 2(3):162-169 (1990).

Ruddle, Nancy H. et al., "An Antibody to Lymphotoxin and Tumor Necrosis Factor Prevents Transfer of Experimental Allergic Encephalomyelitis," *J. Exp. Med.*, 172:1193-1200 (1990).

Galloway, Cynthia J. et al., "Monoclonal anti-tumor necrosis factor (TNF) antibodies protect mouse and human cells from TNF cytotoxicity," *J. of Immunological Methods*, 140:37-43 (1991).

Waldmann, Thomas A., "Monoclonal Antibodies in Diagnosis and Therapy," *Science*, 252:1657-1662 (1991).

Aderka, Dan et al., "The Possible Role of Tumor Necrosis Factor (TNF) and Its Natural Inhibitors, The Soluble-TNF Receptors, In Autoimmune Diseases," *Israel J. Med. Sci.*, 28(2):126-130 (1992).

Pennington, James, "TNF: Therapeutic Target in Patients with Sepsis," *ASM News*, 58(9):479-482 (1992).

Harris, William J. and Emery, Steven, "Therapeutic antibodies—the coming of age," *TBTECH*, 11:42-44 (1993).

Parrillo, Joeseph E., "Pathogenetic Mechanisms of Septic Shock," *N.E. Journal of Medicine*, 328(20):1471-1477 (1993).

Aggarwal, Bharat B. et al., "Human Tumor Necrosis Factor Production, Purification and Characterization," *J. of Biol. Chem.*, 260(4):2345-2354 (1985).

Beutler, B. et al., "Purification of Cachectin, A Liproprotein Lipase-Suppressing Hormone Secreted by Endotoxin-induced RAW 264.7 Cells," *J. Exp. Med.*, 161:984-995 (1985).

Echtenacher, Bernd et al., "Requirement of Endogenous Tumor Necrosis Factor/Cachectin for Recovery from Experimental Peritonitis," *J. of Immunology*, 145(11):3762-3766 (1990).

Smith, Craig R., "Human and Chimeric Antibodies to LPS and TNF," Abstract, *Endotoxemia & Sepsis Conference* (1991).

Bodmer, Mark, "Humanized Antibodies for Anti-TNF Therapy," Abstract, *Endotoxemia & Sepsis Conference* (1991).

Genebank Accession, No. N90300 (Nov. 1, 1989).

Genebank Accession, No. M32046 (Jun. 15, 1990).

Paulus, H., "Preparation and Biomedical Applications of Bispecific Antibodies", *Behring Inst. Mitt*, No. 78:118-132 (1985).

Whittle, Nigel, et al., "Contructions and Expression of a CDR-Grafted Anti-TNF Antibody," *J. Cell Biochem.*, Supl. 13A:96 (1989).

Gorman, S.D. and Clark, M.R., "Humanisation of monoclonal antibodies for therapy," *Sem. Immunol.*, 2:457-466 (1990).

Starnes, H. Fletcher, Jr., et al., "ANTI-IL-6 Monoclonal Antibodies Protect Against Lethal *Escherichia coli* Infection and Lethal Tumor Necrosis Factorα Challenge in Mice," *J. Immunol.*, 145:4185-4191 (1990).

Duncombe, Andrew S. et al., "Tumor Necrosis Factor Mediates Autocrine Growth Inhibition in a Chronic Leukemia," *J. Immunol.*, 143:3828-3834 (1989).

Aderka, Dan et al., "IL-6 Inhibits Lipopolysaccharide-Induced tumor Necrosis Factor Production in Cultured Human Monocytes, U937 Cells, and in Mice," *J. Immunol.*, 143:3517-3523 (1989).

Aderka, Dan, "Role of Tumor Necrosis Factor in the Pathogenesis of Intravascular Coagulopathy of Sepsis: Potential New Therapeutic Implications," *Isr. J. Med. Sci.*, 27:52-60 (1991).

Lassalle, Ph., et al., "Potential Implication of Endothelial Cells in Bronchial Asthma," *Int. Arch. Allergy Appl. Immunol.*, 94:233-238 (1991).

Fong, Yuman and Lowry, Stephen F., "Tumor Necrosis Factor in the Pathophysiology of Infection and Sepsis," *Clin. Immunol. Immunopathol.*, 55:157-170 (1990).

Eck, Michael J. and Sprang, Stephen R., "The Structure of Tumor Necrosis Factor-α at 2.6 Å Resolution," *J. Biol. Chem.*, 264:17595-17605 (1989).

Gillies, Stephen D. et al., "High-level expression of chimeric antibodies using adapted cDNA variable region cassettes," *J. Immunol. Methods*, 125:191-202 (1989).

Kameyama, Koh-zoh, et al., "Convenient plasmid vectors for construction of chimeric mouse/human antibodies," *FEBS Lett.*, 244:301-306 (1989).

Hayashi, H. et al., "An Enzyme-linked Immunosorbent Assay for Recombinant Human Tumor Necrosis Factor Using Monoclonal Antibody," *Recent Adv. Chemother.*, 820-821 (1985).

Hirai, Makoto et al., "Production and characterization of monoclonal antibodies to human tumor necrosis factor," *J. Immunol. Methods*, 96:57-62 (1987).

Sunahara, N. et al., "Simple enzyme immunoassay methods for recombinant human tumor necrosis factor α and its antibodies using a bacterial cell wall carrier," *J. Immunol. Methods*, 109:203-214 (1988).

Oliff, A., et al., "Tumors Secreting Human TNF/Cachectin Induce Cachexia in Mice," *Cell*, 50:555-563 (1987).

Mule, J.J., "Antitumor Activity of Recombinant Interleukin 6 in Mice," *The Journal of Experimental Medicine*, 171:629-636 (1990).

Luettig, B., et al., "Evidence For The Existence Of Two Forms Of Membrane Tumor Necrosis Factor: An Integral Protein And A Molecule Attached To Its Receptor," *The Journal of Immunology*, 143:4034-4038 (1989).

Barbuto, J.A.M., et al., "Production of neutralizing antibodies to tumor necrosis factor by human tumor-infiltrating B lymphocytes," *Proceedings of the American Association for Cancer Research*, 34:487, Abstract 2904, (1993).

Bendtzen, K., et al., "Auto-Antibodies To IL-1α and TNFα In Normal Individuals And In Infectious And Immunoinflammatory Disorders," *The Physiological and Pathological Effects of Cytokines*, 10B:447-452 (1990).

Fromsgaard, A., et al., "Auto-Antibodies To Tumour Necrosis Factor α In Healthy Humans And Patients With Inflammatory Diseases And Gram-Negative Bacterial Infections," *Scand. J. Immunol.*, 30:219-223 (1989).

James, K. and Bell, G.T., "Human Monoclonal Antibody Production Current Status And Future Prospects," *Journal of Immunological Methods*, 100:5-40 (1987).

Alberts, B. et al., Molecular Biology of the Cell, Garland Publishing Inc., pp. 182-183 (1983).

Simpson, S.Q., et al., "Role Of Tumor Necrosis Factor In Sepsis And Acute Lung Injury," *Critical Care Clinics*, 5:27-47 (1989).

Bendtzen, K., et al., "Native inhibitors (autoantibodies) of IL-1α and TNF," *Immunology Today*, 10(7):222 (1989).

Davenport, C., et al., "Stimulation Of Human B Cells Specific For Candida Albicans For Monoclonal Antibody Production," *FEMS Microbiol. Immunol*, 4(6):335-343 Abstract (1992).

Pennica, D., et al., "Human tumour necrosis factor: precursor structure, expression and homology to lymphotoxin," *Nature*, 312(20/27):724-729 (1984).

Gray, P.W., et al., "Cloning and expression of cDNA for human lymphotoxin, a lymphokine with tumour necrosis activity," *Nature*, 312(20/27):721-724 (1984).

Petersen, C.M., et al., "Bioactive human recombinant tumor necrosis factor-α: an unstable dimer?*," *Eur. J. Immunol.*, 19:1887-1894 (1989).

Smith, C. A., et al., "A Receptor for Tumor Necrosis Factor Defines an Unusual Family of Cellular and Viral Proteins," *Science*, 248:1019-1023 (1990).

Brennan, F.M., et al., "Inhibitory Effect Of TNFα Antibodies On Synovial Cell Interleukin-1 Production In Rheumatoid Arthritis," *The Lancet*, 244-247 (1989).

Hahn, T., et al., "Use of monoclonal antibodies to a human cytotoxin for its isolation and for examining the self-induction of resistance to this protein," *Proc. Natl. Acac. Sci. USA* 82:3814-3818 (1985).

Grau, G.E., et al., "Tumor Necrosis Factor (Cachectin) as an Essential Mediator in Murine Cerebral Malaria," *Science*, 237:1210-1212 (1987).

Barbanti, E., et al., "A high-affinity neutralizing anti-human TNF-alpha monoclonal antibody that cross-reacts with human TNF-beta," *Abstracts*, Mar. 6th-9th (1991).

Jones, E.Y., et al., "Structure of tumour necrosis factor," *Nature*, 338:225-228 (1989).

Clark, W. R., "Types of Antibody Reactions," In *The Experimental Foundations of Modern Immunology*, (NY: John Wiley & Sons, Inc.) 4th Ed., pp. 143-155 (1991).

Beutler, B., et al., "Cachectin and tumour necrosis factor as two sides of the same biological coin," *Nature*, 320:584-588 (1986).

Folks, T. M., et al., "Tumor Necrosis factor α induces expression of human immunodeficiency virus in a chronically infected T-cell clone," *Proc. Natl. Acad. Sci. USA*, 86:2365-2358 (1989).

Hird, V., et al., "Immunotherapy with Monoclonal Antibodies," In *Genes and Cancer* (John Wiley & Sons, Ltd.)(1990).

Rhein, R., "Another sepsis drug down-Immunex' TNF receptor," *Biotechnology Newswatch*, Monday, Oct. 4, 1993, pp. 1,3.

Boyle, P., et al., "A Novel Monoclonal Human IgM Autoantibody which Binds Recombinant Human and Mouse Tumor Necrosis Factor-α," *Cellular Immunology*, 152:556-568 (1993).

Boyle, P., et al., "The B5 Monoclonal Human Autoantibody Binds to Cell Surface TNFα on Human Lymphoid Cells and Cell Lines and Appears to Recognize a Novel Epitope," *Cellular Immunology*, 152:569-581 (1993).

Sheehan, K.C.F., et al., "Generation And Characterization Of Hamster Monoclonal Antibodies That Neutralize Murine Tumor Necrosis Factors," *The Journal of Immunology*, 142(11):3884-3893 (1989).

Jacob, C.O., et al., "Tumour necrosis factor-α in murine autoimmune 'lupus' nephritis," *Nature*, 331:356-358 (1988).

Mateo, C. et al., "Removal of Amphipathic Epitopes from Genetically Engineered Antibodies: Production of Modified Immunoglobulins with Reduced Immunogenicity", *Hybridoma*, 19(6):463-471 (2000).

Paul, W.E. (Ed.), *Fundamental Immunology*, 3rd Edition, Pub. Raven Press Ltd., pp. 292-293 (1993).

Herve, P. et al., "Monoclonal Anti TNF α Antibody for the Treatment of Severe Acute GvHD in Humans," Abstract 3.25, *Lymphoma Res. 9*:591 (1990).

Kawasaki, Hajime et al., "Analysis of Endotoxin Fever in Rabbits by Using a Monoclonal Antibody to Tumor Necrosis Factor (Cachectin)," *Infection and Immunity*, 57(10):3131-3135 (1989).

Von Asmuth, E.J.U. et al., "Tumour Necrosis Factor Alpha (TNF-α) and Interleukin 6 in a Zymosan-Induced Shock Model," *Scand. J. Immunol.*, 32:313-319 (1990).

Socher, S. et al., "Antibodies against amino acids 1-15 of tumor necrosis factor block its binding to cell-surface receptor", *Proc. Natl. Acad. Sci.*, USA 84:8829-8833 (1987).

Borrebaeck, C.A.K. (Ed.), *Antibody Engineering*, 2nd Edition,Pub. Oxford University Press, p. 291 (1995).

Fong, Yuman et al., "Antibodies to Cachectin/Tumor Necrosis Factor Reduce Interleukin 1β and Interleukin 6 Appearance During Lethal Bacteremia," *J. Exp. Med., 170*:1627-1633 (1989).

Goh,C., "Tumor Necrosis Factors in Clinical Practice", *Annals of the Academy of Medicine*, 19(2):235-239 (1990).

Yan, L. et al., "Preparation and Characterization of Monoclonal Antibodies Against Recombinant Human Tumor Necrosis Factor Alpha", *Chinese J. Biotechnology*, 7(2):121-126 (1991).

Elliott, M.J., et al., "Repeated Therapy with Monoclonal Antibody to Tumour Necrosis Factor α (cA2) in Patients with Rheumatoid Arthritis," *The Lancet*, 344:1125-1127 (1994).

Knight, D.M., et al., "Construction and Initial Characterization of a Mouse-Human Chimeric Anti-TNF Antibody," *Mol. Immunol.*, 30(16):1443-1453 (1993).

Siegel, S.A., et al., "The Mouse/Human Chimeric Monoclonal Antibody cA2 Neutralizes TNF In Vitro and Protects Transgenic Mice from Cachexia and TNF Lethality In Vivo," *Cytokine*, 7(1):15-25 (1995).

U.S. Appl. No. 11/401,391, filed Apr. 10, 2006, by Junming Le, Jan Vilcek, Peter Daddona, John Ghrayeb, David M. Knight and Scott Siegel.

U.S. Appl. No. 11/400,787, filed Apr. 7, 2006, by Junming Le, Jan Vilcek, Peter Daddona, John Ghrayeb, David Knight and Scott Siegel.

U.S. Appl. No. 11/501,162, filed Aug. 8, 2006, by Junming Le, Jan Vilcek, Peter Daddona, John Ghrayeb, David Knight and Scott Siegel.

* cited by examiner

```
1
Val Arg Ser Ser Ser Arg Thr Pro Ser Asp Lys Pro Val Ala His Val Val Ala Asn Pro
                                        10
21
Gln Ala Glu Gly Gln Leu Gln Trp Leu Asn Arg Arg Ala Asn Ala Leu Leu Ala Asn Gly
                                        30
41
Val Glu Leu Arg Asp Asn Gln Leu Val Val Pro Ser Glu Gly Leu Tyr Leu Ile Tyr Ser
                                        50
61
Gln Val Leu Phe Lys Gly Gln Gly Cys Pro Ser Thr His Val Leu Leu Thr His Thr Ile
                                        70
81
Ser Arg Ile Ala Val Ser Tyr Gln Thr Lys Val Asn Leu Leu Ser Ala Ile Lys Ser Pro
                                        90
101
Cys Gln Arg Glu Thr Pro Glu Gly Ala Glu Ala Lys Pro Trp Tyr Glu Pro Ile Tyr Leu
                            110
121
Gly Gly Val Phe Gln Leu Glu Lys Gly Asp Arg Leu Ser Ala Glu Ile Asn Arg Pro Asp
                            130
141
Tyr Leu Asp Phe Ala Glu Ser Gly Gln Val Tyr Phe Gly Ile Ile Ala Leu
                            150
```

FIG. 13

```
1
    Val Arg Ser Ser Ser Arg Thr Pro Ser Asp Lys Pro Val Ala His Val Val Ala Asn Pro
                                            10

21
    Gln Ala Glu Gly Gln Leu Gln Trp Leu Asn Arg Arg Ala Asn Ala Leu Leu Ala Asn Gly
                                            30

41
    Val Glu Leu Arg Asp Asn Gln Leu Val Pro Ser Glu Gly Leu Tyr Leu Ile Tyr Ser
                                            50

61
    Gln Val Leu Phe Lys Gly Gln Gly Cys Pro Ser Thr His Val Leu Leu Thr His Thr Ile
                                            70

81
    Ser Arg Ile Ala Val Ser Tyr Gln Thr Lys Val Asn Leu Leu Ser Ala Ile Lys Ser Pro
                                            90

101
    Cys Gln Arg Glu Thr Pro Glu Gly Ala Glu Ala Lys Pro Trp Tyr Glu Pro Ile Tyr Leu
                                           110

121
    Gly Gly Val Phe Gln Leu Glu Lys Gly Asp Arg Leu Ser Ala Glu Ile Asn Arg Pro Asp
                                           130

141
    Tyr Leu Asp Phe Ala Glu Ser Gly Gln Val Tyr Phe Gly Ile Ile Ala Leu
                                           150
```

FIG. 15

```
GACATCTTGCTGACTCAGTCTCCAGCCATCCTGTCTGTGAGTCCAGGAGAAAGAGTCAGT
AspIleLeuLeuThrGlnSerProAlaIleLeuSerValSerProGlyGluArgValSer

TTCTCCTGCAGGGCCAGTCAGTTCGTTGGCTCAAGCATCCACTGGTATCAGCAAAGAACA
PheSerCysArgAlaSerGlnPheValGlySerSerIleHisTrpTyrGlnGlnArgThr

AATGGTTCTCCAAGGCTTCTCATAAAGTATGCTTCTGAGTCTATGTCTGGGATCCCTTCC
AsnGlySerProArgLeuLeuIleLysTyrAlaSerGluSerMetSerGlyIleProSer

AGGTTTAGTGGCAGTGGATCAGGGACAGATTTACTCTTAGCATCAACACTGTGGAGTCT
ArgPheSerGlySerGlyGluThrAspPheThrLeuSerIleAsnThrValGluSer

GAAGATATTGCAGATTATTACTGTCAAGAAAGTCATAGCTGGCCATTCACGTTCGGCTCG
GluAspIleAlaAspTyrTyrCysGlnGluSerHisSerTrpProPheThrPheGlySer

GGGACAAATTTGGAAGTAAAA
GlyThrAsnLeuGluValLys
```

FIG. 16A

GAAGTGAAGCTTGAGGAGTCTGGAGGAGGCTTGGTGCAACCTGGAGGATCCATGAAACTC
GluValLysLeuGluGluSerGlyGlyGlyLeuValGlnProGlyGlySerMetLysLeu

TCCTGTGTTGCCTCTGGATTCATTTCAGTAACCACTGGATGAACTGGGTCCGCCAGTCT
SerCysValAlaSerGlyPheIlePheSerAsnHisTrpMetAsnTrpValArgGlnSer

CCAGAGAAGGGGCTTGAGTGGGTTGCTGAAATTAGATCAAAATCTATTAATTCTGCAACA
ProGluLysGlyLeuGluTrpValAlaGluIleArgSerLysSerIleAsnSerAlaThr

CATTATGCGGAGTCTGTGAAAGGGAGGTTCACCATCTCAAGAGATGATTCCAAAAGTGCT
HisTyrAlaGluSerValLysGlyArgPheThrIleSerArgAspAspSerLysSerAla

GTGTACCTGCAAATGACCGACTTAAGAACTGAAGACACTGGCGTTTATTACTGTTCCAGG
ValTyrLeuGlnMetThrAspLeuArgThrGluAspThrGlyValTyrTyrCysSerArg

AATTACTACGGTAGTACCTACGACTACTGGGGCCAAGGCACCACTCTCACAGTCC
AsnTyrTyrGlySerThrTyrAspTyrTrpGlyGlnGlyThrThrLeuThrValSer

FIG. 16B

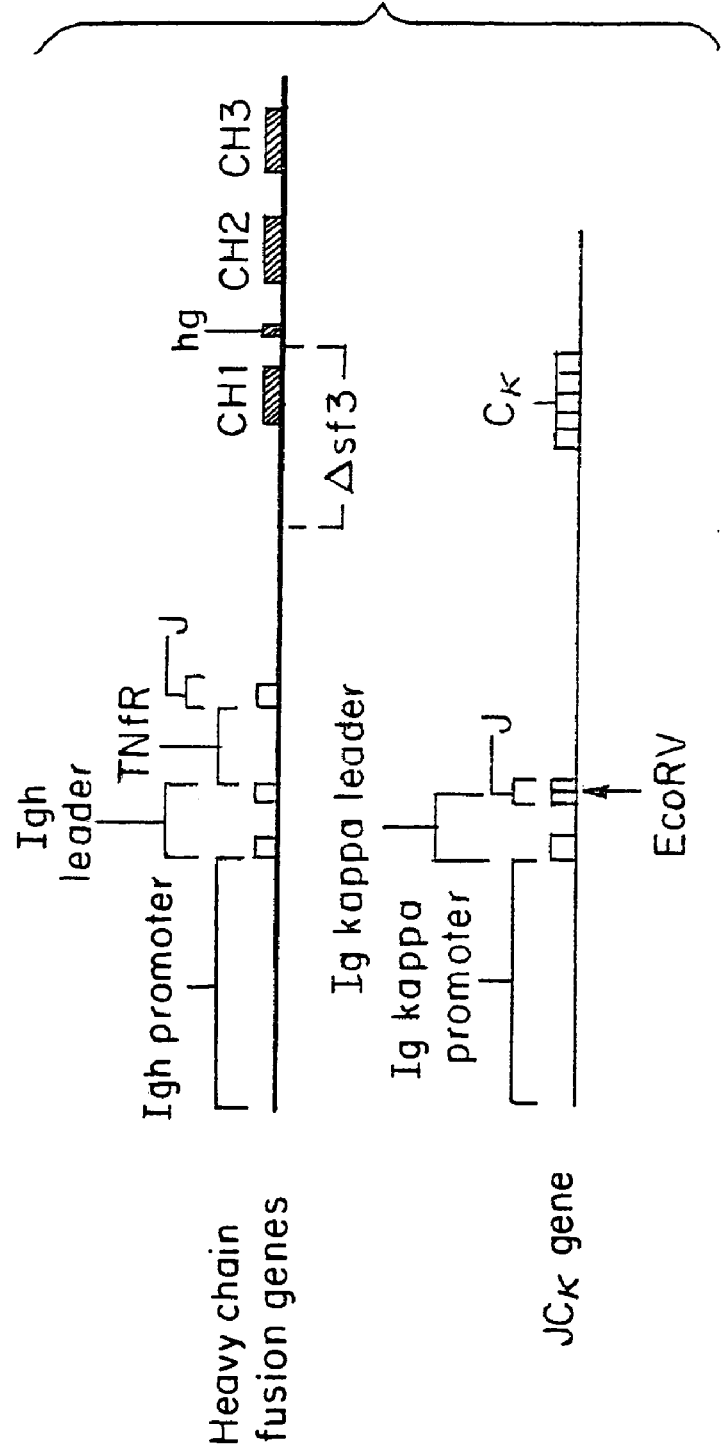

*p≤0.05, p≤0.01, *p≤0.001 *versus* pre-infusion
†p≤0.05, ††p≤0.01, †††p≤0.001 *versus* change in placebo group

SEQUENCE LISTING

```
<160> NUMBER OF SEQ ID NOS: 30

<210> SEQ ID NO 1
<211> LENGTH: 157
<212> TYPE: PRT
<213> ORGANISM: Homo sapiens

<400> SEQUENCE: 1

Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
 65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
               100                 105                 110

Pro Trp Tyr Glu Pro Ile Tyr Leu Gly Gly Val Phe Gln Leu Glu Lys
           115                 120                 125

Gly Asp Arg Leu Ser Ala Glu Ile Asn Arg Pro Asp Tyr Leu Asp Phe
```

```
                130             135             140
Ala Glu Ser Gly Gln Val Tyr Phe Gly Ile Ile Ala Leu
145                 150                 155

<210> SEQ ID NO 2
<211> LENGTH: 321
<212> TYPE: DNA
<213> ORGANISM: Mus Balb/c
<220> FEATURE:
<221> NAME/KEY: CDS
<222> LOCATION: (1)...(321)

<400> SEQUENCE: 2 gac atc ttg ctg act cag tct cca gcc atc ctg tct gtg agt cca gga        48
Asp Ile Leu Leu Thr Gln Ser Pro Ala Ile Leu Ser Val Ser Pro Gly
 1               5                  10                  15 gaa aga gtc agt ttc tcc tgc agg gcc agt cag ttc gtt ggc tca agc        96
Glu Arg Val Ser Phe Ser Cys Arg Ala Ser Gln Phe Val Gly Ser Ser
                20                  25                  30 atc cac tgg tat cag caa aga aca aat ggt tct cca agg ctt ctc ata       144
Ile His Trp Tyr Gln Gln Arg Thr Asn Gly Ser Pro Arg Leu Leu Ile
             35                  40                  45 aag tat gct tct gag tct atg tct ggg atc cct tcc agg ttt agt ggc       192
Lys Tyr Ala Ser Glu Ser Met Ser Gly Ile Pro Ser Arg Phe Ser Gly
 50                  55                  60 agt gga tca ggg aca gat ttt act ctt agc atc aac act gtg gag tct       240
Ser Gly Ser Gly Thr Asp Phe Thr Leu Ser Ile Asn Thr Val Glu Ser
 65                  70                  75                  80 gaa gat att gca gat tat tac tgt caa caa agt cat agc tgg cca ttc       288
Glu Asp Ile Ala Asp Tyr Tyr Cys Gln Gln Ser His Ser Trp Pro Phe
                 85                  90                  95 acg ttc ggc tcg ggg aca aat ttg gaa gta aaa                           321
Thr Phe Gly Ser Gly Thr Asn Leu Glu Val Lys
                100                 105

<210> SEQ ID NO 3
<211> LENGTH: 107
<212> TYPE: PRT
<213> ORGANISM: Mus Balb/c

<400> SEQUENCE: 3

Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Phe Val Gly Ser Ser
                20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys
                100                 105

<210> SEQ ID NO 4
<211> LENGTH: 357
<212> TYPE: DNA
<213> ORGANISM: Mus Balb/c
<220> FEATURE:
```

```
<221> NAME/KEY: CDS
<222> LOCATION: (1)...(357)

<400> SEQUENCE: 4 gaa gtg aag ctt gag gag tct gga gga ggc ttg gtg caa cct gga gga      48
Glu Val Lys Leu Glu Glu Ser Gly Gly Gly Leu Val Gln Pro Gly Gly
 1               5                  10                  15 tcc atg aaa ctc tcc tgt gtt gcc tct gga ttc att ttc agt aac cac      96
Ser Met Lys Leu Ser Cys Val Ala Ser Gly Phe Ile Phe Ser Asn His
             20                  25                  30 tgg atg aac tgg gtc cgc cag tct cca gag aag ggg ctt gag tgg gtt     144
Trp Met Asn Trp Val Arg Gln Ser Pro Glu Lys Gly Leu Glu Trp Val
         35                  40                  45 gct gaa att aga tca aaa tct att aat tct gca aca cat tat gcg gag     192
Ala Glu Ile Arg Ser Lys Ser Ile Asn Ser Ala Thr His Tyr Ala Glu
     50                  55                  60 tct gtg aaa ggg agg ttc acc atc tca aga gat gat tcc aaa agt gct     240
Ser Val Lys Gly Arg Phe Thr Ile Ser Arg Asp Asp Ser Lys Ser Ala
 65                  70                  75                  80 gtc tac ctg caa atg acc gac tta aga act gaa gac act ggc gtt tat     288
Val Tyr Leu Gln Met Thr Asp Leu Arg Thr Glu Asp Thr Gly Val Tyr
                 85                  90                  95 tac tgt tcc agg aat tac tac ggt agt acc tac gac tac tgg ggc caa     336
Tyr Cys Ser Arg Asn Tyr Tyr Gly Ser Thr Tyr Asp Tyr Trp Gly Gln
            100                 105                 110 ggc acc act ctc aca gtc tcc                                         357
Gly Thr Thr Leu Thr Val Ser
        115

<210> SEQ ID NO 5
<211> LENGTH: 119
<212> TYPE: PRT
<213> ORGANISM: Mus Balb/c

<400> SEQUENCE: 5

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Ile Phe Ser Asn His
             20                  25                  30

Trp Met Asn Trp Val Arg Gln Ser Pro Glu Lys Gly Leu Glu Trp Val
         35                  40                  45

Ala Glu Ile Arg Ser Lys Ser Ile Asn Ser Ala Thr His Tyr Ala Glu
     50                  55                  60

Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser
        115

<210> SEQ ID NO 6
<211> LENGTH: 8
<212> TYPE: PRT
<213> ORGANISM: Homo sapiens

<400> SEQUENCE: 6

Gly Thr Leu Val Thr Val Ser Ser
 1               5
```

```
<210> SEQ ID NO 7
<211> LENGTH: 7
<212> TYPE: PRT
<213> ORGANISM: Homo sapiens

<400> SEQUENCE: 7

Gly Thr Lys Leu Glu Ile Lys
 1               5

<210> SEQ ID NO 8
<211> LENGTH: 20
<212> TYPE: DNA
<213> ORGANISM: Artificial Sequence
<220> FEATURE:
<223> OTHER INFORMATION: PCR oligonucleotides

<400> SEQUENCE: 8
cctggatacc tgtgaaaaga                                              20

<210> SEQ ID NO 9
<211> LENGTH: 27
<212> TYPE: DNA
<213> ORGANISM: Artificial Sequence
<220> FEATURE:
<223> OTHER INFORMATION: PCR oligonucleotides

<400> SEQUENCE: 9
cctggtacct tagtcaccgt ctcctca                                      27

<210> SEQ ID NO 10
<211> LENGTH: 27
<212> TYPE: DNA
<213> ORGANISM: Artificial Sequence
<220> FEATURE:
<223> OTHER INFORMATION: PCR oligonucleotides

<400> SEQUENCE: 10
aatagatatc tccttcaaca cctgcaa                                      27

<210> SEQ ID NO 11
<211> LENGTH: 21
<212> TYPE: DNA
<213> ORGANISM: Artificial Sequence
<220> FEATURE:
<223> OTHER INFORMATION: PCR oligonucleotides

<400> SEQUENCE: 11
atcgggacaa agttggaaat a                                            21

<210> SEQ ID NO 12
<211> LENGTH: 16
<212> TYPE: DNA
<213> ORGANISM: Artificial Sequence
<220> FEATURE:
<223> OTHER INFORMATION: PCR oligonucleotides

<400> SEQUENCE: 12
ggcggtctgg taccgg                                                  16

<210> SEQ ID NO 13
<211> LENGTH: 19
<212> TYPE: DNA
<213> ORGANISM: Artificial Sequence
<220> FEATURE:
<223> OTHER INFORMATION: PCR oligonucleotides
```

```
<400> SEQUENCE: 13
gtcaacaaca tagtcatca                                              19

<210> SEQ ID NO 14
<211> LENGTH: 23
<212> TYPE: DNA
<213> ORGANISM: Artificial Sequence
<220> FEATURE:
<223> OTHER INFORMATION: PCR oligonucleotides

<400> SEQUENCE: 14
cacaggtgtg tccccaagga aaa                                         23

<210> SEQ ID NO 15
<211> LENGTH: 18
<212> TYPE: DNA
<213> ORGANISM: Artificial Sequence
<220> FEATURE:
<223> OTHER INFORMATION: PCR oligonucleotides

<400> SEQUENCE: 15
aatctggggt aggcacaa                                               18

<210> SEQ ID NO 16
<211> LENGTH: 17
<212> TYPE: DNA
<213> ORGANISM: Artificial Sequence
<220> FEATURE:
<223> OTHER INFORMATION: PCR oligonucleotides

<400> SEQUENCE: 16
agtgtgtgtc cccaagg                                                17

<210> SEQ ID NO 17
<211> LENGTH: 24
<212> TYPE: DNA
<213> ORGANISM: Artificial Sequence
<220> FEATURE:
<223> OTHER INFORMATION: PCR oligonucleotides

<400> SEQUENCE: 17
cacagctgcc cgcccaggtg gcat                                        24

<210> SEQ ID NO 18
<211> LENGTH: 17
<212> TYPE: DNA
<213> ORGANISM: Artificial Sequence
<220> FEATURE:
<223> OTHER INFORMATION: PCR oligonucleotides

<400> SEQUENCE: 18
gtcgccagtg ctccctt                                                17

<210> SEQ ID NO 19
<211> LENGTH: 20
<212> TYPE: DNA
<213> ORGANISM: Artificial Sequence
<220> FEATURE:
<223> OTHER INFORMATION: PCR oligonucleotides

<400> SEQUENCE: 19
atcggacgtg gacgtgcaga                                             20

<210> SEQ ID NO 20
```

```
<211> LENGTH: 11
<212> TYPE: PRT
<213> ORGANISM: Artificial Sequence
<220> FEATURE:
<223> OTHER INFORMATION: Partial sequence of pHC707

<400> SEQUENCE: 20

Ile Glu Pro Gly Thr Leu Val Thr Val Ser Ser
 1               5                  10

<210> SEQ ID NO 21
<211> LENGTH: 46
<212> TYPE: DNA
<213> ORGANISM: Artificial Sequence
<220> FEATURE:
<223> OTHER INFORMATION: Partial sequence of pHC707

<400> SEQUENCE: 21
cacaggtatc caggcctggt aacttagtca ccgtctcctc aggtaa              46

<210> SEQ ID NO 22
<211> LENGTH: 16
<212> TYPE: DNA
<213> ORGANISM: Artificial Sequence
<220> FEATURE:
<223> OTHER INFORMATION: Partial sequence of pHC707

<400> SEQUENCE: 22
cacaggtatc caggca                                               16

<210> SEQ ID NO 23
<211> LENGTH: 9
<212> TYPE: PRT
<213> ORGANISM: Artificial Sequence
<220> FEATURE:
<223> OTHER INFORMATION: Partial sequence of pHC707

<400> SEQUENCE: 23

Pro Gly Thr Leu Val Thr Val Ser Ser
 1               5

<210> SEQ ID NO 24
<211> LENGTH: 32
<212> TYPE: DNA
<213> ORGANISM: Artificial Sequence
<220> FEATURE:
<223> OTHER INFORMATION: Partial sequence of pHC707

<400> SEQUENCE: 24
cctggtacct tagtcaccgt ctcctcaggt aa                             32

<210> SEQ ID NO 25
<211> LENGTH: 12
<212> TYPE: PRT
<213> ORGANISM: Artificial Sequence
<220> FEATURE:
<223> OTHER INFORMATION: Partial sequence of pLC871

<400> SEQUENCE: 25

Val Glu Gly Asp Ile Gly Thr Lys Leu Glu Ile Lys
 1               5                  10

<210> SEQ ID NO 26
<211> LENGTH: 52
<212> TYPE: DNA
<213> ORGANISM: Artificial Sequence
<220> FEATURE:
```

<223> OTHER INFORMATION: Partial sequence of pLC871

<400> SEQUENCE: 26
tttgcaggtg ttgaaggaga tatcgggaca aagttggaaa taaaacgtaa gt        52

<210> SEQ ID NO 27
<211> LENGTH: 4
<212> TYPE: PRT
<213> ORGANISM: Artificial Sequence
<220> FEATURE:
<223> OTHER INFORMATION: Partial sequence of pLC671

<400> SEQUENCE: 27

Val Glu Gly Asp
 1

<210> SEQ ID NO 28
<211> LENGTH: 21
<212> TYPE: DNA
<213> ORGANISM: Artificial Sequence
<220> FEATURE:
<223> OTHER INFORMATION: Partial sequence of pLC671

<400> SEQUENCE: 28
tttgcaggtg ttgaaggaga t        21

<210> SEQ ID NO 29
<211> LENGTH: 8
<212> TYPE: PRT
<213> ORGANISM: Artificial Sequence
<220> FEATURE:
<223> OTHER INFORMATION: Partial sequence of pLC671

<400> SEQUENCE: 29

Ile Gly Thr Lys Leu Glu Ile Lys
 1               5

<210> SEQ ID NO 30
<211> LENGTH: 31
<212> TYPE: DNA
<213> ORGANISM: Artificial Sequence
<220> FEATURE:
<223> OTHER INFORMATION: Partial sequence of pLC671

<400> SEQUENCE: 30
atcgggacaa agttggaaat aaaacgtaag t        31

METHOD OF TREATING PSORIASIS USING HUMAN ANTI-TNF ANTIBODIES AND FRAGMENTS

RELATED APPLICATIONS

This application is a divisional of U.S. application Ser. No. 09/927,703, filed Aug. 10, 2001, which is a continuation of U.S. application Ser. No. 09/756,398, filed Jan. 8, 2001, now U.S. Pat. No. 6,835,823, issued Dec. 28, 2004, which is a divisional of U.S. application Ser. No. 09/133,119, filed Aug. 12, 1998, now U.S. Pat. No. 6,277,969, issued Aug. 21, 2001, which is a divisional of U.S. application Ser. No. 08/570,674, filed Dec. 11, 1995, now abandoned, which is a continuation-in-part of U.S. application Ser. No. 08/324,799, filed Oct. 18, 1994, now U.S. Pat. No. 5,698,195, issued Dec. 16, 1997, which is a continuation-in-part of U.S. application Ser. No. 08/192,102, now U.S. Pat. No. 5,656,272, issued Aug. 12, 1997, Ser No. 08/192,861, now U.S. Pat. No. 5,919,452, issued Jul. 6, 1999, and Ser. No. 08/192,093, now U.S. Pat. No. 6,284,471, all filed on Feb. 4, 1994 which are continuations-in-part of U.S. application Ser. No. 08/010,406, filed Jan. 29, 1993, now abandoned, and U.S. application Ser. No. 08/013,413, filed Feb. 2, 1993, now abandoned, which is a continuation-in-part of U.S. application Ser. No. 07/943,852, filed Sep. 11, 1992, now abandoned, which is a continuation-in-part of U.S. application Ser. No. 07/853,606, filed Mar. 18, 1992, now abandoned, which is a continuation-in-part of U.S. application Ser. No. 07/670,827, filed Mar. 18, 1991, now abandoned. The entire teachings of the above applications are incorporated herein by reference.

BACKGROUND AND FIELD OF THE INVENTION

The present invention in the field of immunology and medicine relates to anti-tumor necrosis factor (TNF) antibodies, anti-TNF peptides and nucleic acids encoding therefor, and to pharmaceutical and diagnostic compositions and production, diagnostic and therapeutic methods thereof, and to methods for treating human TNF-mediated pathologies.

DESCRIPTION OF THE BACKGROUND ART

Tumor Necrosis Factor

Monocytes and macrophages secrete cytokines known as tumor necrosis factor-α (TNFα) and tumor necrosis factor-β (TNFβ) in response to endotoxin or other stimuli. TNFα is a soluble homotrimer of 17 kD protein subunits (Smith, et al., *J. Biol. Chem.* 262:6951–6954 (1987)). A membrane-bound 26 kD precursor form of TNF also exists (Kriegler, et al., *Cell* 53:45–53 (1988)). For reviews of TNF, see Beutler, et al., *Nature* 320:584 (1986), Old, *Science* 230:630 (1986), and Le, et al., *Lab. Invest.* 56:234.

Cells other than monocytes or macrophages also make TNFα. For example, human non-monocytic tumor cell lines produce TNF (Rubin, et al., *J. Exp. Med.* 164:1350 (1986); Spriggs, et al., *Proc. Natl. Acad. Sci. USA* 84:6563 (1987)). $CD4^+$ and $CD8^+$ peripheral blood T lymphocytes and some cultured T and B cell lines (Cuturi, et al., *J. Exp. Med.* 165:1581 (1987); Sung, et al., *J. Exp. Med.* 168:1539 (1988)) also produce TNFα.

TNF causes pro-inflammatory actions which result in tissue injury, such as inducing procoagulant activity on vascular endothelial cells (Pober, et al., *J. Immunol.* 136:1680 (1986)), increasing the adherence of neutrophils and lymphocytes (Pober, et al., *J. Immunol.* 138:3319 (1987)), and stimulating the release of platelet activating factor from macrophages, neutrophils and vascular endothelial cells (Camussi, et al., *J. Exp. Med.* 166:1390 (1987)).

Recent evidence associates TNF with infections (Cerami, et al., *Immunol. Today* 9:28 (1988)), immune disorders, neoplastic pathologies (Oliff, et al., *Cell* 50:555 (1987)), autoimmune pathologies and graft-versus host pathologies (Piguet, et al., *J. Exp. Med.* 166:1280 (1987)). The association of TNF with cancer and infectious pathologies is often related to the host's catabolic state. Cancer patients suffer from weight loss, usually associated with anorexia.

The extensive wasting which is associated with cancer, and other diseases, is known as "cachexia" (Kern, et al., (*J. Parent. Enter. Nutr.* 12:286–298 (1988)). Cachexia includes progressive weight loss, anorexia, and persistent erosion of body mass in response to a malignant growth. The fundamental physiological derangement can relate to a decline in food intake relative to energy expenditure. The cachectic state causes most cancer morbidity and mortality. TNF can mediate cachexia in cancer, infectious pathology, and other catabolic states.

TNF also plays a central role in gram-negative sepsis and endotoxic shock (Michie, et al., *Br. J. Surg.* 76:670–671 (1989); Debets, et al., *Second Vienna Shock Forum,* p. 463–466 (1989); Simpson, et al., *Crit. Care Clin.* 5:27–47 (1989)), including fever, malaise, anorexia, and cachexia. Endotoxin strongly activates monocyte/macrophage production and secretion of TNF and other cytokines (Kornbluth, et al., *J. Immunol.* 137:2585–2591 (1986)). TNF and other monocyte-derived cytokines mediate the metabolic and neurohormonal responses to endotoxin (Michie, et al., *New. Engl. J. Med.* 318:1481–1486 (1988)). Endotoxin administration to human volunteers produces acute illness with flu-like symptoms including fever, tachycardia, increased metabolic rate and stress hormone release (Revhaug, et al., *Arch. Surg.* 123:162–170 (1988)). Circulating TNF increases in patients suffering from Gram-negative sepsis (Waage, et al., Lancet 1:355–357 (1987); Hammerle, et al., *Second Vienna Shock Forum* p. 715–718 (1989); Debets, et al., *Crit. Care Med.* 17:489–497 (1989); Calandra, et al., *J. Infect. Dis.* 161:982–987 (1990)).

TNF Antibodies

Polyclonal murine antibodies to TNF are disclosed by Cerami et al. (EPO Patent Publication 0212489, Mar. 4, 1987). Such antibodies were said to be useful in diagnostic immunoassays and in therapy of shock in bacterial infections.

Rubin et al. (EPO Patent Publication 0218868, Apr. 22, 1987) discloses murine monoclonal antibodies to human TNF, the hybridomas secreting such antibodies, methods of producing such murine antibodies, and the use of such murine antibodies in immunoassay of TNF.

Yone et al. (EPO Patent Publication 0288088, Oct. 26, 1988) discloses anti-TNF murine antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, *Allergy* 16:178 (1967); Kawasaki, *Shonica (Pediatrics)* 26:935 (1985)) were said to contain elevated TNF levels which were related to progress of the pathology (Yone et al., infra).

Other investigators have described rodent or murine mAbs specific for recombinant human TNF which had neutralizing activity in vitro (Liang, et al., (*Biochem. Biophys. Res. Comm.* 137:847–854 (1986); Meager, et al., *Hybridoma* 6:305–311 (1987); Fendly et al., *Hybridoma* 6:359–369 (1987); Bringman, et al., *Hybridoma* 6:489–507 (1987); Hirai, et al., *J. Immunol. Meth.* 96:57–62 (1987); Moller, et al., (*Cytokine* 2:162–169 (1990)). Some of these mAbs were used to map epitopes of human TNF and develop enzyme immunoassays (Fendly et al., infra; Hirai et al., infra; Moller et al., infra) and to assist in the purification of recombinant TNF (Bringman et al., infra). However, these studies do not provide a basis for producing TNF neutralizing antibodies that can be used for in vivo diagnostic or therapeutic uses in humans, due to immunogenicity, lack of specificity and/or pharmaceutical suitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, et al., *J. Clin. Invest.* 81:1925–1937 (1988); Beutler, et al., *Science* 229: 869–871 (1985); Tracey, et al., *Nature* 330:662–664 (1987); Shimamoto, et al., *Immunol. Lett.* 17:311–318 (1988); Silva, et al., *J. Infect. Dis.* 162:421–427 (1990); Opal, et al., *J. Infect. Dis.* 161:1148–1152 (1990); Hinshaw, et al., *Circ. Shock* 30:279–292 (1990)).

Putative receptor binding loci of hTNF has been disclosed by Eck and Sprang (*J. Biol. Chem.* 264(29), 17595–17605 (1989)), who identified the receptor binding loci of TNF-α as consisting of amino acids 11–13, 37–42, 49–57 and 155–157.

PCT publication W091/02078 (1991) discloses TNF ligands which can bind to monoclonal antibodies having the following epitopes: at least one of 1–20, 56–77, and 108–127; at least two of 1–20, 56–77, 108–127 and 138–149; all of 1–18, 58–65, 115–125 and 138–149; all of 1–18, and 108–128; all of 56–79, 110–127 and 135- or 136–155; all of 1–30, 117–128 and 141–153; all of 1–26, 117–128 and 141–153; all of 22–40, 49–96 or 49–97, 110–127 and 136–153; all of 12–22, 36–45, 96–105 and 132–157; both of 1–20 and 76–90; all of 22–40, 69–97, 105–128 and 135–155; all of 22–31 and 146–157; all of 22–40 and 49–98; at least one of 22–40, 49–98 and 69–97, both of 22–40 and 70–87.

To date, experience with anti-TNF murine mAb therapy in humans has been limited. In a phase I study, fourteen patients with severe septic shock were administered a murine anti-TNF mAb in a single dose from 0.4–10 mg/kg (Exley, A. R. et al., *Lancet* 335:1275–1277 (1990)). However, seven of the fourteen patients developed a human anti-murine antibody response to the treatment, which treatment suffers from the known problems due to immunogenicity from the use of murine heavy and light chain portions of the antibody. Such immunogenicity causes decreased effectiveness of continued administration and can render treatment ineffective, in patients undergoing diagnostic or therapeutic administration of murine anti-TNF antibodies.

Administration of murine TNF mAb to patients suffering from severe graft versus host pathology has also been reported (Herve, et al., *Lymphoma Res.* 9:591 (1990)).

TNF Receptors

The numerous biological effects of TNFα and the closely related cytokine, TNFβ (lymphotoxin), are mediated by two TNF transmembrane receptors, both of which have been cloned. The p55 receptor (also termed TNF-R55, TNF-RI, or TNFRβ) is a 55 kDa glycoprotein shown to transduce signals resulting in cytotoxic, anti-viral, and proliferative activities of TNFα.

The p75 receptor (also termed TNF-R75, TNF-RII, or TNFRα) is a 75 kDa glycoprotein that has also been shown to transduce cytotoxic and proliferative signals as well as signals resulting in the secretion of GM-CSF. The extracellular domains of the two receptors have 28% homology and have in common a set of four subdomains defined by numerous conserved cysteine residues. The p75 receptor differs, however, by having a region adjacent to the transmembrane domain that is rich in proline residues and contains sites for O-linked glycosylation. Interestingly, the cytoplasmic domains of the two receptors share no apparent homology which is consistent with observations that they can transduce different signals to the interior of the cell.

TNFα inhibiting proteins have been detected in normal human urine and in serum of patients with cancer or endotoxemia. These have since been shown to be the extracellular domains of TNF receptors derived by proteolytic cleavage of the transmembrane forms. Many of the same stimuli that result in TNFα release also result in the release of the soluble receptors, suggesting that these soluble TNFα inhibitors can serve as part of a negative feedback mechanism to control TNFα activity.

Aderka, et al., *Isrl. J. Med. Sci.* 28:126–130 (1992) discloses soluble forms of TNF receptors (sTNF-Rs) which specifically bind TNF and thus can compete with cell surface TNF receptors to bind TNF (Seckinger, et al., *J. Exp. Med.* 167:1511–1516 (1988); Engelmann, et al., *J. Biol. Chem.* 264:11974–11980 (1989)).

Loetscher, et al., *Cell* 61:351–359 (Apr. 20, 1990) discloses the cloning and expression of human 55 kd TNF receptor with the partial amino acid sequence, complete cDNA sequence and predicted amino acid sequence.

Schall et al., *Cell* 61:361–370 (Apr. 20, 1990), discloses molecular cloning and expression of a receptor for human TNF with an isolated cDNA clone including a receptor as a 415 amino acid protein with an apparent molecular weight of 28 kDa, as well as the cDNA sequence and predicted amino acid sequence.

Nophar, et al., *EMBO J.* 9(10):3269–3278 (1990) discloses soluble forms of TNF receptor and that the cDNA for type I TNF-R encodes both the cell surface and soluble forms of the receptor. The cDNA and predicted amino acid sequences are disclosed.

Engelmann, et al., *J. Biol. Chem.* 265(3):1531–1536 (1990), discloses TNF-binding proteins, purified from human urine, both having an approximate molecular weight of 30 kDa and binding TNF-α more effectively than TNF-β. Sequence data is not disclosed. See also Engelmann, et al., *J. Biol. Chem.* 264 (20):11974–11980 (1989).

European Patent publication number 0 433 900 A1, published Jun. 26, 1991, owned by YEDA Research and Development Co., Ltd., Wallach, et al., discloses TNF binding protein I (TBP-I), derivatives and analogs thereof, produced expression of a DNA encoding the entire human type I TNF receptor, or a soluble domain thereof.

PCT publication number WO 92/13095, published Aug. 6, 1992, owned by Synergen, Carmichael et al., discloses methods for treating tumor necrosis factor mediated diseases by administration of a therapeutically effective amount of a TNF inhibitor selected from a 30 kDa TNF inhibitor and a 40 kDa TNF inhibitor selected from the full length 40 kDa TNF inhibitor or modifications thereof.

European Patent Publication number 0 526 905 A2, published Oct. 2, 1993, owned by YEDA Research and Development Company, Ltd., Wallach et al., discloses multimers of the soluble forms of TNF receptors produced by either chemical or recombinant methods which are useful for protecting mammals from the deleterious effects of TNF, which include portions of the hp55 TNF-receptor.

PCT publication WO 92/07076, published Apr. 30, 1992, owned by Charring Cross Sunley Research Center, Feldmann et al., discloses modified human TNFα receptor which consists of the first three cysteine-rich subdomains but lacks the fourth cysteine-rich subdomain of the extracellular binding domain of the 55 kDa or 75 kDa TNF receptor for human TNFα, or an amino acid sequence having a homology of 90% or more with the TNF receptor sequences.

European Patent Publication 0 412 486 A1, published Feb. 13, 1991, owned by YEDA Research and Development Co., Ltd., Wallach et al., discloses antibodies to TNF binding protein I (TBP-I), and fragments thereof, which can be used as diagnostic assays or pharmaceutical agents, either inhibiting or mimicking the effects of TNF on cells.

European Patent Publication number 0 398 327 A1, published Nov. 22, 1990, owned by YEDA Research and Development Co., Ltd., Wallach et al., discloses TNF binding protein (TBP), isolated and purified, having inhibitory activity on the cytotoxic effect of TNF, as well as TNF binding protein II and salts, functional derivatives, precursors and active fractions thereof, as well as polyclonal and monoclonal antibodies to TNF binding protein II.

European Patent Publication 0 308 378 A2, published Mar. 22, 1989, owned by YEDA Research and Development Co., Ltd., Wallach, et al., discloses TNF inhibitory protein isolated and substantially purified, having activity to inhibit the binding of TNF to TNF receptors and to inhibit the cytotoxicity of TNF. Additionally disclosed are TNF inhibitory protein, salts, functional derivatives and active fractions thereof, used to antagonize the deleterious effects of TNF.

Accordingly, there is a need to provide novel TNF antibodies or peptides which overcome the problems of murine antibody immunogenicity and which provide reduced immunogenicity and increased neutralization activity.

Citation of documents herein is not intended as an admission that any of the documents cited herein is pertinent prior art, or an admission that the cited documents is considered material to the patentability of any of the claims of the present application. All statements as to the date or representation as to the contents of these documents is based on the information available to the applicant and does not constitute any admission as to the correctness of the dates or contents of these documents.

SUMMARY OF THE INVENTION

It is the object of the present invention to overcome one or more deficiencies of the background art.

It is also an object of the present invention to provide methods having utility for in vitro, in situ and/or in vivo diagnosis and/or treatment of animal cells, tissues or pathologies associated with the presence of tumor necrosis factor (TNF), using anti-TNF antibodies and/or anti-TNF peptides.

Anti-TNF antibodies (Abs) are intended to include at least one of monoclonal rodent-human chimeric antibodies, rodent antibodies, human antibodies or any portions thereof, having at least one antigen binding region of an immunoglobulin variable region, which antibody binds TNF.

Anti-TNF peptides are capable of binding TNF under physiological conditions, and can include, but are not limited to, portions of a TNF receptor and/or portions or structural analogs of anti-TNF antibody antigen binding regions or variable regions. Such antibodies or peptides bind TNF with neutralizing and/or inhibiting biological activity.

Anti-TNF antibodies and/or anti-TNF peptides of the present invention can be routinely made and/or used according to methods of the present invention, such as, but not limited to synthetic methods, hybridomas, and/or recombinant cells expressing nucleic acid encoding such anti-TNF antibodies or peptides.

The present invention also provides antigenic polypeptides of hTNF, corresponding to peptides containing neutralizing epitopes or portions of TNF that, when such epitopes on TNF are bound by anti-TNF antibodies or peptides, neutralize or inhibit the biological activity of TNF in vitro, in situ or in vivo.

The present invention also provides anti-TNF antibodies and peptides in the form of pharmaceutical and/or diagnostic compounds and/or compositions, useful for the diagnostic and/or therapeutic methods of the present invention for diagnosing and/or treating TNF-related pathologies.

Anti-TNF Abs or anti-TNF peptides of the present invention are provided for use in diagnostic methods for detecting TNF in patients or animals suspected of suffering from conditions associated with abnormal TNF production, including methods wherein high affinity anti-TNF antibodies or peptides are contacted with a biological sample from a patient and an antigen-antibody reaction detected. Also included in the present invention are kits for detecting TNF in a solution using anti-TNF antibodies or peptides, preferably in detectably labeled form.

The present invention is also directed to an anti-hTNF chimeric antibody comprising two light chains and two heavy chains, each of the chains comprising at least part of a human constant region and at least part of a variable (V) region of non-human origin having specificity to human TNF, said antibody binding with high affinity to a inhibiting and/or neutralizing epitope of human TNF, such as the antibody cA2. The invention also includes a fragments or a derivative such an antibody, such as one or more portions of the antibody chain, such as the heavy chain constant, joining, diversity or variable regions, or the light chain constant, joining or variable regions.

Methods are also provided for making and using anti-TNF antibodies and peptides for various utilities of the present invention, such as but not limited to, hybridoma, recombinant or chemical synthetic methods for producing anti-TNF antibodies or anti-TNF peptides according to the present invention; detecting TNF in a solution or cell; removing TNF from a solution or cell, inhibiting one or more biological activities of TNF in vitro, in situ or in vitro. Such removal can include treatment methods of the present invention for alleviating symptoms or pathologies involving TNF, such as, by not limited to bacterial, viral or parasitic infections, chronic inflammatory diseases, autoimmune diseases, malignancies, and/or neurodegenerative diseases.

The invention further relates to the unexpected discovery that the inhibition or antagonism of TNF decreases the expression of Vascular Endothelial Growth Factor (VEGF) or Vascular Permeability Factor (VPF). VEGF has been implicated in the angiogenesis in cancer, vascular diseases and rheumatoid arthritis, for example. Thus, a TNF antagonist, such as an anti-TNF antibody, can be administered to a mammal for the treatment to decrease angiogenesis, such as in the treatment of a VEGF-mediated disease.

BRIEF DESCRIPTION OF THE DRAWINGS

FIG. 13 is an amino acid sequence of human TNF as SEQ ID NO:1.

FIG. 14A is a graphical representation of epitope mapping of chimeric mAb cA2 indicating relative binding of cA2 to human TNF peptide pins. FIG. 14B is a graphical representation of epitope mapping of chimeric mAb cA2 indicating relative binding of cA2 to human TNF peptide pins in the presence of human TNF.

FIG. 15 is an amino acid sequence of human TNF showing sequences having portions of epitopes recognized by cA2, corresponding to portions of amino acids 59–80 and/or 87–108 of SEQ ID NO:1.

FIGS. 16A–16B. FIG. 16A is a nucleic acid sequence (SEQ ID NO:2) and corresponding amino acid sequence (SEQ ID NO:3) of a cloned cA2 light chain variable region. FIG. 16B is a nucleic acid sequence (SEQ ID NO:4) and corresponding amino acid sequence (SEQ ID NO:5) of a cloned cA2 heavy chain variable region.

FIGS. 26A–26B. FIG. 26A is a schematic illustration of the genes encoding TNF receptor/IgG fusion proteins and the gene encoding the truncated light chain. The gene encoding Ig heavy chain (IgH) fusion proteins had the same basic structure as the naturally occurring, rearranged Ig genes except that the Ig variable region coding sequence was replaced with TNF receptor coding sequence. Except for the TNF receptor coding sequences and a partial human K sequence derived by modifying the murine J region coding sequence in the cM-T412 IgH gene by PCT mutagenesis, the entire genomic fragment shown originated from the cM-T412 chimeric mouse/human IgH gene. Looney et al., *Hum. Antibody Hybrid.* 3:191–200 (1992). The region deleted in the genes encoding p55-sf3 and p75P-sf3 is marked in the figure. The $JC_K$ gene, encoding a truncated Ig Kappa light chain, was constructed by deleting the variable region coding sequence from the cM-T412 chimeric mouse/human Ig Kappa gene (Looney, infra) and using PCR mutagenesis to change the murine J sequence to a partial human J sequence. The p55-light chain fusion in p55-df2 was made by inserting the p55 coding sequence into the EcoRV site in the $JC_K$ gene. Tracey et al., *Nature* 330:662–666 (1987). FIG. 26B is a schematic illustration of several immunoreceptor molecules of the present invention. The blackened ovals each represent a domain of the IgG1 constant region. The circles represent the truncated light chain. Small circles adjacent to a p55 or p75 subunit mark the positions of human J sequence. The incomplete circles in p75-sf2 and -sf3 are to illustrate that the C-terminal 53 amino acids of the p75 extracellular domain were deleted. Lines between subunits represent disulfide bonds.

FIG. 31A shows p55 fusion proteins. FIG. 31B shows p75 fusion proteins. FIG. 31C shows comparison of the protective ability of the non-fusion form of p55 (p55-nf) to p55-sf2.

DETAILED DESCRIPTION OF THE INVENTION

Figure 1:
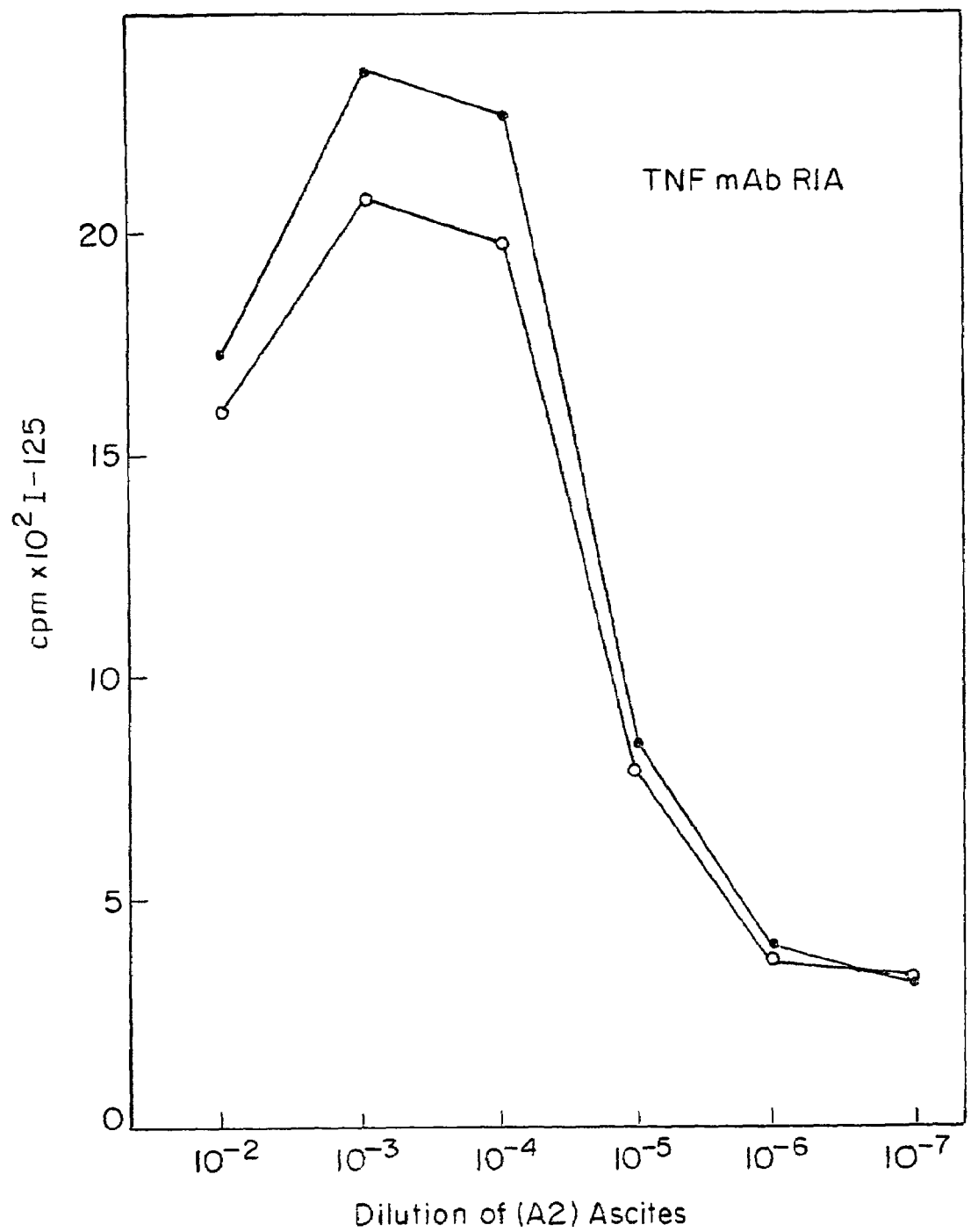
FIG. 1 is a graph showing dose dependent binding of mouse mAb A2 to human TNFα.
Figure 2:
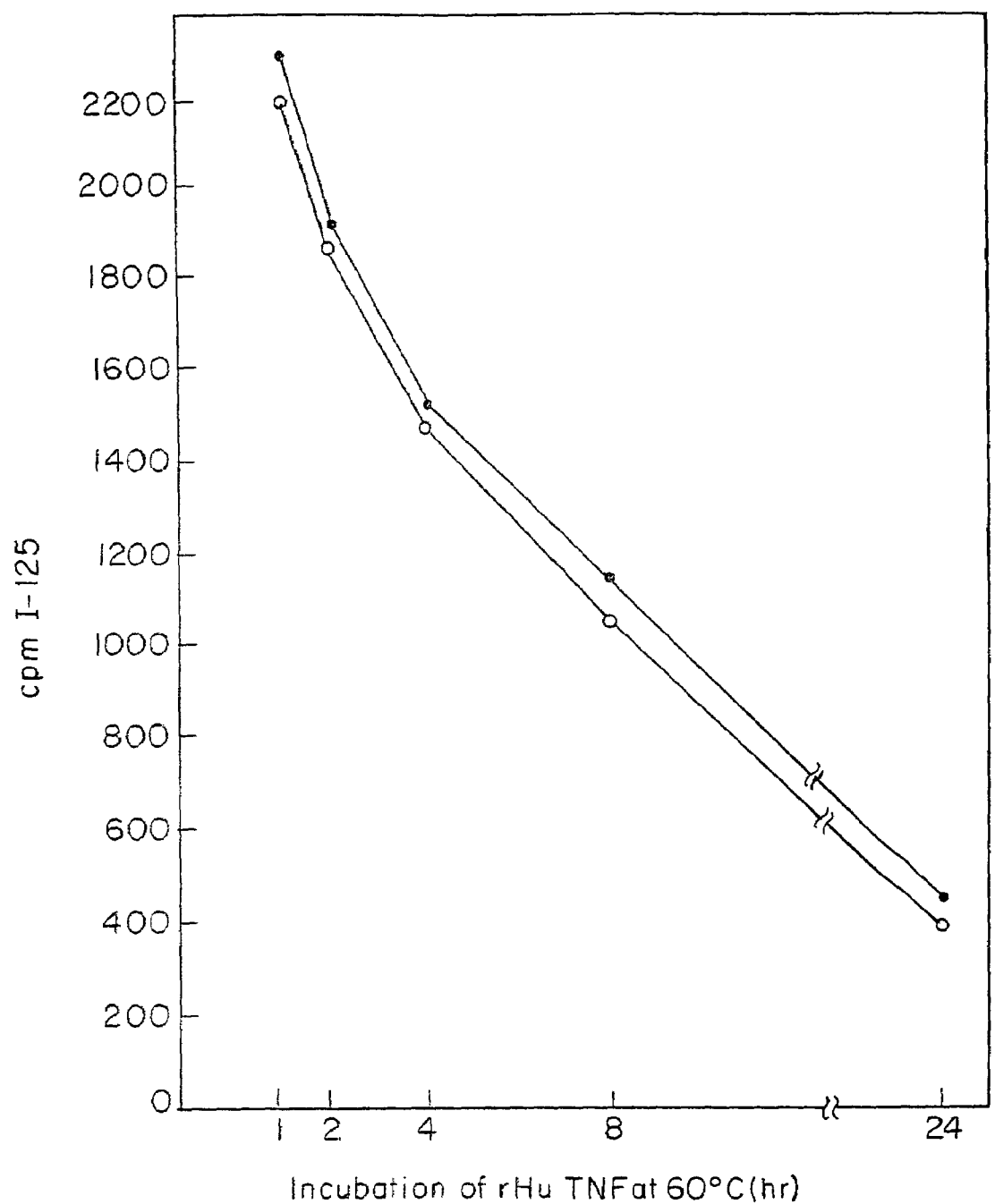
FIG. 2 is a graph showing lack of recognition of heat-inactivated human TNFα by mAb A2.

Tumor necrosis factor (TNF) has been discovered to mediate or be involved in many pathologies, such as, but not limited to, bacterial, viral or parasitic infections, chronic inflammatory diseases, autoimmune diseases, malignancies, and/or neurodegenerative diseases. Accordingly, anti-TNF compounds and compositions of the present invention which have neutralizing and/or inhibiting activity against TNF are discovered to provide methods for treating and/or diagnosing such pathologies.

The present invention thus provides anti-TNF compounds and compositions comprising anti-TNF antibodies (Abs) and/or anti-TNF peptides which inhibit and/or neutralize TNF biological activity in vitro, in situ and/or in vivo, as specific for association with neutralizing epitopes of human tumor necrosis factor-alpha (hTNFα) and/or human tumor necrosis factor β (hTNFβ). Such anti-TNF Abs or peptides have utilities for use in research, diagnostic and/or therapeutic methods of the present invention for diagnosing and/or treating animals or humans having pathologies or conditions associated with the presence of a substance reactive with an anti-TNF antibody, such as TNF or metabolic products thereof. Such pathologies can include the generalized or local presence of TNF or related compounds, in amounts and/or concentrations exceeding, or less than, those present in a normal healthy subject, or as related to a pathological condition.

Anti-TNF Antibodies and Methods

The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques. Such anti-TNF antibodies of the present invention are capable of binding portions of TNF that inhibit the binding of TNF to TNF receptors.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, *Nature* 256:495–497 (1975); U.S. Pat. No. 4,376,110; Ausubel et al., eds., *Current Protocols in Molecular Biology,* Greene Publishing Assoc. and Wiley Interscience, N.Y., (1987, 1992); and Harlow and Lane *ANTIBODIES: A Laboratory Manual* Cold Spring Harbor Laboratory (1988); Colligan et al., eds., *Current Protocols in Immunology,* Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066–1074 (1986); Robinson et al., International Patent Publication #PCT/US86/02269 (published 7 May 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow and Lane *Antibodies: a Laboratory Manual* Cold Spring Harbor Laboratory (1988)). These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Anti-TNF antibodies of the present invention can include at least one of a heavy chain constant region ($H_c$), a heavy chain variable region ($H_v$), a light chain variable region ($L_v$) and a light chain constant region ($L_c$), wherein a polyclonal Ab, monoclonal Ab, fragment and/or regions thereof include at least one heavy chain variable region ($H_v$) or light chain variable region ($L_v$) which binds a portion of a TNF and inhibits and/or neutralizes at least one TNF biological activity.

Preferred antibodies of the present invention are high affinity human-murine chimeric anti-TNF antibodies, and fragments or regions thereof, that have potent inhibiting and/or neutralizing activity in vivo against human TNFα. Such antibodies and chimeric antibodies can include those generated by immunization using purified recombinant hTNFα (SEQ ID NO:1) or peptide fragments thereof. Such fragments can include epitopes of at least 5 amino acids of residues 87–108, or a combination of both of 59–80 and 87–108 of hTNFα (as these corresponding amino acids of SEQ ID NO:1). Additionally, preferred antibodies, fragments and regions of anti-TNF antibodies of the present invention do not recognize amino acids from at least one of amino acids 11–13, 37–42, 49–57 or 155–157 of hTNFα (of SEQ ID NO:1).

Preferred anti-TNF mAbs are also those which will competitively inhibit in vivo the binding to human TNFα of anti-TNFα murine mAb A2, chimeric mAb cA2, or an antibody having substantially the same specific binding characteristics, as well as fragments and regions thereof. Preferred antibodies of the present invention are those that bind epitopes recognized by A2 and cA2, which are included in amino acids 59–80 and/or 87–108 of hTNFα (as these corresponding amino acids of SEQ ID NO:1), such that the epitopes consist of at least 5 amino acids which comprise at least one amino acid from the above portions of human TNFα.

Preferred methods for determining mAb specificity and affinity by competitive inhibition can be found in Harlow, et al., *Antibodies: A Laboratory Manual,* Cold Spring Harbor Laboratory Press, Cold Spring Harbor, N.Y., 1988), Colligan et al., eds., *Current Protocols in Immunology,* Greene Publishing Assoc. and Wiley Interscience, N.Y., (1992, 1993), and Muller, *Meth. Enzymol.* 92:589–601 (1983), which references are entirely incorporated herein by reference.

The techniques to raise antibodies of the present invention to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues.

Preferably, the antigen binding region will be of murine origin. In other embodiments, the antigen binding region can be derived from other animal species, in particular rodents such as rabbit, rat or hamster.

The antigen binding region of the chimeric antibody of the present invention is preferably derived from a non-human antibody specific for human TNF. Preferred sources for the DNA encoding such a non-human antibody include cell lines which produce antibody, preferably hybrid cell lines commonly known as hybridomas. A preferred hybridoma is the A2 hybridoma cell line.

An "antigen" is a molecule or a portion of a molecule capable of being bound by an antibody which is additionally capable of inducing an animal to produce antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens. Preferred antigens that bind antibodies, fragments and regions of anti-TNF antibodies of the present invention include at least 5 amino acids comprising at least one of amino acids residues 87–108 or both residues 59–80 and 87–108 of hTNFα (of SEQ ID NO:1). Preferred antigens that bind antibodies, fragments and regions of anti-TNF antibodies of the present invention do not include amino acids of amino acids 11–13, 37–42, 49–57 or 155–157 of hTNFα (SEQ ID NO:1).

Particular peptides which can be used to generate antibodies of the present invention can include combinations of amino acids selected from at least residues 87–108 or both residues 59–80 and 87–108, which are combined to provide an epitope of TNF that is bound by anti-TNF antibodies, fragments and regions thereof, and which binding provided anti-TNF biological activity. Such epitopes include at least 1–5 amino acids and less than 22 amino acids from residues 87–108 or each of residues 59–80 and 87–108, which in combination with other amino acids of TNF provide epitopes of at least 5 amino acids in length.

TNF residues 87–108 or both residues 59–80 and 87–108 of TNF (of SEQ ID NO:1), fragments or combinations of peptides containing therein are useful as immunogens to raise antibodies that will recognize peptide sequences presented in the context of the native TNF molecule.

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule or organism containing the epitope, in vivo, in vitro or in situ, more preferably in vivo, including binding of TNF to a TNF receptor.

Epitopes recognized by antibodies, and fragments and regions thereof, of the present invention can include 5 or more amino acids comprising at least one amino acid of each or both of the following amino acid sequences of TNF, which provide a topographical or three dimensional epitope of TNF which is recognized by, and/or binds with anti-TNF activity, an antibody, and fragments, and variable regions thereof, of the present invention:

59–80: Tyr-Ser-Gln-Val-Leu-Phe-Lys-Gly-Gln-Gly-Cys-Pro-Ser-Thr-His-Val-Leu-Leu-Thr-His-Thr-Ile (AA 59-80 of SEQ ID NO:1); and 87–108: Tyr-Gln-Thr-Lys-Val-Asn-Leu-Leu-Ser-Ala-Ile-Lys-Ser-Pro-Cys-Gln-Arg-Glu-Thr-Pro-Glu-Gly (AA 87-108 of SEQ ID NO:1).

Preferred antibodies, fragments and regions of anti-TNF antibodies of the present invention recognize epitopes including 5 amino acids comprising at least one amino acid from amino acids residues 87–108 or both residues 59–80 and 87–108 of hTNFα (of SEQ ID NO:1). Preferred antibodies, fragments and regions of anti-TNF antibodies of the present invention do not recognize epitopes from at least one of amino acids 11–13, 37–42, 49–57 or 155–157 of hTNFα (of SEQ ID NO:1). In a preferred embodiment, the epitope comprises at least 2 amino acids from residues 87–108 or both residues 59–80 and 87–108 of hTNFα (of SEQ ID NO:1). In another preferred embodiment, the epitope comprises at least 3 amino acids from residues 59–80 and 87–108 of hTNFα (of SEQ ID NO:1). In another preferred embodiment, the epitope comprises at least 4 amino acids from residues 87–108 or both residues 59–80 and 87–108 of hTNFα (of SEQ ID NO:1). In another preferred embodiment, the epitope comprises at least 5 amino acids from residues 87–108 or both residues 59–80 and 87–108 of hTNFα (of SEQ ID NO:1). In another preferred embodiment, the epitope comprises at least 6 amino acids from residues 87–108 or both residues 59–80 and 87–108 of hTNFα (of SEQ ID NO:1). In another preferred embodiment, the epitope comprises at least 7 amino acids from residues 87–108 or both residues 59–80 and 87–108 of hTNFα (of SEQ ID NO:1).

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ chain).

Murine and chimeric antibodies, fragments and regions of the present invention comprise individual heavy (H) and/or light (L) immunoglobulin chains. A chimeric H chain comprises an antigen binding region derived from the H chain of a non-human antibody specific for TNF, which is linked to at least a portion of a human H chain C region ($C_H$), such as $CH_1$ or $CH_2$.

A chimeric L chain according to the present invention, comprises an antigen binding region derived from the L chain of a non-human antibody specific for TNF, linked to at least a portion of a human L chain C region ($C_L$).

Antibodies, fragments or derivatives having chimeric H chains and L chains of the same or different variable region binding specificity, can also be prepared by appropriate association of the individual polypeptide chains, according to known method steps, e.g., according to Ausubel infra, Harlow infra, and Colligan infra, the contents of which references are incoporated entirely herein by reference.

With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

The hybrid cells are formed by the fusion of a non-human anti-hTNFα antibody-producing cell, typically a spleen cell of an animal immunized against either natural or recombinant human TNF, or a peptide fragment of the human TNFα protein sequence. Alternatively, the non-human anti-TNFα antibody-producing cell can be a B lymphocyte obtained from the blood, spleen, lymph nodes or other tissue of an animal immunized with TNF.

The second fusion partner, which provides the immortalizing function, can be a lymphoblastoid cell or a plasmacytoma or myeloma cell, which is not itself an antibody producing cell, but is malignant. Preferred fusion partner cells include the hybridoma SP2/0-Ag14, abbreviated as SP2/0 (ATCC CRL1581) and the myeloma P3X63Ag8 (ATCC TIB9), or its derivatives. See, e.g, Ausubel infra, Harlow infra, and Colligan infra, the contents of which references are incoporated entirely herein by reference.

Murine hybridomas which produce mAb specific for human TNFα or TNFβ are formed by the fusion of a mouse fusion partner cell, such as SP2/0, and spleen cells from mice immunized against purified hTNFα, recombinant hTNFα, natural or synthetic TNF peptides, including peptides including 5 or more amino acids selected from residues 59–80, and 87–108 of TNF (of SEQ ID NO:1) or other biological preparations containing TNF. To immunize the mice, a variety of different conventional protocols can be followed. For example, mice can receive primary and boosting immunizations of TNF.

The antibody-producing cell contributing the nucleotide sequences encoding the antigen-binding region of the chimeric antibody of the present invention can also be produced by transformation of a non-human, such as a primate, or a human cell. For example, a B lymphocyte which produces anti-TNF antibody can be infected and transformed with a virus such as Epstein-Barr virus to yield an immortal anti-TNF producing cell (Kozbor et al., *Immunol. Today* 4:72–79 (1983)). Alternatively, the B lymphocyte can be transformed by providing a transforming gene or transforming gene product, as is well-known in the art. See, e.g, Ausubel infra, Harlow infra, and Colligan infra, the contents of which references are incorporated entirely herein by reference.

Antibody Production Using Hybridomas

The cell fusions are accomplished by standard procedures well known to those skilled in the field of immunology. Fusion partner cell lines and methods for fusing and selecting hybridomas and screening for mAbs are well known in the art. See, e.g, Ausubel infra, Harlow infra, and Colligan infra, the contents of which references are incoporated entirely herein by reference.

The hTNFα-specific murine or chimeric mAb of the present invention can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

In a preferred embodiment, the antibody is a MAb which binds amino acids of an epitope of TNF, which antibody is designated A2, rA2 or cA2, which is produced by a hybridoma or by a recombinant host. In another preferred embodiment, the antibody is a chimeric antibody which recognizes an epitope recognized by A2. In a more preferred embodiment, the antibody is a chimeric antibody designated as chimeric A2 (cA2).

As examples of antibodies according to the present invention, murine mAb A2 (ATCC Accession No. PTA-7045) of the present invention is produced by a cell line designated c134A. Chimeric antibody cA2 is produced by a cell line designated c168A. c134A was deposited pursuant to the Budapest Treaty requirements with the American Type Culture Collection (ATCC), 10801 University Boulevard, Manassas, Va. 20110-2209, on Sep. 22. 2005. Cell line c134A is deposited as a research cell bank in the Centocor Cell Biology Services Depository, and cell line c168A (RCB) is deposited as a research cell bank in the Centocor Corporate Cell Culture Research and Development Depository, both at Centocor, 200 Great Valley Parkway, Malvern, Pa., 19355. The c168A cell line is also deposited at Centocor BV, Leiden, The Netherlands.

The invention also provides for "derivatives" of the murine or chimeric antibodies, fragments, regions or derivatives thereof, which term includes those proteins encoded by truncated or modified genes to yield molecular species functionally resembling the immunoglobulin fragments. The modifications include, but are not limited to, addition of genetic sequences coding for cytotoxic proteins such as plant and bacterial toxins. The fragments and derivatives can be produced from any of the hosts of this invention. Alternatively, anti-TNF antibodies, fragments and regions can be bound to cytotoxic proteins or compounds in vitro, to provide cytotoxic anti-TNF antibodies which would selectively kill cells having TNF receptors.

Fragments include, for example, Fab, Fab', F(ab')$_2$ and Fv. These fragments lack the Fc fragment of intact antibody, clear more rapidly from the circulation, and can have less non-specific tissue binding than an intact antibody (Wahl et al., *J. Nucl. Med.* 24:316–325 (1983)). These fragments are produced from intact antibodies using methods well known in the art, for example by proteolytic cleavage with enzymes such as papain (to produce Fab fragments) or pepsin (to produce F(ab')$_2$ fragments).

The identification of these antigen binding region and/or epitopes recognized by mAbs of the present invention provides the information necessary to generate additional monoclonal antibodies with similar binding characteristics and therapeutic or diagnostic utility that parallel the embodiments of this application.

In a preferred embodiment, the amino acids of the epitope are not of at least one of amino acids 11–13, 37–42, 49–57 and 155–157 of hTNFα (of SEQ ID NO:1).

Unexpectedly, anti-TNF antibodies or peptides of the present invention can block the action of TNF-α without binding to the putative receptor binding locus such as is presented by Eck and Sprang (*J. Biol. Chem.* 264(29): 17595–17605 (1989), as amino acids 11–13, 37–42, 49–57 and 155–157 of hTNFα (of SEQ ID NO:1).

Recombinant Expression of Anti-TNF Antibodies

Recombinant murine or chimeric murine-human or human-human antibodies that inhibit TNF and bind an epitope included in the amino acid sequences residues 87–108 or both residues 59–80 and 87–108 of hTNFα (of SEQ ID NO:1), can be provided according to the present invention using known techniques based on the teaching provided herein. See, e.g., Ausubel et al., eds. *Current Protocols in Molecular Biology,* Wiley Interscience, N.Y. (1987, 1992, 1993); and Sambrook et al. *Molecular Cloning: A Laboratory Manual,* Cold Spring Harbor Laboratory Press (1989), the entire contents of which are incorporated herein by reference.

The DNA encoding an anti-TNF antibody of the present invention can be genomic DNA or cDNA which encodes at least one of the heavy chain constant region ($H_c$), the heavy chain variable region ($H_v$), the light chain variable region ($L_v$) and the light chain constant regions ($L_c$). A convenient alternative to the use of chromosomal gene fragments as the source of DNA encoding the murine V region antigen-binding segment is the use of cDNA for the construction of chimeric immunoglobulin genes, e.g., as reported by Liu et al. (*Proc. Natl. Acad. Sci., USA* 84:3439 (1987) and *J. Immunology* 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a murine V region antigen-binding segment having anti-TNF activity can be provided using known methods based on the use of the DNA sequence presented in FIG. 16A (SEQ ID NO:2). Alternatively, a cDNA encoding a murine C region antigen-binding segment having anti-TNF activity can be provided using known methods based on the use of the DNA sequence presented in FIG. 16B (SEQ ID NO:3). Probes that bind a portion of the DNA sequence presented in FIG. 16A or 16B can be used to isolate DNA from hybridomas expressing TNF antibodies, fragments or regions, as presented herein, according to the present invention, by known methods.

Oligonucleotides representing a portion of the variable region presented in FIG. 16A or 16B sequence are useful for screening for the presence of homologous genes and for the cloning of such genes encoding variable or constant regions of an anti-TNF antibody. Such probes preferably bind to portions of sequences according to FIGS. 16A or 16B which encode light chain or heavy chain variable regions which bind an activity inhibiting epitope of TNF, especially an epitope of at least 5 amino acids of residues 87–108 or a combination of residues 59–80 and 87–108 (of SEQ ID NO:1).

Such techniques for synthesizing such oligonucleotides are well known and disclosed by, for example, Wu, et al., *Prog. Nucl. Acid. Res. Molec. Biol.* 21:101–141 (1978)), and Ausubel et al., eds. *Current Protocols in Molecular Biology*, Wiley Interscience (1987, 1993), the entire contents of which are herein incorporated by reference.

Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-TNF antibody or fragment. Such "codon usage rules" are disclosed by Lathe, et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding anti-TNF variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-TNF antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region anti-TNF gene (Sambrook et al., infra).

A suitable oligonucleotide, or set of oligonucleotides, which is capable of encoding a fragment of the variable or constant anti-TNF region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing anti-TNF antibodies or variable or constant regions thereof. Single stranded oligonucleotide molecules complementary to the "most probable" variable or constant anti-TNF region peptide coding sequences can be synthesized using procedures which are well known to those of ordinary skill in the art (Belagaje, et al., *J. Biol. Chem.* 254:5765–5780 (1979); Maniatis, et al., *In: Molecular Mechanisms in the Control of Gene Expression,* Nierlich, et al., Eds., Acad. Press, NY (1976); Wu, et al., *Prog. Nucl. Acid Res. Molec. Biol.* 21:101–141 (1978); Khorana, *Science* 203:614–625 (1979)). Additionally, DNA synthesis can be achieved through the use of automated synthesizers. Techniques of nucleic acid hybridization are disclosed by Sambrook et al. (infra), and by Haymes, et al. (In: *Nucleic Acid Hybridization, A Practical Approach,* IRL Press, Washington, D.C. (1985)), which references are herein incorporated by reference. Techniques such as, or similar to, those described above have successfully enabled the cloning of genes for human aldehyde dehydrogenases (Hsu, et al., *Proc. Natl. Acad. Sci. USA* 82:3771–3775 (1985)), fibronectin (Suzuki, et al., *Bur. Mol. Biol. Organ. J.* 4:2519–2524 (1985)), the human estrogen receptor gene (Walter, et al., *Proc. Natl. Acad. Sci. USA* 82:7889–7893 (1985)), tissue-type plasminogen activator (Pennica, et al., *Nature* 301:214–221 (1983)) and human term placental alkaline phosphatase complementary DNA (Keun, et al., *Proc. Natl. Acad. Sci. USA* 82:8715–8719 (1985)).

In an alternative way of cloning a polynucleotide encoding an anti-TNF variable or constant region, a library of expression vectors is prepared by cloning DNA or, more preferably, cDNA (from a cell capable of expressing an anti-TNF antibody or variable or constant region) into an expression vector. The library is then screened for members capable of expressing a protein which competitively inhibits the binding of an anti-TNF antibody, such as A2 or cA2, and which has a nucleotide sequence that is capable of encoding polypeptides that have the same amino acid sequence as anti-TNF antibodies or fragments thereof. In this embodiment, DNA, or more preferably cDNA, is extracted and purified from a cell which is capable of expressing an anti-TNF antibody or fragment. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, infra, Harlow, infra, Colligan, infra; Nyyssonen et al. *Bio/Technology* 11:591–595 (Can 1993); Marks et al., *Bio/Technology* 11:1145–1149 (October 1993). Once nucleic acid encoding such variable or constant anti-TNF regions is isolated, the nucleic acid can be appropriately expressed in a host cell, along with other constant or variable heavy or light chain encoding nucleic acid, in order to provide recombinant MAbs that bind TNF with inhibitory activity. Such antibodies preferably include a murine or human anti-TNF variable region which contains a framework residue having complimentarity determining residues which are responsible for antigen binding. In a preferred embodiment, an anti-TNF variable light or heavy chain encoded by a nucleic acid as described above binds an epitope of at least 5 amino acids including residues 87–108 or a combination of residues 59–80 and 87–108 of hTNF (of SEQ ID NO: 1).

Human genes which encode the constant (C) regions of the murine and chimeric antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including gamma, µ, α, δ or ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or µ (IgM).

The human $C_L$ region can be derived from either human L chain isotype, kappa or lambda.

Genes encoding human immunoglobulin C regions are obtained from human cells by standard cloning techniques (Sambrook, et al. (*Molecular Cloning: A Laboratory Manual*, 2nd Edition, Cold Spring Harbor Press, Cold Spring Harbor, N.Y. (1989) and Ausubel et al., eds. *Current Protocols in Molecular Biology* (1987–1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the $CH_1$ domain and hinge region of the H chain, followed by a translational stop codon to yield the truncated molecule.

Generally, the murine, human or murine and chimeric antibodies, fragments and regions of the present invention are produced by cloning DNA segments encoding the H and L chain antigen-binding regions of a TNF-specific antibody, and joining these DNA segments to DNA segments encoding $C_H$ and $C_L$ regions, respectively, to produce murine, human or chimeric immunoglobulin-encoding genes.

Thus, in a preferred embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the chimeric antibody according to the present invention involves several steps, outlined below:

1. isolation of messenger RNA (mRNA) from the cell line producing an anti-TNF antibody and from optional additional antibodies supplying heavy and light constant regions; cloning and cDNA production therefrom;
2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody;
3. Construction of complete H or L chain coding sequences by linkage of the cloned specific V region gene segments to cloned C region gene, as described above;
4. Expression and production of L and H chains in selected hosts, including prokaryotic and eukaryotic cells to provide murine-murine, human-murine, human-human or human murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region ($C_{gamma-1}$). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human $C_{gamma-1}$ region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions.

Non-Limiting Exemplary Chimeric A2 (cA2) Anti-TNF Antibody of the Present Invention Murine MAbs are undesirable for human therapeutic use, due to a short free circulating serum half-life and the stimulation of a human anti-murine antibody (HAMA) response. A murine-human chimeric anti-human TNFα MAb was developed in the present invention with high affinity, epitope specificity and the ability to neutralize the cytotoxic effects of human TNF. Chimeric A2 anti-TNF consists of the antigen binding variable region of the high-affinity neutralizing mouse antihuman TNF IgG1 antibody, designated A2, and the constant regions of a human IgG1, kappa immunoglobulin. The human IgG1 Fc region is expected to: improve allogeneic antibody effector function; increase the circulating serum half-life; and decrease the immunogenicity of the antibody. A similar murine-human chimeric antibody (chimeric 17-1A) has been shown in clinical studies to have a 6-fold longer in vivo circulation time and to be significantly less immunogenic than its corresponding murine MAb counterpart (LoBuglio et al., *Proc Natl Acad Sci USA* 86: 4220–4224, (1988)).

The avidity and epitope specificity of the chimeric A2 is derived from the variable region of the murine A2. In a solid phase ELISA, cross-competition for TNF was observed between chimeric and murine A2, indicating an identical epitope specificity of cA2 and murine A2. The specificity of cA2 for TNF-α was confirmed by its inability to neutralize the cytotoxic effects of lymphotoxin (TNF-β). Chimeric A2 neutralizes the cytotoxic effect of both natural and recombinant human TNF in a dose dependent manner. From binding assays of cA2 and recombinant human TNF, the affinity constant of cA2 was calculated to be $1.8 \times 10^9$ $M^1$.

ANTI-TNF Immunoreceptor Peptides

Immunoreceptor peptides of this invention can bind to TNFα and/or TNFβ. The immunoreceptor comprises covalently attached to at least a portion of the TNF receptor at least one immunoglobulin heavy or light chain. In certain preferred embodiments, the heavy chain constant region comprises at least a portion of $CH_1$. Specifically, where a light chain is included with an immunoreceptor peptide, the heavy chain must include the area of $CH_1$ responsible for binding a light chain constant region.

An immunoreceptor peptide of the present invention can preferably comprise at least one heavy chain constant region and, in certain embodiments, at least one light chain constant region, with a receptor molecule covalently attached to at least one of the immunoglobulin chains. Light chain or heavy chain variable regions are included in certain embodiments. Since the receptor molecule can be linked within the interior of an immunoglobulin chain, a single chain can have a variable region and a fusion to a receptor molecule.

The portion of the TNF receptor linked to the immunoglobulin molecule is capable of binding TNFα and/or TNFβ. Since the extracellular region of the TNF receptor binds TNF, the portion attached to the immunoglobulin molecule of the immunoreceptor consists of at least a portion of the extracellular region of the TNF receptor. In certain preferred embodiments, the entire extracellular region of p55 is included. In other preferred embodiments, the entire extracellular region of p75 is included. In further preferred embodiments, the extracellular region of p75 is truncated to delete at least a portion of a region of O-linked glycosylation and/or a proline-rich region while leaving intact the intramolecular disulfide bridges. Such immunoreceptors comprise at least a portion of a hinge region wherein at least one heavy chain is covalently linked to a truncated p75 extracellular region capable of binding to TNFα or TNFβ or both. Such a truncated molecule includes, for example, sequences 1–178, 1–182 or at least 5 amino acid portions thereof, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, . . . 50, 60, 70, 80, 90, 100, 110, 120, 130, 140, 150, 160, 170, 180, 190, 200, 210, 220, 230, 240, 250, 260, 270, 280, 290.

Certain embodiments can also include, for example, the C-terminal half of the hinge region to provide a disulfide bridge between heavy chains where both $CH_2$ and $CH_3$ chains are present and $CH_1$ is absent. Alternatively, for example, the N-terminal half of the hinge region can be included to provide a disulfide bridge with a light chain where only the $CH_1$ region is present.

In certain preferred embodiments of this invention, the non-immunoglobulin molecule is covalently linked to the N-terminus of at least one $CH_1$ region. In other preferred embodiments, the non-immunoglobulin molecule is covalently linked to an interior section of at least one heavy and/or light chain region. Thus, a portion of the TNF receptor can be, for example, at the end of the immunoglobulin chain or in the middle of the chain.

Where the TNF receptor is attached to the middle of the immunoglobulin, the immunoglobulin chain can be truncated, for example, to compensate for the presence of foreign amino acids, thus resulting in a fusion molecule of approximately the same length as a natural immunoglobulin chain. Alternatively, for example, the immunoglobulin chain can be present substantially in its entirety, thus resulting in a chain that is longer than the corresponding natural immunoglobulin chain. Additionally, the immunoglobulin molecule can be truncated to result in a length intermediate between the size of the entire chain linked to the receptor molecule and the size of the immunoglobulin chain alone.

In certain preferred embodiments, the heavy chain is an IgG class heavy chain. In other preferred embodiments, the heavy chain is an IgM class heavy chain.

In certain preferred embodiments, the heavy chain further comprises at least about 8 amino acids of a J region.

In certain preferred embodiments, at least a portion of the hinge region is attached to the $CH_1$ region. For example, where $CH_1$ and $CH_2$ are present in the molecule, the entire hinge region is also present to provide the disulfide bridges between the two heavy chain molecules and between the heavy and light chains. Where only $CH_1$ is present, for example, the molecule need only contain the portion of the hinge region corresponding to the disulfide bridge between the light and heavy chains, such as the first 7 amino acids of the hinge.

It will be understood by one skilled in the art, once armed with the present disclosure, that the immunoreceptor peptides of the invention can be, for example, monomeric or dimeric. For example, the molecules can have only one light chain and one heavy chain or two light chains and two heavy chains.

At least one of the non-immunoglobulin molecules linked to an immunoglobin molecule comprises at least a portion of p55 or at least a portion of p75. The portion of the receptor that is included encompasses the TNF binding site.

In certain preferred embodiments, the non-immunoglobulin molecule comprises at least 5 amino acid segments of sequences 2–159 of p55. In other preferred embodiments, the non-immunoglobulin molecule comprises at least 5 amino acid portions of sequences 1–235 of p75. In further preferred embodiments, the non-immunoglobulin molecule comprises at least 5 amino acid portions of sequences 1–182 of p75. The above 5 amino acid portions can be selected from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 50, 60, 70, 80, 90, 100, 110, 120, 130, 140, 150, 160, 170, 180, 190, 200, 210, 220, 230, 240, 250, 260, 270, 280, 290.

Figure 26B:
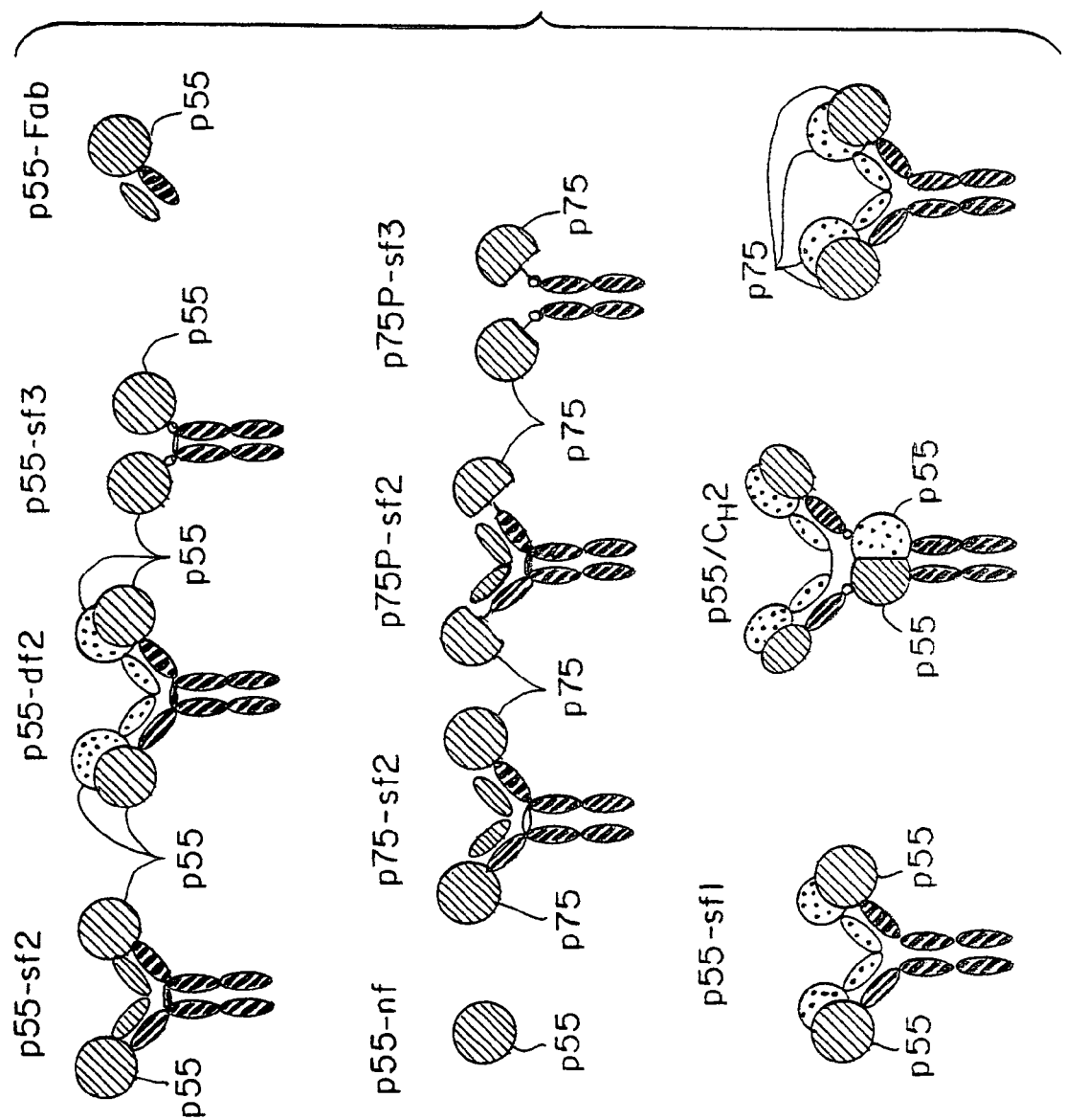

In certain preferred embodiments, each of the two heavy chains and each of the two light chains is linked to a portion of the TNF receptor, thus forming a tetravalent molecule. Such a tetravalent molecule can have, for example, four p55 receptor molecules; two on the two heavy chains and two on the two light chains. Alternatively, a tetravalent molecule can have, for example, a p55 receptor molecule attached to each of the two heavy chains and a p75 receptor molecule attached to each of the two light chains. A tetravalent molecule can also have, for example, p55 receptor attached to the light chains and p75 receptor attached to the heavy chains. Additionally, a tetravalent molecule can have one heavy chain attached to p55, one heavy chain attached to p75, one light chain attached to p75, and one light chain attached to p55. See, for example, the molecules depicted in FIG. 26B. Further, the molecules can have six receptors attached, for example, two within the heavy chains and four at the ends of the heavy and light chains. Other potential multimers and combinations would also be within the scope of one skilled in the art, once armed with the present disclosure.

In further preferred embodiments, at least one of the heavy chains has a variable region capable of binding to a second target molecule. Such molecules include, for example, CD3, so that one half of a fusion molecule is a monomeric anti-CD3 antibody.

Additionally, in other embodiments of the present invention, the immunoreceptor peptides further include an irrelevant variable region on the light chain and/or heavy chain. Preferably, however, such a region is absent due to the lowered affinity for TNF which can be present due to steric hindrance.

In certain preferred embodiments, the heavy chain is linked to a non-immunoglobulin molecule capable of binding to a second target molecule, such as a cytotoxic protein, thus creating a part immunoreceptor, part immunotoxin that is capable of killing those cells expressing TNF. Such cytotoxic proteins, include, but are not limited to, Ricin-A, *Pseudomonas* toxin, Diphtheria toxin and TNF. Toxins conjugated to ligands are known in the art (see, for example, Olsnes, S. et al., *Immunol. Today* 1989, 10, 291–295). Plant and bacterial toxins typically kill cells by disruption of the protein synthetic machinery.

The immunoreceptors of this invention can be conjugated to additional types of therapeutic moieties including, but not limited to, radionuclides, cytotoxic agents and drugs. Examples of radionuclides include $^{212}$Bi, $^{131}$I, $^{186}$Re, and $^{90}$Y, which list is not intended to be exhaustive. The radionuclides exert their cytotoxic effect by locally irradiating the cells, leading to various intracellular lesions, as is known in the art of radiotherapy.

Cytotoxic drugs which can be conjugated to the immunoreceptors and subsequently used for in vivo therapy include, but are not limited to, daunorubicin, doxorubicin, methotrexate, and Mitomycin C. Cytotoxic drugs interfere with critical cellular processes including DNA, RNA, and protein synthesis. For a fuller exposition of these classes of drugs which are known in the art, and their mechanisms of action, see Goodman, A. G., et al., *Goodman and Gilman's The Pharmacological Basis of Therapeutics,* 8th Ed., Macmillan Publishing Col, 1990. Katzung, ed., Basic and Clinical Pharmacology, Fifth Edition, p 768–769, 808–809, 896, Appleton and Lange, Norwalk, Conn.

In preferred embodiments, immunoreceptor molecules of the invention are capable of binding with high affinity to a neutralizing epitope of human TNFα or TNFβ in vivo. Preferably, the binding affinity is at least about $1.6\times10^{10}$ M-1. Additionally, in preferred embodiments, immunoreceptor molecules of the invention are capable of neutralizing TNF at an efficiency of about a concentration of less than 130 pM to neutralize 39.2 pM human TNFα. See, for example, Table 1.

TABLE 1

Summary of affinities of different fusion proteins for TNFα.

| Protein | $IC_{50}$* | Molar ratio fp: TNFα at $IC_{50}$ | $K_D$(pM) |
|---|---|---|---|
| p55-sf2 | 70 | 1.8 | 57 |
| p55-df2 | 55 | 1.4 | 60 |
| p55-sf3 | 100 | 2.6 | 48 |
| p55-nf | 36,000 | 900 | n.d. |
| p75-sf2 | 130 | 3.3 | 33 |
| p75P-sf2 | 70 | 1.8 | 29 |
| p75P-sf3 | 130 | 3.3 | 15 |

*$IC_{50}$ = concentration of fusion protein required to inhibit 2 ng/ml (39.2 pM) TNFα by 50%

Once armed with the present disclosure, one skilled in the art would be able to create fragments of the immunoreceptor peptides of the invention. Such fragments are intended to be within the scope of this invention. For example, once the molecules are isolated, they can be cleaved with protease to generate fragments that remain capable of binding TNF.

Once armed with the present disclosure, one skilled in the art would also be able to create derivatives of the immunoreceptor peptides of the invention. Such derivatives are intended to be within the scope of this invention. For example, amino acids in the immunoreceptor that constitute a protease recognition site can be modified to avoid protease cleavage and thus confer greater stability, such as KEX2 sites.

One skilled in the art, once armed with the present disclosure, would be able to synthesize the molecules of the invention. The immunoreceptor peptides can be constructed, for example, by vector-mediated synthesis, as described in Example XXVI. In general, two expression vectors are preferably used; one for the heavy chain, one for the light chain. A vector for expression of an immunoglobulin preferably consists of a promoter linked to the signal sequence, followed by the constant region. The vector additionally preferably contains a gene providing for the selection of transfected cells expressing the construct. In certain preferred embodiments, sequences derived from the J region are also included.

The immunoglobulin gene can be from any vertebrate source, such as murine, but preferably, it encodes an immunoglobulin having a substantial number of sequences that are of the same origin as the eventual recipient of the immunoreceptor peptide. For example, if a human is treated with a molecule of the invention, preferably the immunoglobulin is of human origin.

TNF receptor constructs for linking to the heavy chain can be synthesized, for example, using DNA encoding amino acids present in the cellular domain of the receptor. Putative receptor binding loci of hTNF have been presented by Eck and Sprange, *J. Biol. Chem.* 264(29), 17595–17605 (1989), who identified the receptor binding loci of TNFα as consisting of amino acids 11–13, 37–42, 49–57 and 155–157. PCT application W091/02078 (priority date of Aug. 7, 1989) discloses TNF ligands which can bind to monoclonal antibodies having the following epitopes of at least one of 1–20, 56–77, and 108–127; at least two of 1–20, 56–77, 108–127 and 138–149; all of 1–18, 58–65, 115–125 and 138–149; all of 1–18, and 108–128; all of 56–79, 110–127 and 135- or 136–155; all of 1–30, 117–128 and 141–153; all of 1–26, 117–128 and 141–153; all of 22–40, 49–96 or -97, 110–127 and 136–153; all of 12–22, 36–45, 96–105 and 132–157; all of both of 1–20 and 76–90; all of 22–40, 69–97, 105–128 and 135–155; all of 22–31 and 146–157; all of 22–40 and 49–98; at least one of 22–40, 9–98 and 69–97, both of 22–40 and 70–87. Thus, one skilled in the art, once armed with the present disclosure, would be able to create TNF receptor fusion proteins using portions of the receptor that are known to bind TNF.

Advantages of using an immunoglobulin fusion protein (immunoreceptor peptide) of the present invention include one or more of (1) possible increased avidity for multivalent ligands due to the resulting bivalency of dimeric fusion proteins, (2) longer serum half-life, (3) the ability to activate effector cells via the Fc domain, (4) ease of purification (for example, by protein A chromatography), (5) affinity for TNFα and TNFβ and (6) the ability to block TNFα or TNFβ cytotoxicity.

TNF receptor/IgG fusion proteins have shown greater affinity for TNFα in vitro than their monovalent, non-fusion counterparts. These types of fusion proteins, which also bind murine TNF with high affinity, have also been shown to protect mice from lipopolysaccharide-induced endotoxemia. Lesslauer et al., *Eur. J. Immunol.* 21, 2883–2886 (1991); and Ashkenazi et al., *Proc. Natl. Acad. Sci. USA* 88:10535–10539 (1991). Unlike the molecules of the present invention, the TNF receptor/IgG fusion proteins reported to date have had the receptor sequence fused directly to the hinge domain of IgGs such that the first constant domain ($CH_1$) of the heavy chain was omitted. Lesslauer et al., *Eur. J. Immunol.* 1:2883–2886; Ashkenzi et al., *Proc. Natl. Acad. Sci. USA* 88:10535–10539 (1991); and Peppel et al., *J. Exp. Med.* 174:1483–1489 (1991).

While this generally permits secretion of the fusion protein in the absence of an Ig light chain, a major embodiment of the present invention provides for the inclusion of the $CH_1$ domain, which can confer advantages such as (1) increased distance and/or flexibility between two receptor molecules resulting in greater affinity for TNF, (2) the ability to create a heavy chain fusion protein and a light chain fusion protein that would assemble with each other and dimerize to form a tetravalent (double fusion) receptor molecule, and (3) a tetravalent fusion protein can have increased affinity and/or neutralizing capability for TNF compared to a bivalent (single fusion) molecule.

Unlike other TNF receptor/IgG fusion proteins that have been reported, the fusion proteins of a major embodiment of the present invention include the first constant domain ($CH_1$) of the heavy chain. The $CH_1$ domain is largely responsible for interactions with light chains. The light chain, in turn, provides a vehicle for attaching a second set of TNF receptor molecules to the immunoreceptor peptide.

It was discovered using the molecules of the present invention that the p55/light chain fusion proteins and p55/heavy chain fusion proteins would assemble with each other and dimerize to form an antibody-like molecule that is tetravalent with respect to p55. The resulting tetravalent p55 molecules can confer more protection against, and have greater affinity for, TNFα or TNFβ than the bivalent p55 molecules. Despite the presumed close proximity of the two light chain p55 domains to the heavy chain p55 domains, they do not appear sterically hinder or reduce the affinity for TNF.

Inclusion of the $CH_1$ domain also meant that secretion of the fusion protein was likely to be inefficient in the absence of light chain. This has been shown to be due to a ubiquitous immunoglobulin binding protein (BiP) that binds to the $CH_1$ domain of heavy chains that are not assembled with a light chain and sequesters them in the endoplasmic reticulum. Karlsson et al., *J. Immunol. Methods* 145:229–240 (1991).

In initial experiments, an irrelevant light chain was co-transfected with the p55-heavy chain construct and subsequent analyses showed that the two chains did assemble and that the resulting fusion protein protected WEHI cells from TNFα. However, it was considered likely that the variable region of the irrelevant light chain would sterically hinder interactions between the p55 subunits and TNFα. For this reason, a mouse-human chimeric antibody light chain gene was engineered by (1) deleting the variable region coding sequence, and (2) replacing the murine J coding sequence with human J coding sequence. Use of this truncated light chain, which was shown to assemble and disulfide bond with heavy chains, increased the efficiency of TNF inhibition by approximately 30-fold compared to use of a complete irrelevant light chain.

Comparison of the abilities of p75-sf2 and p75P-sf2 to inhibit TNF cytotoxicity indicated that the C-terminal 53 amino acids of the extracellular domain of p75, which defines a region that is rich in proline residues and contains the only sites of O-linked glycosylation, are not necessary for high-affinity binding to TNFα or TNFβ. In fact, the p75P-sf2 construct repeatedly showed higher affinity binding to TNFβ than p75-sf2. Surprisingly, there was no difference observed between the two constructs in their affinity for TNFα.

It is possible that a cell-surface version of p75-P would also bind TNFβ with higher affinity than the complete p75 extracellular domain. A similar region is found adjacent to the transmembrane domain in the low affinity nerve growth factor receptor whose extracellular domain shows the same degree of similarity to p75 as p55 does. Mallerr et al., *Immunol. Today* 12:220–223 (1991).

Two groups have reported that in cell cytotoxicity assays, their p55 fusion protein could be present at a 3-fold (Lesslauer et al., *Eur. J. Immunol.* 21:2883–2886 (1991)) or 6–8 fold (Ashkenazi et al., *Proc. Natl. Acad. Sci. USA* 88:10535–10539 (1991)) lower concentration than their monovalent p55 and still get the same degree of protection, while another group (Peppel et al., *J. Exp. Med.* 174:1483–1489 (1991)) showed that their p55 fusion protein could be present at a 1000-fold lower concentration than monomeric p55. Thus, the prior art has shown unpredictability in the great variability in the efficiency of different fusion proteins.

The molecules of the present invention have demonstrated the same degree of protection against TNF in a 5000-fold lower molar concentration than monomeric p55. (See Table 1.) It is believed that the presence of the $CH_1$ chain in the molecules of a major embodiment of the present invention can confer greater flexibility to the molecule and avoid steric hindrance with the binding of the TNF receptor.

Recombinant Expression of Anti-TNF Antibodies and Anti-TNF Peptides

A nucleic acid sequence encoding at least one anti-TNF peptide or Ab fragment of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel, infra, Sambrook, infra, entirely incorporated herein by reference, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-TNF peptides or Ab fragments in recoverable amounts. The precise nature of the regulatory regions needed for gene expression may vary from organism to organism, as is well known in the analogous art. See, e.g., Sambrook, supra and Ausubel supra.

The present invention accordingly encompasses the expression of an anti-TNF peptide or Ab fragment, in either prokaryotic or eukaryotic cells, although eukaryotic expression is preferred.

Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cell or tissue is of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins may be accomplished. The fusion proteins so produced may be processed in vivo or purified and processed in vitro, allowing synthesis of an anti-TNF peptide or Ab fragment of the present invention with a specified amino terminus sequence. Moreover, problems associated with retention of initiation codon-derived methionine residues in direct yeast (or bacterial) expression may be avoided. Sabin et al., *Bio/Technol.* 7(7): 705–709 (1989); Miller et al., *Bio/Technol.* 7(7):698–704 (1989).

Any of a series of yeast gene expression systems incorporating promoter and termination elements from the actively expressed genes coding for glycolytic enzymes produced in large quantities when yeast are grown in mediums rich in glucose can be utilized to obtain anti-TNF peptides or Ab fragments of the present invention. Known glycolytic genes can also provide very efficient transcriptional control signals. For example, the promoter and terminator signals of the phosphoglycerate kinase gene can be utilized.

Production of anti-TNF peptides or Ab fragments or functional derivatives thereof in insects can be achieved, for example, by infecting the insect host with a baculovirus engineered to express a transmembrane polypeptide by methods known to those of skill. See Ausubel et al., eds. *Current Protocols in Molecular Biology* Wiley Interscience, §§16.8–16.11 (1987, 1993).

In a preferred embodiment, the introduced nucleotide sequence will be incorporated into a plasmid or viral vector capable of autonomous replication in the recipient host. Any of a wide variety of vectors may be employed for this purpose. See, e.g., Ausubel et al., infra, §§ 1.5, 1.10, 7.1, 7.3, 8.1, 9.6, 9.7, 13.4, 16.2, 16.6, and 16.8–16.11. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors known in the art include plasmids such as those capable of replication in *E. coli* (such as, for example, pBR322, ColE1, pSC101, pACYC 184, πVX). Such plasmids are, for example, disclosed by Maniatis, T., et al. (*Molecular Cloning, A Laboratory Manual*, Second Edition, Cold Spring Harbra Press, Cold Spring Harbor, N.Y. (1989); Ausubel, infra. *Bacillus* plasmids include pC194, pC221, pT127, etc. Such plasmids are disclosed by Gryczan, T. (In: *The Molecular Biology of the Bacilli*, Academic Press, NY (1982), pp. 307–329). Suitable *Streptomyces* plasmids include pIJ101 (Kendall, K. J., et al., *J. Bacteriol.* 169:4177–4183 (1987)), and *streptomyces* bacteriophages such as ΦC31 (Chater, K. F., et al., In: *Sixth International Symposium on Actinomycetales Biology*, Akademiai Kaido, Budapest, Hungary (1986), pp. 45–54). *Pseudomonas* plasmids are reviewed by John, J. F., et al. (*Rev. Infect. Dis.* 8:693–704 (1986)), and Izaki, K. (*Jpn. J. Bacteriol.* 33:729–742 (1978); and Ausubel et al., supra).

Alternatively, gene expression elements useful for the expression of cDNA encoding anti-TNF antibodies or peptides include, but are not limited to (a) viral transcription promoters and their enhancer elements, such as the SV40 early promoter (Okayama, et al., *Mol. Cell. Biol.* 3:280 (1983)), Rous sarcoma virus LTR (Gorman, et al., *Proc. Natl. Acad. Sci., USA* 79:6777 (1982)), and Moloney murine leukemia virus LTR (Grosschedl, et al., *Cell* 41:885 (1985)); (b) splice regions and polyadenylation sites such as those derived from the SV40 late region (Okayarea et al., infra); and (c) polyadenylation sites such as in SV40 (Okayama et al., infra).

Immunoglobulin cDNA genes can be expressed as described by Liu et al., infra, and Weidle et al., *Gene* 51:21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., *Protein Engineering* 1:499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an anti-TNF peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-TNF peptide or chimeric H and L chains, or portions thereof, are assembled in separate expression vectors that are then used to co-transfect a recipient cell.

Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes.

Examples of selectable genes for use in a bacterial system are the gene that confers resistance to ampicillin and the gene that confers resistance to chloramphenicol. Preferred selectable genes for use in eukaryotic transfectants include the xanthine guanine phosphoribosyl transferase gene (designated gpt) and the phosphotransferase gens from Tn5 (designated neo).

Selection of cells expressing gpt is based on the fact that the enzyme encoded by this gene utilizes xanthine as a substrate for purine nucleotide synthesis, whereas the analogous endogenous enzyme cannot. In a medium containing (1) mycophenolic acid, which blocks the conversion of inosine monophosphate to xanthine monophosphate, and (2) xanthine, only cells expressing the gpt gene can survive. The product of the neo blocks the inhibition of protein synthesis by the antibiotic G418 and other antibiotics of the neomycin class.

The two selection procedures can be used simultaneously or sequentially to select for the expression of immunoglobulin chain genes introduced on two different DNA vectors into a eukaryotic cell. It is not necessary to include different selectable markers for eukaryotic cells; an H and an L chain vector, each containing the same selectable marker can be co-transfected. After selection of the appropriately resistant cells, the majority of the clones will contain integrated copies of both H and L chain vectors and/or anti-TNF peptides.

Alternatively, the fused genes encoding the chimeric H and L chains can be assembled on the same expression vector.

For transfection of the expression vectors and production of the chimeric antibody, the preferred recipient cell line is a myeloma cell. Myeloma cells can synthesize, assemble and secrete immunoglobulins encoded by transfected immunoglobulin genes and possess the mechanism for glycosylation of the immunoglobulin. A particularly preferred recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric antibody construct or anti-TNF peptide of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment (Johnston et al., *Science* 240:1538 (1988)). A preferred way of introducing DNA into lymphoid cells is by electroporation (Potter et al., *Proc. Natl. Acad. Sci. USA* 81:7161 (1984); Yoshikawa, et al., *Jpn. J. Cancer Res.* 77:1122–1133). In this procedure, recipient cells are subjected to an electric pulse in the presence of the DNA to be incorporated. Typically, after transfection, cells are allowed to recover in complete medium for about 24 hours, and are then seeded in 96-well culture plates in the presence of the selective medium. G418 selection is performed using about 0.4 to 0.8 mg/ml G418. Mycophenolic acid selection utilizes about 6 µg/ml plus about 0.25 mg/ml xanthine. The electroporation technique is expected to yield transfection frequencies of about $10^{-5}$ to about $10^{-4}$ for Sp2/0 cells. In the protoplast fusion method, lysozyme is used to strip cell walls from catarrhal harboring the recombinant plasmid containing the chimeric antibody gene. The resulting spheroplasts are fused with myeloma cells with polyethylene glycol.

The immunoglobulin genes of the present invention can also be expressed in nonlymphoid mammalian cells or in other eukaryotic cells, such as yeast, or in prokaryotic cells, in particular bacteria.

Yeast provides substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides) (Hitzman, et al., 11*th International Conference on Yeast, Genetics and Molecular Biology,* Montpelier, France, Sep. 13–17, 1982).

Yeast gene expression systems can be routinely evaluated for the levels of production, secretion and the stability of anti-TNF peptides, antibody and assembled murine and chimeric antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast (see Glover, ed., *DNA Cloning, Vol. II,* pp 45–66, IRL Press, 1985).

Bacterial strains can also be utilized as hosts for the production of antibody molecules or peptides described by this invention, *E. coli* K12 strains such as *E. coli* W3110 (ATCC 27325), and other enterobacteria such as *Salmonella typhimurium* or *Serratia marcescens,* and various *Pseudomonas* species can be used.

Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine and chimeric antibodies, fragments and regions or antibody chains encoded by the cloned immunoglobulin cDNAs in bacteria (see Glover, ed., *DNA Cloning, Vol. I,* IRL Press, 1985, Ausubel, infra, Sambrook, infra, Colligan, infra).

Preferred hosts are mammalian cells, grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61).

Many vector systems are available for the expression of cloned anti-TNF peptides H and L chain genes in mammalian cells (see Glover, ed., *DNA Cloning, Vol. II*, pp143–238, IRL Press, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies and/or anti-TNF peptides. The co-expression can occur by using either the same or different plasmids in the same host. Genes for both H and L chains and/or anti-TNF peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-TNF peptides and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Anti-idiotype Abs

In addition to monoclonal or chimeric anti-TNF antibodies, the present invention is also directed to an anti-idiotypic (anti-Id) antibody specific for the anti-TNF antibody of the invention. An anti-Id antibody is an antibody which recognizes unique determinants generally associated with the antigen-binding region of another antibody. The antibody specific for TNF is termed the idiotypic or Id antibody. The anti-Id can be prepared by immunizing an animal of the same species and genetic type (e.g. mouse strain) as the source of the Id antibody with the Id antibody or the antigen-binding region thereof. The immunized animal will recognize and respond to the idiotypic determinants of the immunizing antibody and produce an anti-Id antibody. The anti-Id antibody can also be used as an "immunogen" to induce an immune response in yet another animal, producing a so-called anti-anti-Id antibody. The anti-anti-Id can be epitopically identical to the original antibody which induced the anti-Id. Thus, by using antibodies to the idiotypic determinants of a mAb, it is possible to identify other clones expressing antibodies of identical specificity.

Accordingly, mAbs generated against TNF according to the present invention can be used to induce anti-Id antibodies in suitable animals, such as BALB/c mice. Spleen cells from such immunized mice can be used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a TNF epitope.

Screening Methods for determining tissue necrosis factor neutralizing and/or inhibiting activity are also provided in the present invention. In the context of the present invention, TNF neutralizing activity or TNF inhibiting activity refers to the ability of a TNF neutralizing compound to block at least one biological activity of TNF, such as preventing TNF from binding to a TNF receptor, blocking production of TNF by intracellular processing, such as transcription, translation or post-translational modification, expression on the cell surface, secretion or assembly of the bioactive trimer of TNF. Additionally, TNF neutralizing compounds can act by inducing regulation of metabolic pathways such as those involving the up or down regulation of TNF production. Alternatively TNF neutralizing compounds can modulate cellular sensitivity to TNF by decreasing such sensitivity. TNF neutralizing compounds can be selected from the group consisting of antibodies, or fragments or portions thereof, peptides, peptido mimetic compounds or organo mimetic compounds that neutralizes TNF activity in vitro, in situ or in vivo is considered a TNF neutralizing compound if used according to the present invention. Screening methods which can be used to determine TNF neutralizing activity of a TNF neutralizing compound can include in vitro or in vivo assays. Such in vitro assays can include a TNF cytotoxicity assay, such as a radioimmuno assay, which determines a decrease in cell death by contact with TNF, such as chimpanzee or human TNF in isolated or recombinant form, wherein the concurrent presence of a TNF neutralizing compound reduces the degree or rate of cell death. The cell death can be determined using ID50 values which represent the concentration of a TNF neutralizing compound which decreases the cell death rate by 50%. For example, MAb's A2 and cA2 are found to have ID50 about 17 mg/ml+/–3 mg/ml, such as 14–20 mg/ml, or any range or value therein. Such a TNF cytotoxicity assay is presented in Example II.

Alternatively or additionally, another in vitro assay which can be used to determine neutralizing activity of a TNF neutralizing compound is an assay which measures the neutralization of TNF induced procoagulant activity, such as presented in Example XI.

Alternatively or additionally, TNF neutralizing activity of a TNF neutralizing compound can be measured by an assay for the neutralization of TNF induced IL-6 secretion, such as using cultured human umbilical vein endothelial cells (HUVEC), for example. Also presented in Example XI.

Alternatively or additionally, in vivo testing of TNF neutralizing activity of TNF neutralizing compounds can be tested using survival of a mouse given lethal doses of Rh TNF with controlled and varied concentrations of a TNF neutralizing compound, such as TNF antibodies. Preferably galactosamine sensitive mice are used. For example, using a chimeric human anti-TNF antibody as a TNF neutralizing compound, a concentration of 0.4 milligrams per kilogram TNF antibody resulted in a 70–100% increase in survival and a 2.0 mg/kg dose of TNF antibody resulted in a 90–100% increase in survival rate using such an assay, for example, as presented in Example XVI.

Additionally, after TNF neutralizing compounds are tested for safety in animal models such as chimpanzees, for example as presented in Example XVII, TNF neutralizing compounds can be used to treat various TNF related pathologies, as described herein, and as presented in Examples XVIII–XXV.

Accordingly, any suitable TNF neutralizing compound can be used in methods according to the present invention. Examples of such TNF neutralizing compound can be selected from the group consisting of antibodies or portions thereof specific to neutralizing epitopes of TNF, p55 receptors, p75 receptors, or complexes thereof, portions of TNF receptors which bind TNF, peptides which bind TNF, any peptido mimetic drugs which bind TNF and any organo mimetic drugs that block TNF.

Such TNF neutralizing compounds can be determined by routine experimentation based on the teachings and guidance presented herein, by those skilled in the relevant arts.

Structural Analogs of Anti-TNF Antibodies and Anti-TNF Peptides

Structural analogs of anti-TNF Abs and peptides of the present invention are provided by known method steps based on the teaching and guidance presented herein.

Knowledge of the three-dimensional structures of proteins is crucial in understanding how they function. The three-dimensional structures of more than 400 proteins are currently available in protein structure databases (in contrast to around 15,000 known protein sequences in sequence databases). Analysis of these structures shows that they fall into recognizable classes of motifs. It is thus possible to model a three-dimensional structure of a protein based on the protein's homology to a related protein of known structure. Many examples are known where two proteins that have relatively low sequence homology, can have very similar three dimensional structures or motifs.

In recent years it has become possible to determine the three dimensional structures of proteins of up to about 15 kDa by nuclear magnetic resonance (NMR). The technique only requires a concentrated solution of pure protein. No crystals or isomorphous derivatives are needed. The structures of a number of proteins have been determined by this method. The details of NMR structure determination are well-known in the art (See, e.g., Wuthrich, *NMR of Proteins and Nucleic Acids,* Wiley, New York, 1986; Wuthrich, K. *Science* 243:45–50 (1989); Clore et al., *Crit. Rev. Bioch. Molec. Biol.* 24:479–564 (1989); Cooke et al., *Bioassays* 8: 52–56 (1988), which references are hereby incorporated herein by reference).

In applying this approach, a variety of $^1$H NMR 2D data sets are collected for anti-TNF Abs and/or anti-TNF peptides of the present invention. These are of two main types. One type, COSY (Correlated Spectroscopy) identifies proton resonances that are linked by chemical bonds. These spectra provide information on protons that are linked by three or less covalent bonds. NOESY (nuclear Overhauser enhancement spectroscopy) identifies protons which are close in space (less than 0.5 nm). Following assignment of the complete spin system, the secondary structure is defined by NOESY. Cross peaks (nuclear Overhauser effects or NOE's) are found between residues that are adjacent in the primary sequence of the peptide and can be seen for protons less than 0.5 nm apart. The data gathered from sequential NOE's combined with amide proton coupling constants and NOE's from non-adjacent amino acids that are adjacent to the secondary structure, are used to characterize the secondary structure of the polypeptides. Aside from predicting secondary structure, NOE's indicate the distance that protons are in space in both the primary amino acid sequence and the secondary structures. Tertiary structure predictions are determined, after all the data are considered, by a "best fit" extrapolation.

Types of amino acid are first identified using through-bond connectivities. The second step is to assign specific amino acids using through-space connectivities to neighboring residues, together with the known amino acid sequence. Structural information is then tabulated and is of three main kinds: The NOE identifies pairs of protons which are close in space, coupling constants give information on dihedral angles and slowly exchanging amide protons give information on the position of hydrogen bonds. The restraints are used to compute the structure using a distance geometry type of calculation followed by refinement using restrained molecular dynamics. The output of these computer programs is a family of structures which are compatible with the experimental data (i.e. the set of pairwise <0.5 nm distance restraints). The better that the structure is defined by the data, the better the family of structures can be superimposed, (i.e., the better the resolution of the structure). In the better defined structures using NMR, the position of much of the backbone (i.e. the amide, Cα and carbonyl atoms) and the side chains of those amino acids that lie buried in the core of the molecule can be defined as clearly as in structures obtained by crystallography. The side chains of amino acid residues exposed on the surface are frequently less well defined, however. This probably reflects the fact that these surface residues are more mobile and can have no fixed position. (In a crystal structure this might be seen as diffuse electron density).

Thus, according to the present invention, use of NMR spectroscopic data is combined with computer modeling to arrive at structural analogs of at least portions of anti-TNF Abs and peptides based on a structural understanding of the topography. Using this information, one of ordinary skill in the art will know how to achieve structural analogs of anti-TNF Abs and/or peptides, such as by rationally-based amino acid substitutions allowing the production of peptides in which the TNF binding affinity is modulated in accordance with the requirements of the expected therapeutic or diagnostic use of the molecule, preferably, the achievement of greater specificity for TNF binding.

Alternatively, compounds having the structural and chemical features suitable as anti-TNF therapeutics and diagnostics provide structural analogs with selective TNF affinity. Molecular modeling studies of TNF binding compounds, such as TNF receptors, anti-TNF antibodies, or other TNF binding molecules, using a program such as MACROMODEL®, INSIGHT®, and DISCOVER® provide such spatial requirements and orientation of the anti-TNF Abs and/or peptides according to the present invention. Such structural analogs of the present invention thus provide selective qualitative and quantitative anti-TNF activity in vitro, in situ and/or in vivo.

Therapeutic Methods for Treating TNF-Related Pathologies

The anti-TNF peptides, antibodies, fragments and/or derivatives of the present invention are useful for treating a subject having a pathology or condition associated with abnormal levels of a substance reactive with an anti-TNF antibody, in particular TNF, such as TNFα or TNFβ, in excess of levels present in a normal healthy subject, where such excess levels occur in a systemic, localized or particular tissue type or location in the body. Such tissue types can include, but are not limited to, blood, lymph, CNS, liver, kidney, spleen, heart muscle or blood vessels, brain or spinal cord white matter or grey matter, cartilage, ligaments, tendons, lung, pancreas, ovary, testes, prostate. Increased TNF concentrations relative to normal levels can also be localized to specific regions or cells in the body, such as joints, nerve blood vessel junctions, bones, specific tendons or ligaments, or sites of infection, such as bacterial or viral infections.

TNF related pathologies include, but are not limited to, the following:

(A) acute and chronic immune and autoimmune pathologies, such as systemic lupus erythematosus (SLE), rheumatoid arthritis, thyroidosis, graft versus host disease, scleroderma, diabetes mellitus, Graves' disease, Beschet's disease, and the like;

(B) infections, including, but not limited to, sepsis syndrome, cachexia, circulatory collapse and shock resulting from acute or chronic bacterial infection, acute and chronic parasitic and/or infectious diseases, bacterial, viral or fungal, such as a HIV, AIDS (including symptoms of cachexia, autoimmune disorders, AIDS dementia complex and infections);

(C) inflammatory diseases, such as chronic inflammatory pathologies and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology:

(D) neurodegenerative diseases, including, but are not limited to, demyelinating diseases, such as multiple sclerosis and acute transverse myelitis; extrapyramidal and cerebellar disorders such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo palsy; Cerebellar and Spinocerebellar Disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and MachadoJoseph)); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, or any subset thereof;

(E) malignant pathologies involving TNF-secreting tumors or other malignancies involving TNF, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); carcinomas (such as colon carcinoma) and metastases thereof; cancer-related angiogenesis; infantile haemangiomas;

(F) alcohol-induced hepatitis; and (G) other diseases related to angiogenesis or VEGF/VPF, such as ocular neovascularization, psoriasis, duodenal ulcers, angiogenesis of the female reproductive tract.

See, e.g., Berkow et al., eds., *The Merck Manual,* 16th edition, chapter 11, pp 1380–1529, Merck and Co., Rahway, N.J., 1992, which reference, and references cited therein, are entirely incorporated herein by reference. See also Folkman, *Nature Medicine,* Volume 1, No. 1 (1995).

Such treatment comprises parenterally administering a single or multiple doses of the antibody, fragment or derivative. Preferred for human pharmaceutical use are high affinity potent hTNFα-inhibiting and/or neutralizing murine and chimeric antibodies, fragments and regions of this invention.

Anti-TNF peptides or MAbs of the present invention can be administered by any means that enables the active agent to reach the agent's site of action in the body of a mammal. In the case of the antibodies of this invention, the primary focus is the ability to reach and bind with TNF released by monocytes and macrophages or other TNF producing cells. Because proteins are subject to being digested when administered orally, parenteral administration, i. e., intravenous, subcutaneous, intramuscular, would ordinarily be used to optimize absorption.

Therapeutic Administration

Anti-TNF peptides and/or MAbs of the present invention can be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 1.0 to 5, and preferably 1 to 10 milligrams per kilogram per day given in divided doses 1 to 6 times a day or in sustained release form is effective to obtain desired results.

As a non-limiting example, treatment of TNF-related pathologies humans or animals can be provided as a daily dosage of anti-TNF peptides, monoclonal chimeric and/or murine antibodies of the present invention 0.1 to 100 mg/kg, such as 0.5, 0.9, 1.0, 1.1, 1.5, 2,3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4, or 2 hours, or any combination thereof.

Since circulating concentrations of TNF tend to be extremely low, in the range of about 10 pg/ml in non-septic individuals, and reaching about 50 pg/ml in septic patients and above 100 pg/ml in the sepsis syndrome (Hammerle, A. F. et al., 1989, infra) or can be only be detectable at sites of TNF-mediated pathology, it is preferred to use high affinity and/or potent in vivo TNF-inhibiting and/or neutralizing antibodies, fragments or regions thereof, for both TNF immunoassays and therapy of TNF-mediated pathology. Such antibodies, fragments, or regions, will preferably have an affinity for hTNFα, expressed as Ka, of at least $10^8$ $M^{-1}$, more preferably, at least $10^9$ $M^{-1}$, such as $10^8$-$10^{10}M^{-1}$, $5\times10^8M^{-1}$, $8\times10^8M^{-1}$, $2\times10^9M^{-1}$, $4\times10^9$ $M^{-1}$, $6\times10^9$ $M^{-1}$, $8\times10^9$ $M^{-1}$, or any range or value therein.

Preferred for human therapeutic use are high affinity murine and chimeric antibodies, and fragments, regions and derivatives having potent in vivo TNFα-inhibiting and/or neutralizing activity, according to the present invention, that block TNF-induced IL-6 secretion. Also preferred for human therapeutic uses are such high affinity murine and chimeric anti-TNFα antibodies, and fragments, regions and derivatives thereof, that block TNF-induced procoagulant activity, including blocking of TNF-induced expression of cell adhesion molecules such as ELAM-I and ICAM-I and blocking of TNF mitogenic activity, in vivo, in situ, and in vitro.

Dosage forms (composition) suitable for internal administration generally contain from about 0.1 milligram to about 500 milligrams of active ingredient per unit. In these pharmaceutical compositions the active ingredient will ordinarily be present in an amount of about 0.5–95% by weight based on the total weight of the composition.

For parenteral administration, anti-TNF peptides or antibodies can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of Remington's Pharmaceutical Sciences, A. Osol, a standard reference text in this field of art.

For example, a parenteral composition suitable for administration by injection is prepared by dissolving 1.5% by weight of active ingredient in 0.9% sodium chloride solution.

Anti-TNF peptides and/or antibodies of this invention can be adapted for therapeutic efficacy by virtue of their ability to mediate antibody-dependent cellular cytotoxicity (ADCC) and/or complement-dependent cytotoxicity (CDC) against cells having TNF associated with their surface. For these activities, either an endogenous source or an exogenous source of effector cells (for ADCC) or complement components (for CDC) can be utilized. The murine and chimeric antibodies, fragments and regions of this invention, their fragments, and derivatives can be used therapeutically as immunoconjugates (see for review: Dillman, R. O., *Ann. Int. Med.* 111:592–603 (1989)). Such peptides or Abs can be coupled to cytotoxic proteins, including, but not limited to ricin-A, *Pseudomonas* toxin and Diphtheria toxin. Toxins conjugated to antibodies or other ligands or peptides are well known in the art (see, for example, Olsnes, S. et al., *Immunol. Today* 10:291–295 (1989)). Plant and bacterial toxins typically kill cells by disrupting the protein synthetic machinery.

Anti-TNF peptides and/or antibodies of this invention can be conjugated to additional types of therapeutic moieties including, but not limited to, radionuclides, therapeutic agents, cytotoxic agents and drugs. Examples of radionuclides which can be coupled to antibodies and delivered in vivo to sites of antigen include $^{212}Bi$, $^{131}I$, $^{186}Re$, and $^{90}Y$, which list is not intended to be exhaustive. The radionuclides exert their cytotoxic effect by locally irradiating the cells, leading to various intracellular lesions, as is known in the art of radiotherapy.

Cytotoxic drugs which can be conjugated to anti-TNF peptides and/or antibodies and subsequently used for in vivo therapy include, but are not limited to, daunorubicin, doxorubicin, methotrexate, and Mitomycin C. Cytotoxic drugs interfere with critical cellular processes including DNA, RNA, and protein synthesis. For a description of these classes of drugs which are well known in the art, and their mechanisms of action, see Goodman et al., *Goodman and Gilman's THE PHARMACOLOGICAL BASIS OF THERAPEUTICS*, 8th Ed., Macmillan Publishing Co., 1990.

Anti-TNF peptides and/or antibodies of this invention can be advantageously utilized in combination with other monoclonal or murine and chimeric antibodies, fragments and regions, or with lymphokines or hemopoietic growth factors, etc., which serve to increase the number or activity of effector cells which interact with the antibodies.

Anti-TNF peptides and/or antibodies, fragments or derivatives of this invention can also be used in combination with TNF therapy to block undesired side effects of TNF. Recent approaches to cancer therapy have included direct administration of TNF to cancer patients or immunotherapy of cancer patients with lymphokine activated killer (LAK) cells (Rosenberg et al., *New Eng. J. Med.* 313:1485–1492 (1985)) or tumor infiltrating lymphocytes (TIL) (Kurnick et al. (*Clin. Immunol. Immunopath.* 38:367–380 (1986); Kradin et al., *Cancer Immunol. Immunother.* 24:76–85 (1987); Kradin et al., *Transplant. Proc.* 20:336–338 (1988)). Trials are currently underway using modified LAK cells or TIL which have been transfected with the TNF gene to produce large amounts of TNF. Such therapeutic approaches are likely to be associated with a number of undesired side effects caused by the pleiotropic actions of TNF as described herein and known in the related arts. According to the present invention, these side effects can be reduced by concurrent treatment of a subject receiving TNF or cells producing large amounts of TIL with the antibodies, fragments or derivatives of the present invention. Effective doses are as described above. The dose level will require adjustment according to the dose of TNF or TNF-producing cells administered, in order to block side effects without blocking the main anti-tumor effect of TNF. One of ordinary skill in the art will know how to determine such doses without undue experimentation.

Treatment of Arthritis

In rheumatoid arthritis, the main presenting symptoms are pain, stiffness, swelling, and loss of function (Bennett J C. *The etiology of rheumatoid arthritis.* In Textbook of Rheumatology (Kelley W N, Harris E D, Ruddy S, Sledge C B, eds.) WB Saunders, Philadelphia pp 879–886, 1985). The multitude of drugs used in controlling such symptoms seems largely to reflect the fact that none is ideal. Although there have been many years of intense research into the biochemical, genetic, microbiological, and immunological aspects of rheumatoid arthritis, its pathogenesis is not completely understood, and none of the treatments clearly stop progression of joint destruction (Harris E D. *Rheumatoid Arthritis. The clinical spectrum.* In Textbook of Rheumatology (Kelley, et al., eds.) W B Saunders, Philadelphia pp 915–990, 1985).

TNFα is of major importance in the pathogenesis of rheumatoid arthritis. TNFα is present in rheumatoid arthritis joint tissues and synovial fluid at the protein and mRNA level (Buchan G, et al., *Clin. Exp. Immunol* 73: 449–455, 1988), indicating local synthesis. However detecting TNFα in rheumatoid arthritis joints even in quantities sufficient for bioactivation does not necessarily indicate that it is important in the pathogenesis of rheumatoid arthritis, nor that it is a good candidate therapeutic target. In order to address these questions, the effects of anti-TNF antibody and peptides (rabbit or monoclonal) on rheumatoid joint cell cultures, and for comparison, osteoarthritic cell cultures, have been studied. IL-1 production was abolished, showing TNFα as a suitable therapeutic target for the therapy of rheumatoid arthritis, since anti-TNFα blocks both TNF and IL-1, the two cytokines known to be involved in cartilage and bone destruction (Brennan et al., *Lancet* 11:244–247, 1989).

Subsequent studies in rheumatoid arthritis tissues have supported this hypothesis. Anti-TNF Abs abrogated the production of another proinflammatory cytokine, GM-CSF (Haworth et al., *Eur. J. Immunol.* 21:2575–2579, 1991). This observation has been independently confirmed (Alvaro-Gracia et al, 1991). It has also been demonstrated that anti-TNF diminishes cell adhesion and HLA class II expression in rheumatoid arthritis joint cell cultures.

Figure 34:
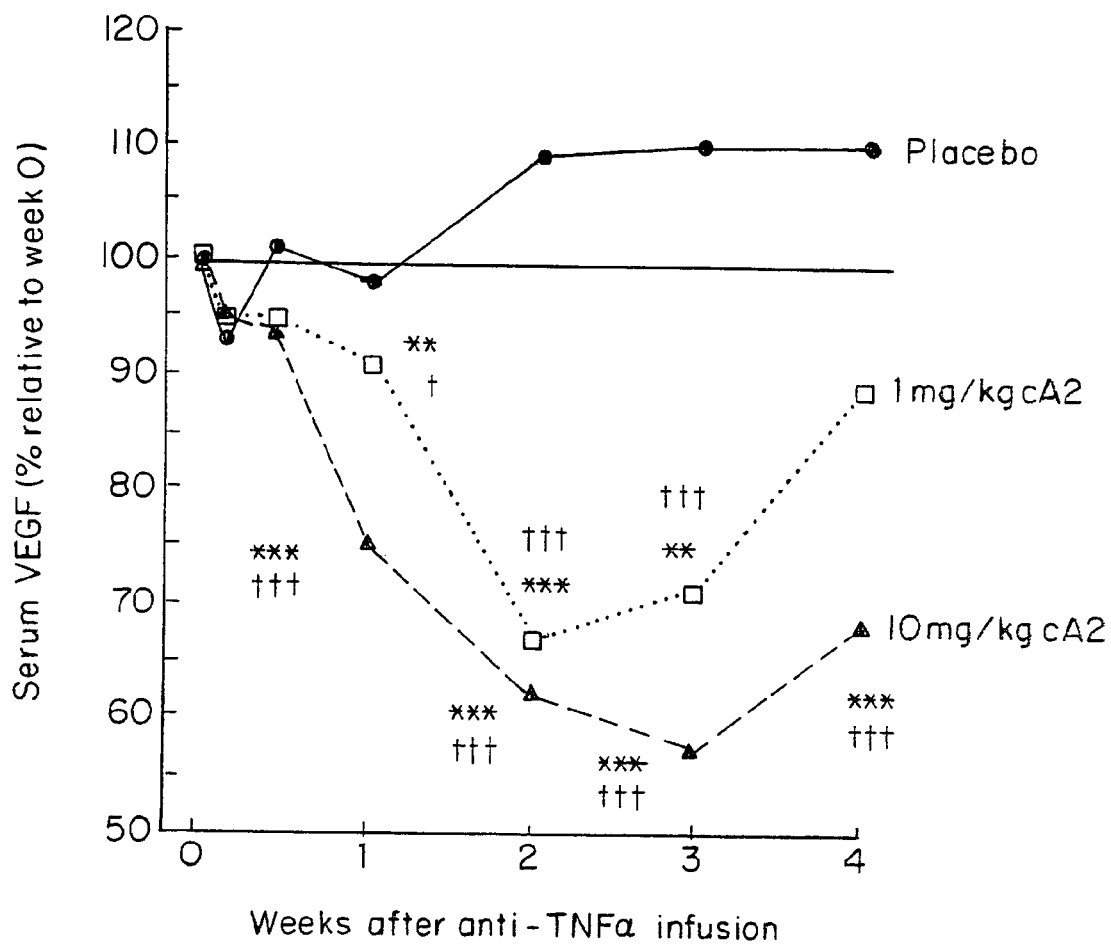
FIG. 34 is a graphic illustration depicting VEGF levels in the serum of rheumatoid arthritis patients treated with placebo (circles), 1 mg/kg cA2 antibody (square) or 10 mg/kg (triangle). The figure shows that the administration of an anti-TNF antibody resulted in decreased levels of VEGF.

The administration of the antibody also established that VEGF/VPF serum levels were significantly decreased (FIG. 34) in rheumatoid arthritis (RA) patients. A prominant feature of rheumatoid arthritis lesions is an infiltrate of inflammatory cells from the blood, together with invading pannus which is associated with prominent new blood formation, thus perpetuating the ingress of nutrients and cells, and the inflammatory reactions which culminate in bone and cartilage destruction. VEGF is a potent inducer to angiogenesis and has been implicated in the formation of blood vessels and activation of microvascular endothelium in RA.

VEGF serum levels are significantly increased in patients with active RA, relative to serum levels in a population of age-matched controls. Furthermore, a time- and dose-dependent decrease in serum VEGF levels in RA patients after infusion with anti-TNFα, cA2, was observed. In patients who received 1 mg/kg cA2 (n=24), the maximal effect (33% decrease, $p<0.001$ versus change in placebo group and versus pre-infusion levels) was detected 2 weeks post-infusion, but subsequently VEGF levels returned to pre-infusion levels. In contrast, patients who received 10 mg/kg cA2 (n=21), the reduction was maintained even 4 weeks post-infusion (32% decrease, $p<0.001$), although serum levels were still higher than in normal individuals. The data indicate that treatment of RA or other VEGF-mediated diseases with TNF antagonists decreases VEGF levels in vivo, thereby leading to reduction in the vascularity of the pannus. Also, since VEGF is a survival factor for newly formed blood vessels and endothelial cell apoptosis, as a consequence of suppression of VEGF secretion, leads to vessel regression, TNF antagonists can exert a beneficial effect by causing regression of existing blood vessels in the arthritic pannus.

Diagnostic Methods

The present invention also provides the above anti-TNF peptides and antibodies, detectably labeled, as described below, for use in diagnostic methods for detecting TNFα in patients known to be or suspected of having a TNFα-mediated condition.

Anti-TNF peptides and/or antibodies of the present invention are useful for immunoassays which detect or quantitate TNF, or anti-TNF antibodies, in a sample. An immunoassay for TNF typically comprises incubating a biological sample in the presence of a detectably labeled high affinity anti-TNF peptide and/or antibody of the present invention capable of selectively binding to TNF, and detecting the labeled peptide or antibody which is bound in a sample. Various clinical assay procedures are well known in the art, e.g., as described in *Immunoassays for the 80's*, A. Voller et al., eds., University Park, 1981.

Thus, an anti-TNF peptide or antibody can be added to nitrocellulose, or another solid support which is capable of immobilizing cells, cell particles or soluble proteins. The support can then be washed with suitable buffers followed by treatment with the detectably labeled TNF-specific peptide or antibody. The solid phase support can then be washed with the buffer a second time to remove unbound peptide or antibody. The amount of bound label on the solid support can then be detected by known method steps.

By "solid phase support" or "carrier" is intended any support capable of binding peptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to TNF or an anti-TNF antibody. Thus, the support configuration can be spherical, as in a bead, or cylindrical, as in the inside surface of a test tube, or the external surface of a rod. Alternatively, the surface can be flat, such as a sheet, culture dish, test strip, etc. Preferred supports include polystyrene beads. Those skilled in the art will know many other suitable carriers for binding antibody, peptide or antigen, or can ascertain the same by routine experimentation.

Well known method steps can determine binding activity of a given lot of anti-TNF peptide and/or antibody. Those skilled in the art can determine operative and optimal assay conditions by routine experimentation.

Detectably labeling a TNF-specific peptide and/or antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the TNF-specific antibodies of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the TNF-specific antibodies, it is possible to detect TNF through the use of a radioimmunoassay (RIA) (see, for example, Work, et al., *Laboratory Techniques and Biochemistry in Molecular Biology*, North Holland Publishing Company, N.Y. (1978)). The radioactive isotope can be detected by such means as the use of a gamma counter or a scintillation counter or by autoradiography. Isotopes which are particularly useful for the purpose of the present invention are: $^3$H, $^{125}$I, $^{131}$I, $^{35}$S, $^{14}$C, and, preferably, $^{125}$I.

It is also possible to label the TNF-specific antibodies with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The TNF-specific antibodies can also be detectably labeled using fluorescence-emitting metals such as $^{125}$Eu, or others of the lanthanide series. These metals can be attached to the TNF-specific antibody using such metal chelating groups as diethylenetriaminepentaacetic acid (DTPA) or ethylenediamine-tetraacetic acid (EDTA).

The TNF-specific antibodies also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the TNF-specific antibody, fragment or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the TNF-specific antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the TNF which is detected by the above assays can be present in a biological sample. Any sample containing TNF can be used. Preferably, the sample is a biological fluid such as, for example, blood, serum, lymph, urine, inflammatory exudate, cerebrospinal fluid, amniotic fluid, a tissue extract or homogenate, and the like. However, the invention is not limited to assays using only these samples, it being possible for one of ordinary skill in the art to determine suitable conditions which allow the use of other samples.

In situ detection can be accomplished by removing a histological specimen from a patient, and providing the combination of labeled antibodies of the present invention to such a specimen. The antibody (or fragment) is preferably provided by applying or by overlaying the labeled antibody (or fragment) to a biological sample. Through the use of such a procedure, it is possible to determine not only the presence of TNF but also the distribution of TNF in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the TNF from the sample by formation of a binary solid phase antibody-TNF complex. After a suitable incubation period, the solid support is washed to remove the residue of the fluid sample, including unreacted TNF, if any, and then contacted with the solution containing a known quantity of labeled antibody (which functions as a "reporter molecule"). After a second incubation period to permit the labeled antibody to complex with the TNF bound to the solid support through the unlabeled antibody, the solid support is washed a second time to remove the unreacted labeled antibody. This type of forward sandwich assay can be a simple "yes/no" assay to determine whether TNF is present or can be made quantitative by comparing the measure of labeled antibody with that obtained for a standard sample containing known quantities of TNF. Such "two-site" or "sandwich" assays are described by Wide (*Radioimmune Assay Method,* Kirkham, ed., Livingstone, Edinburgh, 1970, pp. 199–206).

Other type of "sandwich" assays, which can also be useful with TNF, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes can be used to construct a sensitive three-site immunoradiometric assay.

TNF Removal from Solutions

The murine and chimeric antibodies, fragments and regions, fragments, or derivatives of this invention, attached to a solid support, can be used to remove TNF from fluids or tissue or cell extracts. In a preferred embodiment, they are used to remove TNF from blood or blood plasma products. In another preferred embodiment, the murine and chimeric antibodies, fragments and regions are advantageously used in extracorporeal immunoadsorbent devices, which are known in the art (see, for example, *Seminars in Hematology,* 26 (2 *Suppl.* 1) (1989)). Patient blood or other body fluid is exposed to the attached antibody, resulting in partial or complete removal of circulating TNF (free or in immune complexes), following which the fluid is returned to the body. This immunoadsorption can be implemented in a continuous flow arrangement, with or without interposing a cell centrifugation step. See, for example, Terman, et al., *J. Immunol.* 117:1971–1975 (1976).

Having now generally described the invention, the same will be further understood by reference to certain specific examples which are included herein for purposes of illustration only and are not intended to be limiting unless otherwise specified.

EXAMPLE I

Production a Mouse Anti-Human TNF mAb

To facilitate clinical study of TNF mAb, a high-affinity potent inhibiting and/or neutralizing mouse anti-human TNF IgG1 mAb designated A2 was produced.

Female BALB/c mice, 10 weeks old, were obtained from the Jackson Laboratory (Bar Harbor, Me.). Forty µg of purified E. coli-derived recombinant human TNF (rhTNF) emulsified with an equal volume of complete Freund's adjuvant (obtained from Difco Laboratories) in 0.4 ml was injected subcutaneously and intraperitoneally (i.p.) into a mouse. One week later, an injection of 5 µg of rhTNF in incomplete Freund's adjuvant was given i.p. followed by four consecutive i.p. injections of 10 µg of TNF without adjuvant. Eight weeks after the last injection, the mouse was boosted i.p. with 10 µg of TNF.

Four days later, the mouse was sacrificed, the spleen was obtained and a spleen cell suspension was prepared. Spleen cells were fused with cells of the nonsecreting hybridoma, Sp2/0 (ATCC CRL1581), at a 4:1 ratio of spleen cells to Sp2/0 cells, in the presence of 0.3 ml of 30% polyethylene glycol, PEG 1450. After incubation at 37° C. for 6 hours, the fused cells were distributed in 0.2 ml aliquots into 96-well plates at concentrations of $2 \times 10^4$ SP2/0 cells per well. Feeder cells, in the form of $5 \times 10^4$ normal BALB/c spleen cells, were added to each well.

The growth medium used consisted of RPM1–1640 medium, 10% heat-inactivated fetal bovine serum (FBS) (HYCLONE), 0.1 mM minimum essential medium (MEM) nonessential amino acids, 1 mM sodium pyruvate, 2 mM L-glutamine, 100 U/ml penicillin, 100 µg/ml streptomycin (GIBCO Laboratories) and, for selection, hypoxanthine-aminopterin-thymidine (HAT) (Boehringer Mannheim). A solid-phase radioimmunoassay (RIA) was employed for screening supernatants for the presence of mAbs specific for rhTNFα. This assay is described in Example II, below. The background binding in this assay was about 500 cpm. A supernatant was considered positive if it yielded binding of 2000 cpm or higher.

Of 322 supernatants screened, 25 were positive by RIA. Of these 25, the one with the highest binding (4800 cpm) was designated A2. Positive wells were subcloned at limiting dilution on mouse feeder cells. Upon further analysis of the supernatants in neutralization assays, A2 was found to be the only positive clone showing potent inhibiting and/or neutralizing activity. Thus, the hybridoma line A2 was selected. This line was maintained in RPM1-1640 medium with 10% FBS (GIBCO), 0.1 mM nonessential amino acids, 1 mM sodium pyruvate, 2 mM L-glutamine, 100 U/ml penicillin and 100 µg/ml streptomycin.

Alternatively, anti-TNF antibodies which inhibit TNF biological activity can be screened by binding to peptide including at least 5 amino acids of residues 87–108 or both residues 59–80 and 87–108 of TNF (of SEQ ID NO: 1) or combinations of peptides contained therein, which are used in place of the rTNF protein, as described above.

EXAMPLE II

Characterization of an Anti-TNF Antibody of the Present Invention

Radioimmunoassays

E. coli-derived rhTNF was diluted to 1 µg/ml in BCB buffer, pH 9.6, and 0.1 ml of the solution was added to each assay well. After incubation at 4° C. overnight, the wells were washed briefly with BCB, then sealed with 1% bovine incubated with 40 pg/ml of natural (GENZYME, Boston, Mass.) or recombinant (SUNTORY, Osaka, Japan) human TNFα with varying concentrations of mAb A2 in the presence of 20 µg/ml cycloheximide at 39° C. overnight. Controls included medium alone or medium+TNF in each well. Cell death was measured by staining with naphthol blue-black, and the results read spectrophotometrically at 630 nm. Absorbance at this wave length correlates with the number of live cells present.

Figure 3:
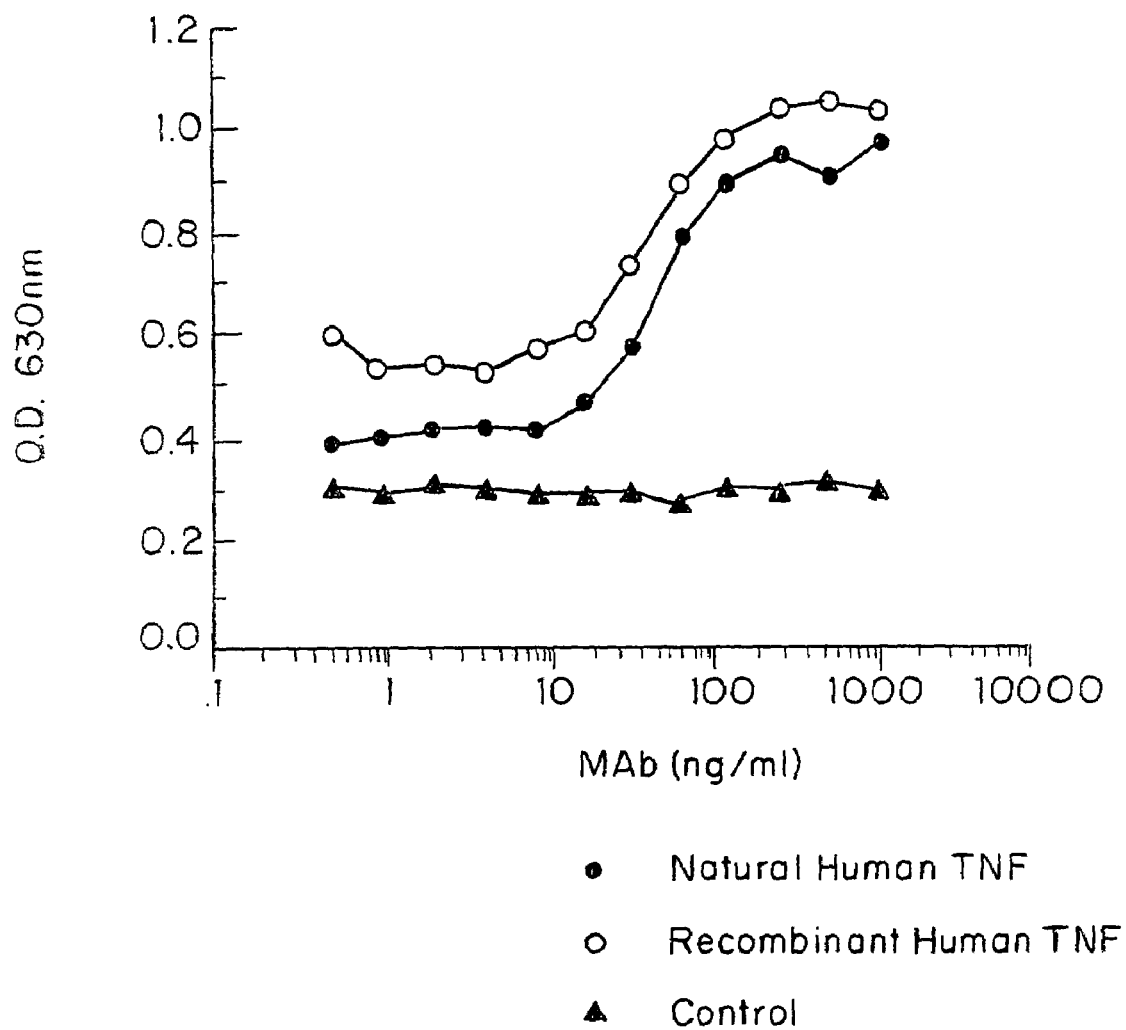
FIG. 3 is a graph showing neutralization of in vitro TNF cytotoxicity by murine A2. Control: murine IgG1 anti-lipid A mAb (8A1) with natural human TNF. Average absorbance values for controls were as follows: no TNF added=1.08; natural TNF, no antibody=0.290; and recombinant TNF, no antibody=0.500.

It was found that A2 inhibited or neutralized the cytotoxic effect of both natural and rhTNF in a dose-dependent manner (FIG. 3).

Figure 4:
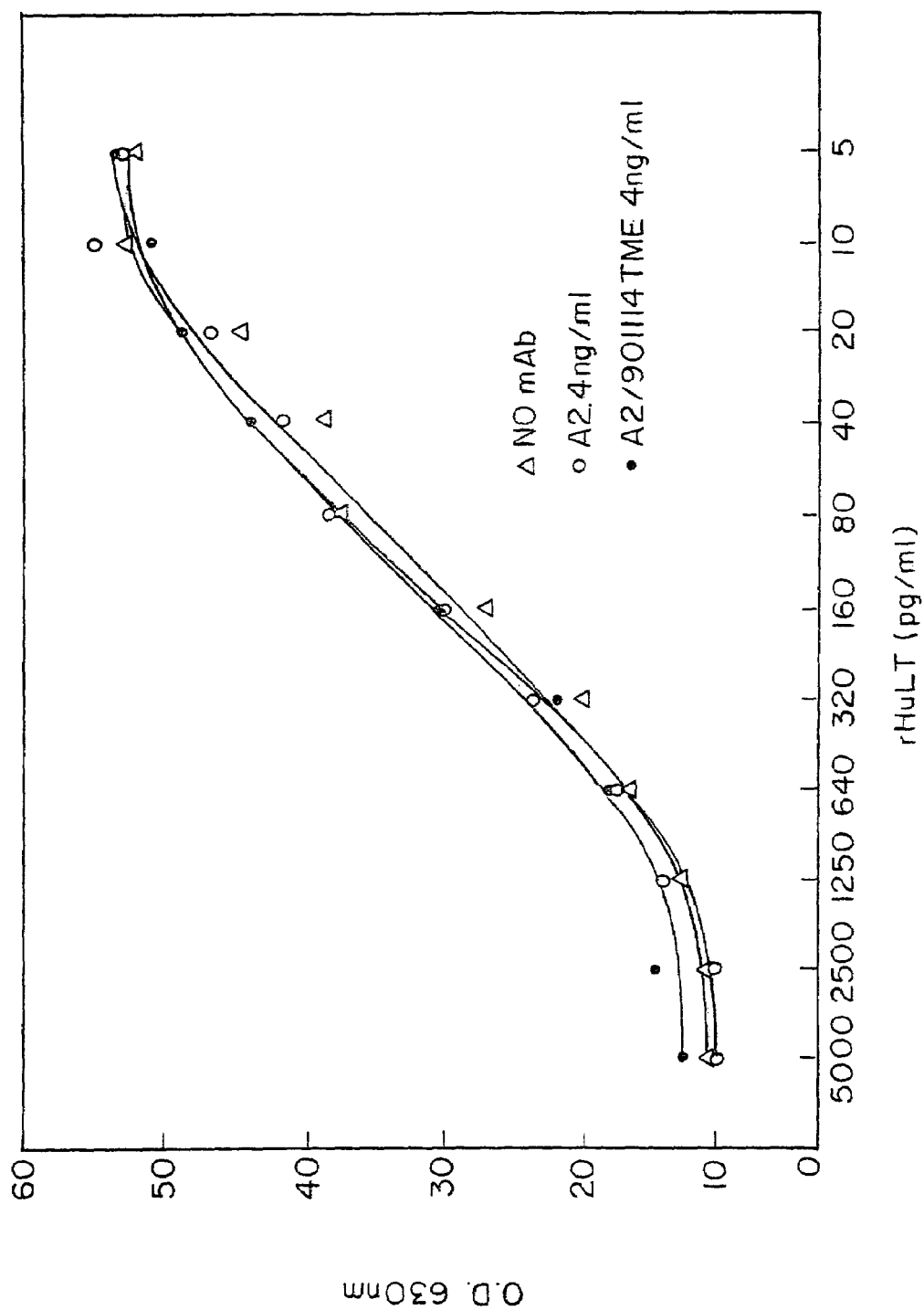
FIG. 4 is a graph showing that mAb A2 and chimeric A2 do not inhibit or neutralize human lymphotoxin (TNFβ).
Figure 5:
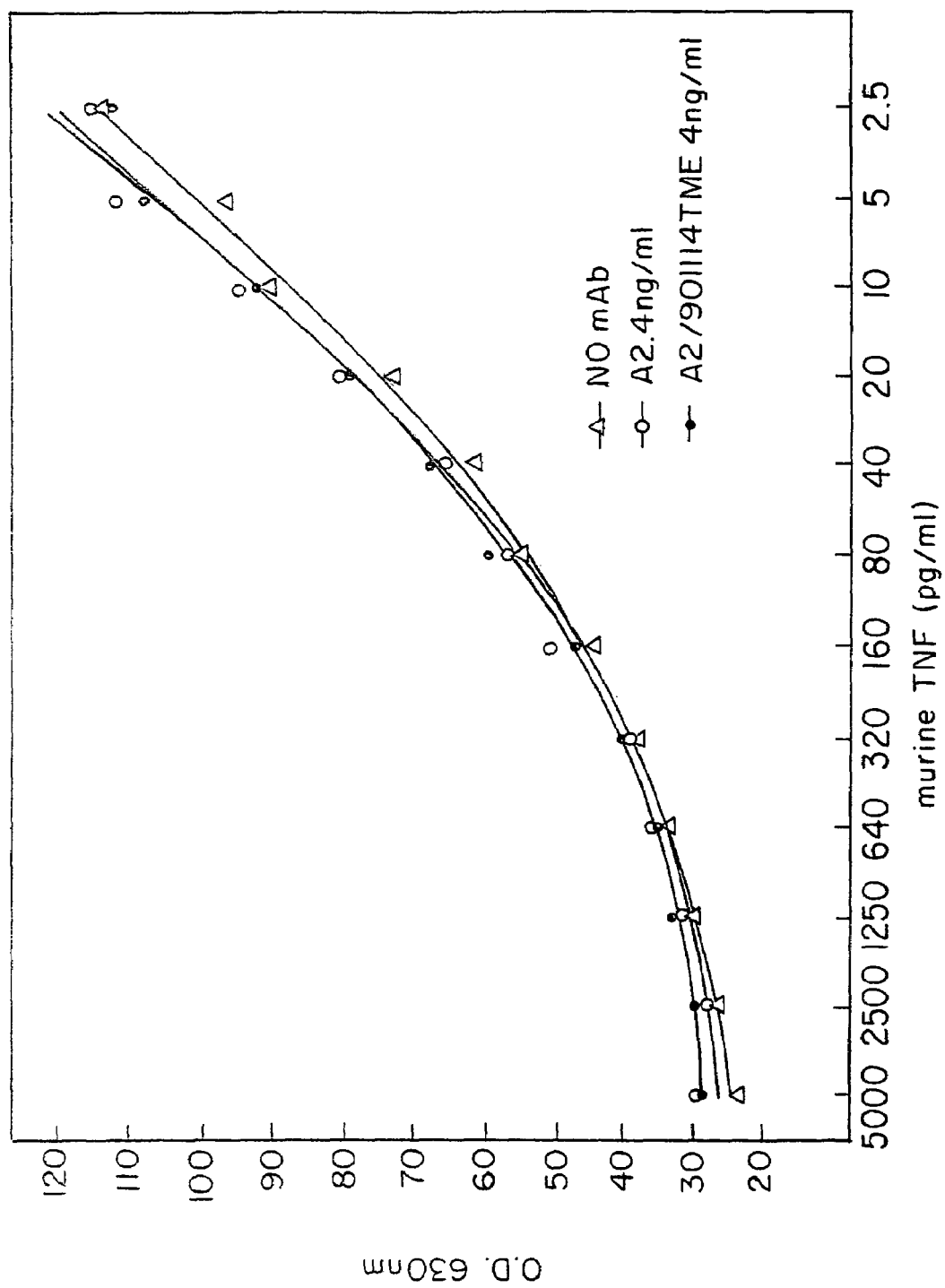
FIG. 5 is a graph showing that mAbs murine A2 and chimeric CA2 do not inhibit or neutralize murine TNFα.

In another experiment, the specificity of this inhibiting and/or neutralizing activity was tested. A673/6 cells were seeded at $3 \times 10^4$ cells/well 20 hr before the TNF bioassay. Two-fold serial dilutions of rhTNF, E. coli-derived recombinant human lymphotoxin (TNFβ), and E. coli-derived recombinant murine TNF were prepared. The A2 hybridoma supernatant was added to an equal volume of the diluted TNF preparations, and the mixtures were incubated at room temperature for 30 min. Aliquots of 0.1 ml were transferred to the wells containing A673/6 cells, 20 µg/ml of cycloheximide was added, and the cells were incubated at 39° C. overnight. The cells were then fixed and stained for evaluation of cytotoxicity. The results indicate that mAb A2 specifically inhibited or neutralized the cytotoxicity of rhTNFα, whereas it had no effect on human lymphotoxin (TNFβ) (FIG. 4) or murine TNF (FIG. 5).

Experiments were next performed to analyze the cross-reactivity of mAb A2 with TNF derived from non-human primates. Monocytes isolated from B514 (baboon), J91 (cynomolgus) and RH383 (rhesus) blood by Ficoll gradient centrifugation and adherence, were incubated at $1 \times 10^5$ cells/well in RPMi 1640 medium with 5% FBS and 2 µg/ml of E. coli LPS for 3 or 16 hr at 37° C. to induce TNF production. Supernatants from duplicate wells were pooled and stored at 4° C. for less than 20 hr until the TNF bioassay was performed, as described above, using A673/6 cells. Two-fold dilutions of the culture supernatants were mixed with either medium or purified mAb A2 at a final concentration of 1 µg/ml, incubated at room temperature for 30 min. and aliquots transferred to the indicator cells. The results showed that mAb A2 failed to significantly inhibit or neutralize the cytotoxic activity of TNF produced by baboon, cynomolgus and rhesus monkey monocytes.

Figure 6:
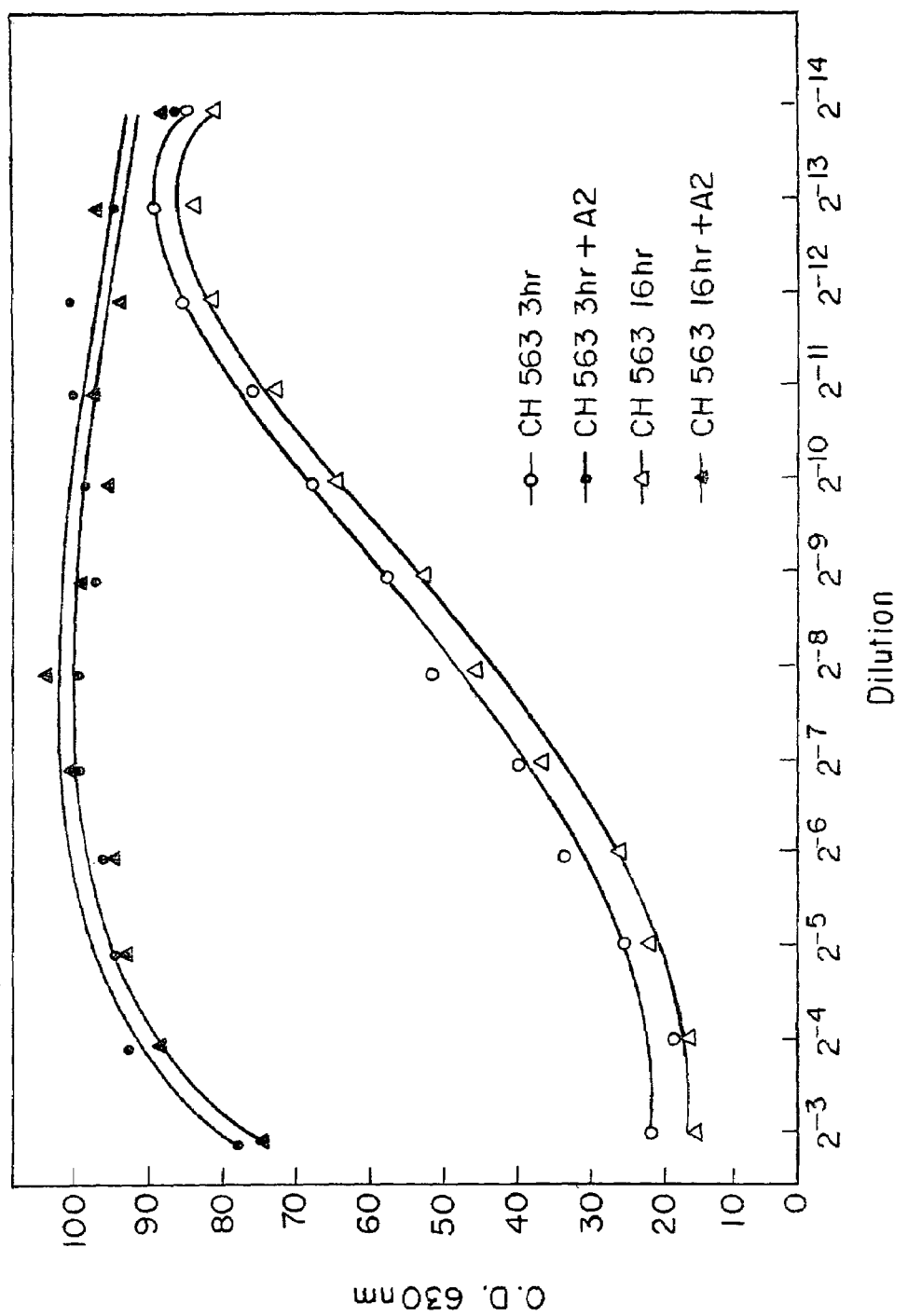
FIG. 6 and FIG. 7 are graphs showing that mAb A2 inhibits or neutralizes TNF produced by chimpanzee monocytes and rhTNFα.
Figure 7:
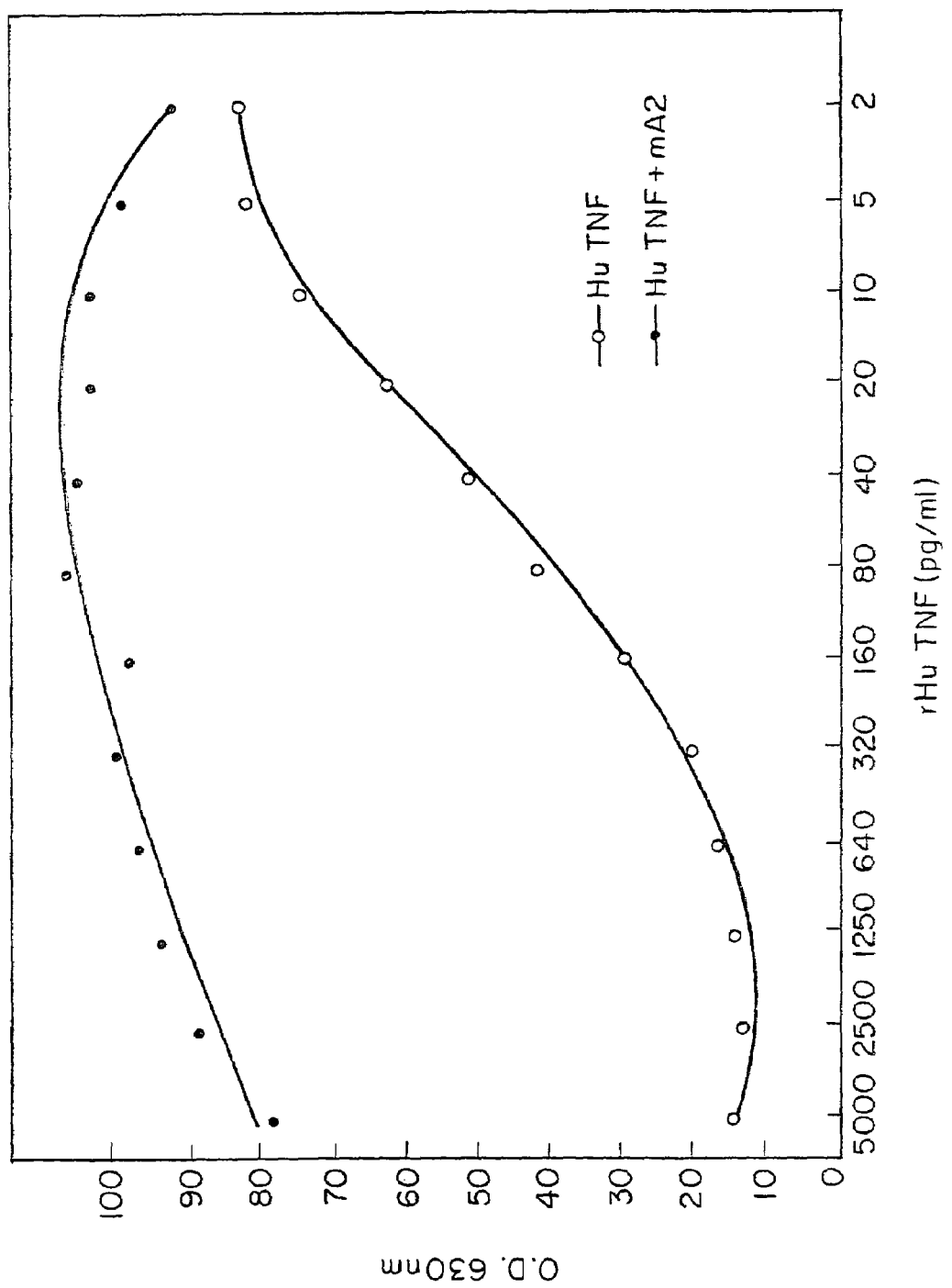

A further experiment was conducted with chimpanzee TNF. Monocytes isolated from CH563 (chimpanzee) blood were incubated as described above to generate TNF-containing supernatants. The ability of 10 µg/ml of mAb A2 to inhibit or neutralize the bioactivity of these supernatants was assayed as above. Human TNF was used as a positive control. Results, shown in FIG. 6, indicate that mAb A2 had potent inhibiting and/or neutralizing activity for chimpanzee TNF, similar to that for human TNF (FIG. 7).

The inhibiting and/or neutralizing activity of mAb A2 was compared with three other murine mAbs specific for human TNF, termed TNF-1, TNF-2 and TNF-3, and a control mAb. Two-fold serial dilutions of purified mAbs were mixed with rhTNF (40 pg/ml), incubated at room temperature for 30 min, and aliquots tested for TNF bioactivity as above. It was found that mAbs TNF-1, TNF-2 and TNF-3 each had a similar moderate degree of inhibiting and/or neutralizing activity. In contrast, mAb A2 had much more potent inhibiting and/or neutralizing activity.

EXAMPLE III

General Strategy for Cloning Antibody V and C Genes

The strategy for cloning the V regions for the H and L chain genes from the hybridoma A2, which secretes the anti-TNF antibody described above, was based upon the linkage in the genome between the V region and the corresponding J (joining) region for functionally rearranged (and expressed) Ig genes. J region DNA probes can be used to screen genomic libraries to isolate DNA linked to the J regions. Although DNA in the germline configuration (i.e., unrearranged) would also hybridize to J probes, this DNA would not be linked to a Ig V region sequence and can be identified by restriction enzyme analysis of the isolated clones.

The cloning utilized herein was to isolate V regions from rearranged H and L chain genes using $J_H$ and $J_K$ probes. These clones were tested to see if their sequences were expressed in the A2 hybridoma by Northern analysis. Those clones that contained expressed sequence were cloned into expression vectors containing human C regions and transfected into mouse myeloma cells to determine if an antibody was produced. The antibody from producing cells was then tested for binding specificity and functionally compared to the A2 murine antibody.

EXAMPLE IV

Construction of a L Chain Genomic Library

To isolate the L chain V region gene from the A2 hybridoma, a size-selected genomic library was constructed using the phage lambda vector charon 27. High molecular weight DNA was isolated from A2 hybridoma cells and digested to completion with restriction endonuclease HindIII. The DNA was then fractionated on a 0.8% agarose gel and the DNA fragments of three different size ranges of approximately 3 kb, 4 kb and 6 kb were isolated from the gel by electroelution. The size ranges for library construction were chosen based upon the size of HindIII fragments that hybridized on a southern blot with the $J_K$ probe. After phenol/chloroform extraction and ethanol precipitation, the DNA fragments from each size class were ligated with lambda charon 27 arms and packaged into phage particles in vitro using Gigapack Gold from Stratagene (LaJolla, Calif.).

These libraries were screened directly at a density of approximately 20,000 plaques per 150 mm petri dish using a $^{32}$P-labeled $J_K$ probe. The mouse L chain $J_K$ probe was a 2.7 kb HindIII fragment containing all five $J_K$ segments. The probe was labeled with $^{32}$P by random priming using a kit obtained from Boehringer Mannheim. Free nucleotides were removed by centrifugation through a Sephadex G-SO column. The specific activities of the probe was approximately $10^9$ cpm/μg.

Plaque hybridizations were carried out in 5×SSC, 50% formamide, 2× Denhardt's reagent, and 200 μg/ml denatured salmon sperm DNA at 42° C. for 18–20 hours. Final washes were in 0.5×SSC, 0.1% SDS at 65° C. Positive clones were identified after autoradiography.

EXAMPLE V

Construction of H Chain Genomic Library

To isolate the V region gene for the A2 H chain, a genomic library was constructed in the lambda gt10 vector system. High molecular weight DNA was digested to completion with restriction endonuclease EcoRI and fragments of approximately 7.5 kb were isolated after agarose gel electrophoresis. These fragments were ligated with lambda gt10 arms and packaged into phage particles in vitro using Gigapack Gold.

This library was screened at a density of 20,000 plaques per 150 mm plate using a $J_H$ probe. The $J_H$ probe was a 2 kb BamHI/EcoRI fragment containing both J3 and J4 segments. The probe was labeled as in Example III and had a similar specific radioactivity. Hybridization and wash conditions were identical to those used in Example III.

EXAMPLE VI

Cloning of the TNF-Specific V Gene Regions

Several positive clones were isolated from the H and L chain libraries after screening approximately $10^6$ plaques from each library using the $J_H$ and $J_K$ probes, respectively. Following plaque purification, bacteriophage DNA was isolated for each positive clone, digested with either EcoRI (H chain clones) or HindIII (L chain clones) and fractionated on 1% agarose gels. The DNA was transferred to nitrocellulose and the blots were hybridized with the $J_H$ or the $J_K$ probe.

Several H chain clones were obtained that contained 7.5 k/D EcoRI DNA encoding fragments of MAbs to the $J_H$ probe. For the light chain libraries, several clones from each of the three size-selected libraries were isolated that contained HindIII fragments that hybridize to the $J_K$ probe. For the L chain, several independently derived HindIII fragments of 2.9 kb from the 2 kb library hybridized with a 1250 bp mRNA from A2, but not with SP2/0 mRNA (see Example VII). In addition, several HindIII fragments derived from the 4 kb library hybridized both to the A2 mRNA and the fusion partner mRNA. A 5.7 kb HindIII fragment from the 6 kb library did not hybridize to either RNA.

The observed lengths of hybridizing A2 mRNA were the correct sizes for H and L chain mRNA, respectively. Because the RNA expression was restricted to the A2 hybridoma, it was assumed that the 7.5 kb H chain fragments and the 2.9 kb L chain fragments contained the correct V region sequences from A2. One example of each type was chosen for further study. The important functional test is the demonstration that these V regions sequences, when combined with appropriate C region sequences, are capable of directing the synthesis of an antibody with a specificity and affinity similar to that of the murine A2 antibody.

The 7.5 kb H chain fragment and the 2.9 kb L chain fragment were subcloned into plasmid vectors that allow expression of the chimeric mouse/human proteins in murine myeloma cells (see Examples VIII and IX). These plasmids were co-transfected into SP2/0 cells to ascertain if intact antibody molecules were secreted, and if so, if they were of the correct specificity and affinity. Control transfections were also performed pairing the putative anti-TNF H chain with an irrelevant, but expressed, L chain; the putative anti-TNF L chain was also paired with an irrelevant, but expressed, H chain. The results indicated that the 7.5 kb H chain fragment could be expressed, whereas the 2.9 kb L chain fragment could not. This was confirmed by DNA sequence analysis that suggested portions of the coding region were not in the proper amino acid reading frame when compared to other known L chain amino acid sequences.

Because the 2.9 kb HindIII fragment appeared not to contain a functional V gene, the 4.0 kb and 5.7 kb HindIII fragments isolated from L chain libraries were cloned into expression vectors and tested for expression of chimeric antibody after co-transfection with the 7.5 kb H chain. The 5.7 kb HindIII fragment was incapable of supporting antibody expression, whereas the 4.0 kb HindIII fragment did support antibody expression. The antibody resulting from the co-transfection of the 7.5 kb putative H chain V region and the 4.0 kb L chain V region was purified, tested in solid phase TNF binding assay, and found to be inactive. It was concluded that the V region contained on the 4.0 kb HindIII fragment was not the correct anti-TNF V region, but was contributed to the hybridoma by the fusion partner. This was subsequently confirmed by sequence analysis of cDNA derived from the A2 hybridoma and from the fusion partner.

Other independently derived L chain clones containing 2.9 kb HindIII fragments that hybridized with A2 mRNA were characterized in more detail. Although the restriction maps were similar, the clones fell into two classes with respect to the presence or absence of an AccI enzyme site. The original (non-functional) 2.9 kb fragment (designated clone 8.3) was missing an AccI site present in some other clones (represented by clone 4.3). The DNA sequence of clone 4.3 was extremely similar to clone 8.3, but contained a single amino acid reading frame with close homology to known L chains, unlike clone 8.3. The 2.9 kb HindIII fragment from clone 4.3 was subcloned into the L chain expression vector and co-transfected with the putative anti-TNF H chain into SP2/0 cells. An antibody was synthesized, purified and tested in the solid phase TNF binding assay. This antibody bound to TNF, and therefore, the clone 4.3 L chain V region was assumed to be the correct one.

The A2 murine hybridoma has been shown to contain at least four rearranged L chain V region genes. At least two of these are expressed as proteins: clone 4.3 (the correct anti-TNF L chain gene) and the gene contained in the 4.0 kb HindIII fragment (contributed by the fusion partner). The expression of two L chains implies that the resulting antibody secreted from the murine hybridoma is actually a mixture of antibodies, some using the correct L chain, some using the incorrect L chain, and some using one of each. The presence of two different L chains in the murine A2 antibody has been confirmed by SDS gel and N-terminal protein sequence analysis of the purified antibody. Because construction of the chimeric A2 antibody involves cloning the individual H and L chain genes and expressing them in a non-producing cell line, the resulting antibody will have only the correct L chain and therefore should be a more potent antibody (see Examples X, XI and XII).

EXAMPLE VII

Northern Analysis of Cloned DNA

Cloned DNA corresponding to the authentic H and L chain V regions from the A2 hybridoma would be expected to hybridize to A2 mRNA. Non-functional DNA rearrangements at either the H or L chain genetic loci should not be expressed.

Ten µg total cellular RNA was subjected to electrophoresis on 1% agarose/formaldehyde gels (Sambrook et al., infra) and transferred to nitrocellulose. Blots were hybridized with random primed DNA probes in 50% formamide, 2× Denhardt's solution, 5×SSC, and 200 µg/ml denatured salmon sperm DNA at 42° C. for 10 hours. Final wash conditions were 0.5×SSC, 0.1% SDS at 65° C.

The subcloned DNA fragments were labeled with $^{32}$p by random priming and hybridized to Northern blots containing total RNA derived from A2 cells or from cells of SP2/0, the fusion partner parent of A2. The 7.5 kb EcoRI H chain fragment hybridized with a 2 kb mRNA from A2, but not with SP2/0 mRNA. Similarly, the 2.9 kb L chain HindIII fragment (clone 4.3) hybridized with a 1250 bp mRNA from A2, but not with SP2/0 mRNA. The observed lengths of A2 mRNA hybridizing were the correct sizes for H and L chain mRNA, respectively, confirming that the V region sequences on these DNA fragments are expressed in A2 hybridoma cells.

EXAMPLE VIII

Construction of Expression Vectors

Figure 8A:
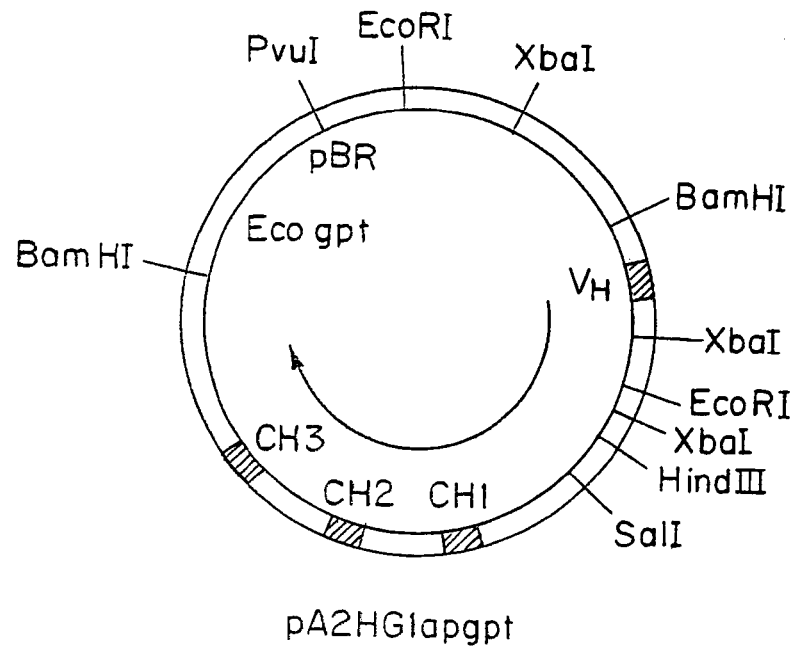
FIGS. 8A and 8B provide schematic diagrams of the plasmids used for expression of the chimeric H (pA2HG1apgpt) and L (pA2HuKapgpt) chains of the chimeric A2 antibody.
Figure 8B:
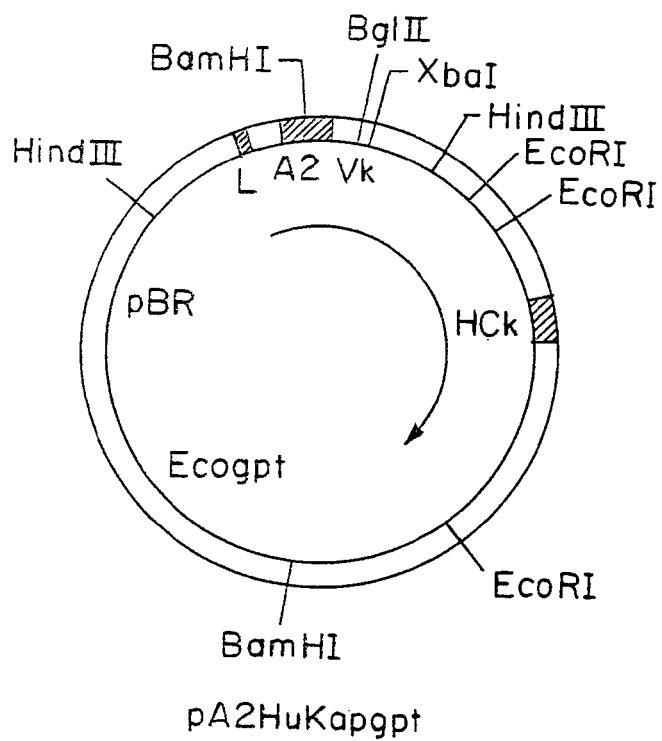

The putative L (clone 4.3) and H chain V genes described above were joined to human kappa and gamma1 constant region genes in expression vectors. The 7.5 kb EcoRI fragment corresponding to the putative $V_H$ region gene from A2 was cloned into an expression vector containing the human $C_{gamma1}$ gene and the Ecogpt gene to yield the plasmid designated pA2HG1apgpt (see FIG. 8).

The 2.9 kb putative VL fragment from clone 4.3 was cloned into a vector containing the human kappa $C_k$ gene and the Ecogpt gene to allow selection in mammalian cells. The resulting plasmid was designated pA2HuKapgpt (See FIG. 8).

EXAMPLE IX

Expression of Chimeric Antibody Genes

To express the chimeric H and L chain genes, the expression plasmids were transfected into cells of the non-producing mouse myeloma cell line, SP2/0. Plasmid DNA to be transfected was purified by centrifuging to equilibrium in ethidium bromide/cesium chloride gradients twice. Plasmid DNA (10–50 µg) was added to $10^7$ SP2/0 cells in medium containing Hank's salts, and the mixture was placed in a BIORAD electroporation apparatus. Electroporation was performed at 20 volts, following which the cells were plated in 96 well microtiter plates.

Mycophenolic acid selection was applied after 24 hours and drug resistant colonies were identified after 1–2 weeks. Resistant colonies were expanded to stable cell lines and tissue culture supernatant from these cell lines was tested for antibody using an ELISA assay with goat anti-human IgG Fc antibody and goat anti-human H+L conjugated with alkaline phosphatase (obtained from Jackson Laboratories).

The chimeric A2 antibody was purified from tissue culture supernatant by Protein A-Sepharose chromatography. The supernatant was adjusted to 0.1M Tris, 0.002M EDTA, pH 8.0 and loaded on a Protein A-Sepharose column equilibrated in the same buffer. The IgG was eluted with 0.1M citrate, pH 3.5, inhibited or neutralized with IM Tris, and dialyzed into phosphate buffered saline (PBS).

The purified chimeric antibody was evaluated for its binding and inhibiting and/or neutralizing activity.

EXAMPLE X

Specificity of an Anti-TNF Chimeric Antibody

Figure 9A:
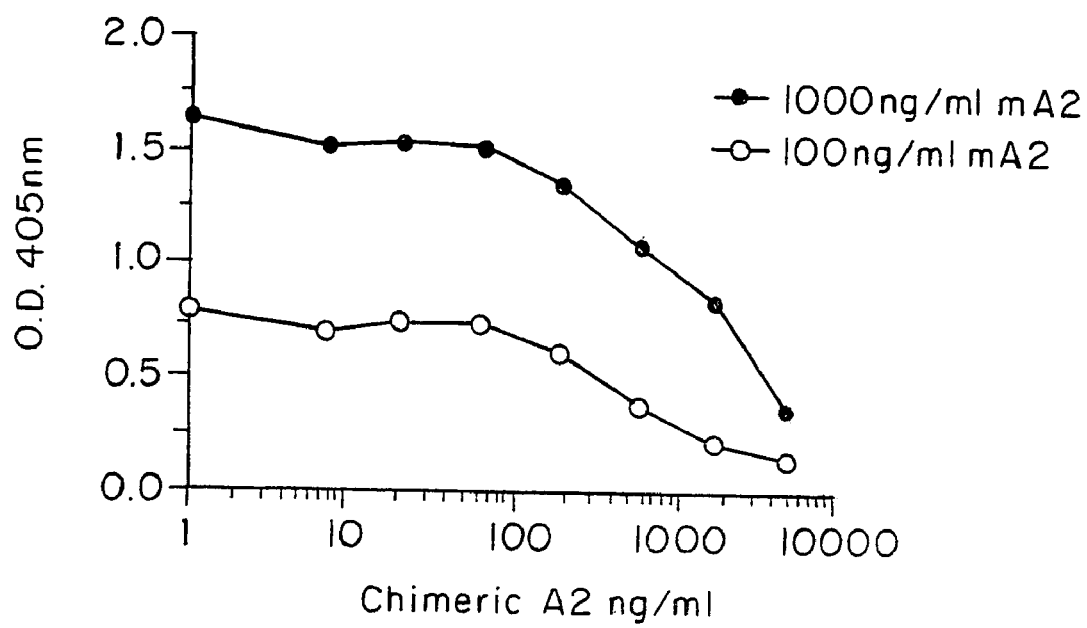
FIGS. 9A and 9B are graphs showing results of a cross-blocking epitope ELISA with murine A2 (mA2) and chimeric (cA2) antibody competitors.
Figure 9B:
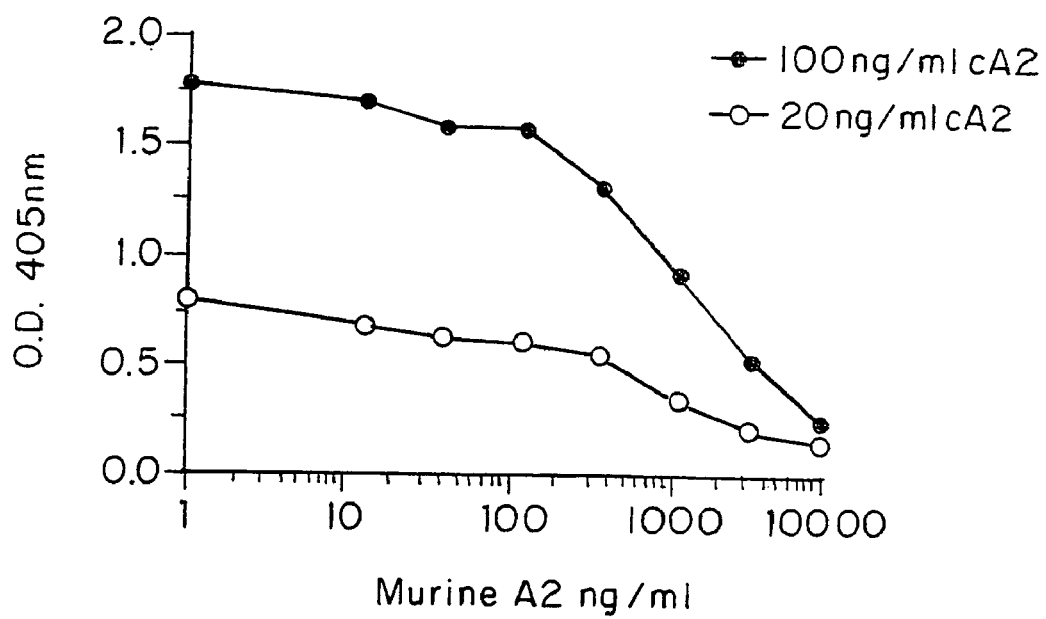

Since the antigen binding domain of cA2 was derived from murine A2, these mAbs would be expected to compete for the same binding site on TNF. Fixed concentrations of chimeric A2 and murine mAb A2 were incubated with increasing concentrations of murine and chimeric A2 competitor, respectively, in a 96-well microtiter plate coated with rhTNF (Dainippon, Osaka, Japan). Alkaline-phosphatase conjugated anti-human immunoglobulin and anti-mouse immunoglobulin second antibodies were used to detect the level of binding of chimeric and murine A2, respectively. Cross-competition for TNF antigen was observed in this solid-phase ELISA format (FIGS. 9A and 9B). This finding is consistent with the expected identical epitope specificity of cA2 and murine A2.

Figure 10A:
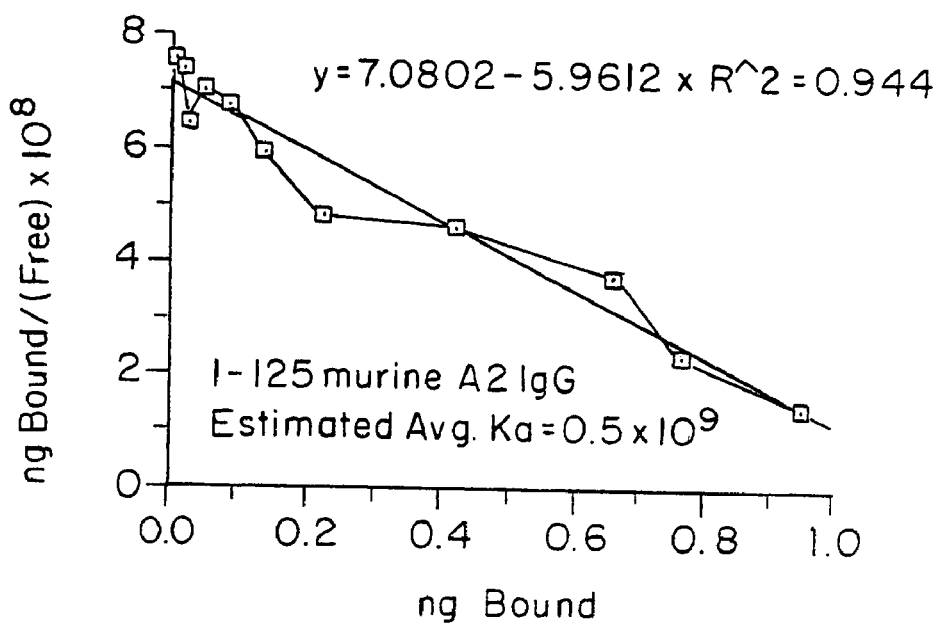
FIGS. 10A and 10B are graphs of a Scatchard analysis of $^{125}$I-labelled mAb A2 (mA2) and chimeric A2 (cA2) binding to recombinant human TNFα immobilized on a microtiter plate. Each Ka value was calculated from the average of two independent determinations.
Figure 10B:
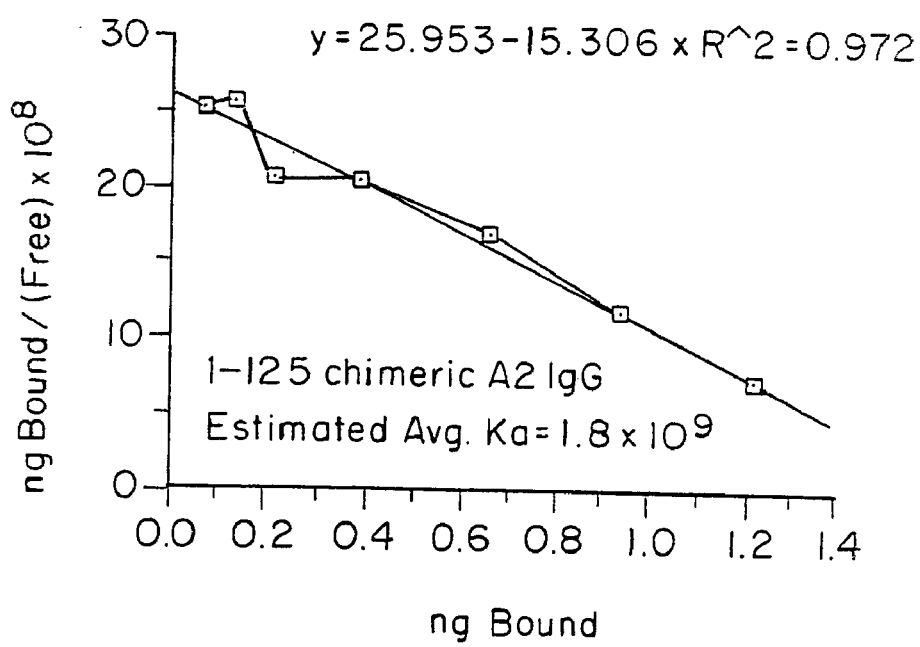

The affinity constant for binding of mouse mAb A2 and cA2 to rhTNFα was determined by Scatchard analysis (see, for example, Scatchard, *Ann. N. Y. Acad. Sci.* 51:660 (1949)). The results are shown in FIG. 10. This analysis involved measuring the direct binding of $^{125}$I labelled cA2 to immobilized rhTNFα in a 96-well plate. The antibodies were each labelled to a specific activity of about 9.7 μCi/μg by the iodogen method. An affinity constant (Ka) of $0.5 \times 10^9$ liters/mole was calculated for the mouse mAb A2. Unexpectedly, the chimeric A2 antibody had a higher affinity, with a Ka of $1.8 \times 10^9$ liters/mole. Thus, the chimeric anti-TNFα antibody of the present invention was shown to exhibit a significantly higher affinity of binding to human TNFα than did the parental murine A2 mAb. This finding was surprising, since murine and chimeric antibodies, fragments and regions would be expected to have affinities that are equal to or less than that of the parent mAb.

Such high affinity anti-TNF antibodies, having affinities of binding to TNFα of at least $1 \times 10^8$ M$^{-1}$, more preferably at least $1 \times 10^9$ M$^{-1}$ (expressed as Ka) are preferred for immunoassays which detect very low levels of TNF in biological fluids. In addition, anti-TNF antibodies having such high affinities are preferred for therapy of TNF-α-mediated conditions or pathology states.

The specificity of cA2 for TNF was confirmed by testing for cross-neutralization of human lymphotoxin (TNF-β). Lymphotoxin shares some sequence homology and certain biological activities, for example, tumor cell cytotoxicity, with TNF (Pennica, et al., *Nature* 312:724–729 (1984)). Cultured human A673 cells were incubated with increasing concentrations of human lymphotoxin (GENENTECH, San Francisco, Calif.) with or without 4 μg/ml chimeric A2 in the presence of 20 μg/ml cycloheximide at 39 C overnight. Cell death was measured by vital staining with naphthol blue-black, as above. The results indicated that cA2 was ineffective at inhibiting and/or neutralizing human lymphotoxin, confirming the TNFα-specificity of the chimeric antibody.

The ability of A2 or cA2 to react with TNF from different animal species was also evaluated. As mentioned earlier, there are multiple epitopes on human TNF to which inhibiting and/or neutralizing mAbs will bind (Moller, et al., infra). Human TNF has bioactivity in a wide range of host animal species. However, certain inhibiting and/or neutralizing epitopes on human TNF are conserved amongst different animal species and others appear to be restricted to humans and chimpanzees.

Neutralization experiments utilized endotoxin-activated cell supernatants from freshly isolated human, chimpanzee, rhesus and cynomolgus monkey, baboon, pig, dog, rabbit, or rat monocytes as the TNF source. As discussed above, murine mAb A2 inhibited or neutralized activity of only human and chimpanzee TNF, and had no effect on TNF derived from other primates and lower animals. A2 also did not inhibit or neutralize the cytotoxic effect of recombinant mouse TNF.

Thus, the epitope recognized by A2 is one shared by human and chimpanzee TNFα. Chimeric A2 was also tested in this manner for cross-reactivity with monocyte-derived TNF from rat, rabbit, dog and pig, as well as with purified recombinant mouse TNFα, and natural and recombinant human TNFα. Chimeric A2 only inhibited or neutralized natural and recombinant human TNFα. Therefore, cA2 appears to share species specificity with murine A2.

EXAMPLE XI

In Vitro Activity and Neutralization Efficacy of a Chimeric Anti-TNF Antibody Both the murine and chimeric anti-TNFα antibodies, A2 and cA2 were determined to have potent TNF-inhibiting and/or neutralizing activity. In the TNF cytotoxicity assay described above, murine A2, at a concentration of about 125 ng/ml completely inhibited or neutralized the biological activity of a 40 pg/ml challenge of rhTNFα. Two separate determinations of inhibiting and/or neutralizing potency, expressed as the 50% Inhibitory Dose (ID50) were determined to be 15.9±1.01 and 17.9±1.6 ng/ml (Mean+Std error). Thus the mAb A2 has an ID50 of about 17 ng/ml.

In this same experimental system, three other murine anti-TNFα antibodies (termed TNF-1, TNF-2 and TNF-3) of comparable binding affinity to TNF were found to have ID50 values of 1–2 orders of magnitude greater, and thus were significantly less potent in neutralization than A2.

Figure 11:
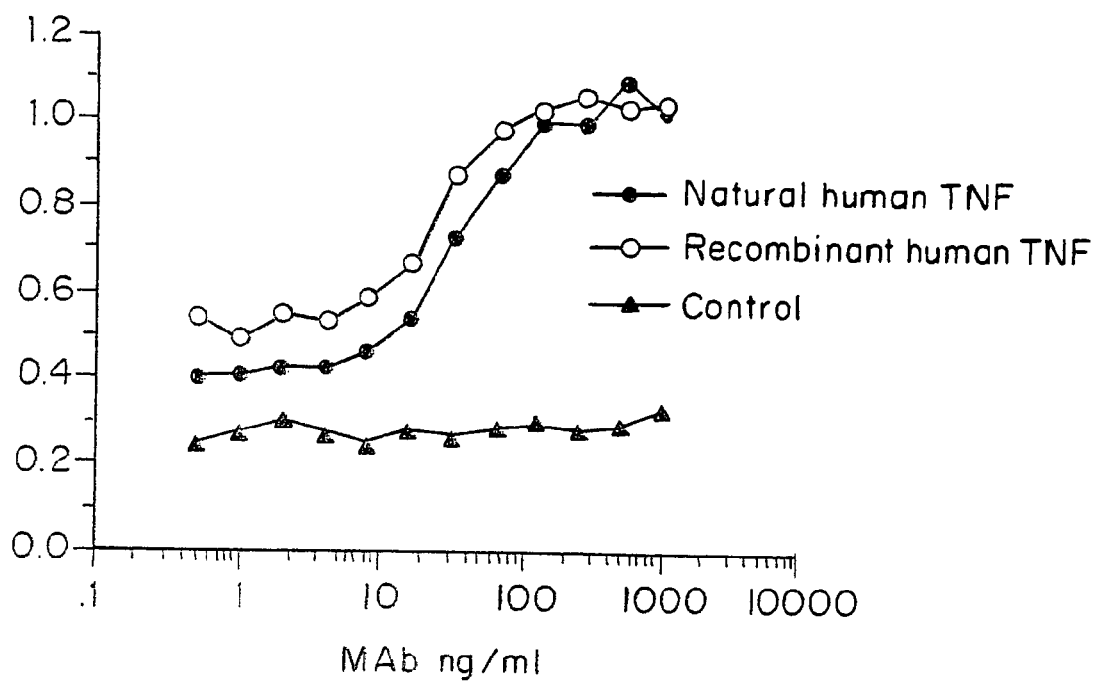
FIG. 11 is a graph showing neutralization of TNF cytotoxicity by chimeric A2. The control is a chimeric mouse/human IgG1 anti-platelet mAb (7E3) reacting with natural human TNF. Average absorbance values for controls were: no TNF added=1.08; natural TNF, no Ab=0.290; and recombinant TNF, no Ab=0.500.

The ability of cA2 to inhibit or neutralize human TNFα bioactivity in vitro was tested using the bioassay system described above. Cultured A673 cells were incubated with 40 pg/ml natural (Genzyme, Boston, Mass.) or recombinant (Suntory, Osaka, Japan) human TNF with or without antibody overnight as above, and cell death was measured by vital staining. As expected based upon the above results with the A2 mouse mAb, cA2 also inhibited or neutralized both natural and rhTNF in a dose-dependent manner in the cytotoxicity assay (FIG. 11). In this assay format, levels of cA2 as low as 125 ng/ml completely abolished the toxic activity of TNF. Upon repeated analysis, the cA2 exhibited greater TNF-inhibiting and/or neutralizing activity than did the parent murine A2 mAb. Such inhibiting and/or neutralizing potency, at antibody levels below 1 μg/ml, can easily be attained in the blood of a subject to whom the antibody is administered. Accordingly, such highly potent inhibiting and/or neutralizing anti-TNF antibodies, in particular the chimeric antibody, are preferred for therapeutic use in TNFα-mediated pathologies or conditions.

As mentioned above, TNF induces cellular secretion of IL-6. Furthermore, there is evidence that IL-6 is involved in the pathophysiology of sepsis, although the precise role of IL-6 in that syndrome is unclear (Fong, et al., *J. Exp. Med.* 170:1627–1633 (1989); Starnes Jr., et al., *J. Immunol.* 145: 4185–4191 (1990)). The ability of cA2 to inhibit or neutralize TNF-induced IL-6 secretion was evaluated using cultured human diploid FS-4 fibroblasts. The results in Table 2 show that cA2 was effective in blocking IL-6 secretion in cells that had been incubated overnight with TNF. TNF-induced IL-6 secretion was not inhibited in the absence of a mAb or in the presence of a control mAb specific for an irrelevant antigen.

TABLE 2

In Vitro Neutralization of TNF-Induced IL-6 Secretion

| Antibody | TNF Concentration (ng/ml) | | | |
|---|---|---|---|---|
| | 0 | 0.3 | 1.5 | 7.5 |
| None | <0.20 | 1.36 | 2.00 | 2.56 |
| Control mAb | <0.20 | 1.60 | 1.96 | 2.16 |
| cA2 | <0.20 | <0.20 | <0.20 | 0.30 |

Values represent mean concentrations of IL-6 of duplicate wells, in ng/ml. RhTNF (Suntory, Osaka, Japan), with or without 4 µg/ml antibody, was added to cultures of FS-4 fibroblasts and after 18 h, the supernatant was assayed for IL-6 using the QUANTIKINE ® Human IL-6 Immunoassay (from R&D Systems, Minneapolis, MN).
Control mAb = chimeric mouse/human IgG1 anti-platelet mAb (7E3).

The ability of TNF to activate procoagulant and adhesion molecule activities of endothelial cells (EC) is thought to be an important component of pathology pathophysiology. In particular, this can be associated with the vascular damage, disseminated intravascular coagulation, and severe hypotension that is associated with the sepsis syndrome. Therefore, the ability of cA2 to block TNF-induced activation of cultured human umbilical vein endothelial cells (HUVEC) was evaluated. TNF stimulation of procoagulant activity was determined by exposing intact cultured HUVEC cells to TNF (with or without antibody) for 4 hours and analyzing a cell lysate in a human plasma clotting assay. The results in Table 3 show the expected upregulation by TNF of HUVEC procoagulant activity (reflected by a decreased clotting time). Chimeric antibody cA2 effectively inhibited or neutralized this TNF activity in a dose-dependent manner.

TABLE 3

In Vitro Neutralization of TNF-Induced Procoagulant Activity

| Antibody | µg/ml | TNF Concentration (ng/ml) | | |
|---|---|---|---|---|
| | | 250 | 25 | 0 |
| None | — | 64 ± 4* | 63 ± 1 | 133 ± 13 |
| Control Ab | 10.00 | 74 ± 6 | N.D. | 178 ± 55 |
| cA2 | 10.00 | 114 ± 5 | 185 ± 61 | 141 ± 18 |
| cA2 | 3.30 | 113 ± 2 | 147 ± 3 | N.D. |
| cA2 | 1.10 | 106 ± 1 | 145 ± 8 | N.D. |
| A2 | 0.37 | 73 ± 17 | 153 ± 4 | N.D. |
| cA2 | 0.12 | 64 ± 1 | 118 ± 13 | N.D. |

*Values represent mean plasma clotting time, in seconds (± S.D.).
Clotting time was determined in normal human plasma after addition of the rhTNF (Dainippon, Osaka, Japan) with or without antibody-treated HUVEC lysate and $Ca^{++}$ at 37° C.
N.D. = not done.
Control Ab is a chimeric mouse/human IgG1 anti-CD4 antibody.

In addition to stimulating procoagulant activity, TNF also induces surface expression of endothelial cell adhesion molecules such as ELAM-1 and ICAM-1. The ability of cA2 to inhibit or neutralize this activity of TNF was measured using an ELAM-1 specific detection radioimmunoassay. Cultured HUVEC were stimulated with 250 ng/ml rhTNF (Dainippon, Osaka, Japan) with or without antibody at 37° C. overnight in a 96-well plate format. Surface expression of ELAM-1 was determined by sequential addition of a mouse anti-human ELAM-1 mAb and $^{125}I$-labelled rabbit anti-mouse immunoglobulin second antibody directly to culture plates at 4° C.

Figure 12:
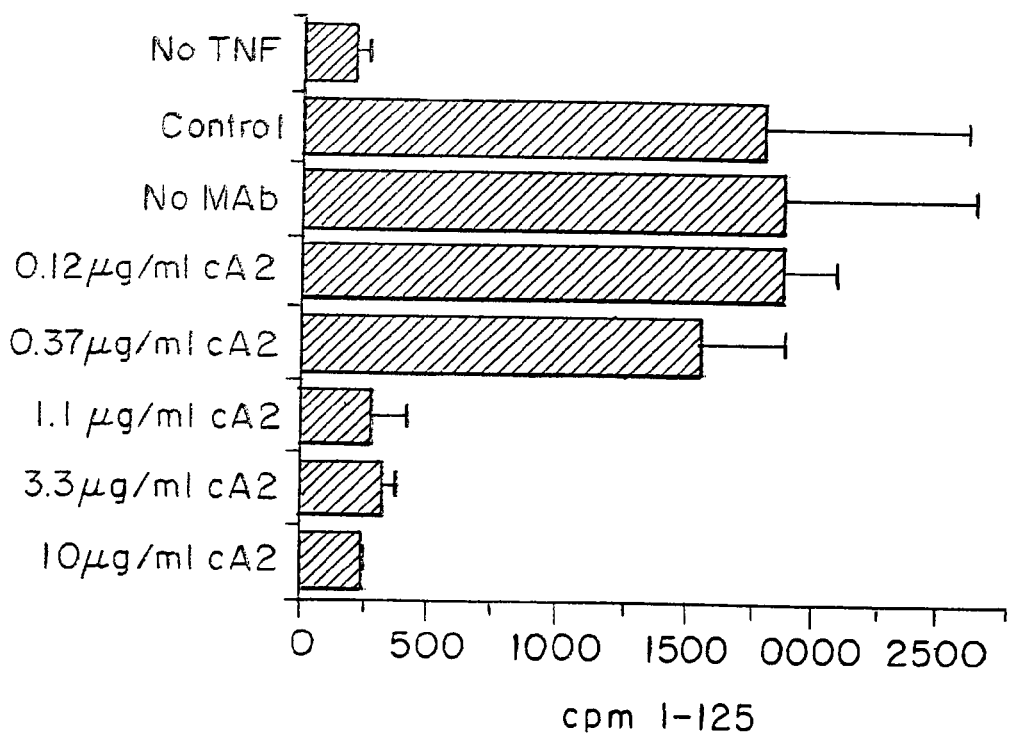
FIG. 12 is a graph showing in vitro neutralization of TNF-induced ELAM-1 expression by chimeric A2. The control is a chimeric mouse/human IgG1 anti-CD4 antibody.

As shown in FIG. 12, TNF induced the expression of ELAM-1 on the surface of cultured HUVEC cells, and this activity was again effectively blocked in a dose-related manner by cA2.

Finally, TNF is known to stimulate mitogenic activity in cultured fibroblasts. Chimeric A2 inhibited or neutralized TNF-induced mitogenesis of human diploid FS-4 fibroblasts cultures, confirming the potent inhibiting and/or neutralizing capability of cA2 against a broad spectrum of in vitro TNF biological activities.

EXAMPLE XII

Determination of Amino Acid Sequences (Epitope) on Human TNF-α Recognized by cA2 mAb Reagents The following reagents are readily available from commercial sources. FMOC-L-Ala-OPfp, FMOC-L-Cys(Trt)-OPfp, FMOC-L-Asp(OtBu)-OPfp, FMOC-L-Giu (OtBu)-OPfp, FMOC-L-Phe-OPfp, FMOC-Gly-OPfp, FMOC-L-His (Boc)-OPfp, FMOC-L-Ile-OPfp, FMOC-L-Lys(Boc)-OPfp, FMOC-L- Leu-OPfp, FMOC-L-Asn-OPfp, FMOC-L-Pro-OPfp, FMOC-L-Gin- OPfp, FMOC-L-Arg(Mtr)-OPfp, FMOC-L-Ser(tBu)-ODhbt, FMOC-L-Thr(tBu)-ODhbt, FMOC-L-Val-OPfp, FMOC-L-Trp-OPfp, FMOC-L-Try(tBu)-OPfp, and 1-hydrox-fbenotriazol (HOBT) were obtained from Cambridge Research Biochemicals. Piperidine and was obtained from Applied Biosystems, Inc. 1-Methyl-2-Pyrrolidinone (NMP) was obtained from EM Science; Methanol from JT Baker; Acetic Anhydride from Applied Biosystems, Inc., Trifluoroaccetic acid (TFA) from Applied Biosystems, Inc.; Diisopropylamne (DIEA), Triethylamine, Dithiothreitol (DTT) and Anisole from Aldrich and Hydrochloric Acid (HCI) from JT Baker.

Abbreviations: FMOC, 9-fluorenylmethoxycarbonyl; tBu t-butyl ether; OrB, t-butyl ester; Boc, t-butyloxycarbonyl; Mtr, 4-methoxy-2,3,6-trimethyl-benzenesulfonyl; Trt, trityl; OPfp, pentafluorophenylester; ODnbt. oxo-benzotriazone ester.

A chimeric antibody of the present invention, designated cA2, was used to determine which portions of the TNF amino acid sequence were involved in inhibitory binding by the antibody by epitope mapping, whereby the amino acid sequences of TNF-α recognized by cA2 have been identified.

Figure 14A:
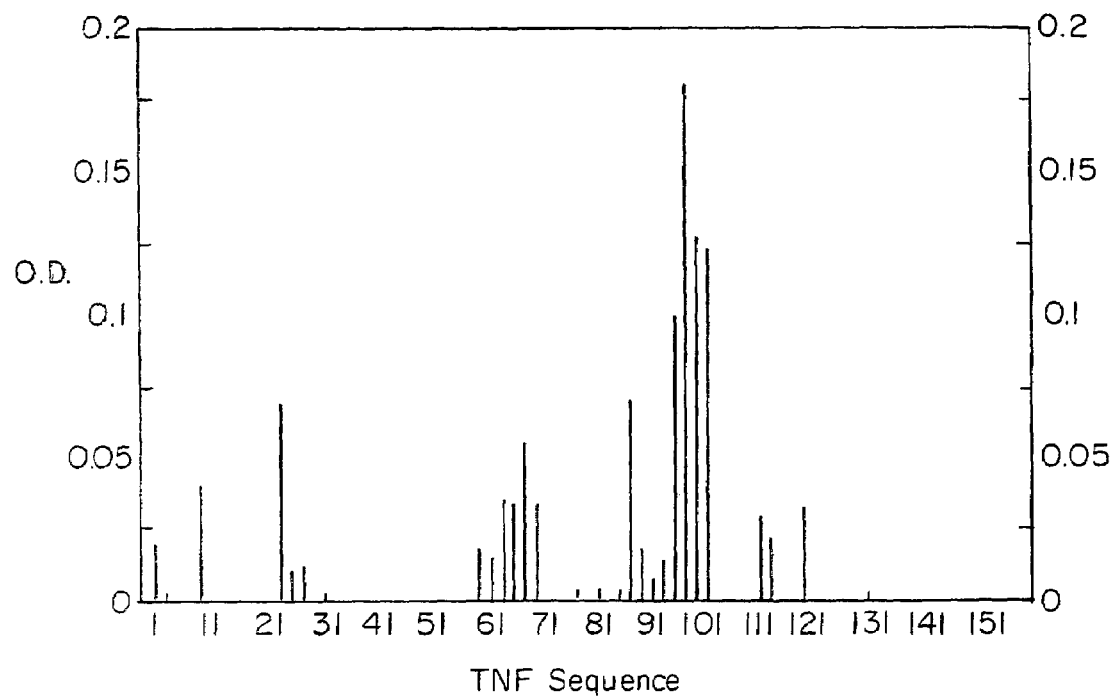
FIGS. 14A–14B.
Figure 14B:
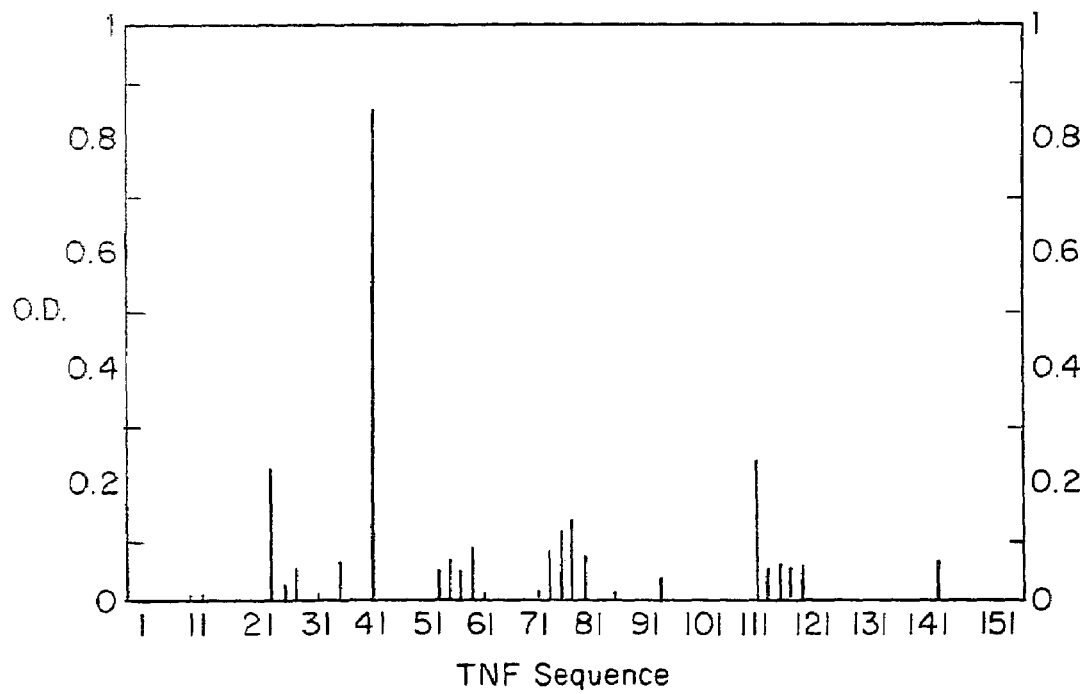
Figure 18:
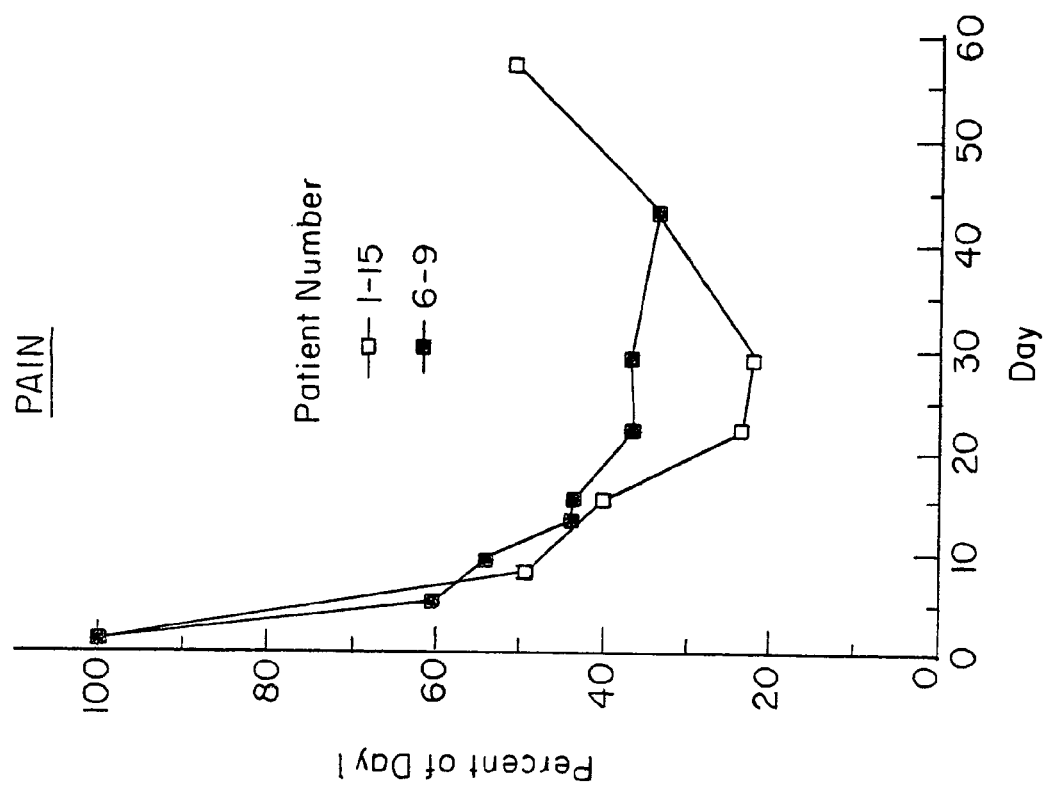
FIG. 18 is a graphical representation of the assessment of pain using a visual analogue scale for the five patients in group I, and the four patients in group II, is plotted as the mean percent of the baseline value versus time. Both groups showed an approximately 60 to 80 percent decrease in pain score which persisted for greater than 40 days.
Figure 17:
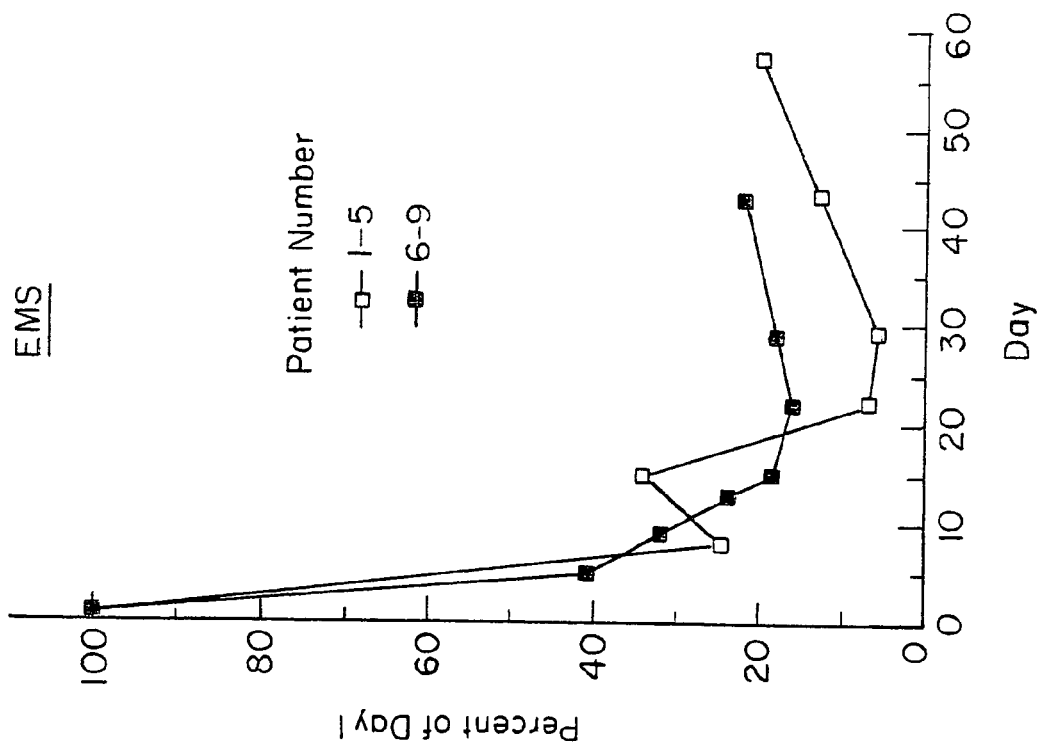
FIG. 17 is a graphical representation of the early morning stiffness for the five patients in group I, and the four patients in group II is plotted as the mean percent of the baseline value versus time. Both groups showed an approximately 80 percent decrease or greater in early morning stiffness, which persisted for greater than 40 days.
Figure 20:
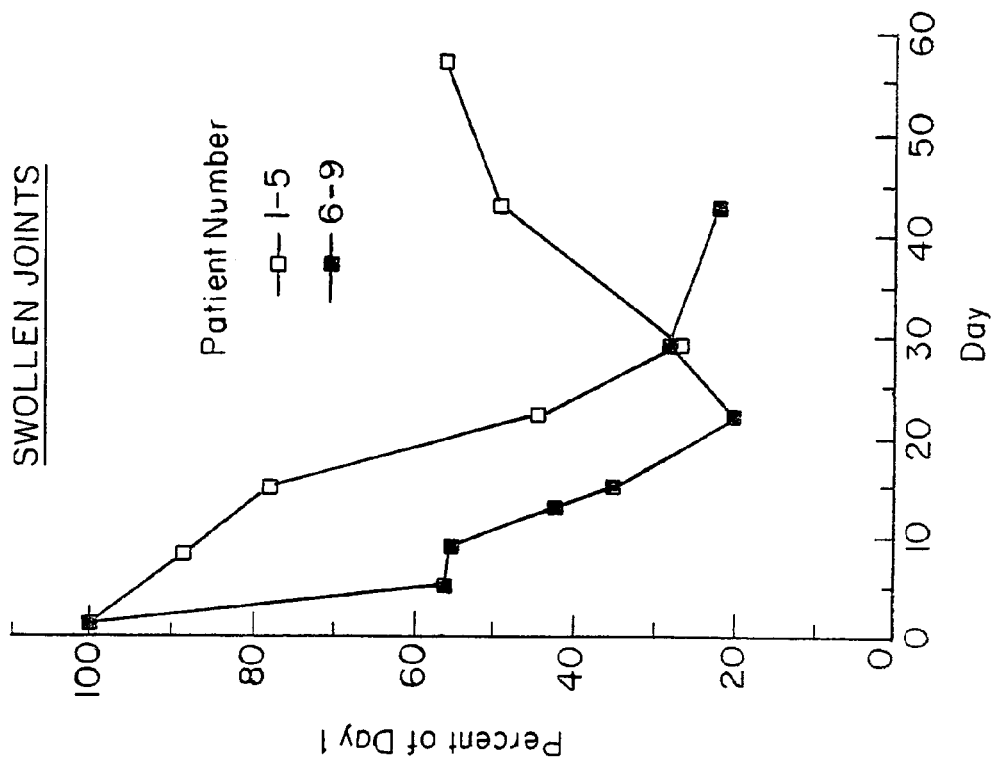
FIG. 20 is a graphical representation of the number of swollen joints for the five patients in group I and the four patients in Group II plotted as the mean percent of baseline value versus time. Both groups showed an approximately 70 to 80 percent decrease in swollen joints, which persisted for 30 to 40 days.
Figure 19:
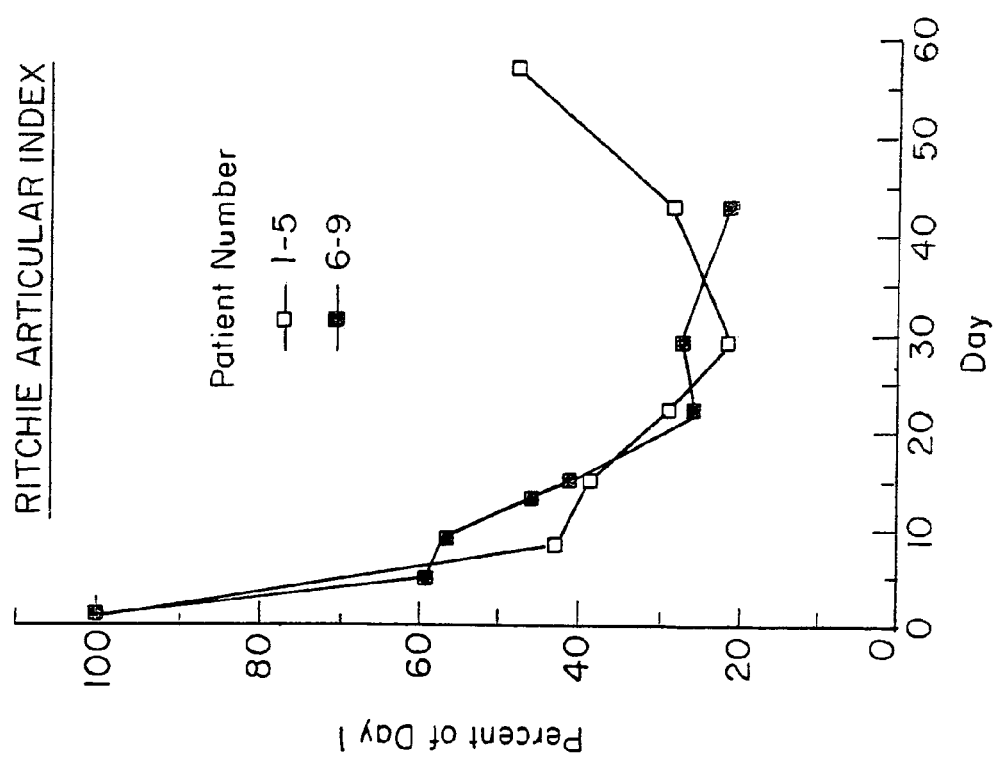
FIG. 19 is a graphical representation of the Ritchie Articular Index, (a scale scored of joint tenderness), plotted as the mean percent of the baseline value versus time. Both groups showed an approximately 80 percent decrease in the Ritchie Articular Index, which persisted for greater than 40 days.
Figure 22:
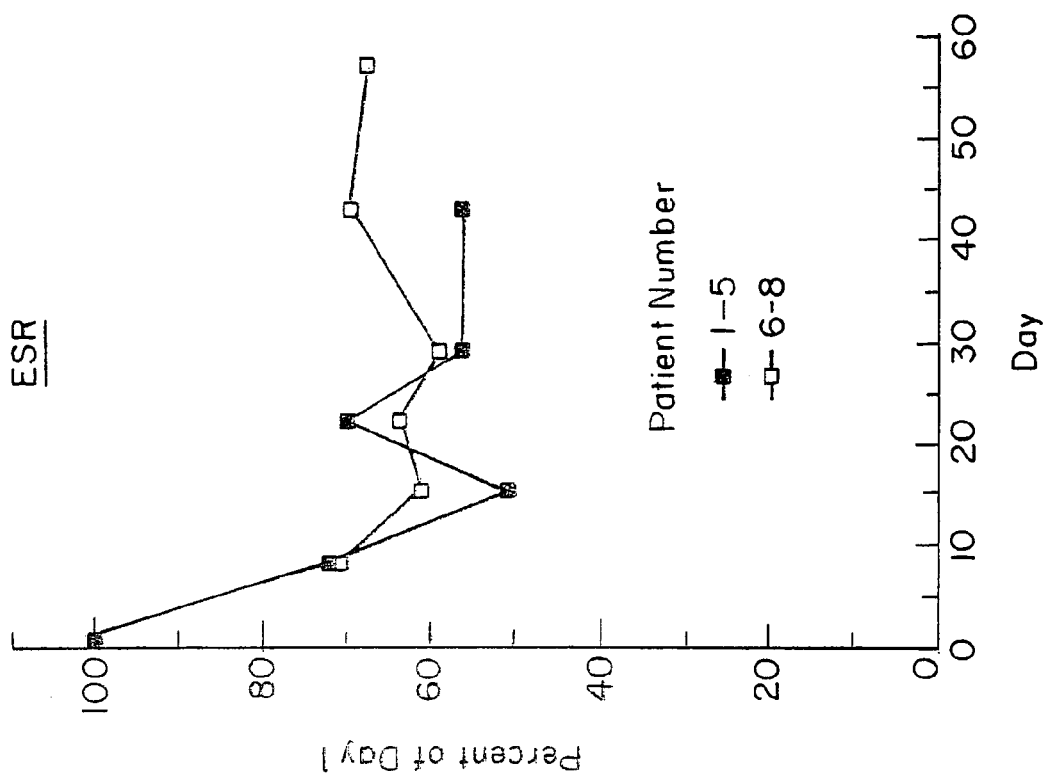
FIG. 22 is a graphical representation of the erythrocyte sedimentation rate for the five patients in group I and three of the patients in group II plotted as the mean percent of the baseline value versus time. Both groups showed an approximately 40 percent reduction in ESR which persisted for at least 40 days. The data from patient number 9 is omitted from the computations on which the plots were based, since this patient did not have an elevated ESR at baseline.
Figure 21:
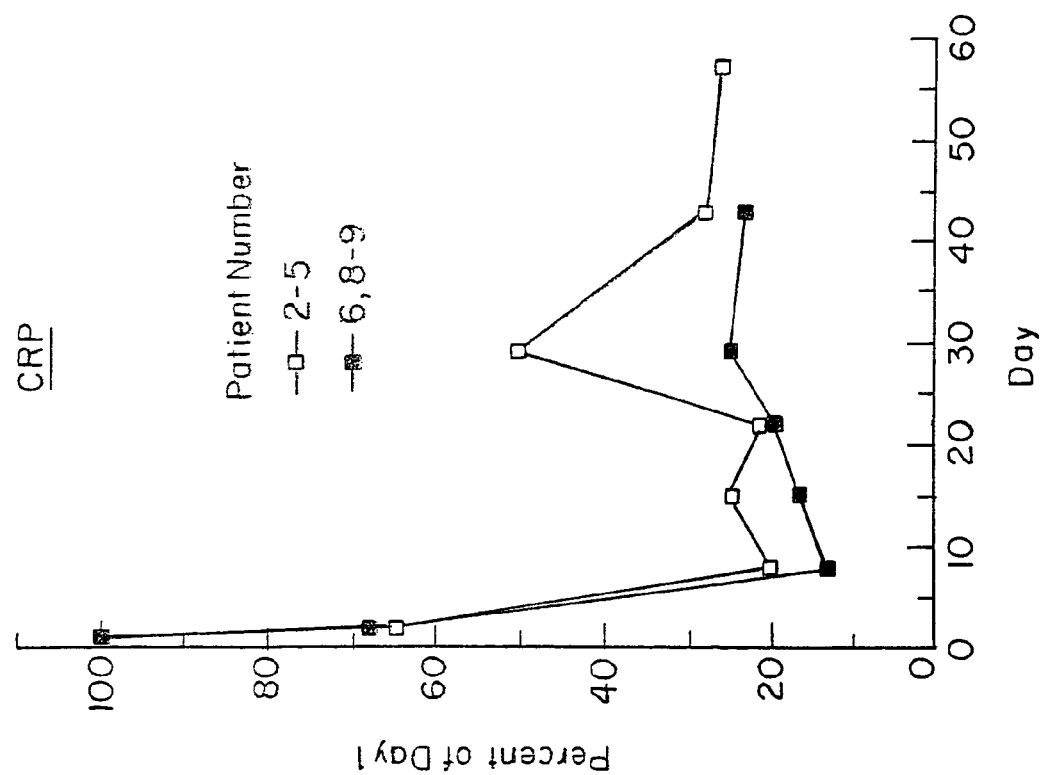
FIG. 21 is a graphical representation of the serum C-reactive protein for four to five patients in group I, and three of the four patients in group II, plotted as the mean percent of the baseline value versus time. Both groups showed an approximately 80 percent reduction in CRP which persisted for 30 to 40 days. The values for patient number 1 and patient number 7 were omitted from the computations on which the plots are based, since these patients did not have elevated CRP values at baseline.
Figure 23:
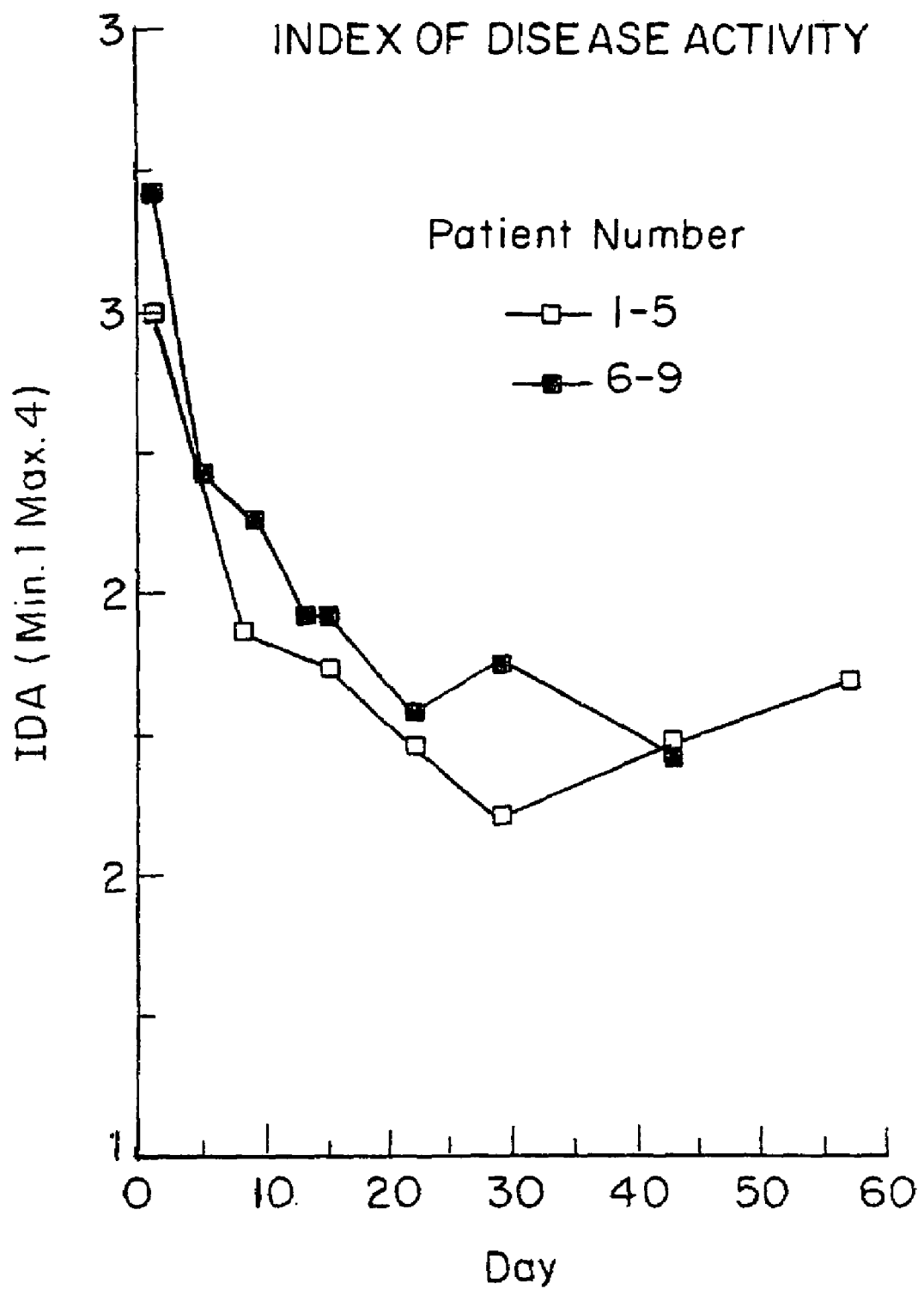
FIG. 23 is a graphical representation of the index of Disease Activity, (a composite score of several parameters of disease activity), for the five patients in group I, and the four patients in group II, plotted as the mean percent of the baseline value versus time. Both groups showed a clinically significant reduction in IDA, which persisted for at least 40 days.

The complete primary sequence of human TNFα, according to Pennica et al., Nature 312:724–729 (1984) is shown in FIG. 13 (SEQ ID NO:1). Overlapping decapeptides beginning with every second amino acid and covering the entire amino acid sequence of human TNF-α were synthesized on polyethylene pins using the method of Geysen (Geysen et al., Peptides: Chemistry and Biological, Proceedings of the Twelfth American Peptide Symposium, p. 519–523, Ed, G. R. Marshall, Escom, Leiden, 1988). Sets of peptide pins bearing free N-terminal amino groups and acetylated N-terminal amino groups were individually prepared. Both sets of peptide pins were incubated in solutions containing the anti-TNF mAb cA2 to determine the amino acid sequences that make up the cA2 epitope on human TNF-α, as described below. FIG. 14A shows the results of binding to the overlapping decapeptides that comprise the entire sequence of human TNFα. The O.D. (optional density) correlates directly with the increased degree of cA2 binding. FIG. 14B shows the results of binding of cA2 to the same set of peptide pins in the presence of human TNFα.

This competitive binding study delineates peptides which can show non-specific binding to cA2.

There are at least two non-contiguous peptide sequences of TNF-α recognized by cA2. Using the conventional protein numbering system wherein the N-terminal amino acid is number 1, the cA2 mAb recognizes an epitope composed at least in part of amino acids located within residues 87–108 or both residues 59–80 and 87–108 of TNF (SEQ ID NO:1). FIG. 15 presents these non-contiguous sequences within the TNF sequence.

Unexpectedly, the mAb cA2 blocks the action of TNF-α without binding to the putative receptor binding locus, which can include one or more of, e.g., 11–13, 37–42, 49–57 or 155–157 of hTNFα (of SEQ ID NO:1). Preferred anti-TNF mAbs are those that inhibit this binding of human TNF-α to its receptors by virtue of their ability to bind to one or more of these peptide sequences. These antibodies can block the activity of TNF by virtue of binding to the cA2 epitope, such binding demonstrated to inhibit TNF activity. The identification of those peptide sequences recognized by cA2 provides the information necessary to generate additional MAbs with binding characteristics and therapeutic utility that parallel the embodiments of this application.

Peptide Pin Synthesis

Using an epitope mapping kit purchased from Cambridge Research Biochemicals, Inc. (CRB), dodecapeptides corresponding to the entire sequence of human TNF-α were synthesized on polyethylene pins.

A synthesis schedule was generated using the CRB epitope mapping software. Prior to the first amino acid coupling, the pins were deprotected with a 20% piperidine in NMP solution for 30 minutes at room temperature. After deprotection, the pins were washed with NMP for five minutes at room temperature, followed by three methanol washes. Following the wash steps, the pins were allowed to air dry for at least 10 minutes.

The following procedure was performed for each coupling cycle:
1) The amino acid derivatives and the HOBT were weighted out according to the weights required in the synthesis schedule.
2) The HOBT was dissolved in the appropriate amount of NMP according to the synthesis schedule.
3) The amino acid derivatives were dissolved in the recommended amount of HOBT solution and 150 microliters were pipeted into the appropriate wells as directed by the well position sheet of the synthesis schedule.
4) The blocks containing the pins were placed into the wells, and the "sandwich" units stored in plastic bags in a 30° C. water bath for 18 hours.
5) The pins were removed from the wells and washed once (for 5 minutes) with NMP, three times (for two minutes) with methanoi and air dried for 10 minutes.
6) The pins were deprotected as described above and the procedure repeated.

To acetylate the peptides on one block of pins, the peptide pins were washed, deprotected and treated with 150 microliters of a solution containing NMP; acetic anhydride:triethylamine (5:2:1) for 90 minutes at 30° C., followed by the washing procedure outlined above. The second set of peptide pins was deprotected by not acetylated to give free N-terminal amino groups.

The final deprotection of the peptides to remove the side chain protecting groups was done using a mixture of TFA: anisole:dithiothreitol, 95:2.5:2.5 (v/v/w) for four hours at ambient temperature. After deprotection, the pins were air dried for 10 minutes, followed by a 15 minute sonication in a solution of 0.1% HCl in methanol/distilled water (1:1). The pins dried over night and were then ready for testing.

ELISA Assay for cA2 Binding to TNF-α Peptide PINs

Reagents: Disruption Buffer

Sodium dihydrogen phosphate (31.2 g, Sigma cat #S-0751 or equivalent) and sodium dodecylsulfate (20.0 g, Sigma cat #L-3771 or equivalent) were dissolved in 2.0 L of MILLI-Q® water. The pH was adjusted to 7.2±0.1 with 50% w/w sodium hydroxide (VWR cat #VW6730-3 or equivalent).

Blocking Buffer

Sodium dihydrogen phosphate (0.39 g, Sigma cat #S-0751 or equivalent) disodium hydrogen phosphate (1.07 g, Baker cat #3828-1 or equivalent) and sodium chloride (8.50 g, Baker cat #3624-5 or equivalent) were dissolved in 1.0 L of MILLI-Q® water. The pH was adjusted to 7.2±0.1 with 50% w/w sodium hydroxide (VWR cat VW6730-3 or equivalent). Chicken egg albumin (10.0 g, Sigma cat #A-5503 or equivalent) and bovine serum albumin (10.0 g, Sigma, cat #A-3294 or equivalent) were dissolved at room temperature with gentle stirring. The solution was filtered, and to the solution was added TWEEN® 20 (2.0 ml, Sigma cat #P-13.79 or equivalent). The solution was stirred gently at room temperature for 30 min, filtered and stored at 40°.

PBS/TWEEN® 20

A 10× concentrate was prepared by dissolving sodium dihydrogen phosphate (3.90 g, Sigma cat #S-075 1 or equivalent), disodium hydrogen phosphate (10.70 g, Baker cat #3828-1 or equivalent) and sodium chloride (85.0 g, Baker cat #3624-5 or equivalent) in 1.0 L of MILLI-Q® water. The pH was adjusted to 7.2±0.1 with 50% w/w sodium hydroxide (VWR cat #VW 6730 or equivalent). To the solution was added TWEEN® 20 (5.0 mL, Sigma cat #P-1379 or equivalent), and the mixture stirred gently. Just prior to use 100 mL of this solution was diluted to 1.0 L with MILLI-Q® water.

Substrate Solution

Substrate buffer was prepared by dissolving citric acid (4.20 g, Malinckrodt cat #0627 or equivalent) and disodium hydrogen phosphate (7.10 g, Baker cat #3828-1 or equivalent) in 1.0 L of MILLI-Q® water. The pH was adjusted to 5.00 with 50% w/w sodium hydroxide (VWR cat #VW6730-3 or equivalent). Immediately prior to use an OPD substrate tablet (30 mg, Sigma cat #P-8412 or equivalent and 30% (v/v) hydrogen peroxide (40 µL, Sigma cat #P-1379 or equivalent) were added to the substrate buffer 25.0 mL). The solution was wrapped in foil and mixed thoroughly.

4 $NH_2SO_4$

Sulfuric acid (53 mL, EM Science cat #SX1244-5 or equivalent) was slowly added to MILLI-Q® water (447 mL) and cooled to room temperature prior to use.

Equipment

Molecular Devices Model nu-max plate reader or equivalent. Scientific Products Model R4140 Oscillating table shaker and equivalent. BRANSON Model 5200 ultra-sonic bath or equivalent. FINNPIPETTE Model 4172317 multi-channel pipeter or equivalent. CORNING Model 25801 96 well disposable polystyrene Elisa Plates.

Prior to use and after each subsequent use the peptide pins were cleaned using the following procedure. Disruption buffer (2.0 L) was heated to 60° and placed in an ultra-sonic bath in a fume hood. To the disruption buffer was added dithiolthreitol (2.5 g, Sigma cat #D-0632 or equivalent). The peptide pins were sonicated in this medium for 30 min, washed thoroughly with MILLI-Q® water, suspended in a boiling ethanol bath for 2 min, and air-dried.

Blocking buffer (200 µL) was added to a 96 well disposable polystyrene Elisa plate and the peptide pins suspended in the wells. The peptide pins and plate were incubated for 2 hours at room temperature on an oscillating table shaker. The plates and peptide pins were washed with PBS/TWEEN® 20 (four times). To each well was added a 20 µg/ml concentration of cA2 antibody (diluted with blocking buffer, 175 µL/well). TNF competition was done by incubation of TNFα (40 µg/ml) and cA2 (20 µg/ml) in BSA/ovalbumin/BBS for three hours at room temperature. The peptide pins were suspended in the plate and incubated at 4° overnight. The peptide pins and plate were washed with PBS/TWEEN® 20 (four times). To each well was added anti-human goat antibody conjugated to horseradish peroxidase (diluted with blocking buffer to ½₀₀₀, 175 µL/well, Jackson IMMUNORESEARCH Labs). The peptide pins were suspended in the plate, and incubated for 1 hour at room temperature on a oscillating table shaker. The plates and peptide pins were washed with PBS/TWEEN® 20 (four times). To each well was added freshly prepared substrate solution (150 µL/well), the peptide pins were suspended in the plate and incubated for 1 hour at room temperature on an oscillating table shaker. The peptide pins were removed and to each well is added 4N $H_2SO_4$ (50 µL). The plates were read in a Molecular Devices plate reader (490 nm, subtracting 650 nm as a blank), and the results are shown in FIGS. 14A and 14B, as described above.

EXAMPLE XIII

Production of Mouse Anti-Human TNF mAb Using TNF Peptide Fragments

Female BALB/c mice, as in Example I above, are injected subcutaneously and intraperitoneally (i.p.) with forty µg of purified *E. coli*-derived recombinant human TNF (rhTNF) fragments comprising anti-TNF epitopes of at least 5 amino acids located within the non-contiguous sequence 59–80, 87–108 or both residues 59–80 and 87–108 of TNF (of SEQ ID NO:1), as presented above, emulsified with an equal volume of complete Freund's adjuvant (obtained from Difco Laboratories) in 0.4 ml is into a mouse. One week later, a booster injection of 5 µg of these rhTNF fragments in incomplete Freund's adjuvant is given i.p. followed by four consecutive i.p. injections of 10 µg of TNF fragments including anti-TNF epitopes including amino acids from residues 59–80, 87–108 or both 59–80 and 87–108 of hTNFα (of SEQ ID NO:1) without adjuvant. Eight weeks after the last injection, the mouse is boosted i.p. with 10 µg of TNF.

Four days later, the mouse is sacrificed, the spleen is obtained and a spleen cell suspension is prepared. Spleen cells are fused with cells of the nonsecreting hybridoma, Sp2/0 (ATCC CRL1581), at a 4:1 ratio of spleen cells to Sp2/0 cells, in the presence of 0.3 ml of 30% polyethylene glycol, PEG 1450. After incubation at 37° C. for 6 hours, the fused cells are distributed in 0.2 ml aliquots into 96-well plates at concentrations of $2\times10^4$ SP2/0 cells per well. Feeder cells, in the form of $5\times10^4$ normal BALB/c spleen cells, are added to each well.

The growth medium used consisted of RPM1-1640 medium, 10% heat-inactivated fetal bovine serum (FBS) (Hyclone), 0.1 mM MEM nonessential amino acids, 1 mM sodium pyruvate, 2 mM L-glutamine, 100 U/ml penicillin, 100 µg/ml streptomycin (GIBCO Laboratories) and, for selection, hypoxanthine-aminopterin-thymidine (HAT) (Boehringer Mannheim). A solid-phase radioimmunoassay (RIA) is employed for screening supernatants for the presence of mAbs specific for rhTNFα fragments including portions of residues 59–80, 87–108 or both 59–80 and 87–108 of hTNFα (of SEQ ID NO:1). This assay is described in Example II, above. The background binding in this assay is about 500 cpm. A supernatant is considered positive if it yielded binding of 2000 cpm or higher.

Of the supernatants screened, one or more positive supernatants are routinely identified by RIA. Of these positive supernatants, the highest binding (as shown by the higher cpm values) are subcloned at limiting dilution on mouse feeder cells. Upon further analysis of the supernatants in neutralization assays, routinely one or more antibodies are found to have potent inhibiting and/or neutralizing activity. These positive and inhibiting and/or neutralizing hybridoma lines are then selected and maintained in RPM1-1640 medium with 10% FBS (GIBCO), 0.1 mM nonessential amino acids, 1 mM sodium pyruvate, 2 mM L-glutamine, 100 U/ml penicillin and 100 µg/ml streptomycin.

EXAMPLE XIV

Production of Murine and Chimeric Antibodies, Fragments and Regions from TNF Peptides Murine and chimeric antibodies, fragments and regions are obtained by construction of chimeric expression vectors encoding the mouse variable region of antibodies obtained in Example XIII and human constant regions, as presented in Examples IV–IX above.

The resulting chimeric A2 antibody is purified from tissue culture supernatant by Protein A-Sepharose chromatography. The supernatant is adjusted to 0.1M Tris, 0.002M EDTA, pH 8.0 and loaded on a Protein A-Sepharose column equilibrated in the same buffer. The IgG is then eluted with 0.1M citrate, pH 3.5, neutralized with 1M Tris, and dialyzed into phosphate buffered saline (PBS).

The purified murine and chimeric antibodies, fragments and regions are evaluated for its binding and inhibiting and/or neutralizing activity.

EXAMPLE XV

In Vitro Activity and Neutralization Efficacy of a Chimeric Anti-TNF Antibody Both the murine and chimeric anti-TNFα antibodies of the present invention, as obtained according to Examples XIII and XIV, are determined to have potent TNF-inhibiting and/or neutralizing activity, as shown for example, in the TNF cytotoxicity assay described above, expressed as the 50% Inhibitory Dose (ID50).

In this same experimental system, three other murine anti-TNFα antibodies (termed TNF-1, TNF-2 and TNF-3) of comparable binding affinity to TNF are found to have ID50 values of 1–2 orders of magnitude greater, and thus have significantly less potency in neutralization, than both the murine and chimeric anti-TNFα antibodies of the present invention.

The ability of both the murine and chimeric anti-TNFα antibodies of the present invention, as obtained according to Examples XIII and XIV, to inhibit or neutralize human TNFα bioactivity in vitro is tested using the bioassay system described above. Cultured cells producing the murine or chimeric anti-TNFα antibodies of the present invention, as obtained according to Examples XIII and XIV, are incubated with 40 pg/ml natural (Genzyme, Boston, Mass.) or recombinant (Suntory, Osaka, Japan) human TNF with or without antibody overnight as above, and cell death is measured by vital staining. As expected, both the murine and chimeric anti-TNFα antibodies of the present invention, as obtained according to Examples XIII and XIV, inhibited or neutralized both natural and rhTNF in a dose-dependent manner in the cytotoxicity assay. Such inhibiting and/or neutralizing potency, at antibody levels below 1 μg/ml, can easily be attained in the blood of a subject to whom the antibody is administered. Accordingly, such highly potent inhibiting and/or neutralizing anti-TNF antibodies, in particular the chimeric antibody, are preferred for therapeutic use in TNFα-mediated pathologies or conditions.

The ability of cA2 to inhibit or neutralize TNF-induced IL-6 secretion is evaluated using cultured human diploid FS-4 fibroblasts. The results are expected to show that both murine and chimeric anti-TNFα antibodies of the present invention, as obtained according to Examples XIII and XIV, are effective in blocking IL-6 secretion in cells that had been incubated overnight with TNF. TNF-induced IL-6 secretion is not inhibited in the absence of a mAb or in the presence of a control mAb specific for an irrelevant antigen.

The ability of TNF to activate procoagulant and adhesion molecule activities of endothelial cells (EC) is thought to be an important component of pathology pathophysiology. In particular, this can be associated with the vascular damage, disseminated intravascular coagulation, and severe hypotension that is associated with the sepsis syndrome. Therefore, the ability of both the murine and chimeric anti-TNFα antibodies of the present invention, as obtained according to Examples XIII and XIV, to block TNF-induced activation of cultured human umbilical vein endothelial cells (HUVEC) is evaluated. TNF stimulation of procoagulant activity is determined by exposing intact cultured HUVEC cells to TNF (with or without antibody) for 4 hours and analyzing a cell lysate in a human plasma clotting assay. The results are expected to show the expected upregulation by TNF of HUVEC procoagulant activity (reflected by a decreased clotting time). Both the murine and chimeric anti-TNFα antibodies of the present invention, as obtained according to Examples XIII and XIV, are expected to effectively inhibit or neutralize this TNF activity in a dose-dependent manner.

In addition to stimulating procoagulant activity, TNF also induces surface expression of endothelial cell adhesion molecules such as ELAM-1 and ICAM-1. Both the murine and chimeric anti-TNFα antibodies of the present invention, as obtained according to Examples XIII and XIV, are expected to inhibit or neutralize this activity of TNF is measured using an ELAM-1 specific detection radioimmunoassay. Cultured HUVEC are stimulated with 250 ng/ml rhTNF (Dainippon, Osaka, Japan) with or without antibody at 37° C. overnight in a 96-well plate format. Surface expression of ELAM-1 is determined by sequential addition of a mouse anti-human ELAM-1 mAb and $^{125}$I-labelled rabbit anti-mouse immunoglobulin second antibody directly to culture plates at 4° C.

TNF is expected to induce the expression of ELAM-1 on the surface of cultured HUVEC cells, and this activity is again expected to be effectively blocked in a dose-related manner by both the murine and chimeric anti-TNFα antibodies of the present invention, as obtained according to Examples XIII and XIV.

Finally, TNF is known to stimulate mitogenic activity in cultured fibroblasts. Both the murine and chimeric anti-TNFα antibodies of the present invention, as obtained according to Examples XIII and XIV, are expected to inhibit or neutralize TNF-induced mitogenesis of human diploid FS-4 fibroblasts cultures, confirming the potent inhibiting and/or neutralizing capability of both the murine and chimeric anti-TNFα antibodies of the present invention, as obtained according to Examples XIII and XIV against a broad spectrum of in vitro TNF biological activities.

EXAMPLE XVI

In Vivo Activity and Efficacy of cA2 Antibody

Evidence that the potent in vitro inhibiting and/or neutralizing capability of cA2 is manifest in vivo was obtained. Earlier animal studies showed that administration of TNF to experimental animals mimics the pathology state obtained with either Gram-negative bacterial infection or direct endotoxin administration (Tracey et al., infra (1986); Tracey et al., infra (1987); Lehmann et al. infra).

An in vivo model wherein lethal doses of human TNF are administered to galactosamine-sensitized mice (Lehmann, V. et al., infra) is substantially modified for testing the capability of both the murine and chimeric anti-TNFα antibodies of the present invention, as obtained according to Examples XIII and XIV above, to inhibit or neutralize TNF in vivo. An i.p. challenge with 5 μg (0.25 mg/kg) of rhTNF resulted in 80–90 percent mortality in untreated control animals and in animals treated i.v. 15–30 minutes later with either saline or 2 mg/kg control antibody (a chimeric IgG1 derived from murine 7E3 anti-platelet mAb). In contrast, treatment with both the murine and chimeric anti-TNFα antibodies of the present invention, as obtained according to Examples XIII and XIV, is expected to reduce mortality to 0–30 percent with 0.4 mg/kg of antibody, and to 0–10 percent with 20 mg/kgs. These expected results indicate that both the murine and chimeric anti-TNFα antibodies of the present invention, as obtained according to Examples XIII and XIV, are capable of inhibiting and/or neutralizing the biological activity of TNF in vivo as well as in vitro.

TABLE 4

Prevention of Human TNF-Induced Lethality by Chimeric A2

| Antibody | Outcome (Survivors/Total) | |
| --- | --- | --- |
| | Experiment #1 | Experiment #2 |
| None | 1/10 | N.D. |
| Control Ab, 2 mg/kg | 2/10 | 1/10 |
| cA2 (2 mg/kg) (p = 0.0001) | 9/10 (p = 0.0055) | 10/10 |
| cA2 (0.4 mg/kg) (p = 0.0001) | 7/10 (p = 0.07) | 10/10 |

Female C3H/HeN mice were administered 5 μg rhTNF (Dainippon, Osaka, Japan) + 18 mg galactosamine i.p. and antibody was administered 15–30 minutes later i.v.
Deaths were recorded 48 hours post-challenge.
Control MAb = chimeric mouse/human IgG1 anti-platelet MAb (7E3).
N.D. = not done.
p values refer to comparison with the control Ab.

EXAMPLE XVII cA2 MAb Safety in Chimpanzees

The epitope specificity of A2 can be for an epitope which predominates in humans and chimpanzees. Therefore, the chimpanzee was chosen as a relevant mammalian species to determine the toxicological potential and provide safety information for cA2. Chimpanzees were dosed at levels of 15 mg/kg for four to five consecutive days and 30 mg/kg once or for three consecutive days. No adverse clinical signs, and no changes considered to be cA2 treatment related were observed in the monitored parameters including routine hematology and blood chemistry. Thus, doses of up to 30 mg/kg for three consecutive days were well tolerated in chimpanzees.

EXAMPLE XVIII

Clinical Activity and Efficacy of cA2 Antibody

Chimeric IgG1 anti-human TNF MAb cA2 was administered to healthy male human volunteers as patients. One hour after receiving 4 ng/kg of an NIH reference endotoxin, the volunteers were administered either saline, as a control, or 0.01, 0.10 or 10 mg/kg of cA2 in a pharmaceutically acceptable form. TNF levels in serum were measured over time and were found to show a dose dependent decrease in peak TNF levels with no TNF being detected in volunteers receiving a 10 mg/kg dose of cA2. Accordingly, therapy with an anti-TNF antibody of the present invention is expected to inhibit TNF-mediated effects in humans.

Patients receiving endotoxin developed pronounced leukopenia thought to be due to margination of white blood cells. As the white blood cells become activated, they can attach to endothelial receptors with resultant endothelial damage. At doses of 1.0 to 10.0 mg/kg, this leukopenia is prevented, whereas, at 0.01 and 0.1 mg/kg dosages, a drop in white cell count was observed. The drop was most pronounced among the polymorph cell line. In all patients there was a subsequent leukocytosis, which was unchanged by treatment with anti-TNF antibody cA2. This blocking effect on white blood cell margination is expected to represent a protective effect against the endothelial damage associated with TNF. It is expected in the art that this TNF-related endothelial damage plays a significant role in the morbidity and mortality associated with sepsis, and it is therefore expected that the anti-TNF antibodies of the present invention will provide a protective effect against these damaging effects, as presented herein.

EXAMPLE XIX

Treatment of Sepsis in Humans Using a Chimeric Anti-TNF Antibody

The chimeric anti-TNF MAb cA2 has been used in two phase I/II studies. In a phase I/II study in septic patients, 20 patients with the sepsis syndrome received a single dose of either 0. 1, 1.0, 5.0 or 10 milligrams of cA2 per kilogram bodyweight. Another 60 patients received 100 milligrams of HA-1A, a human anti-lipid A Mab currently under evaluation for gram negative sepsis, followed with either placebo or 1.0, 5.0, or 10 milligrams cA2 per kilogram bodyweight. The cA2 was administered as a single, intravenous infusion over a 60 minute period. Clinical assessment, vital signs, and laboratory parameters were measured before, during and periodically for 28 days after the infusion. In this study, cA2 was well tolerated. No adverse events were reported as "probably" or "definitely" related to cA2. All deaths were reported as "definitely not" related to cA2.

Accordingly, human treatment of rheumatoid arthritis in human patients was expected, and found, to provide a suitable treatment, as described herein.

EXAMPLE XX

Clinical Treatment of Rheumatoid Arthritis by a Anti-TNF Antibody or Peptide of the Present Invention A Phase I open label study was conducted for methods and compositions of the present invention using a chimeric anti-TNF MAb for the treatment of patients with severe refractory rheumatoid arthritis. Nine patients were enrolled in the study. The first five patients were treated with chimeric anti-TNF antibody (cA2), 10 mg/kg as a single dose infused over a period of two hours. These patients were subsequently retreated with a second infusion of 10 mg/kg on day 14 of the study. The second group of five patients received an infusion of 5 mg/kg on the first day of the study. They were then treated with additional infusions of 5 mg/kg on days 5, 9, and 13. Four of the planned five patients in this second group have been treated to date.

Preparation, Administration, and Storage of Test Material

The chimeric monoclonal anti-TNF antibody was supplied in single-use glass vials containing 20 mL with 100 mg of anti-TNF (5 mg/mL). The anti-TNF antibody was stored at 2–8° C. Prior to infusion, the antibody was withdrawn from the vials and filtered through a low-protein-binding 0.22 µm filter. This filtered antibody was then diluted to a final volume of 300 mL with normal saline. The 300 mL antibody preparation was then infused via an in-line filter over a period of not less than two hours.

Prior to each repeat infusion of study medication a test dose of 0.1 mL of the infusion was diluted in 10 mL of normal saline and administered by slow IV push over 5 minutes. The patient was observed for 15 minutes for signs or symptoms of an immediate hypersensitivity reaction. If no reaction was observed in this time period, the full dose was administered as described above.

Administration Protocol

Group 1 (patients 1–5): a total of 2 infusions, on day 1 and day 15 of the trial; dosage 10 mg/kg on each occasion;

Group 2 (patients 6–9): a total of 4 infusions, on days 1, 5, 9 and 13 of the trial; dosage 5 mg/kg on each occasion.

All infusions were administered iv over 2 hours in a total volume of cA2+saline of 300 ml. Infusions subsequent to the first in any patient were preceded by a small test dose administered as an iv push. All patients had at least three years of disease activity with rheumatoid arthritis. The patients ranged in age from 23 to 63. All patients had failed therapy with at least three different DMARD (Disease Modifying Anti-Rheumatic Drug). Six of the nine patients had serum rheumatoid factors, and all nine patients had erosions present on X-rays.

Clinical Monitoring

Patients were monitored during and for 24 hours after infusions for hemodynamic change, fever or other adverse events. Clinical and laboratory monitoring for possible adverse events was undertaken on each follow-up assessment day. Clinical response parameters were performed at the time-points as specified in the flow charts present in Tables 9A and 9B. These evaluations were performed prior to receiving any infusions.

Clinical response studies will be comprised of the following parameters:

1. Number of tender joints and assessment of pain/tenderness

The following scoring will be used:
   0=No pain/tenderness
   1=Mild pain. The patient says it is tender upon questioning.
   2=Moderate pain. The patient says it is tender and winces.
   3=Severe pain. The patient says it is tender and winces and withdraws.

2. Number of swollen joints

Both tenderness and swelling will be evaluated for each joint separately. MCP's, PIP's etc. will not be considered as one joint for the evaluation.

3. Duration of morning stiffness (in minutes)

4. Grip strength

5. Visual analog pain scale (0–10 cm)

6. Patients and blinded evaluators will be asked to assess the clinical response to the drug. Clinical response will be assessed using a subjective scoring system as follows:

5=Excellent response (best possible anticipated response)
   4=Good response (less than best possible anticipated response)
   3=Fair response (definite improvement but could be better)
   2=No response (no effect)
   1=Worsening (disease worse)

Measurement of index of disease activity is scored according to the following Table 5.

TABLE 5

Clinical Characteristics of Patients 1–5

| Patient Number | Age/Sex | Disease Duration (years) | Rheumat. Factor | Erosions/ Nodules | Previous Treatment (DMARDs only) | Concomitant Anti-rheumatic Therapy |
|---|---|---|---|---|---|---|
| 01 | 48/F | 7 | +ve | −ve/+ve | *Sal, DP, Myo, Aur, MTX, Aza, Chl | **Pred 5 mg |
| 02 | 63/F | 7 | −ve | +ve/−ve | Sal, Myo, DP | Para 1–2 g |
| 03 | 59/M | 3 | +ve | +ve/−ve | Aur, Chl, Myo, MTX, Sal | Pred 10 mg; Ind 225 mg |
| 04 | 56/M | 10 | +ve | +ve/−ve | Myo, DP, Aza, Sal | Pred 12.5 mg, Ibu 2 g, Para 1–2 g |
| 05 | 28/F | 3 | +ve | +ve/−ve | Myo, Sal, DP, Aza | Pred 8 mg, Para 1–2 g, Cod 16 mg |

*Sal = Sulphasalazine; DP = D-penicillamine; Myo = Myocrisin; Aur = auranofin; MTX = methotrexate; Aza = azathioprine; Chl = hydroxychloroquine.
**Pred = prednisolone (dosage/day); Para = paracetamol; Ind = indomethacin; Ibu = ibuprofen; Cod = codeine phosphate.

TABLE 6

Clinical Characteristics of Patients 6–9

| Patient Number | Age/Sex | Disease Duration (years) | Rheumat. Factor | Erosions/ Nodules | Previous Treatment (DMARDs only) | Concomitant Anti-rheumatic Therapy |
|---|---|---|---|---|---|---|
| 06 | 40/M | 3 | +ve | +ve/−ve | *Sal, Chl, Aur | **Nap 1 g |
| 07 | 54/F | 7 | −ve | +ve/−ve | DP, Myo, Sal, Aza, MTX | Para 1–2 g Cod 16–32 mg |
| 08 | 23/F | 11 | +ve | +ve/−ve | Chl, Myo, Sal, MTX, Aza | Pred 7.5 mg, Dicl 100 mg, Para 1–2 g Dext 100–200 mg |
| 09 | 51/F | 15 | −ve | +ve/+ve | Myo, Chl, DP, MTX | Pred 7.5 mg, Dicl 125 mg, Para 1–3 g |

*Sal = Sulphasalazine; Chl = chloroquine or hydroxychloroquine; Aur = auranofin; DP = D-penicillamine; Myo = Myocrisin; Aza = azathioprine; MTX = methotrexate.
**Nap = naprosyn (dosage/day); Para = paracetamol; Cod = codeine phosphate; Pred = prednisolone; Dicl = diclofenac; Dext = dextropropoxyphene.

TABLE 7

Disease Activity at Entry for Patients 1–5

| Patient Number | Morning Stiffness (mins) | Pain (10—10 cm on VAS) | Number Swollen Joints (0–28) | Richie Articular Index (0–69) | Grip Strength L/R (mm/Hg; max 300) | ESR (mm/hr normal ranges: F < 15; M < 10) | CRP (mg/l; normal range <10) | IDA (range 1–4) |
|---|---|---|---|---|---|---|---|---|
| 01 | 60 | 3.9 | 19 | 30 | 108/107 | 35 | 5 | 2.67 |
| 02 | 20 | 2.7 | 25 | 31 | 67/66 | 18 | 14 | 2.0 |
| 03 | 90 | 4.9 | 14 | 16 | 230/238 | 48 | 44 | 2.5 |
| 04 | 30 | 6.9 | 17 | 12 | 204/223 | 24 | 35 | 2.33 |
| 05 | 90 | 5.7 | 28 | 41 | 52/89 | 87 | 107 | 3.0 |

TABLE 8

Disease Activity at Entry for Patients 6–9

| Patient Number | Morning Stiffness (mins) | Pain (0–10 cm on VAS) | Number Swollen Joints (0–28) | Richie Articular Index (0–69) | Grip Strength L/R (mm/Hg; max 300) | ESR (mm/hr normal ranges: F < 15; M < 10) | CRP (mg/l; normal range <10) | IDA (range 1–4) |
|---|---|---|---|---|---|---|---|---|
| 06 | 120 | 5.0 | 3 | 4 | 260/280 | 23 | 33 | 2.33 |
| 07 | 105 | 7.4 | 27 | 31 | 59/80 | 25 | 10 | 2.83 |
| 08 | 270 | 9.3 | 17 | 37 | 73/125 | 35 | 31 | 3.17 |
| 09 | 180 | 4.5 | 20 | 26 | 53/75 | 15 | 33 | 2.5 |

All patients have tolerated the infusions of chimeric anti-CD4 and no serious adverse reactions have been observed. Specifically, no episodes of hemodynamic instability, fevers, or allergic reactions were observed in association with the infusions. Patients have not experienced any infections.

Although this is a non-blinded study, all patients experienced improvement in their clinical assessments of disease status, as well in biochemical parameters of inflammation measured in their serum.

Clinical assessments, including the duration of early morning stiffness; the assessment of pain on a visual analogue scale; total count of swollen joints; Ritchie articular index (a scaled score which assesses the total number of tender joints and the degree of joint tenderness); and Index of Disease Activity (a scaled score which incorporates several clinical and laboratory parameters), showed impressive improvements compared to controls. These improvements were typically in the range of an 80% drop from the baseline score; a degree of improvement which is well beyond the amount of improvement that can be attributed to placebo response. In addition, the duration of these improvements was for six to eight weeks in most cases, a duration of response far longer than would be anticipated from a placebo.

The improvements in clinical assessments were corroborated by improvements in biochemical inflammatory parameters measured in serum. The patients showed rapid drops of serum C-reactive protein, usually in the range of 80% from the baseline. Reductions in the erythrocyte sedimentation rate, usually in the range of 40%, were also observed. Circulating soluble TNF receptors were also decreased following therapy. The durations of the biochemical responses were similar to the duration of the clinical responses.

Preliminary assessment of immune responses to the chimeric anti-TNF antibody has shown no antibody response in the first four patients.

In summary, the preliminary evaluation of the results of this Phase I trial indicate that treatment of patients with advanced rheumatoid arthritis with anti-TNF MAb of the present invention is well tolerated and anti-TNF treatment is associated with rapid and marked improvement in clinical parameters of disease activity, including early morning stiffness, pain, and a number of tender and swollen joints; and is accompanied by improvement of biochemical parameters of inflammation.

Although this was an open label study, the magnitude of the clinical improvements is well beyond the degree of improvement that would be anticipated from a placebo response, such that the present invention is shown to have significant clinical efficacy for treating rheumatoid arthritis.

TABLE 9A

Flowchart for Chimeric Anti-TNF Study C0168TRA Group I
(10 mg/kg at day 1 and day 14)

|  | Pre-Scr | Screening | Wk 0 D 1 | Wk 0 D 2 | Wk 1 | Wk 2 D 14 | Wk 3 | Wk 4 | Wk 6 | Wk 8 |
|---|---|---|---|---|---|---|---|---|---|---|
| Consent | X | | | | | | | | | |
| Demography | | X | | | | | | | | |
| Physical Examination | | X | | | | | | | | X |
| Pregnancy Test | | X | | | | | | | | |
| Weight | | X | X | | | X | | | | X |
| Vital Signs | | X | X* | X | X | X* | X | X | X | X |
| Anti-TNF Infusion | | | X | | | X | | | | |
| Labs, see Chart | | X | X' | X | X | X' | X | X | X | X |
| Clinical (Safety) | | | | X | X | X' | X | X | X | X |
| Clinical (Response) | | X | X' | | X | X' | X | X | X | X |
| Synovial Biopsy | | X | | | X7 | | | | | |
| Response Evaluation | | | | | | | | | | X |
| Hematology + ESR | | X | X' | | X | X' | X | X | X | X |
| Biochemistry | | X | X' | | X | X' | X | X | X | X |
| Urinalysis | | | X' | | X | X' | X | X | X | X |
| CRP + RF | | | X' | | X | X' | X | X | X | X |
| Serum Cytokines | | | X' | | X | X' | X | X | X | X |
| PBL | | | X | X | X | | | | | |
| Pharmacokinetic | | | X# | X# | | X$ | | | | |
| HACA Response | | | X' | | X | X' | X | X | X | X |

X* = Vital signs will be obtained prior to infusion, every 30 minutes during the infusion and every 30 minutes for 2 hours after the infusion;
X' = Needs to be done prior to the infusion;
X# = Serum samples will be obtained prior to the infusion and at 1, 2, 4, 8, 12, and 24 hours after the end of the infusion;
X$ = Serum samples will be obtained to the infusion and at 2 hours after the end of the infusion.

TABLE 9B

Flowchart for Chimeric Anti-TNF Study C0168TRA Group 2
(5 mg/kg at days 1, 5, 9 and 13, 4 times total)

|  | Pre-Scr | Screening | Wk 0 D 1 | Wk 0 D 2 | Wk 0 D 5 | Wk 0 D 9 | Wk 1 D 13 | Wk 2 | Wk 3 | Wk 4 | Wk 6 | Wk 8 |
|---|---|---|---|---|---|---|---|---|---|---|---|---|
| Consent | X | | | | | | | | | | | |
| Demography | | X | | | | | | | | | | |
| Physical Examination | | X | | | | | | | | | | X |
| Pregnancy Test | | X | | | | | | | | | | |
| Weight | | X | X | | X | X | X | | | | | X |
| Vital Signs | | X | X* | X | X* | X* | X* | X | X | X | X | X |
| Anti-TNF Infusion | | | X | | X | X | X | | | | | |
| Labs, see Chart | | X | X' | X | X' | X' | X' | X | X | X | X | X |
| Clinical (Safety) | | | | X | X' | X' | X' | X | X | X | X | X |
| Clinical (Response) | | X | X' | | | X' | | X | X | X | X | X |
| Synovial Biopsy | | X | | | | | X7 | | | | | |
| Response Evaluation | | | | | | | | | | | | X |
| Hematology + ESR | | X | X' | | | X' | | X | X | X | X | X |
| Biochemistry | | X | X' | | | X' | | X | X | X | X | X |
| Urinalysis | | | X' | | | X' | | X | X | X | X | X |
| CRP + RF | | | X' | | | X' | | X | X | X | X | X |
| Serum Cytokines | | | X' | | | X' | | X | X | X | X | X |
| PBL | | | X | X | | X | | | | X | | |

TABLE 9B-continued

Flowchart for Chimeric Anti-TNF Study C0168TRA Group 2
(5 mg/kg at days 1, 5, 9 and 13, 4 times total)

| | Pre-Scr | Screening | Wk 0 D 1 | Wk 0 D 2 | Wk 0 D 5 | Wk 0 D 9 | Wk 1 D 13 | Wk 2 | Wk 3 | Wk 4 | Wk 6 | Wk 8 |
|---|---|---|---|---|---|---|---|---|---|---|---|---|
| Pharmacokinetic | | | X# | X# | X$ | X$ | X$ | | | | | |
| HACA Response | | | X' | | | X' | | X | X | X | X | X |

X* = Vital signs will be obtained prior to infusion, every 30 minutes during the infusion and every 30 minutes for 2 hours after the infusion;
X' = Needs to be done prior to the infusion;
X# = Serum samples will be obtained prior to the infusion and at 1, 2, 4, 8, 12, and 24 hours after the end of the infusion;
X$ = Serum samples will be obtained to the infusion and at 2 hours after the end of the infusion.

TABLE 10

Measurement of the Index of Disease Activity (DA) Variables of Disease Activity

| IDA Score | Morning Stiffness (min) | Pain (VAS, cm)* | Grip Strength (mmHg) | Ritchie Articular Index | Hemoglobin (g/dl) Male | Hemoglobin (g/dl) Female | ESR |
|---|---|---|---|---|---|---|---|
| 1 | <10 | 0–2.4 | >200 | 0 | >14.1 | >11.7 | 0.20 |
| 2 | 10–30 | 2.5–4.4 | 50–200 | 1–7 | 13–14 | 10.8–11.6 | 21–45 |
| 3 | 31–120 | 4.5–6.4 | 30–49 | 8–17 | 10–12.9 | 8.4–10.7 | 46–80 |
| 4 | >120 | 6.5–10 | <30 | >18 | <9.9 | <8.3 | >81 |

*Pain was measured on a visual analog scale (VAS) 0–10 cm.

Conclusions (1)

Safety of anti-TNF in RA

Anti-TNF was safe and very well tolerated:
no hemodynamic, febrile or allergic episodes;
no infections;
no clinical adverse events;
a single laboratory adverse event only, probably unrelated to anti-TNF.

Conclusions (2)

Efficacy of anti-TNF in RA

Anti-TNF therapy resulted in:
rapid and marked improvements in EMS, pain and articular index in most patients;
slower but marked improvement in swollen joint score, maximal by 3–4 weeks;
rapid and impressive falls in serum CRP, and a slower fall in ESR;
normalization of CRP and ESR in some patients;
rapid falls in serum C4d (a complement breakdown product) and IL-6 in patients where these indices were elevated at entry.
Duration of clinical improvements variable, with rebound in some patients at 6–8 weeks.

Accordingly, the present invention has been shown to have clinical efficacy in human patients for treating TNF involved pathologies using TNF MAbs of the present invention, such as for treating rheumatoid arthritis. Additionally, the human clinical use of TNF antibodies of the present invention in humans is also shown to correlate with in vitro data and in vivo animal data for the use of anti-TNF antibodies of the present invention for treating TNF-related pathologies.

EXAMPLE XXI

Treatment of Crohn's Disease in Humans Using Anti-TNFα Antibodies

Case History SB.

This 16 year old patient has a history of Crohn's disease since age 12. She was suffering from diarrhoea, rectal blood loss, abdominal pain, fever and weight loss. She showed perianal lesions, severe colitis and irregularity of the terminal ileum. She was treated with prednisolone (systemic and local) and PENTASA®. This resulted in remission of the disease, but she experienced extensive side effects of the treatment. She experienced severe exacerbations at age 12 and 12 yrs, 5 months, (IMMURAN™ added), 12 yrs, 9 months, 13 yrs, 5 months, and 14 yrs, 10 months. She experienced severe side effects (growth retardation, morbus Cushing, anemia, muscle weakness, delayed puberty, not able to visit school).

At 15 yrs, 11 months, she was diagnosed with a mass in the right lower quadrant. She had a stool frequency of 28 times per week (with as much as 10 times per day unproductive attempts). The Crohn's index was 311, the pediatric score 77.5. The sedimentation rate was elevated. Albumen and hemoglobin reduced. Before the first treatment the score was 291 and pediatric score was 60, and she would possibly have to lose her colon. She was infused on compassionate grounds with 10 mg/kg cA2, without any side effects noticed. One week after treatment her sedimentation rate was reduced from 66 to 32 mm. The Crohn's index was 163 and pediatric score 30. She was reported to feel much better and the frequency of the stools was reduced greatly. There was apparently no more diarrhoea, but normal faeces. On October 15th, before the second infusion she had gained weight, had a sedimentation rate of 20 mm, an albumen of 46 h/l, Crohn's index 105, pediatric score 15. There seemed to be improvement on video endoscopy. A second infusion was performed at 16 yrs.

The patient was greatly improved after the second infusion. A endoscopy showed only 3 active ulcers and scar tissue.

This is in contrast with her colon on admission when the thought was that her colon should be removed. This case history shows a dramatic improvement of severe Crohn's disease upon treatment with cA2 anti-TNF antibody.

TABLE 11

| | | Case History SB |
|---|---|---|
| 11 y, 8 m | Physical Examination | Diarrhoea, rectal blood loss, abdominal pain, fever (40%) weight loss perianal lesions |
| | Sigmoidoscopy | Severe colitis, probably M. Crohn |
| | Enterolysis | Irregularity terminal ileum |
| | Therapy | Prednisolone 10 mg 3 dd PENTASA ® 250 mg 3 dd Enema (40 mg prednisone, 2 g 5 ASA) ml 1 dd |
| | Result | Remission, however: extensive side effects of prednisone and stunting growth |
| | Action | Prednisone |
| 11 y, 11 m | Exacerbation | Same clinical picture as 11 y, 8 m |
| | Sigmoidoscopy | Recurrence of colitis (grade IV) in last 60 cm and anus |
| | Therapy | Prednisolone 40 mg 1 dd PENTASA ® 500 mg 3 dd Enema 1 dd |
| | Result | Better |
| 12 y, 5 m | Severe Exacerbation | Despite intensive treatment |
| | Sigmoidoscopy | Extensive perianal and sigmoidal lesions; active disease |
| | Therapy | Continued + IMMURAN ™ 25 mg 1 dd |
| | Result | Slight improvement, however still growth retardation, cushing, anaemia, muscle weakness |
| | Action | Prednisone |
| 12 y, 9 m | Exacerbation | |
| | Sigmoidoscopy | Extensive (active colitis, polyps) |
| | Action | Prednisone: 30 mg 1 dd, IMMURAN ™ 50 mg 1 dd PENTASA ® 500 mg 3 dd Enema 2 dd |
| | Result | Still needs enemas with prednisone and oral prednisone. Delayed puberty, stunting growth |
| 14 y, 10 m | Severe Exacerbation | Weight loss, abdominal pain, fever |
| | Ileoscopy | Active colitis (grade IV), perianal lesions. Terminal ileum normal |
| | Result | No remission still fever, poor appetite, weight loss, diarrhea, not able to visit school |
| | | Important Findings |
| 14 y, 11 m | | 151.9 cm; 34 kg; t = 38° C., Abdominal mass in right lower quadrant; stool frequency 28 per week (however goes 10–15 times a day but most often without success); ESR 55 mm; Hb 6.2 mmol/l; Ht 0, 29 l/l; alb. 38.4 g/l Crohn's Dis./Act Index: 311 Pediatric score: 77.5 |
| 14 y, 11.2 m | | 151.8 cm; 34.6 kg; (before 1st infusion) Crohn's Dis/Act Index: 291 Pediatric score: 60 |
| 14 y, 11.4 m | | 151.8 cm; 34.6 kg; ESR 332 mm; Hb 5.7 mmol/l Crohn's Dis/Act Index: 163 Pediatric score: 30 |
| 15 y, 0 m | | 152.1 cm: 34.8 kg (before 2nd infusion) Feels like she has never felt before. Parents also very enthusiastic; ESR 30 mm: Hb 6.3 mol/l; Ht 0, 32 11; Alb 46 g/l Crohn Dis/Act Index: 105 Pediatric Score: 15 Videoendoscopy: Improvement No problems or side effects observed during and following infusion. |

Accordingly, anti-TNF antibodies according to the present invention, as exemplified by cA2, are shown to provide successful treatment of TNF related pathologies, as exemplified by Crohn's disease, in human patients with no or little side effects.

EXAMPLE XXII

Treatment of Arthritis in Humans Using Chimeric Immunoglobulin Chain of the Present Invention Patient Selection Twenty patients were recruited, each of whom fulfilled the revised American Rheumatism Association criteria for the diagnosis of RA (Arnett et al., *Arthritis Rheum.* 31:315–324 (1988). The clinical characteristics of the patients are shown in Table 12. The study group comprised 15 females and 5 males, with a median age of 51 years (range 23–72), a median disease duration of 10.5 years (range 3–20) and a history of failed therapy with standard disease-modifying anti-rheumatic drugs (DMARDs; median number of failed DMARDs: 4, range 2–7). Seventeen were seropositive at entry or had been seropositive at some stage of their disease, all had erosions on X-Rays of hands or feet, and 3 had rheumatoid nodules. All patients had active disease at trial entry, as defined by an Index of Disease Activity (IDA; Mallya et al., *Rheumatol. Rehab.* 20:14–17 (1981) of at least 1.75, together with at least 3 swollen joints, and were classed as anatomical and functional activity stage 2 or 3' (Steinbrocker et al., *JAMA* 140:659–662 (1949). The pooled data for each of the clinical and laboratory indices of disease activity at the time of screening for the trial (up to 4 weeks prior to trial entry), and on the day of trial entry itself (week 0), are shown in Tables 13 and 14.

TABLE 12

Demographic Features of 20 Patients with Refractory Rheumatoid Arthritis

| Pat | Age/Sex | DD (yr) | Previous DMARDs | Concomitant therapy |
|---|---|---|---|---|
| 1 | 48/F | 7 | SSZ, DP, GST, AUR, MTX, AZA, HCQ | Pred 5 mg |
| 2 | 63/F | 7 | SSZ, GST, DP | Para 1–2 g |
| 3 | 59/M | 3 | AUR, HCQ, GST, MTX, SSZ | Pred 10 mg; Indo 225 mg |
| 4 | 56/M | 10 | GST, DP, AZA, SSZ | Pred 12.5 mg; Ibu 2 g; Para 1–2 g |
| 5 | 28/F | 3 | GST, SSZ, DP, AZA | Pred 8 mg; Para 1–2 g; Cod 16 mg |
| 6 | 40/M | 3 | SSZ, HCQ, AUR | Nap 1 g |
| 7 | 54/F | 7 | DP, GST, SSZ, AZA, MTX | Para 1–2 g; Cod 16–32 mg |
| 8 | 23/F | 11 | HCQ, GST, SSZ, MTX, AZA | Pred 7.5 mg; Dicl 100 mg; Para 1–2 g; Dex 100–200 mg |
| 9 | 51/F | 15 | GST, HCQ, DP, MTX | Pred 7.5 mg; Dicl 125 mg; Para 1–3 g |
| 10 | 47/F | 12 | SSZ, CYC, MTX | Ben 4 g |
| 11 | 34/F | 10 | DP, SSZ, MTX | Pred 10 mg; Para 1.5 g; Cod 30–90 mg |
| 12 | 57/F | 12 | GST, MTX, DP, AUR | Asp 1.2 g |
| 13 | 51/F | 7 | SSZ, AZA | Para 1–4 g |
| 14 | 72/M | 11 | GST, DP, AZA, MTX | Pred 5 mg; Para 1–4 g; Cod 16–63 mg |
| 15 | 51/F | 17 | HCQ, DP, SSZ, MTX | Asp 0.3 g |
| 16 | 62/F | 16 | GST, DP, SSZ, MTX, AZA | Para 1–4 g; Cod 16–64 mg |
| 17 | 56/F | 11 | SSZ, DP, GST, MTX, HCQ, AZA | Pred 7.5 mg; Eto 600 mg; Para 1–2 g; Dext 100–200 mg |
| 18 | 48/F | 14 | GST, MTX, DP, SS, ZAUR, AZA | Pred 7.5 mg; Indo 100 mg; Para 1–3 g |
| 19 | 42/F | 3 | SSZ, MTX | Fen 450 mg; Ben 6 g; Cod 30 mg |
| 20 | 47/M | 20 | GST, DP, SSZ, AZA | Pred 10 mg; Para 1–3 g |

Pat. = Patient;
DD(yrs) = Disease duration (years);
DMARDs = disease-modifying anti-rheumatic drugs;
SSZ = sulphasalazine;
DP = D-penicillamine;
GST = gold sodium thiomalate;
AUR = auranofin;
MTX = methotrexate;
AZA = azathioprine;
HCQ = (hydroxy)chloroquine;
CYC = cyclophosphamide.
Pred = prednisolone (dose/day);
Para = paracetamol;
Indo = Indomethacin;
Ibu = ibuprofen;
Cod = codeine phosphate;
Nap = naprosyn;
Dicl = diclofenac;
Dext = dextropropoxyphene;
Ben = benorylate;
Asp = aspirin;
eto = etodolac;
Fen = fenbufen.

TABLE 13

Changes in Clinical Assessments Following Treatment of Rheumatoid Arthritis Patients with cA2

| Week of Trial | Morning Stiffness (min) | Pain Score (0–10) cm | Ritchie Index (0–69) | Swollen Joints (0–28) number | Grip Strength (L) (0–300) mm Hg | Grip Strength (R) (0–300) mm Hg | IDA (1–4) | Patient Assessment (grades improved 0–3) |
|---|---|---|---|---|---|---|---|---|
| Screen | 135 | 7.4 | 23 | 16 | 84 | 96 | 3 | NA |
|  | (0–600) | (4–9.7) | (4–51) | (4–28) | (45–300) | (57–300) | (2.3–3.3) |  |
| p value 0 | 180 | 7.1 | 28 | 18 | 77 | 92 | 2 | NA |
|  | (20–600) | (2.7–9.7) | (4–52) | (3–27) | (52–295) | (50–293) | (2–3.5) |  |
| p value 1 | 20 | 2.6 | 13 | 13.5 | 122 | 133 | 2 | 1 |
|  | (0–180) | (0.6–7.8) | (2–28) | (1–25) | (66–300) | (57–300) | (1.5–3.3) | (1–3) |
|  | <0.001 | <0.001 | <0.001; <0.002 | >0.05 | >0.05 | >0.05 | <0.001 | NA |
| p value 2 | 15 | 3.0 | 13 | 11.5 | 139 | 143 | 2 | 1.5 |
|  | (0–150) | (0.2–6.4) | (1–28) | (1–22) | (75–300) | (59–300) | (1.5–3.2) | (1–3) |
|  | <0.001 | <0.001 | <0.001 | <0.003; <0.02 | <0.03; >0.05 | >0.05 | <0.001 | NA |
| p value 3 | 5 | 2.2 | 8 | 6 | 113 | 142 | 2 | 2 |
|  | (0–150) | (0.2–7.4) | (0–22) | (1–19) | (51–300) | (65–300) | (1.2–3.2) | (1–2) |
|  | <0.001 | <0.001 | <0.001 | <0.001; <0.002 | >0.05 | >0.05 | <0.001 | NA |
| p value 4 | 15 | 1.90 | 10 | 6 | 124 | 148 | 1.8 | 2 |
|  | (0–90) | (0.1–5.6) | (0–17) | (0–21) | (79–300) | (64–300) | (1.3–2.7) | (1–2) |
|  | <0.001 | <0.001 | <0.001 | <0.001; <0.002 | <0.02; >0.05 | <0.03; >0.05 | <0.001 | NA |
| p value 6 | 5 | 1.9 | 6 | 5 | 119 | 153 | 1.7 | 2 |
|  | (0–90) | (0.1–6.2) | (0–18) | (1–14) | (68–300) | (62–300) | (1.3–2.8) | (1–2) |
|  | <0.001 | <0.001 | <0.001 | <0.001 | <0.04; >0.05 | <0.05; >0.05 | <0.001 | NA |
| p value 8 | 15 | 2.1 | 8 | 7 | 117 | 167 | 1.8 | 2 |
|  | (0–60) | (0.2–7.7) | (1–28) | (1–18) | (69–300) | (52–300) | (1.5–2.8) | (1–3) |
|  | <0.001 | <0.001 | <0.001 | <0.001 | <0.03; >0.05 | <0.03; >0.05 | <0.001 | NA |

Datas are expressed as the median (range) of values from 20 patients;
data from patient 15 were not included after week 2 (dropout);
P values show significance by Mann-Whitney test compared with week 0 values; adjusted for multiple statistical comparisons.
IDA = Index of disease activity;
NA = not applicable.

TABLE 14

Changes in Laboratory Measures Following Treatment of Rheumatoid Arthritis patients with cA2

| Week of Trial | Hgb g/liter | WBC × 10/ liter | Platelet Count × 10/ liter | ESR mm/hour | CRP mg/liter | SAA mg/ml | RF Inverse titer |
|---|---|---|---|---|---|---|---|
| Screen | 117 | 7.9 | 353 | 59 | 42 | ND | ND |
|  | (98–146) | (3.9–15.2) | (274–631) | (18–87) | (9–107) |  |  |
| P value 0 | 113 | 9.0 | 341 | 55 | 39.5 | 245 | 2,560 |
|  | (97–144) | (4.9–15.7) | (228–710) | (15–94) | (5–107) | (18–1900) | (160–10,240) |
| p value 1 | 114 | 8.5 | 351 | 26 | 5 | 58 | ND |
|  | (96–145) | (3.6–13.6) | (223–589) | (13–100) | (0–50) | (0–330) |  |
|  | >0.05 | >0.05 | >0.05 | >0.05 | <0.001 | <0.001; <0.003 |  |
| p value 2 | 112 | 8.2 | 296 | 27 | 5.5 | 89 | ND |
|  | (95–144) | (4.3–12.7) | (158–535) | (10–90) | (0–80) | (11–900) |  |
|  | >0.05 | >0.05 | <0.04; >0.05 | <0.02; >0.05 | <0.001; <0.003 | <0.02; <0.04 |  |
| p value 3 | 110 | 9.0 | 289 | 27 | 7 | ND | ND |
|  | (89–151) | (3.7–14.4) | (190–546) | (12–86) | (0–78) |  |  |
|  | >0.05 | >0.05 | <0.03; >0.05 | <0.04; >0.05 | <0.01; <0.002 |  |  |
| p value 4 | 112 | 8.2 | 314 | 23 | 10 | ND | ND |
|  | (91–148) | (4.7–13.9) | (186–565) | (10–87) | (0–91) |  |  |
|  | >0.05 | >0.05 | >0.05 | <0.04; >0.05 | <0.004; <0.02 |  |  |
| p value 6 | 116 | 9.1 | 339 | 23 | 8 | ND | ND |
|  | (91–159) | (2.9–13.9) | (207–589) | (12–78) | (0–59) |  |  |
|  | >0.05 | >0.05 | >0.05 | <0.03; >0.05 | <0.001 |  |  |

TABLE 14-continued

Changes in Laboratory Measures Following Treatment
of Rheumatoid Arthritis patients with cA2

| Week of Trial | Hgb g/liter | WBC × 10/ liter | Platelet Count × 10/ liter | ESR mm/hour | CRP mg/liter | SAA mg/ml | RF Inverse titer |
|---|---|---|---|---|---|---|---|
| p value 8 | 114 (94–153) >0.05 | 7.6 (4.2–13.5) >0.05 | 339 (210–591) >0.05 | 30 (7–73) >0.05 | 6 (0–65) <0.001 | ND | 480 (40–05,120) >0.05 |

Data are expressed as the median (range) of values from 20 patients; data from patient 15 were not included after week 2 (dropout).
For rheumatoid factor (RF), only those patients with week 0 titers >1/160 in the particle agglutination assay were included (No. = 14).
P values show significance by Mann-Whitney test compared with week 0 values; adjusted for multiple statistical comparisons;
ND = not done.
Normal ranges: hemoglobin (Hgb) 120–160 g/liter (F), 135–175 g/liter (M); white blood cell count (WBC) 3–11 × $10^9$/liter; platelet count 150–400 × $10^9$/liter; erythrocyte sedimentation rate (ESR) <15 mm/hour (F), <10 mm/hour (M); C-reactive protein (CRP) <10 mg/liter; serum amyloid A(SAA) <10 mg/ml.

All DMARDs were discontinued at least 1 month prior to trial entry. Patients were allowed to continue on a nonsteroidal anti-inflammatory drug and/or prednisolone (<12.5 mg/day) during the trial. The dosage of these agents was kept stable for 1 month prior to trial entry and during the course of the trial, and no parenteral corticosteroids were allowed during these periods. Simple analgesics were allowed ad libitum. Patients with other serious medical conditions were excluded. Specific exclusions included serum creatinine >150 umol/liter (normal range 60–120 umol/liter), hemoglobin (Hgb) <90 gm/liter (normal range 120–160 gm/liter [females]; 135–175 gm/liter [males]), white blood cell count (WBC) <4×10 g/liter (normal range 4–11×$10^9$/liter), platelet count <100×10 g/liter (normal range 150–400×$10^9$/liter), and abnormal liver function tests or active pathology on chest X-Ray.

All patients gave their informed consent for the trial, and approval was granted by the local ethics committee.

Treatment

The cA2 antibody was stored at 4° C. in 20 ml vials containing 5 mg of cA2 per milliliter of 0.01 M phosphate buffered saline in 0.15M sodium chloride at a pH of 7.2 and was filtered through a 0.2 μm sterile filter before use. The appropriate amount of cA2 was then diluted to a total volume of 300 ml in sterile saline and administered intravenously via a 0.2 μm in-line filter over a 2 hour period.

Patients were admitted to hospital for 8–24 hours for each treatment, and were mobile except during infusions. The trial was of an open, uncontrolled design, with a comparison of two treatment schedules. Patients 1 to 5 and 11 to 20 received a total of 2 infusions, each of 10 mg/kg cA2, at entry to the study (week 0) and 14 days later (week 2). Patients 6 to 10 received 4 infusions of 5 mg/kg activity included complete blood counts, C-reactive protein (CRP; by rate nephelometry) and the erythrocyte sedimentation rate (ESR; Westergren). Follow-up assessments were made at monthly intervals after the conclusion of the formal trial period, in order to assess the duration of response.

Analysis of improvement in individual patients was made using two separate indices. Firstly, an index of disease activity (IDA) was calculated for each time point according to the method of Mallya and Mace (Mallya et al., Rheumatol. Rehab. 20:14–17 (1981), with input variable of morning stiffness, pain score, Ritchie Index, grip strength, ESR and Hgb. The second index calculated was that of Paulus (Paulus et al., Arthritis Rheum. 33:477–484 (1990) which uses input variables of morning stiffness, ESR, joint pain/tenderness, joint swelling, patient's and physician's global assessment of disease severity. In order to calculate the presence or otherwise of a response according to this index, two approximations were made to accommodate our data. The 28 swollen joint count used by us (nongraded; validated in Fuchs et al., Arthritis Rheum. 32:531–537 (1989)) was used in place of the more extensive graded count used by Paulus, and the patient's and physician's global assessments of response recorded by us were approximated to the global assessments of disease activity used by Paulus infra. In addition to determining response according to these published indices, we selected 6 disease activity assessments of interest (morning stiffness, pain score, Ritchie index, swollen joint count, ESR and CRP) and calculated their mean percentage improvement. We have used FIGS. 24 and 25 to give an indication of the degree of improvement seen in responding patients.

Immunological Investigations

Rheumatoid factors were measured using the rheumatoid arthritis particle agglutination assay (PAPA, FujiBerio Inc., Tokyo, Japan), in which titers of 1/160 or greater were considered significant. Rheumatoid factor isotypes were measured by ELISA (Cambridge Life Sciences, Ely, UK). The addition of cA2 at concentrations of up to 200 μg/ml to these assay cA2, at entry, and days 4, 8 and 12. The total dose received by the 2 patient groups was therefore the same at 20 mg/kg.

Assessment Safety Monitoring

Vital signs were recorded every 15 to 30 minutes during infusions, and at intervals for up to 24 hours post infusion. Patients were questioned concerning possible adverse events before each infusion and at weeks 1, 2, 3, 4, 6, and 8 of the trial. A complete physical examination was performed at screening and week 8. In addition, patients were monitored by standard laboratory tests including complete blood count, C3 and C4 components of complement, IgG, IgM and IgA, serum electrolytes, creatinine, urea, alkaline phosphatase, aspartate transaminase and total bilirubin. Sample times for these tests were between 0800 and 0900 hours (pre-infusion) and 1200–1400 hours (24 hours post completion of the infusion). Blood tests subsequent to day 1 were performed in the morning, usually between 0700 and 1200 hours. Urine analysis and culture were also performed at each assessment point.

Response Assessment

The patients were assessed for response to cA2 at weeks 1, 2, 3, 4, 6 and 8 of the trial. The assessments were all made between 0700 and 1300 hours by the same observer. The following clinical assessments were made: duration of morning stiffness (minutes), pain score (0 to 10 cm on a visual analog scale), Ritchie Articular Index (maximum 69; Ritchie et al., *Quart. J. Med.* 147:393–406 (1968)), number of swollen joints (28 joint count; validated in Fuchs et al., *Arthritis Rheum.* 32:531–537 (1989), grip strength (0 to 300 mm Hg, mean of 3 measurements per hand by sphygmomanometer cuff) and an assessment of function (the Stanford Health Assessment Questionnaire (HAQ) modified for British patients; 34). In addition, the patients' global assessments of response were recorded on a 5-point scale (worse, no response, fair response, good response, excellent response). Routine laboratory indicators of disease systems did not alter assay results (data not shown). Antinuclear antibodies were detected by immunofluorescence on HEpo 2 cells (Biodiagnostics, Upton, Worcs. UK) and antibodies to extractable nuclear antigens were measured by counter immunoelectrophoresis with poly-antigen extract (Biodiagnostics). Sera positive by immunofluorescence were also screened for antibodies to DNA by the Farr assay (Kodak Diagnostics, Amersham, UK). Anti-cardiolipin antibodies were measured by ELISA (Shield Diagnostics, Dundee, Scotland). Serum amyloid A (SAA) was measured by sandwich ELISA (Biosource International, Camarillo, Calif., USA). Antiglobulin responses to the infused chimeric antibody were measured by an in-house ELISA, using cA2 as a capture reagent.

Cytokine Assays

Bioactive TNF was measured in sera using the WEHI 164 clone 13 cytotoxicity assay (Espevik et al., *J. Imm. Methods* 95:99–105 (1986). Total IL -6 was measured in sera using a commercial immunoassay (Medgenix Diagnostics, SA, Belgium) and by a sandwich ELISA developed "in house" using monoclonal antibodies provided by Dr. F. di Padova (Basel, Switzerland). Microtiter plates were coated with monoclonal antibody LNI 314-14 at a concentration of 3 ug/ml for 18 hours at 4° C. and blocked with 3% bovine serum albumin in 0.1M phosphate buffered saline, pH 7.2. Undiluted sera or standards (recombinant hIL 6, 0–8.1 ug/ml) were added to the wells in duplicate and incubated for 18 hours at 4° C. Bound IL-6 was detected by incubation with monoclonal antibody LNI 110-14 for 90 minutes at 37° C., followed by biotin labeled goat anti-murine IgG2b for 90 minutes at 37° C. (Southern Biotechnology, Birmingham, Ala.). The assay was developed using streptavidin-alkaline phosphatase (Southern Biotechnology) and p-nitrophenylphosphate as a substrate and the optical density read at 405 nm.

Statistics

Comparisons between week 0 and subsequent time points were made for each assessment using the Mann-Whitney test. For comparison of rheumatoid factor (RAPA) titers, the data were expressed as dilutions before applying the test.

This was an exploratory study, in which prejudgements about the optimal times for assessment were not possible. Although it has not been common practice to adjust for multiple statistical comparisons in such studies, a conservative statistical approach would require adjustment of p values to take into account analysis at several time points. The p values have therefore been presented in two forms: unadjusted, and after making allowance for analysis at multiple time points by use of the Bonferroni adjustment. Where p values remained <0.001 after adjustment, a single value only is given. A p value of <0.05 is considered significant.

Results

Safety of cA2

The administration of cA2 was exceptionally well tolerated, with no headache, fever, hemodynamic disturbance, allergy or other acute manifestation. No serious adverse events were recorded during the 8-week trial. Two minor infective episodes were recorded, patient 15 presented at week 2 with clinical features of bronchitis and growth of normal commensals only on sputum culture. She had a history of smoking and of a similar illness 3 years previously. The illness responded promptly to treatment with amoxicillin, but her second cA2 infusion was withheld and the data for this patient are therefore not analyzed beyond week 2. Patient 18 showed significant bacteriuria on routine culture at week 6 (>$10^5$/ml; lactose fermenting coliform), but was asymptomatic. This condition also responded promptly to amoxicillin.

Routine analysis of blood samples showed no consistent adverse changes in hematological parameters, renal function, liver function, levels of C3 or C4 or immunoglobulins during the 8 weeks of the trial. Four minor, isolated and potentially adverse laboratory disturbances were recorded. Patient 2 experienced a transient rise in blood urea, from 5.7 mmol/liter to 9.2 mmol/liter (normal range 2.5 to 7 mmol/liter), with no change in serum creatinine. This change was associated with the temporary use of a diuretic, prescribed for a non-rheumatological disorder. The abnormality normalized within 1 week and was classified as "probably not" related to cA2. Patient 6 experienced a transient fall in the peripheral blood lymphocyte count, from 1.6 to $0.8 \times 10^9$/liter (normal range $1.0 – 4.8 \times 10^9$/liter). This abnormality normalized by the next sample point (2 weeks later), was not associated with any clinical manifestations and was classified as "possible related" to cA2. Patients 10 and 18 developed elevated titers of anti-DNA antibodies at weeks 6 and 8 of the trial, with elevated anti-cardiolipin antibodies being detected in patient 10 only. Both patients had a pre-existing positive antinuclear antibody and patient 10 had a history of borderline lymphocytopenia and high serum IgM. There were no clinical features of systemic lupus erythematosus and the laboratory changes were judged 'possibly related' to cA2.

Efficacy of cA2 Disease Activity

Figure 24:
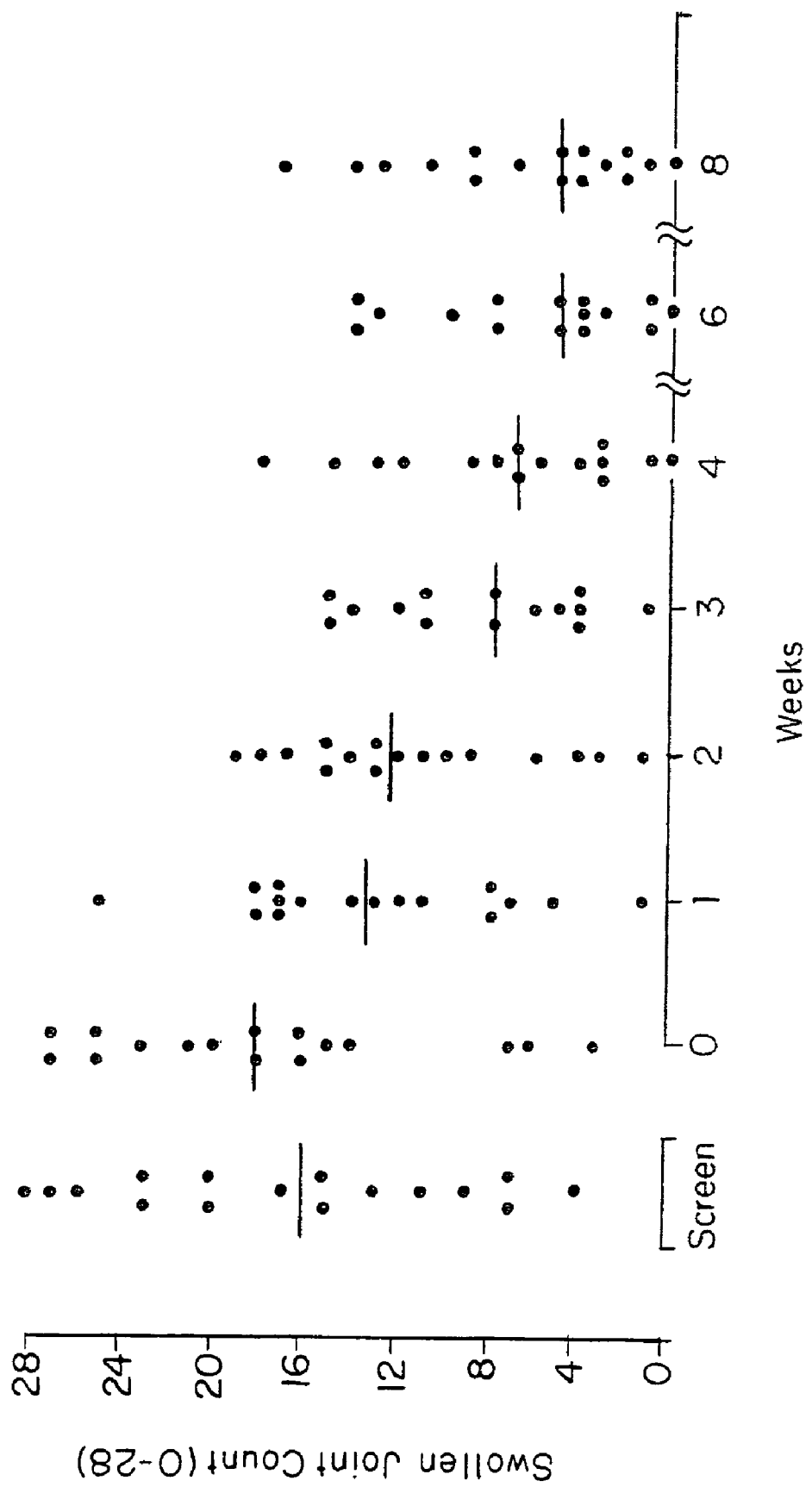
FIG. 24 is a graphical representation of swollen joint counts (maximum 28), as recorded by a single observer. Circles represent individual patients and horizontal bars show median values at each time point. The screening time point was within 4 weeks of entry to the study (week 0); data from patient 15 were not included after week 2 (dropout). Significance of the changes, relative to week 0, by Mann Whitney test, adjusted: week 1, p>0.05; week 2, p<0.02; weeks 3–4, p<0.002; weeks 6–8, p<0.001.
Figure 25:
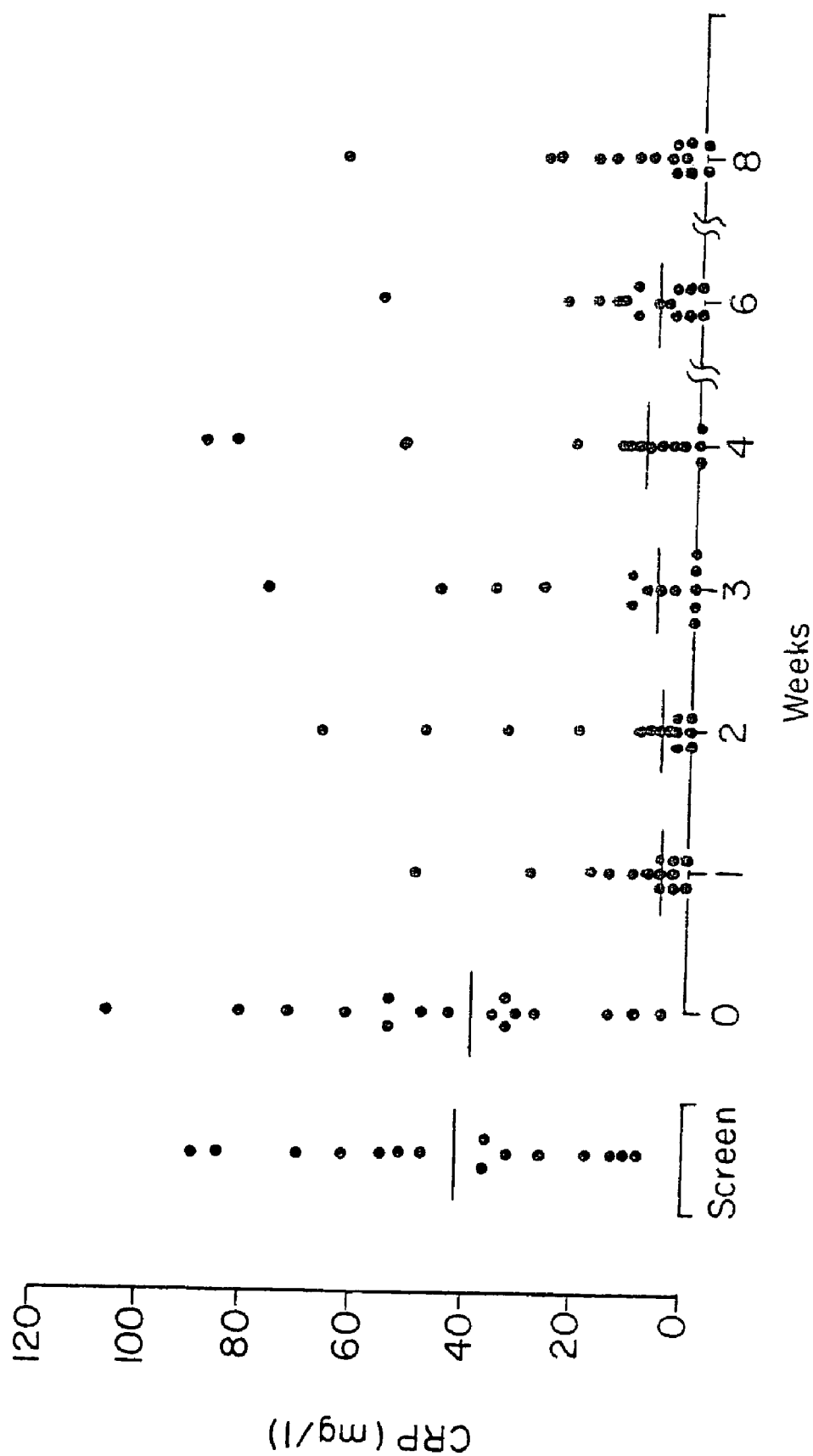
FIG. 25 is a graphical representation of levels of serum C—reactive protein (CRP)—Serum CRP (normal range 0–10 mg/liter), measured by nephelometry. Circles represent individual patients and horizontal bars show median values at each time point. The screening time point was within 4 weeks of entry to the study (week 0); data from patient 15 were not included after week 2 (dropout). Significance of the changes, relative to week 0, by Mann-Whitney test, adjusted: week 1, p<0.001; week 2, p<0.003; week 3, p<0.002; week 4, p<0.02; week 6,8, p<0.001.

The pattern of response for each of the clinical assessments of disease activity and the derived IDA are shown in Table 13. All clinical assessments showed improvement following treatment with cA2, with maximal responses from week 3. Morning stiffness fell from a median of 180 minutes at entry to 5 minutes at week 6 ($p<0.001$, adjusted), representing an improvement of 73%. Similarly, the Ritchie Index improved from 28 to 6 at week 6, ($p<0.001$, adjusted, 79% improvement) and the swollen joint count fell from 18 to 5, ($p<0.001$, adjusted, 72% improvement). The individual swollen joint counts for all time points are shown in FIG. 24. Grip strength also improved; the median grip strength rose from 77 (left) and 92 (right) mm Hg at entry to 119 (left) and 153 (right) mmHg at week 6 ($p<0.04$, $p<0.05$, left and right respectively; $p>0.05$ after adjustment for multiple comparisons). The IDA showed a fall from a median of 3 at entry to 1.7 at week 6 (p<0.001, adjusted). Patients were asked to grade their responses to cA2 on a 5 point scale. No patient recorded a response of "worse" or "no change" at any point in the trial. "Fair", "good" and "excellent" responses were classed as improvements of 1, 2 and 3 grades respectively. At week 6, the study group showed a median of 2 grades of improvement (Table 13).

We also measured changes in the patients' functional capacity, using the HAQ modified for British patients (range 0–3). The median (range) HAQ score improved from 2 (0.9–3) at entry to 1.1 (0–2.6) by week 6, (p<0.001;p<0.002 adjusted).

The changes in the laboratory tests which reflect disease activity are shown in Table 14. The most rapid and impressive changes were seen in serum CRP, which fell from a median of 39.5 mg/liter at entry to 8 mg/liter by week 6 of the trial (p<0.001, adjusted; normal range <10 mg/liter), representing an improvement of 80%. Of the 19 patients with elevated CRP at entry, 17 showed falls to the normal range at some point during the trial. The improvement in CRP was maintained in most patients for the assessment period (Table 14 and FIG. 25); the exceptions with high values at 4 and 6 weeks tended to be those with the highest starting values (data not shown). The ESR also showed improvement, with a fall from 55 mm/hour at entry to 23 mm/hour at week 6 (p<0.03; p>0.05 adjusted; 58% improvement; normal range <10 mm/hour, <15 mm/hour, males and females respectively). SAA levels were elevated in all patients at trial entry, and fell from a median of 245 mg/ml to 58 mg/ml at week 1 (p<0.003, adjusted; 76% improvement; normal range <10/mg/ml) and to 80 mg/ml at week 2 (p<0.04, adjusted). No significant changes were seen in Hgb, WBC or platelet count at week 6, although the latter did improve at weeks 2 and 3 compared with trial entry (Table 14).

The response data have also been analyzed for each individual patient. The majority of patients had their best overall responses at week 6, at which time 13 assessed their responses as "good" while 6 assessed their responses as "fair". Eighteen of the 19 patients who completed the treatment schedule achieved an improvement in the index of Disease Activity (Mallya et al., *Rheumatol. Rehab.* 20:14–17 (1981) of 0.5 or greater at week 6, and 10 achieved an improvement of 1.0 or greater. All patients achieved a response at week 6 according to the index of Paulus (Paulus et al., *Arthritis Rheum.* 33:477–484 (1990). Finally, all patients showed a mean improvement at week 6 in the 6 selected measures of disease activity (as presented above) of 30% or greater, with 18 of the 19 patients showing a mean improvement of 50% or greater.

Although the study was primarily designed to assess the short-term effects of cA2 treatment, follow-up clinical and laboratory data are available for those patients followed for sufficient time (number=12). The duration of response in these patients, defined as the duration of a 30% (or greater) mean improvement in the 6 selected disease activity measures, was variable, ranging from 8 to 25 (median 14) weeks.

Comparison of the clinical and laboratory data for patients treated with 2 infusions of cA2 (each at 10 m/kg) compared with those treated with 4 infusions (each at 5 mg/kg) showed no significant differences in the rapidity or extent of response (data not shown).

Immunological Investigations and Cytokines

Measurement of rheumatoid factor by RAPA showed 14 patients with significant titers (>1/160) at trial entry. Of these, 6 patients showed a fall of at least 2 titers on treatment with cA2, while the remaining patients showed a change of 1 titer or less. No patient showed a significant increase in RF titer during the trial. The median RF titer in the 11 patients fell from 1/2, 560 at entry to 1/480 by week 8 (p>0.05; Table 14). Specific RF isotypes were measured by ELISA, and showed falls in the 6 patients whose RAPA had declined significantly, as well as in some other patients. Median values for the three RF isotypes in the 14 patients seropositive at trial entry were 119, 102 and 62 IU/ml (IgM, IgG and IgA isotypes respectively) and at week 8 were 81, 64 and 46 IU/ml (p>0.05).

We tested sera from the first 9 patients for the presence of bioactive TNF, using the WEHI 164 clone 13 cytotoxicity assay (Espevik et al., *J. Imm. Methods* 95:99–105 (1986). In 8 patients, serum sets spanning the entire trial period were tested, while for patient 9, one pre-trial, one period were tested, patient, one pre, one intermediate and the last available sample only were tested. The levels of bioactive TNF were below the limit of sensitivity of the assay in the presence of human serum (1 pg/ml). Since production of CRP and SAA are thought to be regulated in large part by IL-6, we also measured serum levels of this cytokine, using 2 different assays which measure total IL-6. In the Medgenix assay, IL-6 was significantly elevated in 17 of the 20 patients at entry. In this group, levels fell from 60 (18–500) pg/ml to 40 (0–230) pg/ml at week 1 (p>0.05; normal range <10 pg/ml) and to 32 (0–210) pg/ml at week 2 (p<0.005, p<0.01, adjusted). These results were supported by measurement of serum IL-6 in the first 16 patients in a separate ELISA developed in-house. IL-6 was detectable in 11 of the 16, with median (range) levels falling from 210 (25–900) pg/ml at entry to 32 (01,700) pg/ml at week 1 (p<0.02, p<0.04, adjusted; normal range <10 pg/ml) and to 44 (0–240) pg/ml at week 2 (p<0.02, p<0.03, adjusted).

We tested sera from the first 10 patients for the presence of anti-globulin responses to the infused chimeric antibody, but none were detected. In many patients however, cA2 was still detectable in serum samples taken at week 8 and this can have interfered with the ELISA.

Discussion

This is the first report describing the use of anti-TNFα antibodies in human autoimmune disease. Many cytokines are produced in rheumatoid synovium, but we chose to target specifically TNFα because of mounting evidence that it was a major molecular regulator in RA. The study results presented here support that view and allow three important conclusions to be drawn.

First, treatment with cA2 was safe and the infusion procedure was well tolerated. Although fever, headache, chills and hemodynamic disturbance have all been reported following treatment with anti CD4 or anti CDw52 in RA, such features were absent in our patients. Also notable was the absence of any allergic event despite repeated treatment with the chimeric antibody, although the interval between initial and repeat infusions can have been too short to allow maximal expression of any anti-globulin response. The continuing presence of circulating cA2 at the conclusion of the trial may have precluded detection of antiglobulin responses, but also implied that any such responses were likely to be of low titre and/or affinity. Although we recorded 2 infective episodes amongst the study group, these were minor and the clinical courses were unremarkable. TNFα has been implicated in the control of listeria and other infections in mice (Havell et al., *J. Immunol.* 143:2894–2899 (1989), but our limited experience does not suggest an increased risk of infections after TNFα blockade in man.

The second conclusion concerns the clinical efficacy of cA2. The patients we treated had long-standing, erosive, and for the most part seropositive disease, and had each failed therapy with several standard DMARDs. Despite this, the major clinical assessments of disease activity and outcome (morning stiffness, pain score, Ritchie index, swollen joint count and HAQ score) showed statistically significant improvement, even after adjustment for multiple comparisons. All patients graded their response as at least "fair", with the majority grading it as "good". In addition, all achieved a response according to the criteria of Paulus and showed a mean improvement of at least 30% in 6 selected disease activity measures.

The improvements in clinical assessments following treatment with cA2 appear to be at least as good as those reported following treatment of similar patients with anti-leukocyte antibodies. The two therapeutic approaches can already be distinguished, however, by their effects on the acute phase response, since in several studies of antileukocyte antibodies, no consistent improvements in CRP or ESR were seen. In contrast, treatment with cA2 resulted in significant falls in serum CRP and SAA, with normalization of values in many patients. The changes were rapid and marked, and in the case of CRP, sustained for the duration of the study (Table 14). The falls in ESR were less marked, achieving statistical significance only when unadjusted (Table 14).

These results are consistent with current concepts that implicate TNFα in the regulation of hepatic acute phase protein synthesis, either directly, or by control of other, secondary, cytokines such as IL-6 (Fong et al., *J. Exp. Med.* 170:1627–1633 (1989); Guerne et al., *J. Clin. Invest.* 83:585–592 (1989)). In order to investigate the mechanism of control of the acute phase response in our patients, we measured serum TNFα and IL-6 before and after cA2 treatment. Bioactive TNFα was not detectable in baseline or subsequent sera. We used 2 different assays for IL-6, in view of previous reports of variability between different immunoassays in the measurement of cytokines in biological fluids (Roux-Lombard et al., *Clin. Exp. Rheum.* 10:515–520 (1992), and both demonstrated significant falls in serum IL-6 by week 2. These findings support the other objective laboratory changes induced by cA2, and provide in vivo evidence that TNFα is a regulatory cytokine for IL-6 in this disease. Amongst the other laboratory tests performed, rheumatoid factors fell significantly in 6 patients.

Neutralization of TNFα can have a number of beneficial consequences, including a reduction in the local release of cytokines such as IL-6 and other inflammatory mediators and modulation of synovial endothelial/leukocyte interactions. cA2 can also bind directly to synovial inflammatory cells expressing membrane TNFα, with subsequent in situ cell lysis.

The results obtained in this small series have important implications, both scientifically and clinically. At the scientific level, the ability of the neutralizing antibody, cA2, to reduce acute phase protein synthesis, reduce the production of other cytokines such as IL-6, and significantly improve the clinical state demonstrates that it is possible to interfere with the cytokine network in a useful manner without untoward effects. Due to the many functions and overlapping effects of cytokines such as IL-1 and TNFα, and the fact that cytokines induce the production of other cytokines and of themselves, there had been some pessimism as to whether targeting a single cytokine in vivo would have any beneficial effect (Kingsley et al., *Immunol. Today* 12:177–179 (1991), Trentham, *Curr. Opin. Rheumatol.* 3:369–372 (1991)). This view is clearly refuted. On the clinical side, the results of short-term treatment with cA2 are significant and confirm that TNFα is useful as a new therapeutic target in RA.

EXAMPLE XXIII

Treatment with Chimeric Anti-TNF in a Patient with Severe Ulcerative Colitis

The patient is a 41 year old woman with long term ulcerative colitis, which was diagnosed by endoscopy and histology. She has a pancolitis, but the main disease activity was left-sided. There were no extra-intestinal complications in the past. Maintenance therapy consisted of ASACOL®. Only one severe flair-up occurred 4 years previously and was successfully treated with steroids.

At beginning month one, she was admitted elsewhere because of a very severe flair-up of the ulcerative colitis. Treatment consisted of high doses of steroids intravenously, antibiotics, ASACOL® and Total Parental Nutrition. Her clinical condition worsened and a colectomy was considered.

At end of month one, she was admitted at the internal ward of the AMC. Her main complaints consisted of abdominal pains, frequent water stools with blood and mucopus and malaise.

Medication:
ASACOL® 2 dd 500 mg, orally
Di-Adresone-T 1 dd 100-mg, intravenously
Flagyl 3 dd 500 mg, intravenously
Fortum 3 dd 1 gram, intravenously
Total parental nutrition via central venous catheter On physical examination the patient was moderately ill with a weight of 55 kg and a temperature of 36° C. Jugular venous pressure was not elevated. Blood pressure was 110/70 mm Hg with a pulse rate of 80 per minute. No lymphadenopathy was found. Oropharynx was normal. Central venous catheter was inserted in situ with no signs of inflammation at the place of insertion. Normal auscultation of the lungs and heart. The abdomen was slightly distended and tender. Bowel sounds where reduced. Liver and spleen where not enlarged. No signs of peritonitis. Rectal examination was normal.

All cultures of the stools where negative.
Plain x-ray of the abdomen; slightly dilated colon. No thumb-printing, no free air, no toxic megacolon.
Sigmoidoscopy; (video-taped) Very severe inflammation with deep ulcers. Dilated rectum and sigmoid. Because of danger of perforation the color, the endoscopy was limited to the racto-sigmoid. No biopsies where taken.
Conclusion at time of admission: Severe steroid resistant flair-up of ulcerative colitis.

Antibiotics were stopped, because no improvement was noticed and there was no temperature.

After informed consent of the patient, treatment was started with 10 mg/kg bodyweight (a 550 mg) of cA2 chimeric monoclonal anti-TNF (Centocor) given intravenously over 2 hours (according the protocol of cA2 used in severe Crohn's disease).

During the infusion there were no complaints. Vital signs were monitored and were all normal. Before and after infusion blood samples were drawn. Two days after infusion she had less abdominal pain, the stool frequency decreased and no blood was seen in the stools any more. However she developed high temperature (40° C.). Blood cultures were positive for *Staphylococcus epidermidis*. Infection of the central venous catheter was suspected. The catheter was removed and the same *Staphylococcus* was cultured from the tip of the central venous catheter. During this period she was treated with antibiotics for three days. After this her temperature dropped and she recovered substantially. Steroids were tapered off to 40 mg of prednisone daily.

After 14 days sigmoidoscopy was repeated and showed a remarkable improvement of the mucosa with signs of reepithelization. There were no signs of bleeding, less mucopus and even some normal vascular structures were seen.

At four months she was discharged.

At the outpatient clinic further monitoring was done weekly. Patient is still improving. Stool frequency is two times per day without blood or mucopus. Her laboratory improved, but there is still anaemia, probably due to iron deficiency. A colonoscopy is planned in the nearby future.

Our conclusion is that this patient had a very severe flair-up of her ulcerative colitis. She was refractory to treatment and a total colectomy was seriously considered. After infusion of cA2 the clinical course improved dramatically in spite of the fact that there was a complication of a sepsis which was caused by the central venous catheter.

EXAMPLE XXIV

Treatment of Rheumatoid Arthritis in Humans with cA2 Antibody Patients

Patients were recruited from the clinics of four cooperating trial centers or after referral from outside physicians. Patients aged 18–75 were included if they met the criteria of the American College of Rheumatology for the diagnosis of rheumatoid arthritis, had had disease for at least six months, had a history of failed treatment with at least one disease modifying anti-rheumatic drug (DMARD) and had evidence of erosive disease on radiography of hands and feet. In addition, patients had to have active disease, as defined by the presence of six or more swollen joints plus at least three of four secondary criteria (duration of morning stiffness $\geq 45$ minutes; $\geq 6$ tender or painful joints; erythrocyte sedimentation rate (ESR) $\geq 28$ mm/h; C-reactive protein (CRF) $\geq 20$ mg/L). Patients with severe physical incapacity (Steinbrocker class IV) or with clinically evident joint ankylosis were excluded. Other exclusion criteria included: severe anaemia (haemoglobin <8.5 g/dL); leucopenia (white cells <3.5×10$^9$/L, neutrophils <1.5×10$^9$/L) or thrombocytopenia (100×10$^9$/L); elevation of liver function tests to over three times the upper limit of normal or of serum creatine to over 150 μmol/L; or active pathology on chest film. Patients were also excluded if they had a history of previous administration of murine monoclonal antibodies, a history of cancer or HIV infection, or current other serious medical conditions. Female patients of child-bearing age had to be using an effective method of birth control and to have a negative pregnancy test before entry.

No patient had received other experimental drugs targeted to TNF (e.g., oxpentifylline) in the previous three months. Patients taking disease-modifying anti-rheumatic drugs at screening were withdrawn from their therapy at least four weeks before entry. Patients taking low-dose oral corticosteroids (prednisolone $\leq 12.5$ mg per day) or non-steroidal anti-inflammatory drugs at screening were allowed to continue on stable doses. Additional steroids by injection or other routes were not allowed. Simple analgesics were freely allowed.

All patients gave their informed consent for the trial, which was approved by each of the local regional ethics committees.

Study Infusions

The cA2 antibody was supplied as a sterile solution containing 5 mg cA2 per ml of 0.01 mol/L phosphate-buffered saline in 0.15 mol/L sodium chloride with 0.01% polysorbate 80, pH 7.2. The placebo vials contained 0.1% human serum albumin in the same buffer. Before use, the appropriate amount of cA2 or placebo was diluted to 300 mL in sterile saline by the pharmacist, and administered intravenously via a 0.2 μm in-line filter over 2 hours. The characteristics of the placebo and cA2 infusion bags were identical, and the investigators and patients did not know which infusion was being administered.

Assessments

Patients were seen at an initial screening visit and if eligible, were entered within four weeks. On the day of entry, patients were admitted to the hospital and randomized (in blocks of 6, stratified for center) to one of three groups (24 per group). The first group received a single infusion of placebo. The other two groups received one infusion of cA2, 1 mg/kg ("low dose") and 10 mg/kg ("high dose"). The doses of cA2 were chosen on the basis of experience in the open-label trial and by extrapolation from the anti-TNF-treated collagen-arthritis mice.

Patients were monitored for adverse events during infusions and regularly thereafter, by interviews, physical examination, and laboratory testing.

Before the start of the trial, all clinical observers agreed on a standard technique to assess joints, and to establish protocols for the collection of other clinical data. In each center, patients were assessed by the same clinical observer at each evaluation visit, usually between 0800 and 1100 hour. Clinical observers were additionally blinded to the results of laboratory testing for acute-phase measures (ESR and CRP).

The six primary disease-activity assessments were chosen to allow analysis of the response in individual patients according to the Paulus index. The assessments contributing to this index were the tender and swollen joint scores (60 and 58 joints, respectively, hips not assessed for swelling; graded 0–3), the duration of morning stiffness (minutes), the patient's and observer's assessment of disease severity (on a 5 point scale, ranging from 1 (symptom-free) to 5 (very severe) and ESR. Patients were considered to have responded if at least four of the six variables improved, defined as at least 20% improvement in the continuous variables, and at least two grades of improvement or improvement from grade 1 to 1 in the two disease-severity assessments (Paulus 20% response). Improvements of at least 50% in the continuous variables were also used (Paulus 50%).

Other disease-activity assessments included the pain score (0–10 cm on a visual analogue scale (VAS)), an assessment of fatigue (0–10 cm VAS), and grip strength (0–300 mm Hg, mean of three measurements per hand by sphygmomanometer cuff).

The ESR was measured at each study site with a standard method (Westergen). CRP (Abbott fluorescent polarizing immunoassay) and rheumatoid factor (rheumatoid-arthritis particle-agglutination assay (RAPA, FujiBerio, Tokyo); titres $\geq 160$ were taken to be important) were measured in stored frozen serum samples shipped to a central laboratory.

Statistics

The analysis was on the basis of intention to treat. The sample size was chosen as having an 80% probability of achieving a statistically significant (p<0.05) result if the true response rates were 10% and 40% in the placebo and 10 mg/kg cA2 groups, respectively. Fisher's exact test was used to compare the groups for baseline sex ratio and rheumatoid factor status and for Paulus response rates. Comparisons between groups for other demographic features and for individual disease activity assessments were by analysis of variance, or Cochran-Mantel-Haenszel statistics where appropriate (baseline comparison of disease-modifying anti-rheumatic drugs usage, patient's and observer's assessments of disease severity/activity). The Paulus 20% response rate at week 4 was defined as the primary efficacy endpoint, with other time points and variables considered supportive. Levels of significance were therefore not adjusted for multiple comparisons.

Results

Seventy-two patients were initially randomized. One patient presented two weeks after treatment with 1 mg/kg cA2 with probable pneumonia that required admission to the hospital. The patient was withdrawn and, according to protocol, another patient was recruited. Thus, the intention-to-treat analysis brought the number analyzed in the 1 mg/kg group to 25 patients and the total number to 73.

The three groups were well-matched at entry, with no significant differences in age, sex ratio, disease duration, number of failed disease-modifying anti-rheumatic drugs, or percentage of patients with significant titre of rheumatoid factor (Table 15). Demographic data were similar between the four sites. The patients had active disease at entry, as judged by the presence of multiple tender and swollen joints, high pain scores, substantial morning stiffness, raised acute-phase measures (Table 16). Comparison between groups revealed no significant differences for any of the clinical and laboratory indices of disease activity at entry.

The response rates at Paulus 20% and 50% are shown in Table 17. Only 2 of 24 placebo recipients achieved a 20% response at week 4. By contrast, 19 of 24 patients treated with 10 mg/kg cA2 achieved a response by week 4 (p0.0001 compared with placebo). The response rates in the 1 mg/kg group were intermediate, with 11 of 25 patients responding at week 4 (p=0.0083). Analysis of the Paulus 50% response showed similar differences between the groups, with 14 of 24 high-dose cA2 patients responding (p=0.0005), compared with 2 of 24 patients in the placebo group. Analysis of the response data for corticosteroid use showed that patients who were taking steroids behaved no differently in their responses from non-steroid-treated patients.

Although secondary to the differences in overall response rates, analysis of changes in individual disease-activity assessments was also of interest (Table 16). Significant improvements were seen in both cA2 groups for each of the clinical assessments. For many assessments, maximum mean improvements in cA2-treated groups exceeded 60%. Among the laboratory measures, significant falls were seen in both cA2 groups for ESR, CRP, and platelet counts, with the best improvements seen in the high-dose group. The changes in CRP were particularly rapid in onset and impressive in extent, with many individual patients achieving normal concentrations (10 mg/L, data not shown). In addition, significant improvements relative to placebo were seen for haemoglobin, especially in the high-dose cA2 group. Trends towards a fall in white cell count (from increased counts at entry) in both cA2 groups supported the changes in other laboratory measures, but did not reach statistical significance (Table 16).

Detailed time response profiles for six disease-activity assessments common to the American College of Rheumatology and the European League Against Rheumatism coresets showed rapid and highly significant falls in the cA2-treated groups compared with placebo, with significant inter-group differences evident as early as 24 and 72 h (CRP and all other assessments, respectively).

Seeking possible dose-response relations, we compared response rates between the cA2 groups. We found no difference in 20% or 50% Paulus responses at week 2, but significantly higher response rates for the high-dose group at week 4 (likelihood ratio 1.8, 95% CI 1.1, 2.9, p=0.0186; 2.1, 1.1, 4.1, p=0.0450, for Paulus 20% and 50%, respectively). A similar analysis for each of the individual disease-activity assessments showed no greater benefit with the higher dose at week 2 of the study, except for haemoglobin (least squares mean difference 0.5, 95% CI 0.1, 0.9, p=0.021). By week 4, however, some diminution of the response in the 1 mg/kg group was evident for several assessments; responses in the 120 mg/kg group were maintained (Table 16). As a result, significantly better responses were seen at this time in the high-dose group, including pain score (least-squares mean difference −1.8, 95% CI −3.4 −0.2, p=0.036), right (28.4, 5.4, 51.3, p=0.018) and left grip strength (20.6, 3.3, 37.9, p=0.022), observer's assessment of disease severity (−0.8, −1.3, −0.4, p<0.035), ESR (−15.0, −23.6 to −1.4 p=0.035), CRP (−20.7, −32.1, −9.2, p<0.001), and haemoglobin (0.5, 0.0, 1.0, p=0.042).

The infusions of cA2 and placebo were well tolerated, with no episodes of fever or hemodynamic disturbance. The adverse events recorded during the 4 weeks after treatment are shown in Table 18. In all, two-thirds of the adverse events occurred in the cA2 groups. Infections formed the largest group, with 5 infections recorded in the 1 mg/kg group and 1 each in those receiving 10 mg/kg cA2 and placebo.

Of the 72 initially randomized, 2 patients had severe adverse events. One was the patient with probable pneumonia. The patient recovered fully with treatment, but was withdrawn and replaced. This event was judged "possibly" related to cA2. A second patient presented 1 week after treatment with 10 mg/kg cA2 with a pathological fracture of the clavicle, but continued in the study. In retrospect, a minor bony abnormality was evident on an X-ray film taken pretreatment, and the event was judged "probably not" related to cA2.

TABLE 15

Demographic Features

| | Group | | |
|---|---|---|---|
| | Placebo (n = 24) | 1 mg/kg cA2 (n = 25) | 10 mg/kg cA2 (n = 24) |
| Age (yr) | 48–1 (11–9) | 56–2 (12–2) | 50–6 (13–1) |
| M/F | 7/17 | 5/25 | 4/20 |
| Disease Duration | 9–0 (7–3) | 7–5 (4–8) | 7–3 (5–2) |
| Previous Drugs* | 3–7 (1–9) | 2–8 (1–5) | 3–1 (1–7) |
| Rheumatoid Factor (seropositive) | 7% | 96% | 75% |

Mean (SC).
*Number of disease-modifying anti-rheumatic drugs previously used.

TABLE 16

Disease Activity Assessments

| | Data Summary | | | Statistical analysis vs. Placebo | | | | | |
|---|---|---|---|---|---|---|---|---|---|
| | | 1 mg/kg | 10 mg/kg | 1 mg/kg cA2 | | | 10 mg/kg cA2 | | |
| Assess Wk | Placebo | cA2 | cA2 | Least-sq | 95% CI | P | Least-sq | 95% CI | p |
| Tender joint count | | | | | | | | | |
| 0 | 27.8 (13.5) | 29.1 (14.1) | 28.1 (12.7) | | | | | | |
| 2 | 25.7 (16.6) | 12.1 (10.2) | 11.1 (6.9) | −14.8 | −21.2, −8.4 | <0.001 | −14.8 | −20.2, −9.5 | <0.001 |
| 4 | 26.2 (15.5) | 16.9 (12.1) | 11.3 (9.8) | −10.9 | −16.4, −5.3 | <0.001 | −15.2 | −21.2, −9.2 | <0.001 |
| Swollen Joint count (0–58) | | | | | | | | | |
| 0 | 23.4 (10.5) | 21.4 (10.6) | 21.8 (11.5) | | | | | | |
| 2 | 24.2 (12.1) | 11.1 (8.1) | 8.2 (5.5) | −10.9 | −15.6, −6.3 | <0.001 | −14.4 | −19.6, −9.2 | <0.001 |
| 4 | 23.0 (11.2) | 12.9 (8.8) | 8.6 (6.4) | −8.2 | −12.8, −3.6 | 0.001 | −12.7 | −17.8, −7.5 | <0.001 |
| Pain Score (0–10 cm) | | | | | | | | | |
| 0 | 6.8 (1.8) | 6.6 (2.6) | 6.7 (2.5) | | | | | | |
| 2 | 6.9 (2.6) | 2.5 (2.6) | 2.6 (2.1) | −1.3 | −5.7, −2.9 | <0.001 | −4.3 | −5.8, −2.8 | <0.001 |
| 4 | 6.9 (2.5) | 4.2 (2.9) | 2.5 (1.8) | −2.6 | −4.2, −0.9 | 0.003 | −4.3 | −5.8, −2.9 | <0.001 |
| Morning Stiffness (min) | | | | | | | | | |
| 0 | 132.3 (286.7) | 142.0 (122.0) | 143.1 (106.5) | | | | | | |
| 2 | 150.6 (284.0) | 27.4 (48.7) | 10.3 (14.9) | −88.9 | −147.5, −30.3 | 0.004 | −101.2 | −156.4, −16.1 | <0.001 |
| 4 | 172.3 (300.1) | 99.6 (286.3) | 8.3 (13.6) | −33.4 | −156.4, 89-6 | 0.592 | −124.8 | −188.9, −60.8 | <0.001 |
| Fatigue Score (0–10 cm) | | | | | | | | | |
| 0 | 6.3 (2.3) | 6.5 (2.6) | 5.6 (2.4) | | | | | | |
| 2 | 5.8 (2.9) | 3.2 (2.7) | 2.8 (2.3) | −2.6 | −4.3, −1.0 | −0.003 | −2.3 | −3.9, −0.7 | 0.006 |
| 4 | 5.6 (3.0) | 3.8 (2.8) | 2.3 (1.7) | −1.9 | −3.6, −0.2 | 0.028 | −2.6 | 4.3, −1.0 | 0.003 |
| Grip Strength, right (0–300 mm Hg) | | | | | | | | | |
| 0 | 120.7 (50.2) | 102.4 (48.8) | 117.0 (64.1) | | | | | | |
| 2 | 122.7 (51.5) | 161.8 (78.3) | 175.3 (79.1) | 55.8 | 32.6, 79.0 | <0.001 | 56.4 | 35.0, 77.3 | <0.001 |
| 4 | 119.1 (50.2) | 131.8 (65.0) | 175.2 (78.6) | 31.3 | 15.6, 46.9 | <0.001 | 59.9 | 35.9, 83.9 | <0.001 |
| Grip Strength, left (0–300 mm Hg) | | | | | | | | | |
| 0 | 120.0 (58.4) | 100.8 (46.8) | 108.4 (50.5) | | | | | | |
| 2 | 123.3 (64.9) | 152.4 (72.0) | 157.2 (65.1) | 46.7 | 23.7, 69.6 | <0.001 | 45.4 | 28.9, 52.0 | <0.001 |
| 4 | 120.9 (58.4) | 126.6 (65.8) | 155.1 (60.9) | 25.0 | 6.5, 43.5 | 0.010 | 45.8 | 28.9, 62.7 | <0.001 |
| Disease Severity, patient (1–5) | | | | | | | | | |
| 0 | 3.8 (0.5) | 3.7 (0.5) | 3.6 (0.6) | | | | | | |
| 2 | 3.8 (0.8) | 3.5 (0.7) | 2.6 (1.0) | −1.2 | −1.6, −0.8 | <0.001 | −1.1 | −1.6 −0.6 | <0.001 |
| 4 | 3.3 (0.8) | 3.0 (0.8) | 2.6 (0.8) | −0.7 | −1.2, −0.3 | 0.002 | −1.2 | −1.7 −0.8 | <0.001 |
| Disease Severity, Observer | | | | | | | | | |
| 0 | 3.7 (0.7) | 3.7 (0.5) | 3.6 (0.7) | | | | | | |
| 2 | 3.5 (0.8) | 2.5 (0.8) | 2.3 (0.6) | −1.0 | −1.5, −0.6 | <0.001 | −1.2 | −1.6, −0.8 | <0.001 |
| 4 | 3.6 (2.0) | 3.0 (1.0) | 2.2 (0.6) | −0.6 | −1.1, −0.1 | 0.036 | −1.4 | −1.9, −1.0 | <0.001 |
| ESR (mm/h) | | | | | | | | | |
| 0 | 63.1 (24.8) | 58.1 (25.5) | 63.1 (27.6) | | | | | | |
| 2 | 67.0 (27.4) | 41.8 (24.6) | 42.4 (25.2) | −23.1 | −35.9, −10.4 | <0.001 | −24.9 | −39.0, −10.9 | <0.001 |
| 4 | 65.1 (29.8) | 52.4 (32.3) | 42.7 (24.6) | −10.7 | −26.4, 5.1 | 0.185 | −22.5 | −38.7, −6.3 | 0.009 |
| CRP (mg/L) | | | | | | | | | |
| 0 | 64 (42) | 67 (41) | 64 (36) | | | | | | |
| 2 | 53 (30) | 39 (39) | 28 (29) | −19.1 | −34.1, −4.1 | 0.016 | −24.3 | −38.8, −9.8 | 0.002 |

TABLE 16-continued

Disease Activity Assessments

| | Data Summary | | | Statistical analysis vs. Placebo | | | | | |
|---|---|---|---|---|---|---|---|---|---|
| | | 1 mg/kg | 10 mg/kg | 1 mg/kg cA2 | | | 10 mg/kg cA2 | | |
| Assess Wk | Placebo | cA2 | cA2 | Least-sq | 95% CI | P | Least-sq | 95% CI | p |
| 4 | 60 (42) | 58 (39) | 35 (29) | −7.7 | −20.5, 5.1 | 0.239 | −28.8 | −33.7, −12.9 | <0.001 |
| Haemoglobin g/dL | | | | | | | | | |
| 0 | 11.6 (1.6) | 11.8 (1.3) | 11.0 (1.1) | | | | | | |
| 2 | 10.9 (1.5) | 11.5 (1.2) | 11.2 (1.1) | 0.4 | 0.0, 0.7 | 0.052 | 0.8 | 0.5, 1.2 | <0.001 |
| 4 | 10.9 (1.7) | 11.7 (1.2) | 11.4 (1.2) | 0.6 | 0.1, 1.0 | 0.022 | 1.1 | 0.6, 1.5 | <0.001 |
| WBC ($\times 10^9$/L) | | | | | | | | | |
| 0 | 10.7 (3.5) | 10.1 (3.5) | 9.0 (2.1) | | | | | | |
| 2 | 10.5 (2.9) | 9.2 (3.2) | 8.4 (2.5) | −0.8 | −1.9, 0.4 | 0.202 | −0.4 | −1.4, 0.6 | 0.414 |
| 4 | 10.3 (3.2) | 9.3 (4.3) | 7.7 (2.0) | −0.4 | −1.6, 0.8 | 0.500 | −0.9 | −1.9, 0.2 | 0.096 |
| Platelets ($\times 10^9$/L) | | | | | | | | | |
| 0 | 447 (126) | 421 (132) | 400 (127) | | | | | | |
| 2 | 471 (135) | 375 (111) | 368 (117) | −69 | −108, −30 | 0.001 | −56 | −89, −22 | 0.002 |
| 4 | 462 (115) | 406 (131) | 345 (120) | −29 | −073, 16 | 0.208 | −69 | −103, −36 | <0.001 |

Mean (SD)
*0.2 1 = baseline and after 2 and 4 weeks of study.
Least sq. = least-squares mean difference.
WBC = white blood cells.
Normal values: ESR, female <15, male <10; CRP <10; haemoglobin, female 12–16, male 13.5–17.5; WBC 4–11, platelets 150–400.

TABLE 17

Responses According to Paulus 20% and 50% Criteria at Each Evaluation Point

| | Data Summary | | | Statistical Analysis vs. Placebo | | | | | |
|---|---|---|---|---|---|---|---|---|---|
| | | 1 mg/kg | 10 mg/kg | | | | | | |
| | Placebo | cA2 | cA2 | 1 mg/kg cA2 | | | 10 mg/kg cA2 | | |
| | n = 24 | n = 25 | n = 24 | LR | 95% CI | p | LR | 95% CI | p |
| Paulus 20% | | | | | | | | | |
| Day 3 | 2 (8%) | 8 (32%) | 7 (29%) | 3.8 | 1.1, 14.0 | 0.0738 | 3.5 | 0.9, 13.4 | 0.1365 |
| Wk 1 | 2 (8%) | 13 (52%) | 16 (67%) | 6.2 | 2.1, 18.6 | 0.0015 | 8.0 | 3.0, 21.5 | 0.0001 |
| Wk 2 | 3 (13%) | 15 (60%) | 18 (75%) | 5.0 | 2.1, 12.2 | 0.0008 | 6.0 | 2.7, 13.5 | <0.0001 |
| Wk 3 | 4 (17%) | 12 (48%) | 21 (88%) | 2.9 | 1.2, 7.1 | 0.0322 | 5.3 | 2.7, 10.3 | <0.0001 |
| Wk 4 | 2 (8%) | 11 (44%) | 19 (79%) | 5.3 | 1.7, 16.9 | 0.0083 | 9.5 | 3.9, 23.4 | <0.0001 |
| Paulus 50% | | | | | | | | | |
| Day 3 | 1 (4%) | 6 (24%) | 2 (9%) | 5.8 | 1.0, 33.1 | 0.0983 | 2.0 | 0.2, 20.0 | 1.000 |
| Wk 1 | 1 (4) | 11 (44%) | 12 (50%) | 10.6 | 2.5, 44.6 | 0.0019 | 12.0 | 3.0, 47.5 | 0.007 |
| Wk 2 | 0 | 11 (44%) | 12 (50%) | NA | NA | 0.0002 | NA | NA | <0.0001 |
| Wk 3 | 2 (8%) | 7 (28%) | 13 (54%) | 3.4 | 0.9, 13.0 | 0.1383 | 6.5 | 2.2, 19.2 | 0.0013 |
| Wk 4 | 2 (8%) | 7 (28%) | 14 (58%) | 3.4 | 0.9, 13.0 | 0.1383 | 7.0 | 2.5, 20.0 | 0.0005 |

LR = likelihood ratio,
NA = not applicable (ratio could not be calculated because no placebo recipients responded at that time).

TABLE 18

All Adverse Events Recorded During 4 Weeks After Entry

| System | Event | Placebo | 1 mg/kg cA2 | 10 mg/kg cA2 |
|---|---|---|---|---|
| Respiratory | URTI | 1(0) | 2(0) | 1(1) |
|  | Probable pneumonia | — | 1(1) | — |
|  | Pleuritis | — | 1(0) | — |
| Gastro intestinal | Nausea | 2(0) | — | — |
|  | Diarrhoea | 1(1) | — | — |
|  | Abdominal Pain | — | 2(0) | — |
|  | Peptic Ulcer | — | 1(0) | — |
|  | Blood loss per rectum | — | 1(0) | — |
| Cardiovascular | Hypertension | 1(0) | 1(1) | 1(1) |
|  | Peripheral oedema | — | 1(0) | 1(0) |
| Skin | Rash | 3(1) | 1(0) | — |
|  | Infection | — | 2(2) | — |
|  | Injection site reaction | — | 1(1) | — |
| Neurological | Dizziness | 3(1) | — | — |
|  | Headache | — | — | 1(0) |
| Musculoskeletal | Rheumatoid nodules | — | 1(0) | — |
|  | Popliteal cyst | — | 1(0) | — |
|  | Fracture | — | — | 1(0) |
| Other | Malaise | — | 1(0) | — |
|  | Rigors | — | 1(1) | — |
|  | Facial oedema | — | 1(0) | — |
|  | Scleritis/conjunctivitis | — | 1(0) | — |
|  | Vasculitis | 1(0) | — | — |

URTI = upper respiratory tract infection.
Those events judged by blinded observers to be reasonably related to infusion shown in brackets.

EXAMPLE XXV

Treatment of Crohn's Disease with cA2 Antibody

This patient is a 25 year old female known with Crohn's disease with an eight year history, who has had several exacerbations of Crohn's disease. Following the birth of a child the patient developed again an exacerbation. Prednisone treatment was increased to 30 mg about 15 months earlier. It was not possible to sufficiently taper off prednisone, and azathioprine was added to the therapy six months prior to antibody treatment. Remission could not be achieved, and in the end the patient was enrolled in this trial.

At enrollment her Crohn's medication had been stable for four months and consisted of mesalazine 3×250 mg, prednisone 20 mg, and azathioprine 100 mg. Her main symptoms were frequent diarrhoea, abdominal cramps and poor general well being. Her CDAI was 216, CRP 14 and ESR 32. Endoscopy prior to treatment showed severe inflammation with pseudopolyps and deep ulcerations of the ascending and transverse colon.

The patient was infused with 840 mg of cA2 (10 mg/kg). From day 5 and onwards through week 8 there was considerable improvement of her symptoms, as is also reflected by a marked decrease in the CDAI. For the first time in many years the patient had formed stools again. CRP and ESR also decreased a little, although not as markedly as the CDAI, but these were not that much elevated prior to the treatment. This improvement is also objectivated by the endoscopic findings, which show a greatly improved image at week 4 and a complete remission at week 8.

Prior to the infusion of cA2, the patient already had on her buttocks skin eruptions which were identified as pyoderma gangrenosum. These skin lesions also improved substantially during treatment, although they have not vanished completely. Before the treatment with cA2, the patient already had problems with decreased vision but she did not report this. During the follow up after three weeks she reported this and she was immediately sent to the ophthalmologist who concluded that the reduced vision was a result of cataract due to prednisone. This was the rationale for tapering off prednisone to 15 mg at week 6.

Colon biopsies taken during the 8 week endoscopy showed a mild to moderate focal epithelial dysplasia in one of the biopsy specimens. This is a common finding in patients with chronic inflammatory bowel disease. However, differentiation between epithelial dysplasia associated with inflammatory bowel disease or a fragment of tubular adenoma could not be made.

Pre-treatment Endoscopy

Smooth introduction of the scope till the bottom of the cecum. Because of slight edema it is not possible to enter the terminal ileum. Also the patient indicates that these attempts are quite painful. While retracting the scope the colon is inspected. Especially the promixal part till approximately the flexural lienalis is severely inflamed and has pseudopolyps and deep ulcerations. Also the mucosa is edematous. More distally the mucosa looks more normal. At about 15 cm, there is a small lesion, which could be the exit of a fistula. Biopsies are taken and the entire endoscopy is taken on video. Conclusion: Unchanged image compared to previous endoscopy.

Four Week Endoscopy

Smooth introduction of the scope till in the terminal ileum. While withdrawing, the terminal ileum and cecum are inspected. The inflammation is considerably less than compared to the endoscopy of 4 weeks ago. There are still a few pseudopolyps and left and right a small ulceration, but compared to the endoscopy of 4 weeks ago, there is a dramatic improvement of the endoscopic image. Distally the mucosa looks normal. A diligent search has been made for the fistula opening which was seen last time at 15 cm of the anal ring. At this location we do see a scar with a slightly indurated edge, but at this moment it does not appear to be a real fistula opening. Conclusion: Greatly improved endoscopic image, compared to the endoscopy of 4 weeks ago.

Eight Week Endoscopy

There are only pseudopolyps left. Conclusion: Complete remission.

EXAMPLE XXVI p55 Fusion Protein Structure

Figure 27:
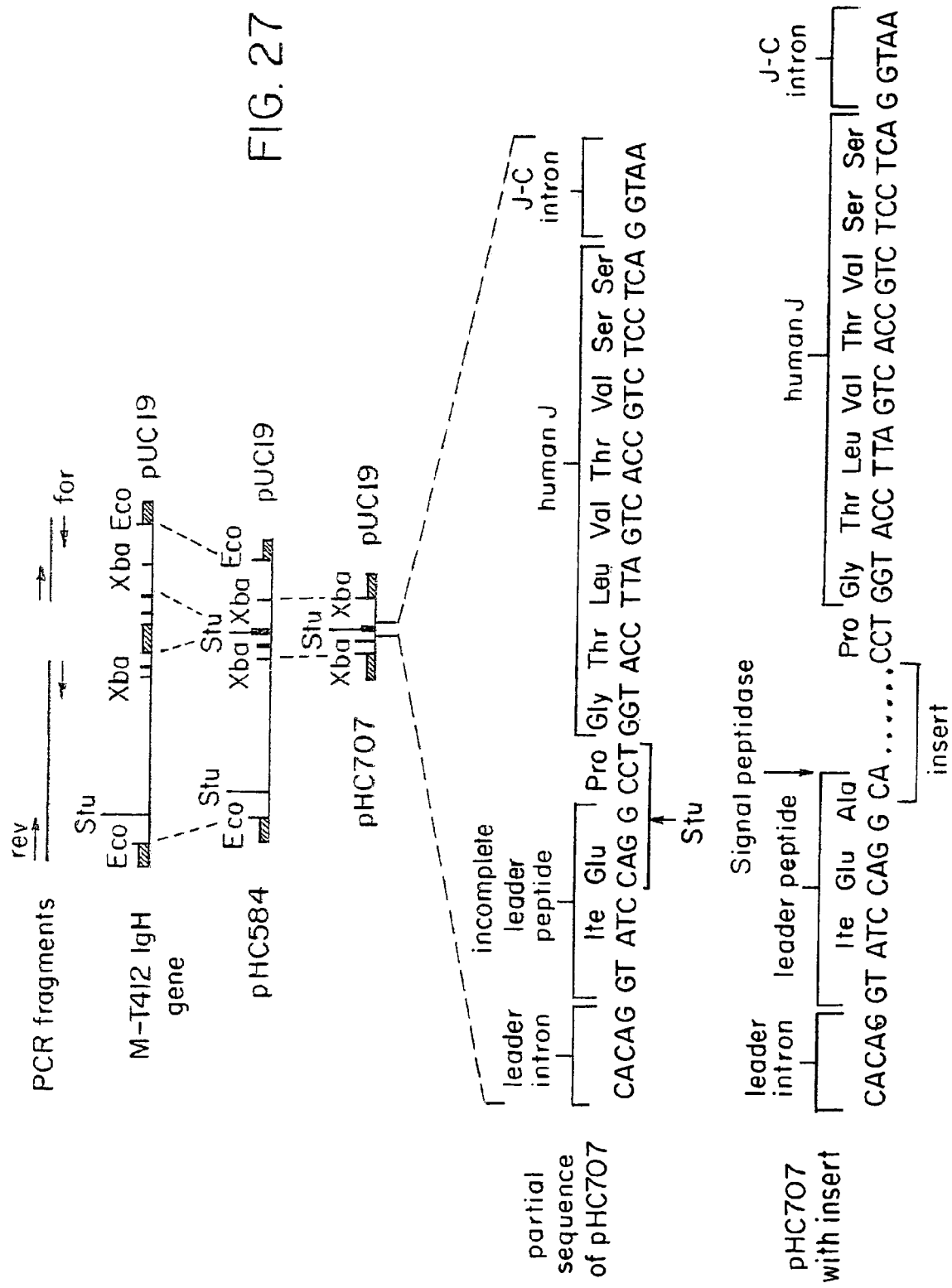
FIG. 27 is a schematic illustration of the construction of a cM-T412 heavy chain so that it has a unique cloning site for insertion of foreign genes such as p55 and p75.
Figure 29:
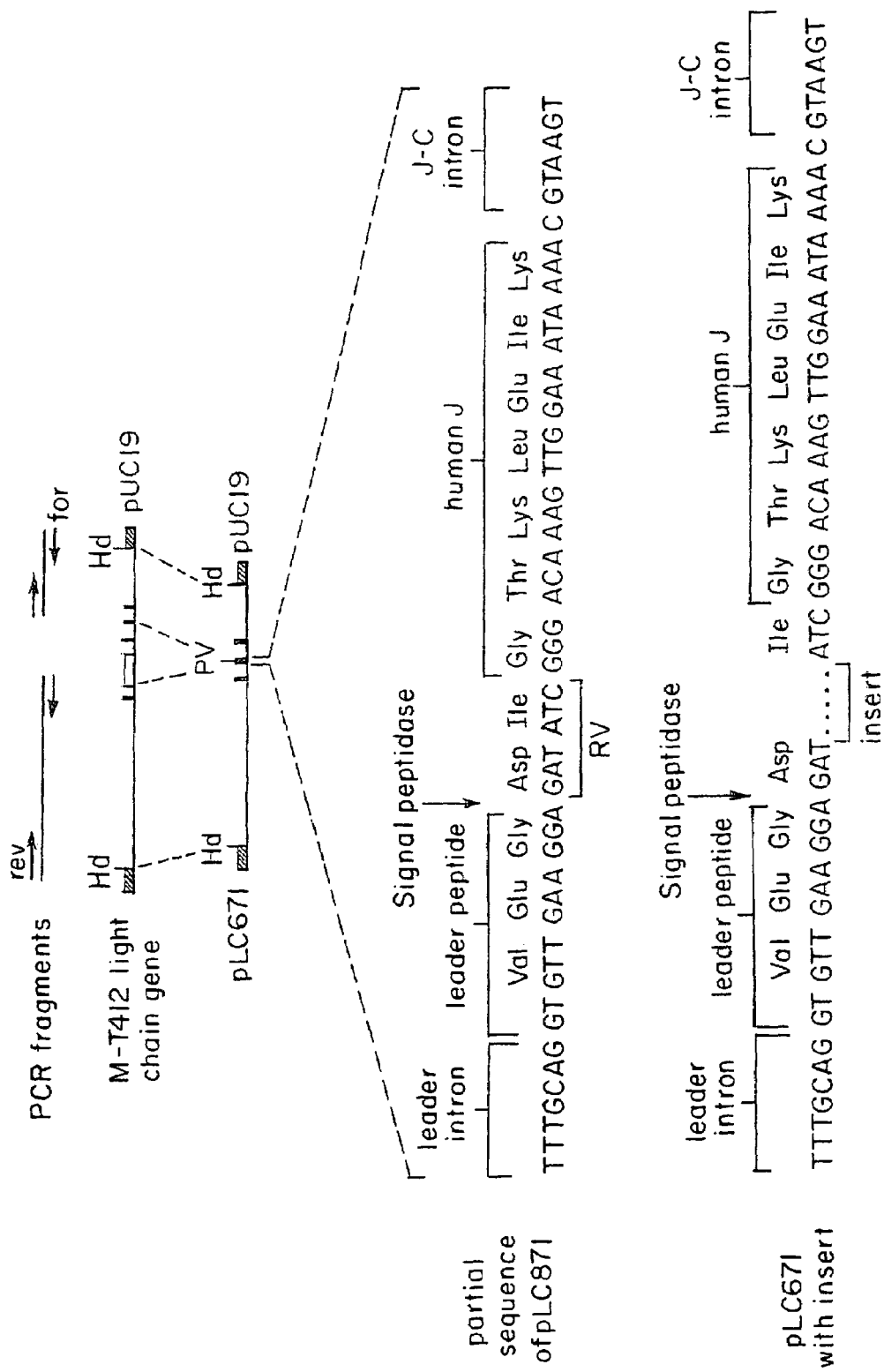
FIG. 29 is a schematic illustration of the construction of a cM-T412 light chain so that it has a unique cloning site for insertion of foreign genes such as p55 and p75.

The extracellular domains of the p55 and p75 receptors were expressed as Ig fusion proteins from DNA constructs designed to closely mimic the structure of naturally occurring, rearranged Ig genes. Thus, the fused genes included the promoter and leader peptide coding sequence of a highly expressed chimeric mouse-human antibody (cM-T412, Looney et al., *Hum. Antibody Hybridomas* 3:191–200 (1992)) on the 5' side of the TNF receptor insert, and codons for eight amino acids of human J sequence and a genomic fragment encoding all three constant domains of human IgG1 on the 3' side of the receptor insert position (FIGS. 27 and 29).

Minor changes were introduced at the N-terminal ends of the heavy chain fusion proteins so that the first two amino acids would be identical or similar to the first two amino acids (Gln-Ile) encoded by the cM-T412 antibody gene (from which the leader peptide originated). This was done to increase the likelihood that any interactions between the N-terminal end of the mature protein and the leader peptide would still result in efficient transport into the lumen of the endoplasmic reticulum. Boyd et al., *Cell* 62: 1031–1033 (1990). Therefore, the Asp$^1$ and Ser$^2$ residues of naturally occurring p55 were replaced with a Gln residue, and the Leu$^1$ residue of p75 was preceded by a Gln residue in all p75 constructs. No amino acid changes were introduced at the N-terminal end of the p55 light chain fusion.

Expression Vectors

PCR methodology was used to engineer cloned genes. Oligonucleotides were purchased from National Biosciences (Plymouth, Minn.). PCR amplification kits were from Perkin Elmer (CA) and DNA sequencing kits from U.S. Biochemical Corporation (Cleveland, Ohio). Alkaline phosphatase-conjugated goat anti-human IgG was purchased from Jackson ImmunoResearch (West Grove, Pa.). $^{125}$I-labeled human TNF was obtained from Du Pont Company, NEN (Boston, Mass.) and unlabeled recombinant human TNF from R&D Systems (Minneapolis, Minn.). Protein A-Sepharose beads was purchased from PHARMACIA (Piscataway, N.J.).

PCR methodology was used to engineer two cloned genes encoding the heavy chain or light chain of an efficiently expressed murine antibody, cM-T412 (see Looney et al.), for the purpose of directing the expression of foreign genes in a mammalian cell system. The approaches were to effectively delete the coding region of the antibody variable region and to place a unique restriction site in its place (StuI for the heavy chain vector and EcoRV for the light chain vector).

The resulting vector contained 2.5 kb of 5' flanking genomic DNA, the promoter, the leader peptide coding sequence (including the leader intron), a StuI cloning site to introduce inserts, coding sequence for eight amino acids of human J sequence Gly Thr Leu Val Thr Val Ser Ser (SEQ ID NO:6) followed by genomic sequences for the human IgG1 constant region. An analogous vector was made from the cM-T412 light chain gene except that an EcoRV cloning site was introduced at the carboxyl terminal end of the light chain leader peptide and a different human J sequence was encoded by the vector Gly Thr Lys Leu Glu Ile Lys (SEQ ID NO:7). Both vectors are based on plasmid pSV2-gpt and subsequent vector derivatives that contain genomic sequences for either the heavy chain or light chain constant regions. See Mulligan et al., *Science* 209:1422–1427 (1980). The *E. coli* gpt gene allows selection of transfected cells with mycophenolic acid.

Heavy Chain Vector

A previously cloned EcoRI fragment containing the cM-T412 heavy chain gene (Goeddel et al., *Cold Spring Harbor Symp. Quant. Biol.* 51: 597–609 (1986)) was subcloned into pUC19. This recombinant plasmid was used as a template for two PCR reactions. In one reaction, an oligo corresponding to the "reverse" primer of the pUC plasmids and the 3' oligo 5'-CCTGGATACCTGTGAAAAGA-3' (SEQ ID NO:8) (with half of a StuI site; oligo was phosphorylated prior to the PCR reaction) were used to amplify a fragment containing 3 kb of 5' flanking DNA, the promoter, transcription start site and leader peptide coding sequence (including the leader intron). In the second reaction, the 5' oligo 5' CCTGGTACCTTAGTCACCGTCT CCTCA-3' (SEQ ID NO:9) (with half of a StuI site; oligo phosphorylated prior to the PCR reaction) and an oligo corresponding to the "forward" primer of pUC plasmids amplified a fragment encoding eight amino acids of human J sequence Gly Thr Leu Val Thr Val Ser Ser (SEQ ID NO:6) and a splice donor to allow splicing to the human constant region coding sequence provided in another vector. The two PCR fragments were digested with EcoRI and then simultaneously ligated into EcoRI-digested pUC19 to make pHC684 (FIG. 27).

Because the StuI site formed at the junction of the two PCR fragments was followed by a "GG" dinucleotide sequence, a dcm methylation site was formed preventing StuI from digesting that site when the DNA was grown in HB101 strain of *E. coli*. Therefore, the plasmid DNA was introduced into dcm-JM110 *E. coli* cells and reisolated. StuI was then able to cut at the junction but a second StuI site in the 5' flanking DNA was a apparent (DNA sequencing showed that StuI site to also be followed by a GG dinucleotide and therefore also methylated). To make the StuI cloning site at the junction be unique, a 790 bp XbaI fragment that included only one of the two StuI sites was subcloned into pUC19 to make the vector pHC707 (FIG. 27) which was then grown in JM110 cells. The StuI cloning site formed at the junction of the two PCR fragments second and third nucleotides (i.e., "CA") of the last codon (Ala) of the signal sequence in order to maintain the appropriate translation reading frame (FIG. 27).

Figure 28:
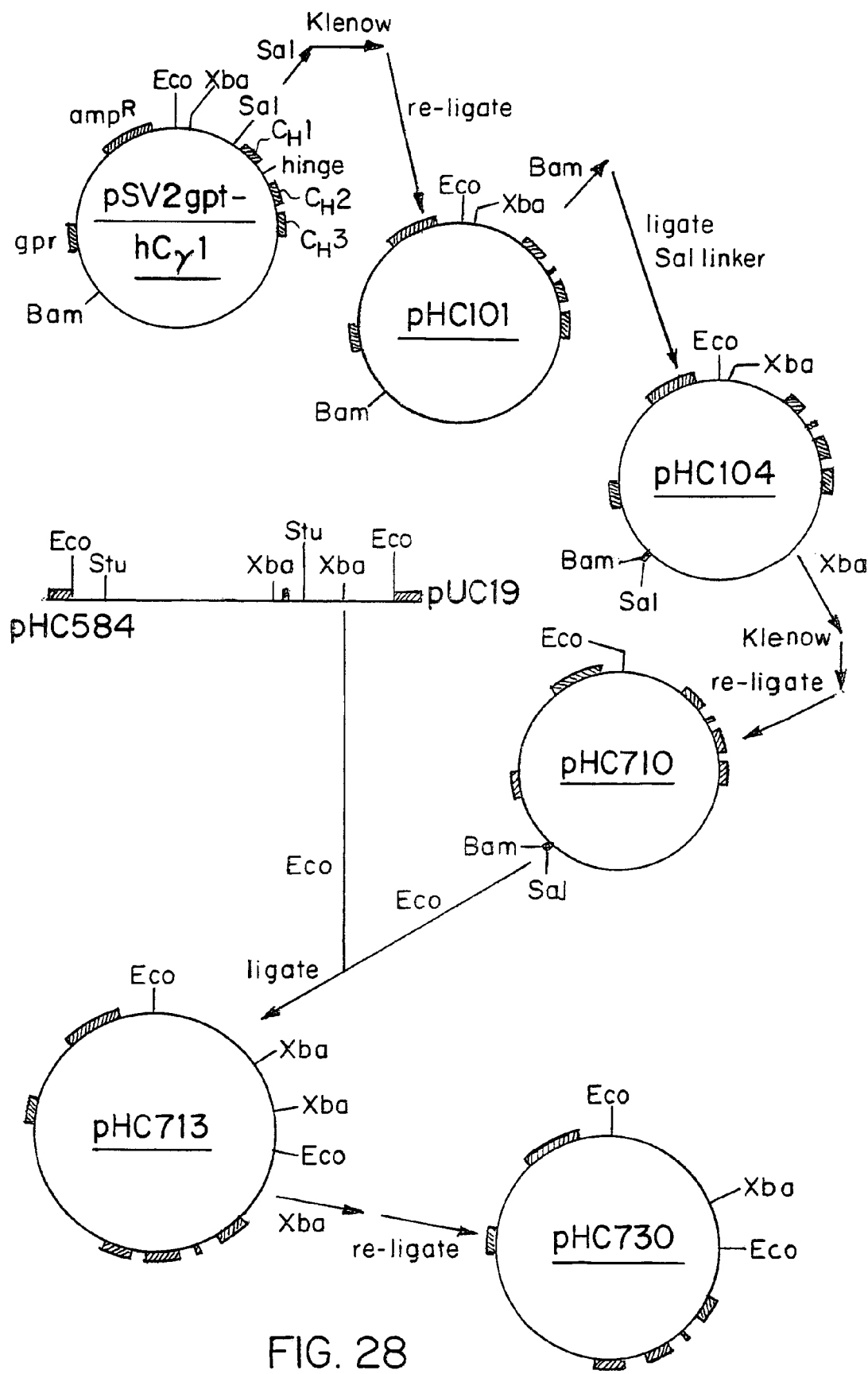
FIG. 28 is a schematic illustration of the construction of the vectors used to express the heavy chain of the immunoreceptors.

A PCR fragment encoding a protein of interest can then be ligated into the unique StuI site of pHC707. The insert can include a translation stop codon that would result in expression of a "non-fusion" protein. Alternatively, a fusion protein could be expressed by the absence of a translation stop codon, thus allowing translation to proceed through additional coding sequences positioned downstream of the StuI cloning site. pH 730 contains coding sequences for all three constant domains of human IgG1 and was designed to accomodate the XbaI fragments of pHC707 at a unique XbaI site upstream of the IgG1 coding sequences (FIG. 28). Coding sequences in the StuI site of pHC707 would not be fused directly to the IgG1 coding sequences in pHC730 but would be separated by an intron sequence that partially originates from pHC707 and partially from pHC730. These intron sequences would be deleted in the cell following transcription resulting in an RNA molecule that is translated into a chimeric protein with the protein of interest fused directly to the IgG1 constant domains.

The plasmid pHC730 was a modified form of an IgG1 expression, pSV2gpt-hCy1 vector described previously (Goeddel et al., *Cold Spring Harbor Symp. Quant. Biol.* 51:597–609 (1986)) (FIG. 28). The modifications were (1) removal of the unique SalI and XbaI sites upstream of the constant region coding sequence, (2) insertion of a SalI linker into the unique BamHI site to allow use of SalI to linearize the plasmid prior to transfections, and (3) ligation into the unique EcoRI site the cloned cM-T412 EcoRI fragment but with the XbaI fragment flanking the V gene deleted (FIG. 28). The resulting expression vector had a unique XbaI site for inserting the XbaI fragments from pHC707.

Light Chain Vector

A previously cloned HindIII fragment containing the cM-T412 light chain gene (Goeddel et al., *Cold Spring Harbor Symp. Quant. Biol.* 51:597–609 (1986)) was subcloned into pUC19 and the resulting plasmid used as template for PCR reactions. In one PCR reaction the "reverse" pUC primer and the 3' oligo 5'-AATAGATATCTCCT-TCAACACCTGCAA-3' (SEQ ID NO:10) (with an EcoRV site) were used to amplify a 2.8 kb fragment containing 5' flanking DNA, the promoter, transcription start site and leader peptide coding sequence (including the leader intron) of the cloned light chain gene. This fragment was then digested with HindIII and EcoRV. In a second PCR reaction, the 5' oligo 5'-ATCGGG ACAAAGTTGG AAATA-3' (SEQ ID NO:11) (with half of an EcoRV site) and the "forward" pUC primer were used to amplify a fragment encoding seven amino acids of human J sequence (Gly Thr Lys Leu Glu Ile Lys) and an intron splice donor sequence. This fragment was digested with HindIII and ligated along with the other PCR fragment into pUC cut with HindIII. The resulting plasmid, pLC671 (FIG. 29), has a unique EcoRV cloning site at the junction of the two PCR fragments with the EcoRV site positioned such that the first three nucleotides of the EcoRV site encoded the first amino acid of the mature protein (Asp).

Figure 30:
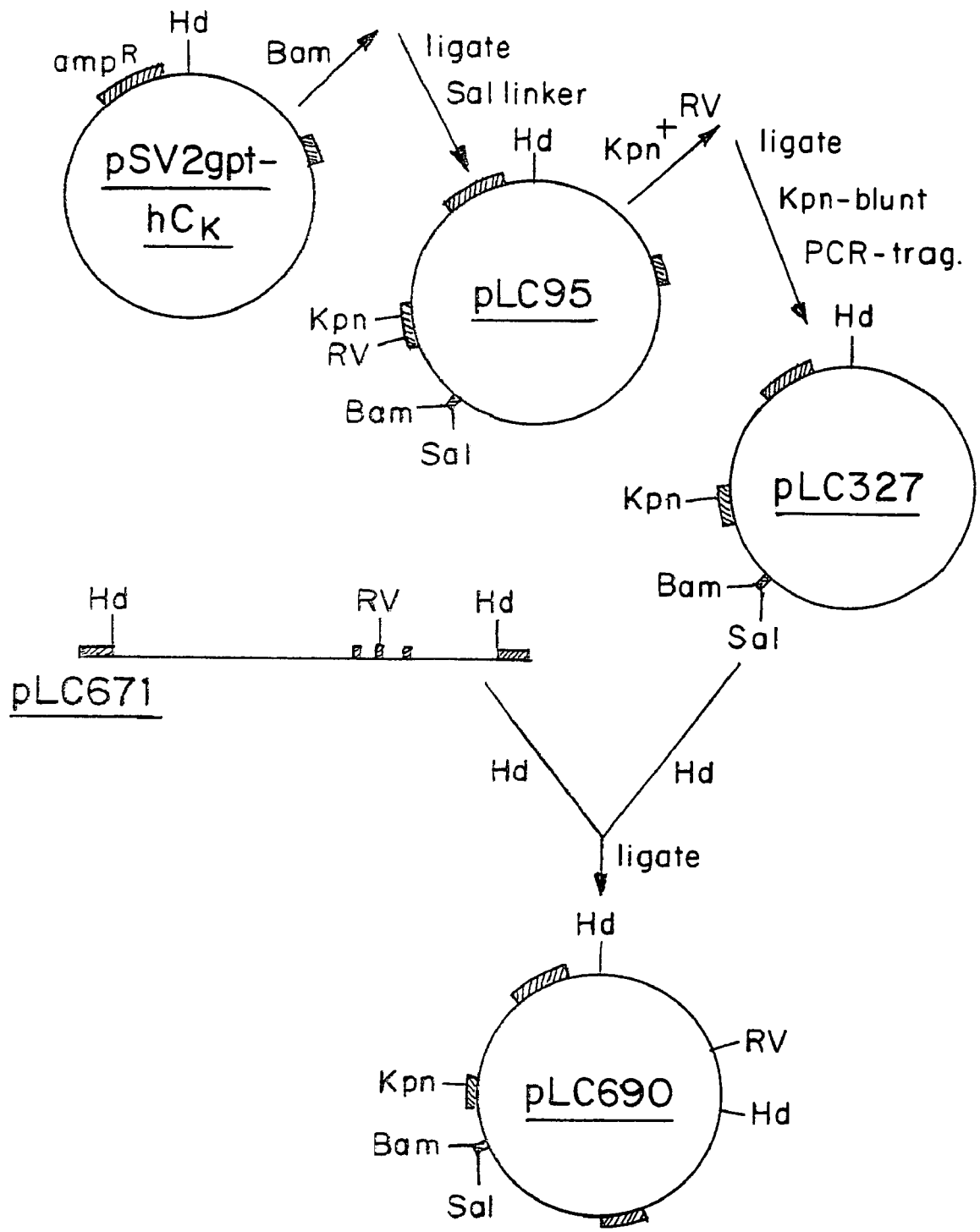
FIG. 30 is a schematic illustration of the construction of the vectors used to express the light chain of the immunoreceptors.

The pLC671 HindIII insert was designed to be positioned upstream of coding sequences for the human kappa light chain constant region present in a previously described expression vector, pSV2gpt-hCk (FIG. 30). However, pSV2gpt-hCk contained an EcoRV site in its gpt gene. Because it was desired that the EcoRV site in the pLC671 HindIII fragment be a unique cloning site after transferring the fragment into pSV2gpt-hCk, the EcoRV site in pSV2gpt-hCk was first destroyed by PCR mutagenesis. Advantage was taken of the uniqueness of this EcoRV site in pSV2gpt-hCk and a Kpn1 site 260 bp upstream of the EcoRV site. Therefore, the 260 bp Kpn1-EcoRV fragment was removed from pSV2gpt-hCk and replaced with a PCR fragment that has identical DNA sequence to the 260 bp fragment except for a single nucleotide change that destroys the EcoRV site. The nucleotide change that was chosen was a T to a C in the third position of the EcoRV recognition sequence (i.e., GATATC changed to GACATC). Because the translation reading frame is such that GAT is a codon and because both GAT and GAG codons encode an Asp residue, the nucleotide change does not change the amino acid ended at that position. Specifically, pSV2gpt-hCk was used as template in a PCR reaction using the 5' oligo 5'GGCGGTCT GGTAC-CGG-3' (SEQ ID NO:12) (with a Kpn1 site) and the 3' oligo 5'-GTCAACAACATAGTCATCA-3' (SEQ ID NO:13) (with the complement of the Asp codon). The 260 bp PCR fragment was treated with the Klenow fragment of DNA polymerase to fill-in the DNA ends completely and then digested with Kpn1. The fragment was ligated into pSV2gpt-hCk that had its Kpn1-EcoRV fragment removed to make pLC327 (FIG. 30).

The HindIII fragment of pLC671 was cloned into the unique HindIII site of pLC327 to make the light chain expression vector, pLC690 (FIG. 30). This plasmid can be introduced into cells without further modifications to encode a truncated human kappa light chain, JCk, that contains the first two amino acids of the cM-T412 light chain gene, seven amino acids of human J sequences, and the light chain constant region. Alternatively, coding sequence of interest can be introduced into the unique EcoRV site of pLC690 to make a light chain fusion protein.

TNF Receptor DNA Constructs

For the p55 heavy chain fusion, amino acids 3–159 of the p55 extracellular domain were encoded in a PCR fragment generated using the 5' oligo 5' CACAGGTGTGTC-CCCAAGGAAAA-3' (SEQ ID NO:14) (with the Val$^3$ codon) and the 3' oligo 5'-AATCTGGGGTAGGCACAA-3' (SEQ ID NO:15) (with the complement of the Ile$^{159}$ codon). For the p55 light chain fusion, amino acids 2–159 were encoded in a PCR fragment made using the 5' oligo 5,-AGT-GTGTGTCCCCAAGG3' (SEQ ID NO:16) (with the Ser$^2$ codon) and the same 3' oligo shown above. The light chain vector contained the codon for Asp$^1$ of p55. The DNA template for these PCR reactions was a previously reported human p55 cDNA clone. (Gray et al., *Proc. Natl. Acad. Sci. USA* 87:7380–7384 (1990)).

A truncated light chain that lacked a variable region was expressed by transfecting cells with the light chain vector with no insert in the EcoRV cloning site. The resulting protein, termed $JC_K$, consisted of the first two amino acids of the cM-T412 light chain gene, seven amino acids of human J sequence (Gly Thr Lys Leu GluIle Lys) (SEQ ID NO:7), and the human light chain constant region.

A non-fusion form of p55 (p55-nf) was expressed in CHO-K1 cells using the CMV-major immediate early promoter after introducing a translation stop codon immediately after Ile$^{159}$. Secreted p55 was purified by affinity chromatography on a TNFα column.

Transfections and ELISA Assays

All plasmids were linearized with a restriction enzyme prior to introducing them into cells. Cells of the myeloma cell line X63-Ag8.653 were transfected with 12 μg of DNA by electroporation. Cell supernatants were assayed for IgG domains. Briefly, supernatants were incubated in plates coated with anti-human IgG Fc and then bound protein detected using alkaline phosphatase-conjugated anti-human and light chains.

Purification of Fusion Proteins

Cell supernatants were clarified by centrifugation followed by passage through a 0.45 micron filter. Supernatants were adjusted to 20 mM Tris-HCl, pH 8.3, 150 mM NaCl, and 1 mM EDTA (1× protein A buffer) and passed over a column of protein A-Sepharose beads. The column was washed in 1× protein A buffer followed by 100 mM Na Citrate, pH 5.0 to elute bound bovine IgG originating from the cell media. Bound fusion protein was then eluted in 100 mM Na Citrate, pH 3.5, neutralized with 0.2 volumes 1 M Tris, and dialyzed against PBS.

TNF Cytotoxicity Assays

TNF-sensitive WEHI-164 cells (Espevik et al., *J. Immunol. Methods* 95:99–105 (1986)) were plated in 1 μg/ml actinomycin D at 50,000 cells per well in 96-well microtiter plates for 3–4 hours. Cells were exposed to 40 pM TNFα or TNFβ and varying concentrations of fusion protein. The mixture was incubated overnight at 37° C. Cell viability was determined by adding 3-[4,5-dimethyl-thiazol-2-yl]-2, 5diphenyltetrazolium bromide dye (MTT) to a final concentration of 0.5 mg/ml, incubating for 4 hours at 37° C., lysing the cells in 0.1 N HCl, 0.1% SDS and measuring the optical density at 550 nm wavelength.

Saturation Binding Analyses

Fusion proteins were captured while at a concentration of 10 ng/ml in 96-well microtiter plates coated with goat anti-human Fc antibodies. Varying concentrations of $^{125}$I-TNF (34.8 μCi/μg) were added in PBS/1% BSA and allowed to bind for two hours at room temperature. Plates were washed and bound cpm determined. Non-specific binding was determined using an irrelevant antibody.

Several different versions of the p55 fusion proteins were expressed. Unlike what was reported for CD4 (Capon et al., *Nature* 337:525–531 (1989)) and IL-2 (Landolfi, *J. Biol. Chem.* 146:915–919 (1991)) fusion proteins that also included the CHI domain of the heavy chain, inclusion of a light chain proved to be necessary to get secretion of the Ig heavy chain fusion proteins from the murine myeloma cells. The light chain variable region was deleted to enable the TNF R domain on the heavy chain to bind TNF without steric hindrance from the light chain.

The "double fusion" (df) protein, p55-df2, has p55 fused to both the heavy chain and light chain and is therefore tetravalent with regard to p55. p55-sf3 has the p55 receptor (and the same eight amino acids of human J sequence present in p55-sf2 and p55-df2) linked to the hinge region, i.e., the $CH_H1$ domain of the constant region is deleted.

After one or two rounds of subcloning, spent cell supernatant from the various cell lines were yielding 20 μg/ml (for p55-sf2) of fusion protein. The proteins were purified from the spent supernatant by protein A column chromatography and analyzed by SDS-PAGE with or without a reducing agent. Each fusion protein was clearly dimeric in that their $M_r$ estimates from their migration through a non-reducing gel was approximately double the estimated $M_r$ from a reducing gel. However, two bands were seen for p55-sf2 (lane 1) and p55-df2. Two lines of evidence indicated that, in each case, the lower bands did not include a light chain while the upper bands did include a light chain. First, when p55-sf2 containing both bands were passed over an anti-kappa column, the upper band bound to the column (lane 3) while the lower band passed through the column. Second, Western blots have shown that only the upper bands were reactive with anti-kappa antibodies.

It is believed that the versions of these fusion proteins that do not have a light chain (k) were not secreted to a significant degree but rather were primarily released from dead cells because 1) supernatants from cells transfected with the p55 heavy chain fusion gene and no light chain gene did not have detectable fusion protein until after there was significant cell death, and 2) the ratio of the k– to k+versions of p55-sf2 increased as cell cultures went from 95% viability to 10% viability.

EXAMPLE XXVII p75

To make a p75 heavy chain fusion (p75-sf2), amino acids 1–235 (Smith et al., Science 248: 1019–1023 (1990) and Kohno et al., Proc. Natl. Acad. Sci. 87:8331–8335 (1990)) were encoded in a fragment prepared using the 5' oligo 5'CACAGCTGCCCGCCCAGGTGGCAT-3' (SEQ ID NO:17) (with the $Leu^1$ codon) and the 3' oligo 5'-GTCGC-CAGTGCTCCC TT-3' (SEQ ID NO:18) (with the complement of the $Asp^{235}$ codon). Two other p75 heavy chain fusions (p75P-sf2 and p75P-sf3) were made using the same 5' oligo with the 3' oligo 5'ATCGGACGTGGACGTG-CAGA-3' (SEQ ID NO:19). The resulting PCR fragment encoded amino acids 1–182. The PCR fragments were blunt-end ligated into the Stu1 or EcoRV site of the appropriate vector and checked for the absence of errors by sequencing the inserts completely.

Several different versions of the p75 fusion proteins were also expressed. p75-sf2 has the complete extracellular domain of p75 fused to the heavy chain while p75P-sf2 lacks the C-terminal 53 amino acids of the p75 extracellular domain. p75P-sf3 is the same as p75P-sf2 except that it lacks the $C_H1$ domain. The region deleted in p75P-sf2 and -sf3 contains sites of O-linked glycosylation and a proline-rich region, neither of which is present in the extracellular domain of p55. Seckinger et al., Proc. Nat. Acad. Sci. USA 87:5188–5192 (1990).

Similar to p55-sf2, two bands were seen for p75-sf2 (lane 7) and p75P-sf2 (lane 8).

WEHI Cytotoxicity Assays

The ability of the various fusion proteins to bind and neutralize human TNFα or TNFβ was tested in a TNF-mediated cell killing assay. Overnight incubation of the murine fibrosarcoma cell line, WEHI 164 (Espevik et al., J. Immunol. Methods 95:99–105 (1986)), with 20 pM (1 ng/ml) TNFα results in essentially complete death of the culture. When the fusion proteins were pre-incubated with TNFα (FIGS. 31A, B and C and Table 1 above) or TNFβ (FIG. 32) and the mixture added to cells, each fusion protein demonstrated dose-dependent protection of the cells from TNF cytotoxicity. Comparison of the viability of control cells not exposed to TNF to cells incubated in both TNF and fusion protein showed that the protection was essentially complete at higher concentrations of fusion protein.

Figure 31A:
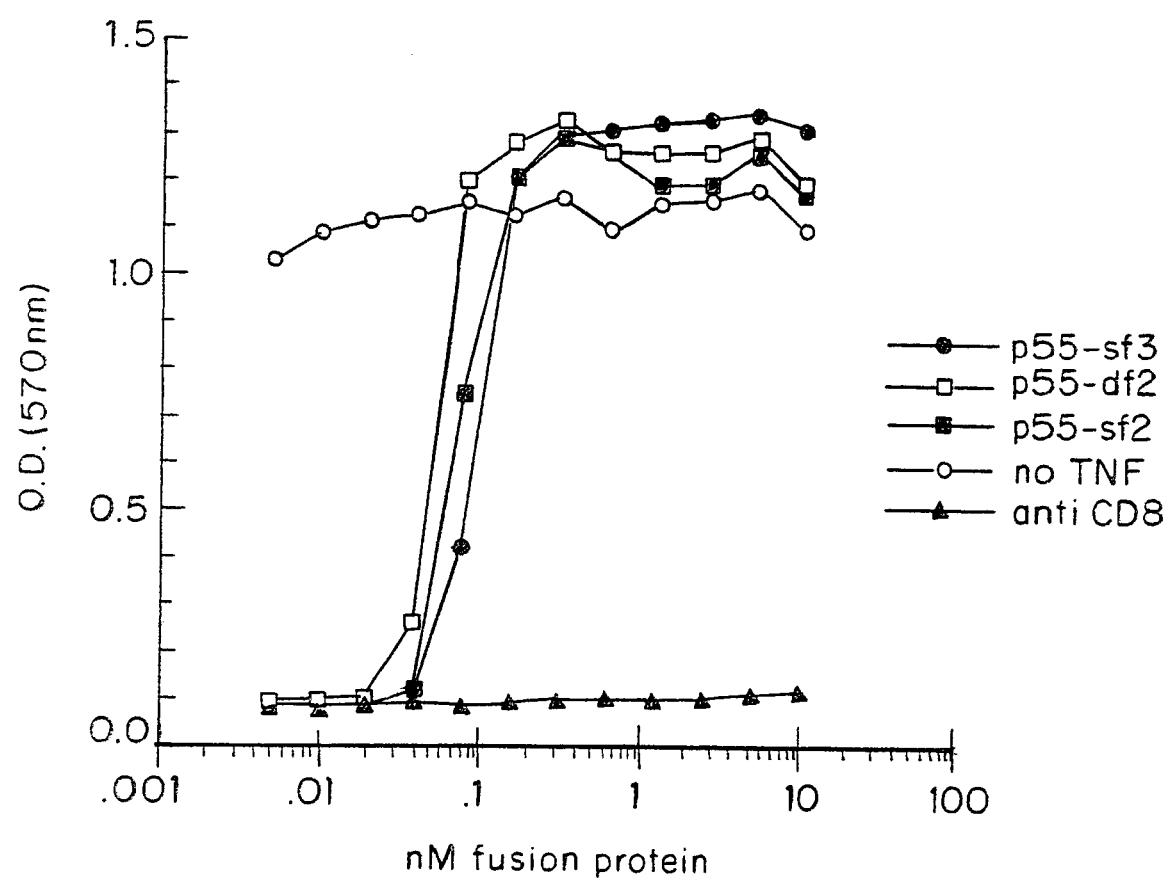
FIGS. 31A–31C are graphical representations showing that fusion proteins protected WEHI 164 cells from TNFα cytotoxicity. Cells were first sensitized to TNFα with actinomycin D and then incubated in 2 ng/ml TNFα with varying concentrations of TNFα overnight at 37° C. Cell viability was determined by measuring their uptake of MTT dye.
Figure 31B:
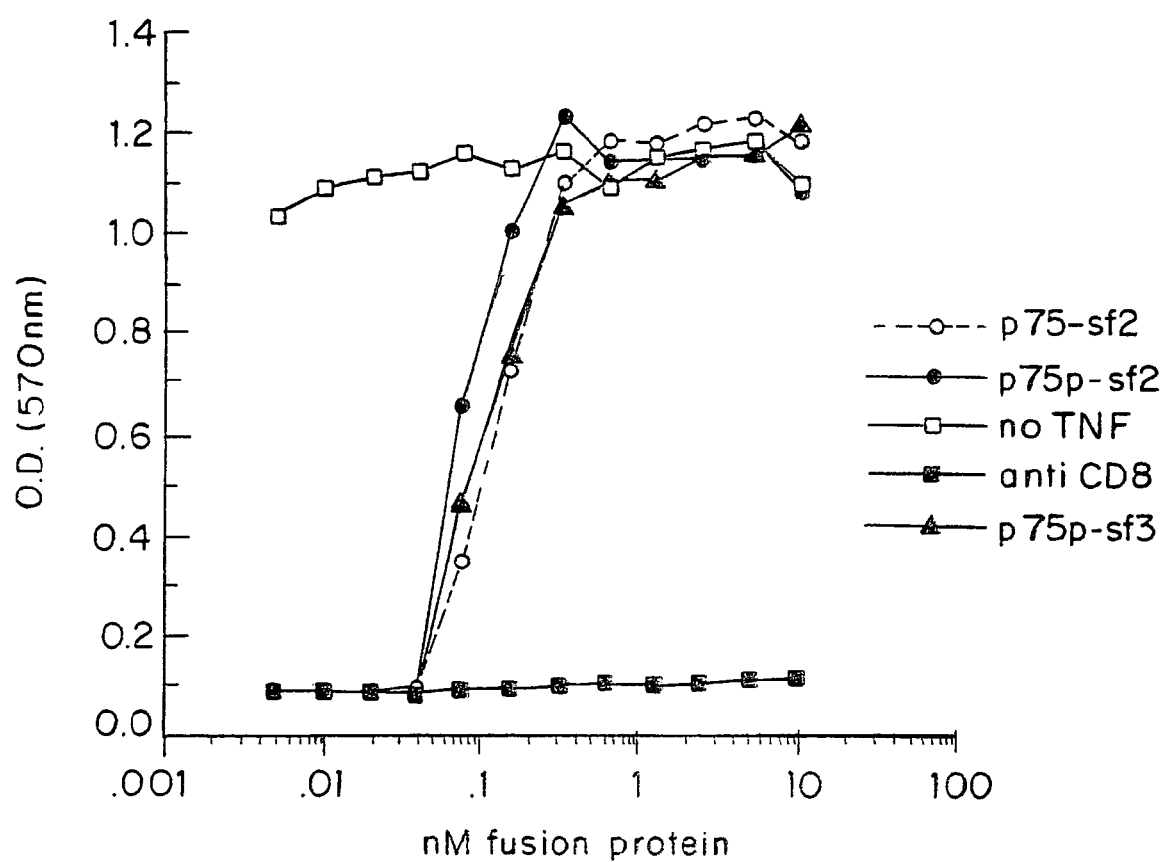
Figure 31C:
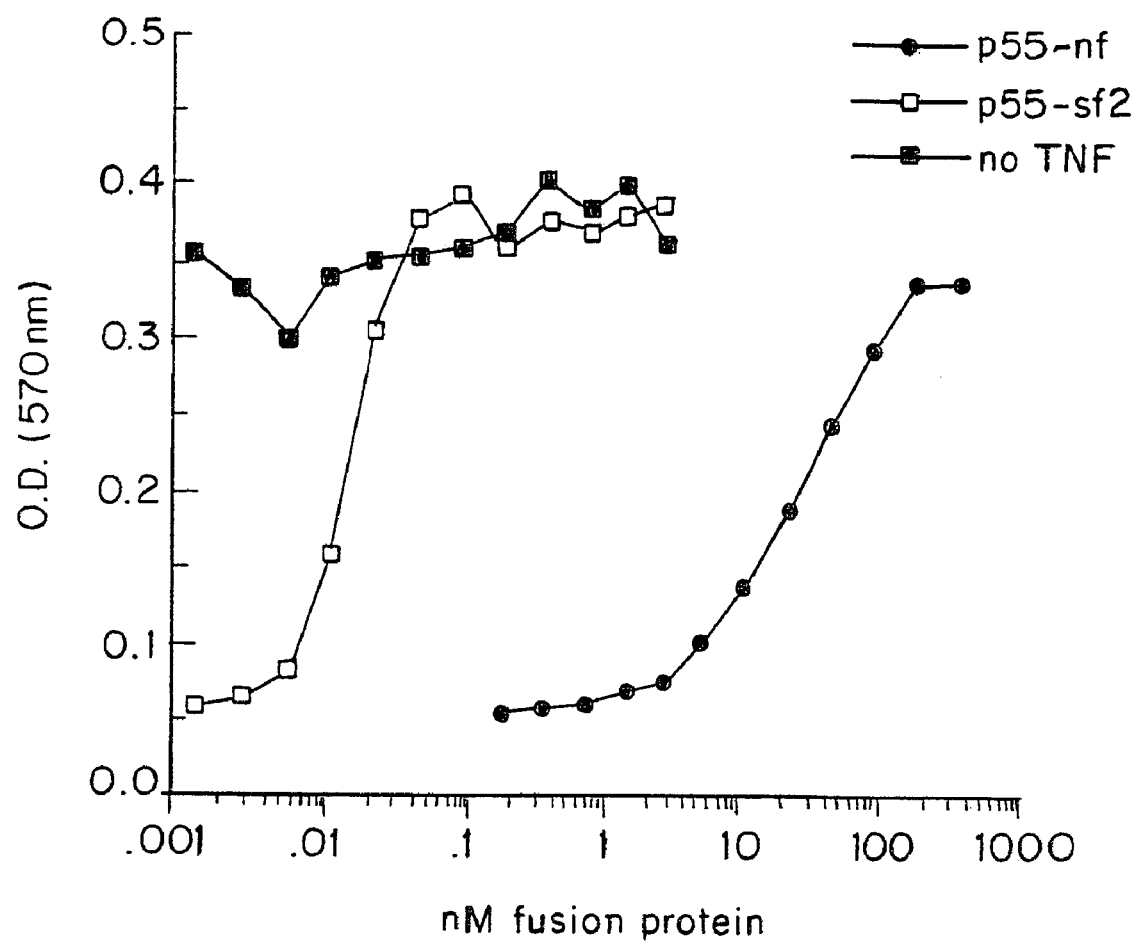

Tetravalent p55-df2 showed the greatest affinity for TNFα requiring a concentration of only 55 pM to confer 50% inhibition of 39 pM (2 ng/ml) TNFα (FIG. 31A and Table 1). Bivalent p55-sf2 and p75P-sf2 were nearly as efficient, requiring concentrations of 70 pM to half-inhibit TNFα. Approximately two times as much p75-sf2 was required to confer 50% inhibition compared to p55-sf2 at the TNF concentration that was used. The monomeric, non-fusion form of p55 was much less efficient at inhibiting TNFα requiring a 900-fold molar excess over TNFα to inhibit cytotoxicity by 50%. This much-reduced inhibition was also observed with a monomeric, Fab-like p55 fusion protein that was required at a 2000-fold molar excess over TNFα to get 50% inhibition. The order of decreasing inhibitory activity was therefore p55-df2>p55-sf2=p75P-sf2>p75-sf2>>>monomeric p55.

Figure 32:
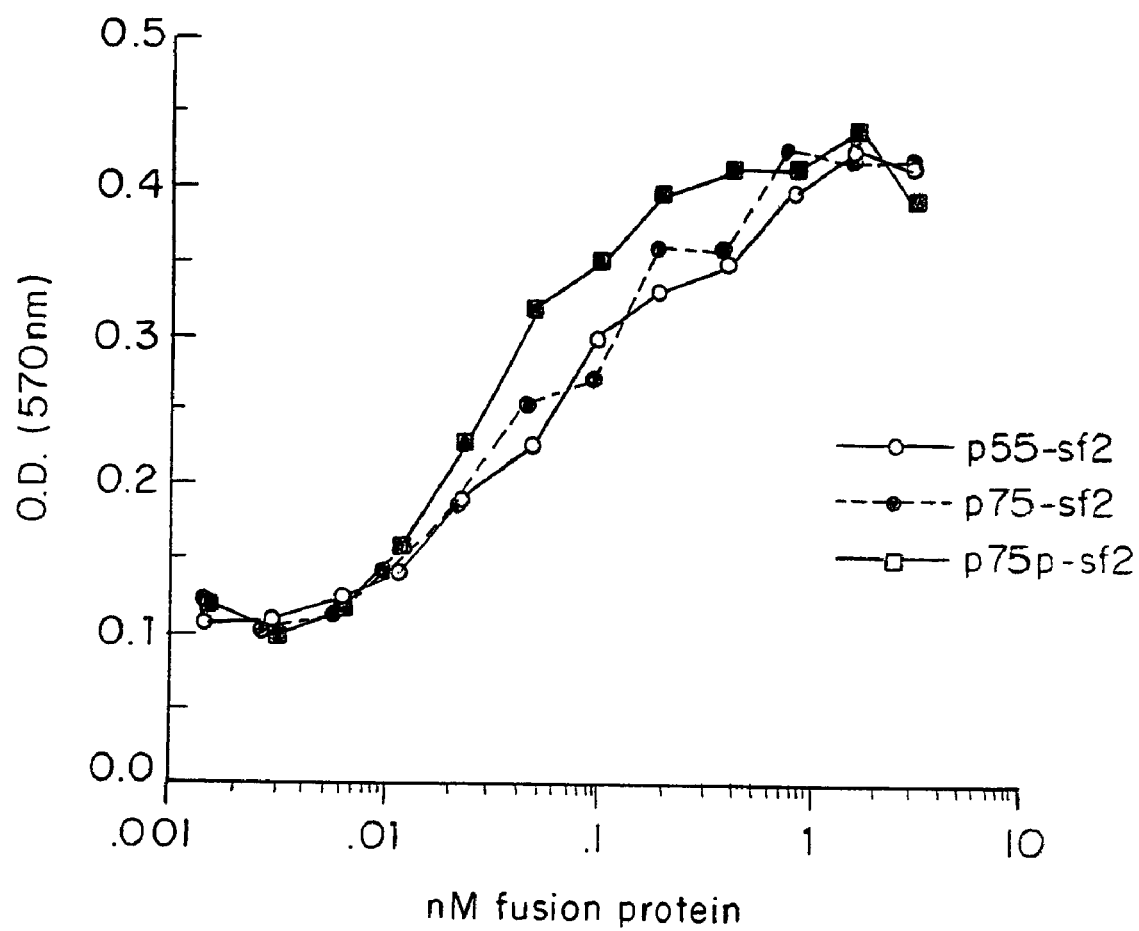
FIG. 32 is a graphical representation of data showing that fusion proteins also effectively protect WEHI 164 cells from TNFβ cytotoxicity.

Surprisingly, the order of decreasing inhibitory activity was different for TNFβ, as presented in FIG. 32. p75P-sf2 was most efficient at inhibition requiring a concentration of 31 pM to half-inhibit human TNFβ at 2 pM. Compared to p75P-sf2, three times as much p75-sf2 and three times as much p55-sf2 were necessary to obtain the same degree of inhibition. The order of decreasing inhibitory activity was therefore p75P-sf2>p75-sf2=p55-sf2.

Affinity Measurements

Figure 33A:
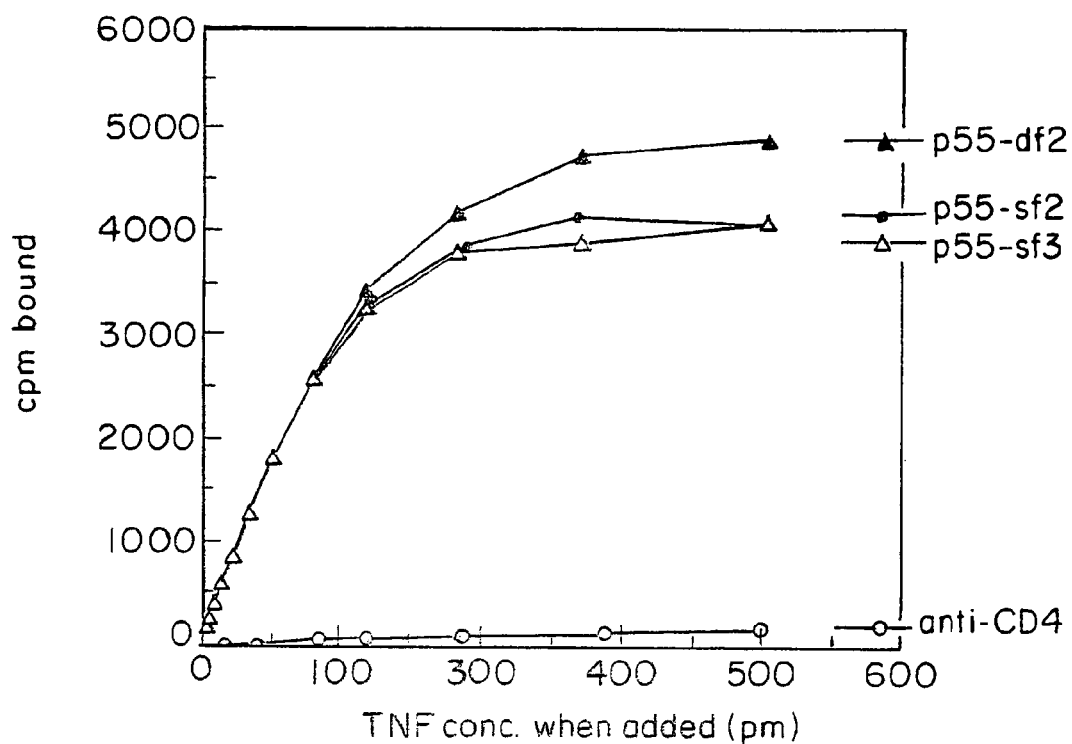
FIGS. 33A–33H are graphical representations of analyses of binding between the various fusion proteins and TNFα by saturation binding (FIGS. 33A and 33B) and Scatchard analysis (FIGS. 33C–33H). A microtiter plate was coated with excess goat anti-Fc polyclonal antibody and incubated with 10 ng/ml of fusion protein in TBST buffer (10 mM Tris-HCl, pH 7.8, 150 mM NaCl, 0.05% TWEEN® 20) for 1 hour. Varying amounts of $^{125}$I labeled TNFα (specific activity—34.8 µCi/µg) were then incubated with the captured fusion protein in PBS (10 mM Na Phosphate, pH 7.0, 150 mM NaCl) with 1% bovine serum albumin for 2 hours. Unbound TNFα was washed away with four washes in PBS and the cpm bound was quantitated using a y-counter. All samples were analyzed in triplicate. The slope of the lines in (FIGS. 33C–H) represent the affinity constant, $K_a$. The dissociation constant ($K_d$) values (see Table 1) were derived using the equation $K_d=1/K_a$.
Figure 33B:
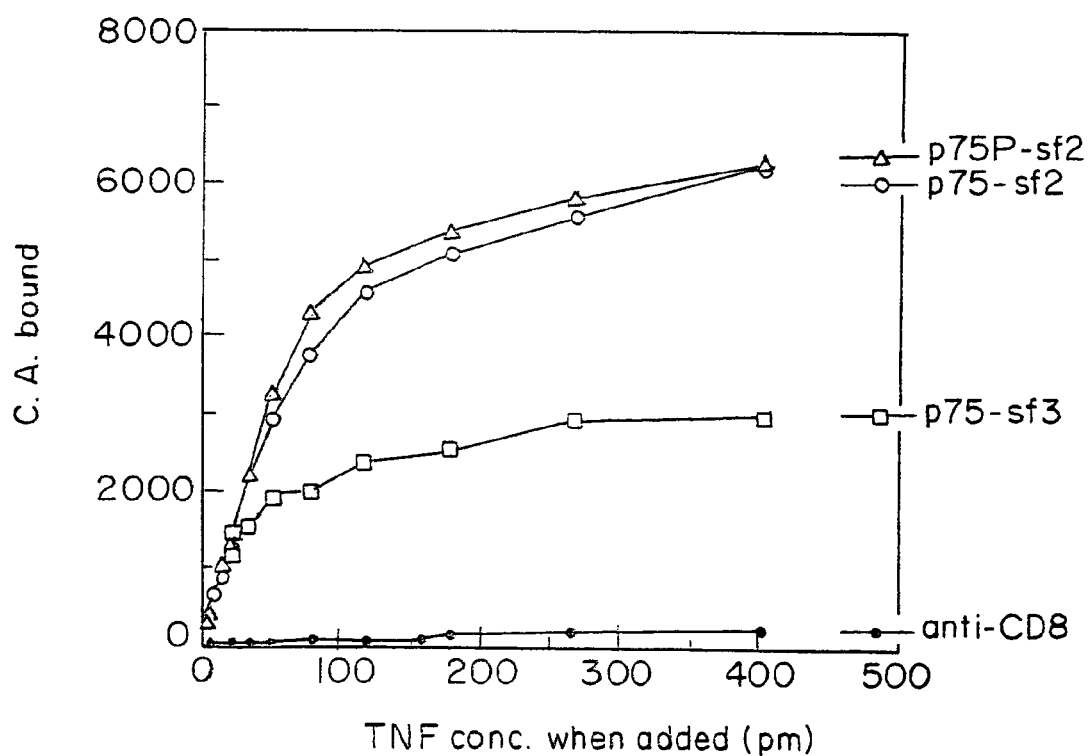
Figure 33D:
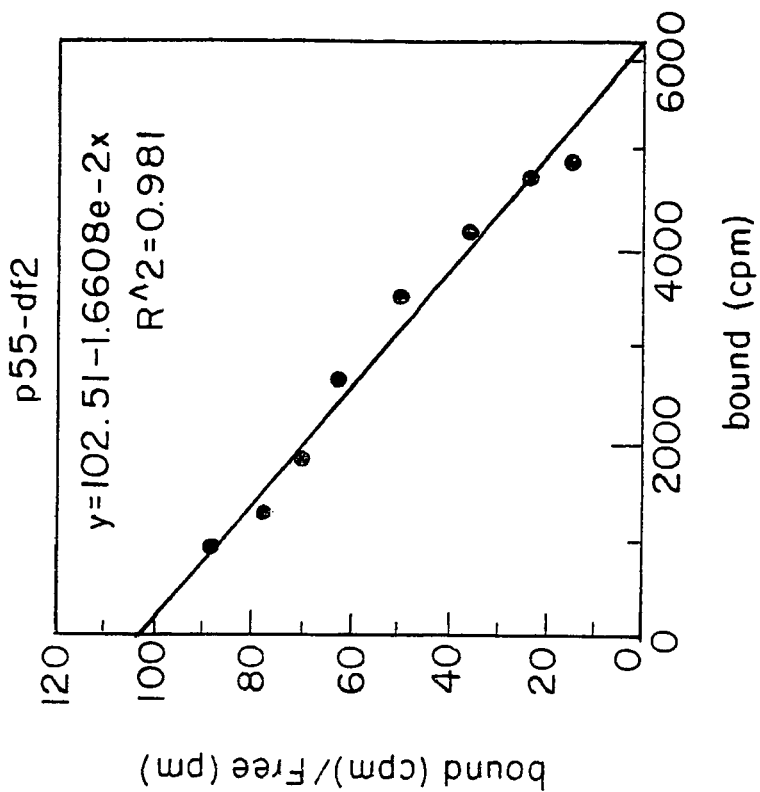
Figure 33C:
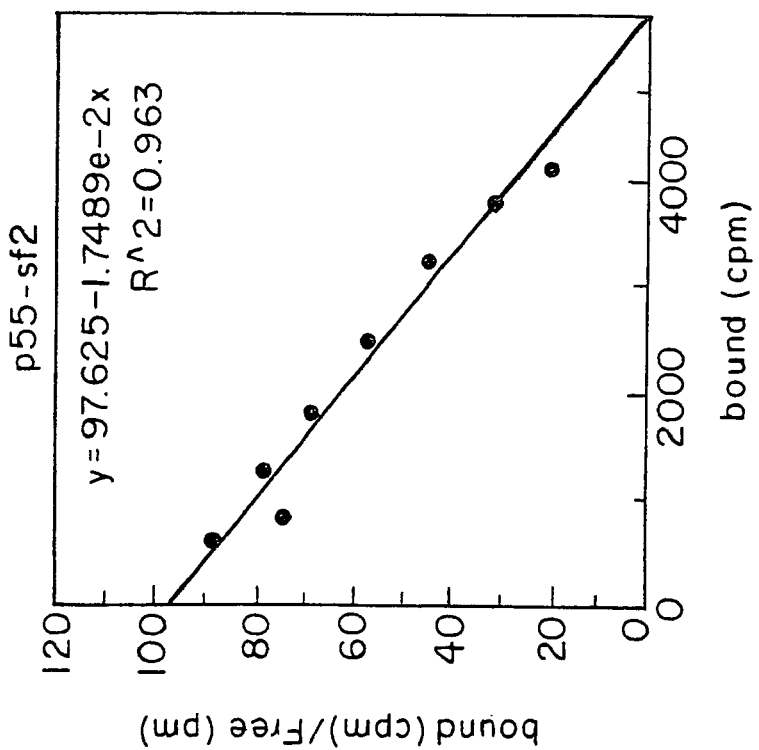
Figure 33F:
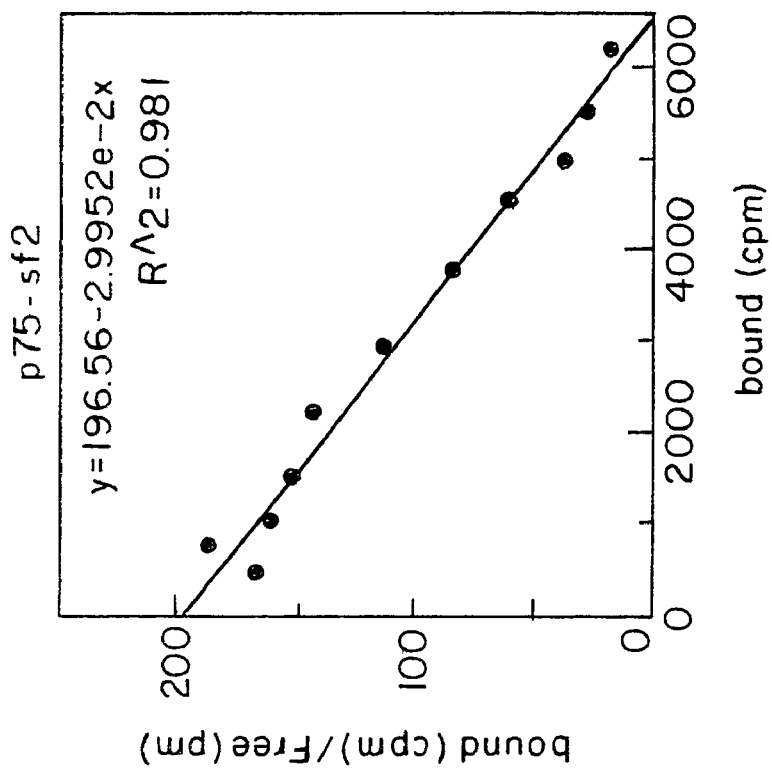
Figure 33E:
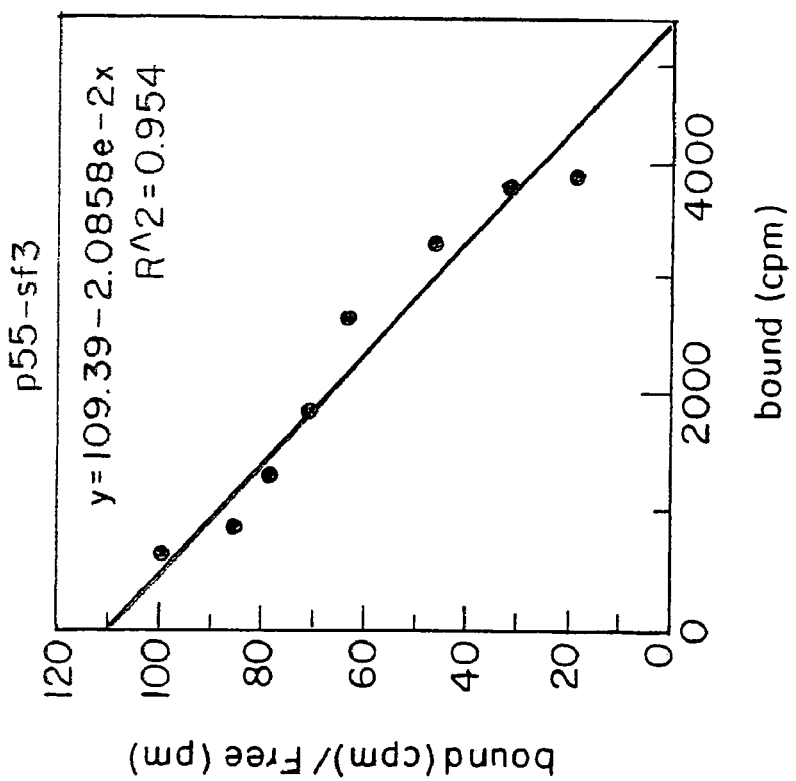
Figure 33H:
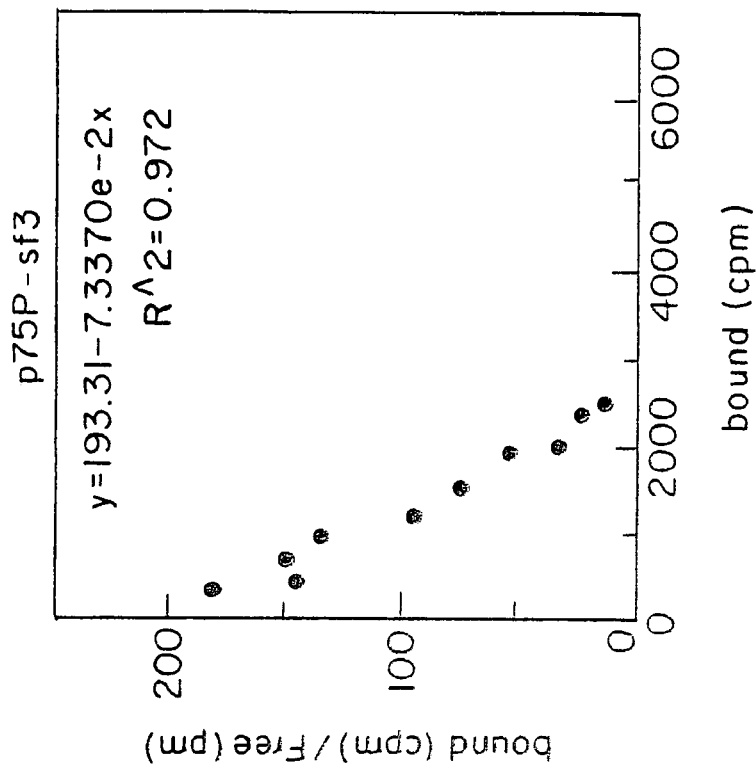
Figure 33G:
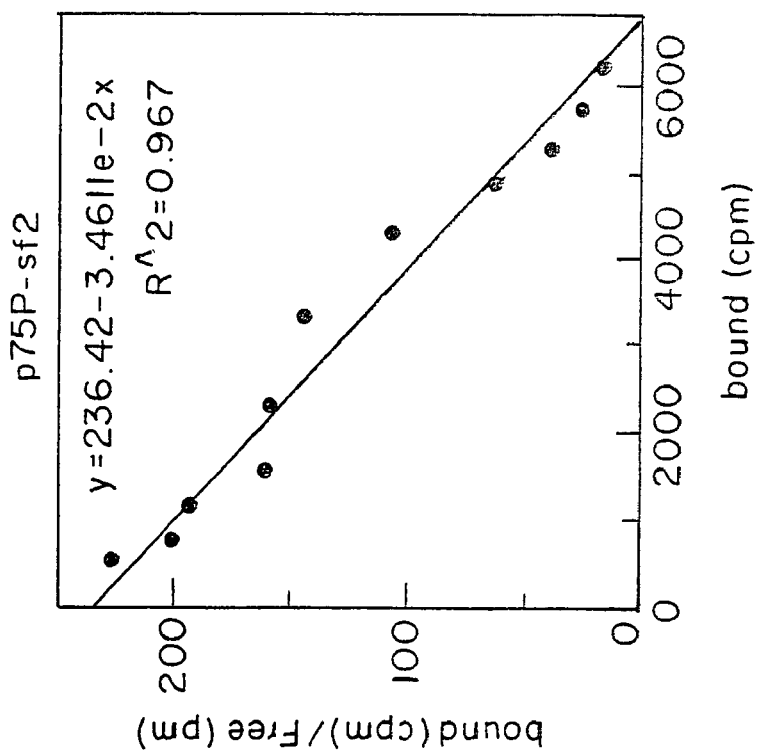

A comparison was made of the binding affinity of various fusion proteins and TNFα by saturation binding (FIGS. 33A and 33B) and Scatchard analysis (FIGS. 33C–33H). A microtiter plate was coated with excess goat anti-Fc polyclonal antibody and incubated with 10 ng/ml of fusion protein in TBST buffer (10 mM Tris-HCl, pH 7.8, 150 NaCl, 0.05% TWEEN® 20) for 1 hour. Varying amounts of $^{125}I$ labeled TNFα (specific activity—34.8 μCi/μg) was then incubated with the captured fusion protein in PBS (10 mM Na Phosphate, pH 7.0, 150 mM NaCl) with 1% bovine serum albumin for 2 hours. Unbound TNFα was washed away with four washes in PBS and the cpm bound was quantitated using a y-counter. All samples were analyzed in triplicate. The slope of the lines in (FIGS. 33C–H) represent the affinity constant, $K_a$. The dissociation constant $(K_d)$ values (see Table 1) were derived using the equation $K_d=1/K_a$.

EXAMPLE XXVIII

In vivo Results

C3H mice were challenged with 5 μg of human TNFα after treatment with an immunoreceptor molecule of the invention. The effect of the treatment was compared with two control treatments. The first control, cA2, is a chimeric mouse/human $IgG_1$ monoclonal antibody that binds human TNF, and thus is a positive control. The second control, c17-1A, is a chimeric mouse/human $IgG_1$ irrelevant monoclonal antibody and is thus a negative control. The results of the treatments were as presented in the following Table 19.

TABLE 19

| Treatment | Dead Fraction | % Dead |
|---|---|---|
| 1 µg cA2 | 5/14 | 36% |
| 10 µg cA2 | 1/15 | 7% |
| 50 µg c17-1A | 13/15 | 87% |
| 1 µg p55-sf2 | 8/15 | 53% |
| 10 µg p55-sf2 | 0/15 | 0% |
| 50 µg p55-sf2 | 0/15 | 0% |

Mice were injected with 25 µg of p55 fusion protein or a control antibody and 1 hour later were challenged with 1 µg lipopolysaccharide (type J5). Mice were checked 24 hourts later. The results are presented in the following Table 20.

TABLE 20

| Treatment | Dead Fraction | % Dead |
|---|---|---|
| Control Antibody | 11/11 | 100% |
| p55-sf2 | 0/13 | 0% |

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method of inhibiting TNFα in a human patient, wherein said human patient has psoriasis, comprising administering to the human patient an effective TNFα-inhibiting amount of an anti-TNFα antibody or antigen-binding fragment thereof, said antibody comprising a human IgG4 constant region, wherein the antigen-binding fragment is a Fab' fragment, and wherein said anti-TNFα antibody or antigen-binding fragment thereof (i) competitively inhibits binding of A2 (ATCC Accession No. PTA-7045) to human TNFα, and (ii) binds to a neutralizing epitope of human TNFα with an affinity of at least $1 \times 10^8$ liter/mole, measured as an association constant (Ka), as determined by Scatchard analysis.

2. The method of claim 1, wherein the antibody or antigen-binding fragment thereof comprises a human constant region and a human variable region.

3. The method of claim 1, wherein the antibody or antigen-binding fragment thereof comprises at least one human light chain and at least one human heavy chain.

4. The method of claim 3, wherein the light chain comprises all antigen-binding regions of the light chain A2 (ATCC Accession No. PTA-7045).

5. The method of claim 3, the heavy chain comprises all antigen-binding regions of the heavy chain of A2 (ATCC Accession No. PTA-7045).

6. The method of claim 3, wherein the light chain comprises all antigen-binding regions of the light chain of A2 (ATCC Accession No. PTA-7045) and the heavy chain comprises all antigen-binding regions of the heavy chain of A2 (ATCC Accession No. PTA-7045).

7. The method of claim 1, wherein said anti-TNFα antibody or antigen-binding fragment thereof binds with high affinity to a neutralizing epitope of TNFα in vivo.

8. The method of claim 1, wherein said binding of the antibody or antigen-binding fragment to human TNFα neutralizes TNFα activation of procoagulant activities of endothelial cells.

9. The method of claim 1, wherein the anti-TNFα antibody or antigen-binding fragment thereof is administered to the human patient by means of parenteral administration.

10. The method of claim 1, wherein the anti-TNFα antibody or antigen-binding fragment thereof is administered to the human patient by means of intravenous administration, subcutaneous administration or intramuscular administration.

11. The method of claim 1, wherein the anti-TNFα antibody or antigen-binding fragment thereof is administered to the human patient by means of oral administration.

12. The method of claim 1, wherein said TNFα-inhibiting amount of the anti-TNFα antibody or antigen-binding fragment thereof comprises a single or divided dose of about 0.1–50 mg/kg.

13. The method of claim 12, wherein the single or divided dose of the anti-TNFα antibody or antigen-binding fragment thereof is one selected from 0.5, 0.9, 1, 1.1, 1.5, 2,3, 4,5, 6, 7, 8, 9, 10, 11, 12, 13, 14 or 15 mg/kg per day on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or at least one of week 1, 2, 3, 4, 5, 6, 7, 8, 9, 10, 11, 12, 13, 14, 15, 16, 17, 18, 19 or 20.

14. A method of inhibiting TNFα in a human patient, wherein said human patient has psoriasis, comprising administering to the human an effective TNFα-inhibiting amount of an antibody light chain that specifically binds human TNFα and competitively inhibits binding of A2 (ATCC Accession No. PTA-7045) to human TNFα, said light chain comprising a human IgG4 light chain constant region and a human light chain framework region, wherein said human light chain binds to a neutralizing epitope of human TNFα with an affinity of at least $1\times10^8$ liter/mole, measured as an association constant (Ka), as determined by Scatchard analysis.

15. A method of inhibiting TNFα in a human patient, wherein said human patient has psoriasis, comprising administering to the human an effective TNFα-inhibiting amount of an antibody heavy chain that specifically binds human TNFα and competitively inhibits binding of A2 (ATCC Accession No. PTA-7045) to human TNFα, said heavy chain comprising a human IgG4 heavy chain constant region and a human heavy chain framework region, wherein said human heavy chain binds to a neutralizing epitope of human TNFα with an affinity of at least $1\times10^8$ liter/mole, measured as an association constant (Ka), as determined by Scatchard analysis.

16. A method of inhibiting TNFα in a human patient, wherein said human patient has psoriasis, comprising administering to the human an effective TNFα-inhibiting amount of an anti-TNFα antibody or antigen-binding fragment thereof, said antibody comprising a human IgG4 constant region, wherein the antigen-binding fragment is a Fab fragment, and wherein said antibody or antigen binding fragment (i) competitively inhibits binding of A2 (ATCC Accession No. PTA-7045) to human TNFα, and (ii) binds to a neutralizing epitope of human TNFα with an affinity of at least $1\times10^8$ liter/mole, measured as an association constant (Ka), as determined by Scatchard analysis.

17. A method of inhibiting TNFα in a human patient, wherein said human patient has psoriasis, comprising administering to the human an effective TNFα-inhibiting amount of an anti-TNFα antibody or antigen-binding fragment thereof, said antibody comprising a human IgG4 constant region, wherein the antigen-binding fragment is a $F(ab')_2$ fragment, and wherein said antibody or antigen binding fragment (i) competitively inhibits binding of A2 (ATCC Accession No. PTA-7045) to human TNF-α, and (ii) binds to a neutralizing epitope of human TNFα with an affinity of at least $1\times10^8$ liter/mole, measured as an association constant (Ka), as determined by Scatchard analysis.

18. The method of claim 1, wherein said Scatchard analysis comprises labeling the anti-TNFα antibody or antigen-binding fragment thereof and measuring direct binding of $^{125}I$ labeled anti-TNFα antibody or antigen-binding fragment thereof to immobilized rhTNFα, and wherein said antibodies are labelled to a specific activity of about 9.7 μCi/μg by the iodogen method.

* * * * *

UNITED STATES PATENT AND TRADEMARK OFFICE
CERTIFICATE OF CORRECTION

PATENT NO. : 7,160,542 B2 Page 1 of 1
APPLICATION NO. : 11/170753
DATED : January 9, 2007
INVENTOR(S) : Junming Le et al.

It is certified that error appears in the above-identified patent and that said Letters Patent is hereby corrected as shown below:

Title Page, Item (54) Title:
please delete "Method" and insert --Methods--.

Signed and Sealed this

Twentieth Day of March, 2007

JON W. DUDAS
*Director of the United States Patent and Trademark Office*